(12) United States Patent
Schwarz et al.

(10) Patent No.: US 9,776,967 B2
(45) Date of Patent: Oct. 3, 2017

(54) CARBOXAMIDE DERIVATIVES AS PESTICIDAL COMPOUNDS

(71) Applicant: Bayer Animal Health GmbH, Leverkusen (DE)

(72) Inventors: Hans-Georg Schwarz, Dorsten (DE); Anne Decor, Langenfeld (DE); Martin Füβlein, Düsseldorf (DE); Ulrich Görgens, Ratingen (DE); Kerstin Ilg, Köln (DE); Claudia Welz, Düsseldorf (DE); Peter Lümmen, Idstein (DE); Adeline Köhler, Langenfeld (DE); Kirsten Börngen, Köln (DE)

(73) Assignee: BAYER ANIMAL HEALTH GMBH, Leverkusen (DE)

( * ) Notice: Subject to any disclaimer, the term of this patent is extended or adjusted under 35 U.S.C. 154(b) by 0 days.

(21) Appl. No.: 15/022,583

(22) PCT Filed: Oct. 10, 2014

(86) PCT No.: PCT/EP2014/071778
§ 371 (c)(1),
(2) Date: Mar. 17, 2016

(87) PCT Pub. No.: WO2015/055535
PCT Pub. Date: Apr. 23, 2015

(65) Prior Publication Data
US 2016/0221950 A1  Aug. 4, 2016

(30) Foreign Application Priority Data

Oct. 14, 2013  (EP) .................................... 13188513

(51) Int. Cl.
| | | |
|---|---|---|
| *C07D 213/38* | (2006.01) |
| *C07D 213/40* | (2006.01) |
| *C07D 401/10* | (2006.01) |
| *C07D 401/12* | (2006.01) |
| *C07D 405/04* | (2006.01) |
| *A01N 43/40* | (2006.01) |
| *C07D 213/61* | (2006.01) |
| *A01N 43/30* | (2006.01) |
| *A01N 47/00* | (2006.01) |
| *A01N 43/60* | (2006.01) |
| *A01N 43/84* | (2006.01) |

(52) U.S. Cl.
CPC ........... *C07D 213/40* (2013.01); *A01N 43/30* (2013.01); *A01N 43/40* (2013.01); *A01N 43/60* (2013.01); *A01N 43/84* (2013.01); *A01N 47/00* (2013.01); *C07D 213/38* (2013.01); *C07D 213/61* (2013.01); *C07D 401/10* (2013.01); *C07D 401/12* (2013.01); *C07D 405/04* (2013.01)

(58) Field of Classification Search
CPC .. C07D 213/38; C07D 213/40; C07D 401/10; C07D 401/12; C07D 405/04
See application file for complete search history.

(56) References Cited

U.S. PATENT DOCUMENTS

| | | | |
|---|---|---|---|
| 4,885,026 | A | 12/1989 | Lee et al. |
| 6,034,106 | A | 3/2000 | Biftu et al. |
| 6,388,084 | B1 | 5/2002 | Kaplan et al. |
| 2004/0242644 | A1 | 12/2004 | Buckley et al. |
| 2006/0247289 | A1 | 11/2006 | Qian et al. |
| 2007/0197481 | A1 | 8/2007 | Qian et al. |

FOREIGN PATENT DOCUMENTS

| | | |
|---|---|---|
| CA | 2828060 | 9/2012 |
| CN | 101337940 | 5/2012 |
| CN | 102057925 | 4/2013 |
| EP | 0952154 | 10/1999 |
| EP | 1171440 | 4/2004 |
| EP | 1548007 | 6/2005 |
| EP | 1674455 | 6/2006 |
| EP | 1997800 | 12/2008 |
| EP | 2132987 | 12/2009 |
| EP | 2289880 | 3/2011 |
| WO | 97/24343 | 7/1997 |
| WO | 99/36393 | 7/1999 |
| WO | 01/11965 | 2/2001 |
| WO | 03/076415 | 9/2003 |
| WO | 03/106457 | 12/2003 |
| WO | 2004/074280 | 9/2004 |
| WO | 2004/099160 | 11/2004 |
| WO | 2005/007627 | 1/2005 |
| WO | 2005/014545 | 2/2005 |
| WO | 2005/058828 | 6/2005 |
| WO | 2005/058833 | 6/2005 |
| WO | 2005/077915 | 8/2005 |
| WO | 2005/077934 | 8/2005 |
| WO | 2005/085216 | 9/2005 |
| WO | 2005/085238 | 9/2005 |

(Continued)

OTHER PUBLICATIONS

European Patent Office, International Search Report for International Patent Application No. PCT/EP2014/071778, dated Dec. 2, 2014, 3 pages.

(Continued)

*Primary Examiner* — Timothy R Rozof
(74) *Attorney, Agent, or Firm* — Morrison & Foerster LLP

(57) ABSTRACT

Disclosed are compounds of formula (I) which possess pesticidal, especially nematicidal properties wherein in the structural elements have the meaning as indicated in the description.

(I)

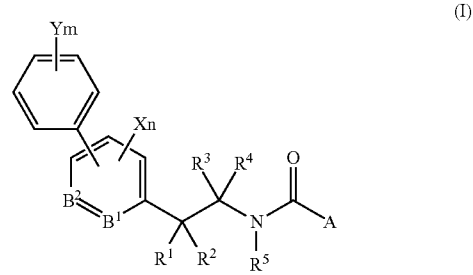

17 Claims, No Drawings

(56) References Cited

FOREIGN PATENT DOCUMENTS

| | | |
|---|---|---|
| WO | 2005/103004 | 11/2005 |
| WO | 2005/103006 | 11/2005 |
| WO | 2006/003494 | 1/2006 |
| WO | 2006/008191 | 1/2006 |
| WO | 2006/008192 | 1/2006 |
| WO | 2006/008193 | 1/2006 |
| WO | 2006/008194 | 1/2006 |
| WO | 2006/029829 | 3/2006 |
| WO | 2006/043635 | 4/2006 |
| WO | 2006/067103 | 6/2006 |
| WO | 2006/122952 | 11/2006 |
| WO | 2006/122955 | 11/2006 |
| WO | 2007/060408 | 5/2007 |
| WO | 2007/108483 | 9/2007 |
| WO | 2008/124757 | 10/2008 |
| WO | 2008/134969 | 11/2008 |
| WO | 2009/002809 | 12/2008 |
| WO | 2009/049851 | 4/2009 |
| WO | 2009/080250 | 7/2009 |
| WO | 2009/099929 | 8/2009 |
| WO | 2010/060231 | 6/2010 |
| WO | 2010/069266 | 6/2010 |
| WO | 2010/069502 | 6/2010 |
| WO | 2010/129500 | 11/2010 |
| WO | 2012/029672 | 3/2012 |
| WO | 2012/034472 | 3/2012 |
| WO | 2012/118139 | 9/2012 |
| WO | 2013/064460 | 5/2013 |
| WO | 2013/064461 | 5/2013 |
| WO | 2013/064518 | 5/2013 |
| WO | 2013/064519 | 5/2013 |
| WO | 2013/064520 | 5/2013 |
| WO | 2013/064521 | 5/2013 |
| WO | 2013/076230 | 5/2013 |
| WO | 2013/120940 | 8/2013 |
| WO | 2013/143811 | 10/2013 |
| WO | 2014/004064 | 1/2014 |
| WO | 2014/034750 | 3/2014 |
| WO | 2014/034751 | 3/2014 |

OTHER PUBLICATIONS

European Patent Office, Written Opinion for International Patent Application No. PCT/EP2014/071778, dated Apr. 23, 2015, 5 pages.

European Patent Office, Extended European Search Report for European Patent Application No. 13188513.9, dated Nov. 27, 2013, 6 pages.

International Bureau of WIPO, International Preliminary Report on Patentability for International Patent Application No. PCT/EP2014/071778, dated Apr. 19, 2016, 6 pages.

Kers, "Phenethyl nicotionamides, a novel class of Nav1.7 channel blockers: Structure and activity relationship", Bioorganic & Medicinal Chemistry Letters, 22, 2012, pp. 6018-6115.

Michels, et al., "Concise Formal Synthesis of Porothramycins A and B via Zincke Pyridinium Ring-Opening/Ring-Closing Cascade", Organic Letters, vol. 12, No. 13, 2010, pp. 3093-3095.

CARBOXAMIDE DERIVATIVES AS PESTICIDAL COMPOUNDS

CROSS REFERENCE TO RELATED APPLICATIONS

This application is a National Phase application under 35 U.S.C. §371 of International Application No. PCT/EP2014/071778, filed Oct. 10, 2014, which claims priority benefit of European Application No. 13188513.9, filed Oct. 14, 2013, the disclosures of each of which are hereby incorporated by reference in their entireties for all purposes.

The present invention relates to certain pyridylalkyl carboxamide derivatives as to processes for their preparation, to compositions comprising those compounds and their use in agriculture and veterinary fields and fields relying on pest management. The compounds are active for controlling plant damaging pests; they are particularly active for the control of nematodes. Furthermore, the compounds act as anthelmintic agents against endoparasites in animals and humans.

Nematodes cause a substantial loss in agricultural product including food and industrial crops and are combated with chemical compounds having nematicidal activity. These compounds should have high activity, broad spectrum activity against different strains of nematodes and should not be toxic to non-target organisms.

The occurrence of resistances against all commercial anthelmintics seems to be a growing problem in the area of veterinary medicine. Therefore, endoparasiticides with new molecular modes of actions are urgently desired. The new active ingredients should perform with excellent efficacy against a broad spectrum of helminths and nematodes without any adverse toxic effects to the treated vertebrate organism. Endoparasiticides are pharmaceuticals for combat or suppression of endoparasites in animals or humans.

The use of certain N-2-(pyridyl)ethyl-carboxamide derivatives for controlling nematodes is described in WO2007/108483 A1 and EP 2 132 987 A1.

The use of certain carboxamides as parasiticides is described in WO2012/118139 A1, WO2013/076230 A1, WO2014/004064 A1, WO2014/034750 A1 and WO2014/034751 A1.

Furthermore, certain carboxamides are described as pesticides in WO2013/064518 A1, WO2013/064519 A1, WO2013/064520 A1, WO2013/064521 A1 or as nematicides in WO2013/064460 A1, WO2013/064461 A1, WO2013/120940 A2 and WO2013/143811 A1.

It is an object of the present invention to provide compounds which can be used as nematicides with a satisfactory or improved nematicidal activity, particularly at relatively low application rates, with a high selectivity and high compatibility in crop-plant cultures. Another object of the present invention is to provide compounds which can be used as endoparasiticides with a satisfactory or improved anthelmintic activity against a broad spectrum of helminths and nematodes, particularly at relatively low dosages, without any adverse toxic effects to the treated vertebrate organism.

The present invention relates to a compound of formula (I)

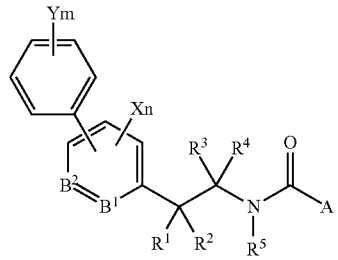

wherein (embodiment 1-1)
$B^1$, $B^2$ represent C—X or N, wherein at least $B^1$ or $B^2$ is N,
n is 0, 1, 2, 3 or 4, limited by the number of available positions in the ring to which a substituent X can be connected,
each X is independently selected from the group consisting of hydrogen, halogen, nitro, cyano, hydroxy, amino, —SH, —SF$_5$, —CHO, —OCHO, —NHCHO, —COOH, —CONH$_2$, —CONH(OH), —OCONH$_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_8$-halogenoalkylcarbonyl having 1 to 5 halogen atoms, —CONH($C_1$-$C_8$-alkyl), —CON($C_1$-$C_8$-alkyl)$_2$, —CONH(OC$_1$-$C_8$-alkyl), —CON(OC$_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(OC$_1$-$C_8$-alkyl), —OCO(OC$_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, ($C_1$-$C_6$-alkoxyimino)-$C_1$-$C_6$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)-$C_1$-$C_6$-alkyl, benzyloxy, —S-benzyl, benzylamino, phenoxy, —S-phenyl and phenylamino,
m is 0, 1, 2, 3, 4 or 5, and
each Y is independently selected from the group consisting of hydrogen, halogen, nitro, cyano, hydroxy, amino, —SH, —SF$_5$, —CHO, —OCHO, —NHCHO, —COOH, —CONH$_2$, —CONH(OH), —OCONH$_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_8$- halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON(O$C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(O$C_1$-$C_8$-alkyl), —OCO(O$C_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_1$-halogenoalkyl having 1 to 5 halogen atoms, —CH$_2$—S—$C_1$-$C_8$-alkyl, —CH$_2$—S(O)—$C_1$-$C_8$-alkyl, —CH$_2$—S(O)$_2$—$C_1$-$C_8$-alkyl, ($C_1$-$C_6$-alkoxyimino)-$C_1$-$C_8$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)-$C_1$-$C_6$-alkyl, benzyloxy, —S-benzyl, benzylamino, phenoxy, —S-phenyl and phenylamino, or m is 2, 3, 4 or 5, and at least two substituents Y are vicinal and, together with the carbon atoms to which they are bonded, form an annellated 5- or 6-membered carbocycle or a 5- or 6-membered heterocycle with one or two heteroatoms selected from the group consisting of oxygen and nitrogen, whereat two oxygen atoms are not directly connected, the carbocycle or heterocycle being independently substituted by 0 to 4 halogen atoms, 0 to 2 oxo-groups, 0 to 8 $C_1$-$C_8$-alkyl, 0 to 8 $C_1$-$C_8$-alkoxy or 0 to 4 $C_1$-$C_8$-halogenoalkyl having 1 to 5 halogen atoms, and the remaining substituents Y are independently selected from the group consisting of hydrogen, halogen, nitro, cyano, hydroxy, amino, —SH, —SF$_5$, —CHO, —OCHO, —NHCHO, —COOH, —CONH$_2$, —CONH(OH), —OCONH$_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkylamino, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_3$-halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON(O$C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(O$C_1$-$C_8$-alkyl), —OCO(O$C_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, —CH$_2$—S—$C_1$-$C_8$-alkyl, —CH$_2$—S(O)—$C_1$-$C_8$-alkyl, —CH$_2$—S(O)$_2$—$C_1$-$C_8$-alkyl, ($C_1$-$C_6$-alkoxyimino)-$C_1$-$C_6$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)-$C_1$-$C_8$-alkyl, benzyloxy, —S-benzyl, benzylamino, phenoxy, —S-phenyl and phenylamino, $R^1$, $R^2$, $R^3$ and $R^4$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_8$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_6$-alkyl), —CON(O$C_1$-$C_6$-alkyl)($C_1$-$C_6$-alkyl), $C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl), —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$—$C_1$-$C_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^1$ and $R^2$ together with the carbon atom to which they are bonded form a 4-, 5- or 6-membered carbocycle and $R^3$ and $R^4$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_8$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_8$-alkyl), —CON(O$C_1$-$C_6$-alkyl)($C_1$-$C_6$-alkyl), $C_1$-$C_8$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$—$C_1$-$C_6$-halogenoalkyl having 1 to 5 halogen atoms, benzyl, benzyloxy, —S-benzyl, —S(O)-benzyl, —S(O)₂-benzyl, benzylamino, phenoxy, —S-phenyl, —S(O)-phenyl, —S(O)₂-phenyl, phenylamino, phenylcarbonylamino, 2,6-dichlorophenyl-carbonylamino, 2-chlorophenylcarbonylamino and phenyl, or $R^3$ and $R^4$ together with the carbon atom to which they are bonded form a 3-, 4-, 5- or 6-membered carbocycle and $R^1$ and $R^2$ are the same or different and are selected from the group consisting of hydrogen, halogen, cyano, hydroxy, amino, —SH, —CHO, —OCHO, —NHCHO, —COOH, —CONH₂, —CONH(OH), —OCONH₂, a (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)₂, —CONH(O$C_1$-$C_6$-alkyl), —CON(O$C_1$-$C_6$-alkyl)($C_1$-$C_6$-alkyl), $C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)₂, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)₂—$C_1$-$C_6$-alkyl, —S(O)₂—$C_1$-$C_6$-halogenoalkyl having 1 to 5 halogen atoms, benzyl, benzyloxy, —S-benzyl, —S(O)-benzyl, —S(O)₂-benzyl, benzylamino, phenoxy, —S-phenyl, —S(O)-phenyl, —S(O)₂-phenyl, phenylamino, phenylcarbonylamino, 2,6-dichlorophenyl-carbonylamino, 2-chlorophenylcarbonylamino and phenyl, or $R^2$ and $R^4$ together with the carbon atoms to which they are bonded form a 4-, 5- or 6-membered non-aromatic carbocycle optionally substituted by substituents selected from the group consisting of one to four $C_1$-$C_8$-alkyl groups and one to four halogen atoms, and $R^1$ and $R^3$ are the same or different and are selected from the group consisting of hydrogen, halogen, cyano, hydroxy, amino, —SH, —CHO, —OCHO, —NHCHO, —COOH, —CONH₂, —CONH(OH), —OCONH₂, a (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)₂, —CONH(O$C_1$-$C_6$-alkyl), —CON(O$C_1$-$C_6$-alkyl)($C_1$-$C_6$-alkyl), $C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)₂, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)₂—$C_1$-$C_6$-alkyl, —S(O)₂—$C_1$-$C_6$-halogenoalkyl having 1 to 5 halogen atoms, benzyl, benzyloxy, —S-benzyl, —S(O)-benzyl, —S(O)₂-benzyl, benzylamino, phenoxy, —S-phenyl, —S(O)-phenyl, —S(O)₂-phenyl, phenylamino, phenylcarbonylamino, 2,6-dichlorophenyl-carbonylamino, 2-chlorophenylcarbonylamino and phenyl, or $R^1$ and $R^3$ together with the carbon atoms to which they are bonded form a 4-, 5- or 6-membered non-aromatic carbocycle optionally substituted by substituents selected from the group consisting of one to four $C_1$-$C_8$-alkyl groups and one to four halogen atoms, and $R^2$ and $R^4$ are the same or different and are selected from the group consisting of hydrogen, halogen, cyano, hydroxy, amino, —SH, —CHO, —OCHO, —NHCHO, —COOH, —CONH₂, —CONH(OH), —OCONH₂, a (hydroxyimino)-$C_1$-$C_6$-alkyl group, $C_1$-$C_6$-alkyl, $C_2$-$C_5$-alkenyl, $C_2$-$C_5$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)₂, —CONH(O$C_1$-$C_6$-alkyl), —CON(O$C_1$-$C_6$-alkyl)($C_1$-$C_6$-alkyl), $C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)₂, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)₂—$C_1$-$C_6$-alkyl, —S(O)₂—$C_1$-$C_6$-halogenoalkyl having 1 to 5 halogen atoms, benzyl, benzyloxy, —S-benzyl, —S(O)-benzyl, —S(O)₂-benzyl, benzylamino, phenoxy, —S-phenyl, —S(O)-phenyl, —S(O)₂-phenyl, phenylamino, phenylcarbonylamino, 2,6-dichlorophenyl-carbonylamino, 2-chlorophenylcarbonylamino and phenyl, $R^5$ is selected from the group consisting of hydrogen, cyano, —CHO, —OH, $C_1$-$C_6$-alkyl, $C_1$-$C_6$-halogenoalkyl having 1 to 5 halogen atoms, $C_1$-$C_6$-alkoxy, $C_1$-$C_6$-halogenoalkoxy having 1 to 5 halogen atoms, $C_3$-$C_7$-cycloalkyl, $C_3$-$C_7$-halogenocycloalkyl having 1 to 5 halogen atoms, $C_3$-$C_7$-cycloalkyl-$C_1$-$C_6$-alkyl, —CONH($C_1$-$C_6$-alkyl), $C_2$-$C_6$-alkenyl, $C_2$-$C_6$-alkynyl, $C_1$-$C_6$-alkoxy-$C_1$-$C_6$-alkyl, $C_3$-$C_7$-cycloalkyl-$C_1$-$C_6$-alkyl, cyano-$C_1$-$C_8$-alkyl, amino-$C_1$-$C_6$-alkyl, $C_1$-$C_6$-alkylamino-$C_1$-$C_6$-alkyl, di-($C_1$-$C_6$-alkyl)amino-$C_1$-$C_6$-alkyl, $C_1$-$C_6$-alkylcarbonyl, $C_1$-$C_6$-halogenoalkylcarbonyl having 1 to 5 halogen atoms, $C_1$-$C_6$-alkoxycarbonyl, $C_1$-$C_6$-benzyloxycarbonyl, $C_1$-$C_6$-alkoxy-$C_1$-$C_6$-alkylcarbonyl, —S—$C_1$-$C_6$-alkyl, —S—$C_1$-$C_6$-halogenoalkyl having 1 to 5 halogen atoms, —S(O)$_2$—$C_1$-$C_6$-alkyl, and S(O)$_2$—$C_1$-$C_6$-halogenoalkyl having 1 to 5 halogen atoms, A represents a phenyl group of the formula (A1)

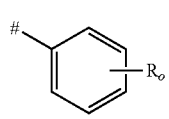

(A1)

wherein
o is 0, 1, 2, 3, 4 or 5, and
each R is independently selected from the group consisting of halogen, nitro, —OH, NH$_2$, SH, SF$_5$, CHO, OCHO, NHCHO, COOH, cyano, $C_1$-$C_8$-alkyl, $C_1$-$C_8$-halogenoalkyl having 1 to 9 halogen atoms, $C_2$-$C_8$-alkenyl, $C_2$-$C_8$-alkynyl, $C_3$-$C_6$-cycloalkyl, —S—$C_1$-$C_8$-alkyl, —S—$C_1$-$C_8$-halogenoalkyl having 1 to 5 halogen atoms, $C_1$-$C_8$-alkoxy, $C_1$-$C_8$-halogenoalkoxy having 1 to 5 halogen atoms, $C_1$-$C_8$-alkoxy-$C_2$-$C_8$-alkenyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, $C_1$-$C_8$-alkylsulfonamide, —NH($C_1$-$C_8$-alkyl), N($C_1$-$C_8$-alkyl)$_2$, phenyl (optionally substituted by $C_1$-$C_6$-alkoxy) and phenoxy, or two R bonded to adjacent carbon atoms together represent O(CH$_2$)$_p$O—, wherein p represents 1 or 2, or A represents a heterocycle of the formula (Het-1)

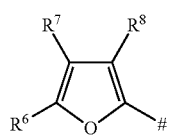

(Het-1)

in which
$R^6$ and $R^7$ may be the same or different and are selected from the group consisting of hydrogen, halogen, amino, nitro, $C_1$-$C_4$-alkyl and $C_1$-$C_4$-halogenoalkyl having 1 to 5 halogen atoms, and
$R^8$ is selected from the group consisting of hydrogen, halogen, nitro, $C_1$-$C_4$-alkyl and $C_1$-$C_4$-halogenoalkyl having 1 to 5 halogen atoms, or A represents a heterocycle of the formula (Het-2)

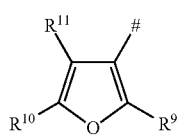

(Het-2)

in which
$R^9$ is selected from the group consisting of hydrogen, halogen, $C_1$-$C_4$-alkyl and $C_1$-$C_4$-halogenoalkyl having 1 to 5 halogen atoms, and
$R^{10}$ and $R^{11}$ may be the same or different and are selected from the group consisting of hydrogen, halogen, amino, $C_1$-$C_4$-alkyl, $C_1$-$C_4$-halogenoalkyl having 1 to 5 halogen atoms and phenyl (optionally substituted by halogen or $C_1$-$C_4$-alkyl), or A represents a heterocycle of the formula (Het-3)

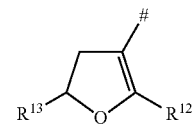

(Het-3)

in which
$R^{12}$ is selected from the group consisting of halogen, $C_1$-$C_4$-alkyl and $C_1$-$C_4$-halogenoalkyl having 1 to 5 halogen atoms, and
$R^{13}$ is selected from the group consisting of hydrogen, $C_1$-$C_4$-alkyl and $C_1$-$C_4$-halogenoalkyl having 1 to 5 halogen atoms, or A represents a heterocycle of the formula (Het-4)

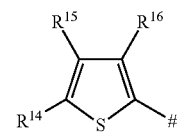

(Het-4)

in which
$R^{14}$ and $R^{15}$ may be the same or different and are selected from the group consisting of hydrogen, halogen, $C_1$-$C_4$-alkyl, $C_1$-$C_4$-halogenoalkyl having 1 to 5 halogen atoms, —S—$C_1$-$C_4$-alkyl, —S(O)$_2$—$C_1$-$C_4$-alkyl, phenyl optionally substituted by halogen or $C_1$-$C_4$-alkyl and pyridyl (optionally substituted by halogen or $C_1$-$C_4$-alkyl), and
$R^{16}$ is selected from the group consisting of hydrogen, halogen, cyano, $C_1$-$C_4$-alkyl, $C_1$-$C_4$-halogenoalkyl having 1 to 5 halogen atoms and $C_1$-$C_4$-halogenoalkoxy having 1 to 5 halogen atoms, or A represents a heterocycle of the formula (Het-5)

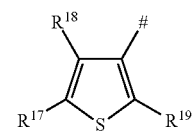

(Het-5)

in which
$R^{17}$ and $R^{18}$ may be the same or different and are selected from the group consisting of hydrogen, halogen, $C_1$-$C_4$-alkyl, $C_1$-$C_4$-alkyloxy and $C_1$-$C_4$-halogenoalkyl having 1 to 5 halogen atoms, and
$R^{19}$ is selected from the group consisting of hydrogen, halogen, $C_1$-$C_4$-alkyl and $C_1$-$C_4$-halogenoalkyl having 1 to 5 atoms, or A represents a heterocycle of the formula (Het-6)

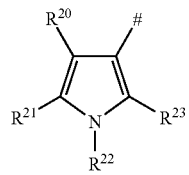
(Het-6)

in which
R²⁰ is selected from the group consisting of hydrogen, halogen, cyano, $C_1$-$C_4$-alkyl and $C_1$-$C_4$-halogenoalkyl having 1 to 5 halogen atoms, and
R²¹ and R²³ may be the same or different and are selected from the group consisting of hydrogen, halogen, $C_1$-$C_4$-alkyl and $C_1$-$C_4$-halogenoalky having 1 to 5 halogen atoms, and
R²² is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, hydroxyl-$C_1$-$C_4$-alkyl, —S(O)₂—$C_1$-$C_4$-alkyl, —S(O)₂—N($C_1$-$C_4$-alkyl)₂, $C_1$-$C_6$-alkylcarbonyl, —S(O)₂-phenyl (optionally substituted by halogen or $C_1$-$C_4$-alkyl) and benzoyl (optionally substituted by halogen or $C_1$-$C_4$-alkyl), or
A represents a heterocycle of the formula (Het-7)

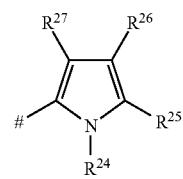
(Het-7)

in which
R²⁴ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, hydroxy-$C_1$-$C_4$-alkyl, —S(O)₂—$C_1$-$C_4$-alkyl, —S(O)₂—N($C_1$-$C_4$-alkyl)₂, $C_1$-$C_6$-alkylcarbonyl, —S(O)₂-phenyl (optionally substituted by halogen or $C_1$-$C_4$-alkyl) and benzoyl (optionally substituted by halogen or a $C_1$-$C_4$-alkyl), and
R²⁵, R²⁶ and R²⁷ may be the same or different and are selected from the group consisting of hydrogen, halogen, cyano, $C_1$-$C_4$-alkyl, $C_1$-$C_4$-halogenalkyl having 1 to 5 halogen atoms and $C_1$-$C_4$-alkylcarbonyl, or
A represents a heterocycle of the formula (Het-8)

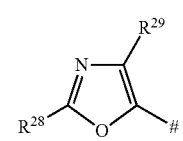
(Het-8)

in which
R²⁸ is selected from the group consisting of hydrogen and $C_1$-$C_4$-alkyl, and
R²⁹ is selected from the group consisting of halogen, $C_1$-$C_4$-alkyl and $C_1$-$C_4$-halogenoalkyl having 1 to 5 halogen atoms, or A represents a heterocycle of the formula (Het-9)

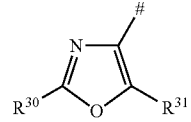
(Het-9)

in which
R³⁰ is selected from the group consisting of hydrogen and $C_1$-$C_4$-alkyl, and
R³¹ is selected from the group consisting of halogen, $C_1$-$C_4$-alkyl, $C_1$-$C_4$-halogenoalkyl having 1 to 5 halogen atoms and phenyl (optionally substituted by halogen or $C_1$-$C_4$-alkyl), or
A represents a heterocycle of the formula (Het-10)

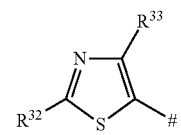
(Het-10)

in which
R³² is selected from the group consisting of hydrogen, halogen, amino, cyano, $C_1$-$C_4$-alkylamino, di-($C_1$-$C_4$-alkyl)amino, $C_1$-$C_4$-alkyl, $C_1$-$C_4$-halogenoalkyl having 1 to 5 halogen atoms and phenyl (optionally substituted by halogen or $C_1$-$C_4$-alkyl), and
R³³ is selected from the group consisting of halogen, $C_1$-$C_4$-alkyl and $C_1$-$C_4$-halogenoalkyl having 1 to 5 halogen atoms, $C_1$-$C_8$-halogenoalkoxy having 1 to 9 halogen atoms, amino, substituted or unsubstituted $C_1$-$C_8$-alkylamino or substituted or unsubstituted di-($C_1$-$C_8$-alkyl)-amino, or
A represents a heterocycle of the formula (Het-11)

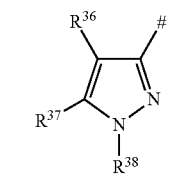
(Het-11)

in which
R³⁴ is selected from the group consisting of hydrogen, halogen, amino, cyano, $C_1$-$C_4$-alkylamino, di-($C_1$-$C_4$-alkyl)amino, $C_1$-$C_4$-alkyl and $C_1$-$C_4$-halogenoalkyl having 1 to 5 halogen atoms, and
R³⁵ is selected from the group consisting of halogen, $C_1$-$C_4$-alkyl and $C_1$-$C_4$-halogenoalkyl having 1 to 5 halogen atoms, or
A represents a heterocycle of the formula (Het-12)

(Het-12)

in which
R³⁶ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, —S(O)$_2$—C$_1$-C$_4$-alkyl, —S—C$_1$-C$_4$-halogenoalkyl having 1 to 5 halogen atoms, aminocarbonyl and aminocarbonyl-C$_1$-C$_4$-alkyl, and R$^{37}$ is selected from the group consisting of hydrogen, halogen, cyano, nitro, C$_1$-C$_4$-alkyl, C$_1$-C$_4$-alkoxy, —S—C$_1$-C$_4$-alkyl, —S(O)—C$_1$-C$_4$-alkyl, and —S(O)$_2$—C$_1$-C$_4$-alkyl, and R$^{38}$ is selected from the group consisting of hydrogen, phenyl, C$_1$-C$_4$-alkyl, C$_1$-C$_4$-halogenoalkyl having 1 to 5 halogen atoms, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkyl-S(O)—C$_1$-C$_4$-alkyl, C$_1$-C$_4$-alkyl-S(O)$_2$—C$_1$-C$_4$-alkyl, C$_1$-C$_4$-halogenoalkylthio-C$_1$-C$_4$-alkyl having 1 to 5 halogen atoms, C$_1$-C$_4$-alkoxy-C$_1$-C$_4$-alkyl and C$_1$-C$_4$-halogenoalkoxy-C$_1$-C$_4$-alkyl having 1 to 5 halogen atoms, or A represents a heterocycle of the formula (Het-13)

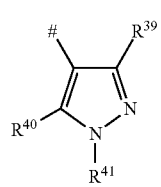
(Het-13)

in which

R$^{39}$ is selected from the group consisting of hydrogen, halogen, cyano, nitro, C$_1$-C$_4$-alkyl, C$_1$-C$_4$-halogenoalkyl having 1 to 5 halogen atoms, C$_3$-C$_6$-cycloalkyl, C$_1$-C$_4$-alkoxy, C$_1$-C$_4$-halogenoalkoxy having 1 to 5 halogen atoms, —S—C$_1$-C$_4$-alkyl, S(O)—C$_1$-C$_4$-alkyl, —S(O)$_2$—C$_1$-C$_4$-alkyl, —S—C$_1$-C$_4$-halogenoalkyl having 1 to 5 atoms, aminocarbonyl and aminocarbonyl-C$_1$-C$_4$-alkyl, and R$^{40}$ is selected from the group consisting of hydrogen, halogen, cyano, C$_1$-C$_4$-alkyl, C$_1$-C$_4$-alkoxy, C$_1$-C$_4$-halogenoalkoxy having 1 to 5 halogen atoms, —S—C$_1$-C$_4$-alkylS(O)—C$_1$-C$_4$-alkyl, and —S(O)$_2$—C$_1$-C$_4$-alkyl, and R$^{41}$ is selected from the group consisting of hydrogen, C$_1$-C$_4$-alkyl, C$_1$-C$_4$-halogenoalkyl having 1 to 5 halogen atoms, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkyl-S(O)—C$_1$-C$_4$-alkyl, C$_1$-C$_4$-alkyl-S(O)$_2$—C$_1$-C$_4$-alkyl, C$_1$-C$_4$-halogenoalkylthio-C$_1$-C$_4$-alkyl having 1 to 5 halogen atoms, C$_1$-C$_4$-alkoxy-C$_1$-C$_4$-alkyl, C$_1$-C$_4$-halogenoalkoxy-C$_1$-C$_4$-alkyl having 1 to 5 halogen atoms and phenyl (optionally substituted by halogen, C$_1$-C$_4$-alkyl, C$_1$-C$_4$-alkoxy-C$_1$-C$_4$-alkyl or nitro), or A represents a heterocycle of the formula (Het-14)

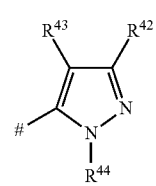
(Het-14)

in which

R$^{42}$ is selected from the group consisting of hydrogen, halogen, cyano, nitro, C$_1$-C$_4$-alkyl, C$_1$-C$_4$-halogenoalkyl having 1 to 5 halogen atoms, C$_3$-C$_6$-cycloalkyl, C$_1$-C$_4$-alkoxy, C$_1$-C$_4$-halogenoalkoxy having 1 to 5 halogen atoms, —S—C$_1$-C$_4$-alkyl, S(O)—C$_1$-C$_4$-alkyl, —S(O)$_2$—C$_1$-C$_4$-alkyl, —S—C$_1$-C$_4$-halogenoalkyl having 1 to 5 halogen atoms, aminocarbonyl and aminocarbonyl-C$_1$-C$_4$-alkyl, and R$^{43}$ is selected from the group consisting of hydrogen, halogen, cyano, C$_1$-C$_4$-alkyl, C$_1$-C$_4$-alkoxy, —S—C$_1$-C$_4$-alkyl, S(O)—C$_1$-C$_4$-alkyl, —S(O)$_2$—C$_1$-C$_4$-alkyl, and C$_1$-C$_4$-halogenoalkyl having 1 to 5 halogen atoms, and R$^{44}$ is selected from the group consisting of hydrogen, phenyl, benzyl, C$_1$-C$_4$-alkyl, C$_1$-C$_4$-halogenoalkyl having 1 to 5 halogen atoms, hydroxy-C$_1$-C$_4$-alkyl, C$_2$-C$_6$-alkenyl, C$_3$-C$_6$-cycloalkyl, C$_1$-C$_4$-alkylthio-C$_1$-C$_4$-alkyl, C$_1$-C$_4$-alkyl-S(O)—C$_1$-C$_4$-alkyl, C$_1$-C$_4$-alkyl-S(O)$_2$—C$_1$-C$_4$-alkyl, C$_1$-C$_4$-halogenoalkylthio-C$_1$-C$_4$-alkyl having 1 to 5 halogen atoms, C$_1$-C$_4$-alkoxy-C$_1$-C$_4$-alkyl and C$_1$-C$_4$-halogenoalkoxy-C$_1$-C$_4$-alkyl having 1 to 5 halogen atoms, or A represents a heterocycle of the formula (Het-15)

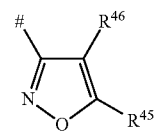
(Het-15)

in which

R$^{45}$ and R$^{46}$ may be the same or different and are selected from the group consisting of hydrogen, halogen, C$_1$-C$_4$-alkyl and C$_1$-C$_4$-halogenoalkyl having 1 to 5 halogen atoms, or A represents a heterocycle of the formula (Het-16)

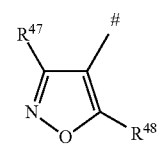
(Het-16)

in which

R$^{47}$ and R$^{48}$ may be the same or different and are selected from the group consisting of hydrogen, halogen, C$_1$-C$_4$-alkyl, C$_1$-C$_4$-halogenoalkyl having 1 to 5 halogen atoms, phenyl (optionally substituted by halogen or a C$_1$-C$_4$-alkyl), and heterocyclyl like pyridyl, pyrimidinyl and thiadiazolyl (each optionally substituted by halogen or C$_1$-C$_4$-alkyl), or A represents a heterocycle of the formula (Het-17)

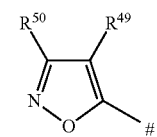
(Het-17)

in which

R$^{49}$ and R$^{50}$ may be the same or different and are selected from the group consisting of hydrogen, halogen, C$_1$-C$_4$-alkyl and C$_1$-C$_4$-halogenoalkyl having 1 to 5 halogen atoms, or A represents a heterocycle of the formula (Het-18)

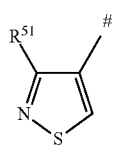

(Het-18)

in which
R$^{51}$ is selected from the group consisting of halogen, C$_1$-C$_4$-alkyl and C$_1$-C$_4$-halogenoalkyl having 1 to 5 halogen atoms, or A represents a heterocycle of the formula (Het-19)

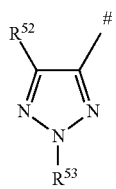

(Het-19)

in which
R$^{52}$ is selected from the group consisting of halogen, C$_1$-C$_4$-alkyl and C$_1$-C$_4$-halogenoalkyl having 1 to 5 halogen atoms, and
R$^{53}$ is selected from the group consisting of hydrogen, C$_1$-C$_4$-alkyl, C$_1$-C$_4$-halogenoalkyl having 1 to 5 halogen atoms and phenyl (optionally substituted by halogen or C$_1$-C$_4$-alkyl), or A represents a heterocycle of the formula (Het-20)

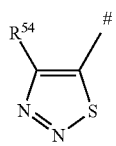

(Het-20)

in which
R$^{54}$ is selected from the group consisting of halogen, C$_1$-C$_4$-alkyl and C$_1$-C$_4$-halogenoalkyl having 1 to 5 halogen atoms, or A represents a heterocycle of the formula (Het-21)

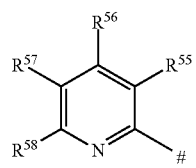

(Het-21)

in which
R$^{55}$ is selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, S(O)—C$_1$-C$_4$-alkyl, —S(O)$_2$—C$_1$-C$_4$-alkyl, —S—C$_1$-C$_4$-halogenoalkyl having 1 to 5 halogen atoms and C$_1$-C$_4$-halogenoalkoxy having 1 to 5 halogen atoms, and R$^{56}$, R$^{57}$ and R$^{58}$, which may be the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, C$_1$-C$_4$-halogenoalkoxy having 1 to 5 halogen atoms, —S(O)—C$_1$-C$_4$-alkyl and S(O)$_2$—C$_1$-C$_4$-alkyl, or A represents a heterocycle of the formula (Het-22)

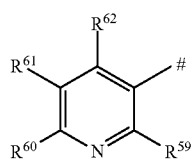

(Het-22)

in which
R$^{59}$ is selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$ alkoxy, —S—C$_1$-C$_5$-alkyl, S(O)—C$_1$-C$_4$-alkyl, —S(O)$_2$—C$_1$-C$_4$-alkyl, —S—C$_2$-C$_5$-alkenyl, —S—C$_1$-C$_4$-halogenoalkyl having 1 to 5 halogen atoms, C$_1$-C$_4$-halogenoalkoxy having 1 to 5 halogen atoms, phenyloxy (optionally substituted by halogen or C$_1$-C$_4$-alkyl) and S-phenyl (optionally substituted by halogen or C$_1$-C$_4$-alkyl), and R$^{60}$, R$^{61}$ and R$^{62}$, which may the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, C$_1$-C$_4$-halogenoalkoxy having 1 to 5 halogen atoms, —S(O)—C$_1$-C$_4$-alkyl, —S(O)$_2$—C$_1$-C$_4$-alkyl, N-morpholine optionally substituted by halogen or C$_1$-C$_4$-alkyl, and thienyl (optionally substituted by halogen or a C$_1$-C$_4$-alkyl), or A represents a heterocycle of the formula (Het-23)

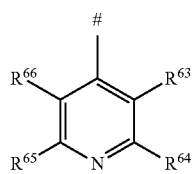

(Het-23)

in which
R$^{63}$, R$^{64}$, R$^{65}$ and R$^{66}$, which may be the same or different, are selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, —S—C$_1$-C$_4$-halogenoalkyl having 1 to 5 halogen atoms, C$_1$-C$_4$-halogenoalkoxy having 1 to 5 halogen atoms, —S(O)—C$_1$-C$_4$-alkyl and S(O)$_2$—C$_1$-C$_4$-alkyl, or A represents a heterocycle of the formula (Het-24)

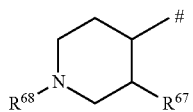
(Het-24)

in which

R$^{67}$ is selected from the group consisting of hydrogen, halogen, C$_1$-C$_4$-alkyl and C$_1$-C$_4$-halogenoalkyl having 1 to 5 halogen atoms, and R$^{68}$ is selected from the group consisting of hydrogen, C$_1$-C$_4$-alkyl, C$_1$-C$_4$-halogenoalkyl having 1 to 5 halogen atoms, C$_1$-C$_6$-alkoxycarbonyl, benzyl (optionally substituted by 1 to 3 halogen atoms), benzyloxycarbonyl (optionally substituted by 1 to 3 halogen atoms), and heterocyclyl like pyridyl and pyrimidinyl (each optionally substituted by halogen, C$_1$-C$_4$-alkyl, C$_1$-C$_4$-halogenoalkyl having 1 to 5 halogen atoms), or A represents a heterocycle of the formula (Het-25)

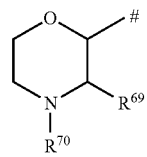
(Het-25)

in which

R$^{69}$ is selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, —S—C$_1$-C$_4$-halogenoalkyl having 1 to 5 halogen atoms and C$_1$-C$_4$-halogenoalkoxy having 1 to 5 halogen atoms, and R$^{70}$ is selected from the group consisting of hydrogen, C$_1$-C$_4$-alkyl, C$_1$-C$_4$-halogenoalkyl having 1 to 5 halogen atoms, and benzyl, or A represents a heterocycle of the formula (Het-26)

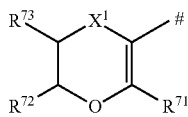
(Het-26)

in which

X$^1$ is selected from the group consisting of sulphur, —SO—, —SO$_2$— and CH$_2$—, and R$^{71}$ is selected from the group consisting of C$_1$-C$_4$-alkyl and C$_1$-C$_4$-halogenoalkyl having 1 to 5 halogen atoms, and R$^{72}$ and R$^{73}$ may be the same or different and are selected from the group consisting of hydrogen and C$_1$-C$_4$-alkyl, or A represents a heterocycle of the formula (Het-27)

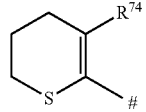
(Het-27)

in which

R$^{74}$ is selected from the group consisting of C$_1$-C$_4$-alkyl and C$_1$-C$_4$-halogenoalkyl having 1 to 5 halogen atoms, or A represents a heterocycle of the formula (Het-28)

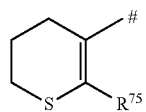
(Het-28)

in which

R$^{75}$ is selected from the group consisting of C$_1$-C$_4$-alkyl and C$_1$-C$_4$-halogenoalkyl having 1 to 5 halogen atoms, or A represents a heterocycle of the formula (Het-29)

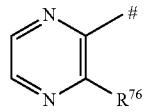
(Het-29)

in which

R$^{76}$ is selected from the group consisting of hydrogen, halogen, C$_1$-C$_4$-alkyl and C$_1$-C$_4$-halogenoalkyl having 1 to 5 halogen atoms.

In formulae (Het-1) to (Het-29) # depicts the bond which connects A to the C(O)NR$^5$-moiety in the compounds of formula (I). In general, in the present application # depicts the connecting bond of the structural element, unless otherwise indicated.

Any of the compounds according to the invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions), and to the mixtures of all the possible stereoisomers, in all proportions. The diastereoisomers and/or the optical isomers can be separated according to the methods which are known per se by the man ordinary skilled in the art.

The invention also relates to salts, N-oxides, metal complexes and metalloid complexes of compounds of formula (I) and the uses thereof.

Compounds of the present invention can also exist in one or more geometric isomer forms depending on the number of double bonds in the compound. The invention thus relates equally to all geometric isomers, especially all syn/anti (or cis/trans) isomers and to all possible syn/anti (or cis/trans) mixtures, and to all possible mixtures, in all proportions. The geometric isomers can be separated according to general methods, which are known per se by the man ordinary skilled in the art.

Compounds of formula (I) may be found in its tautomeric form resulting from the shift of the proton of a hydroxy, sulfanyl or amino group. Such tautomeric forms of such compounds are also part of the present invention. More generally speaking, all tautomeric forms of compounds of formula (I), as well as the tautomeric forms of the compounds which can optionally be used as intermediates in the preparation processes and which will be defined in the description of these processes, are also part of the present invention.

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

In the above recitations, the term "alkyl", used either alone or in compound words such as "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. "Cycloalkenyl" includes groups such as cyclopentenyl and cyclohexenyl as well as groups with more than 10 one double bond such as 1,3- and 1,4-cyclohexadienyl. The term "cycloalkylcycloalkyl" denotes cycloalkyl substitution on another cycloalkyl ring, wherein each cycloalkyl ring independently has from 3 to 7 carbon atom ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl).

The term "halogen", either alone or in compound words such as "haloalkyl", or when used in descriptions such as "alkyl substituted with halogen" includes fluorine, chlorine, bromine or iodine.

Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", "haloalkenyl", "haloalkynyl", and the like, are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$.

The chemical abbreviation C(O) as used herein represents a carbonyl moiety. For example, $C(O)CH_3$ represents an acetyl group. The chemical abbreviations $CO_2$ and C(O)O as used herein represent an ester moiety. For example, $CO_2Me$ and C(O)OMe represent a methyl ester. CHO represents an aldehyde moiety.

"OCN" means —O—C≡N, and "SCN" means —S—C≡N.

The total number of carbon atoms in a substituent group is indicated by the "Ci-Cj" prefix where i and j are numbers from 1 to 14. $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

When a compound is substituted with a substituent bearing a subscript that indicates the number of said substituents can exceed 1, said substituents (when they exceed 1) are independently selected from the group of defined substituents, e.g. n=0, 1, 2, 3 or 4. When a group contains a substituent which can be hydrogen, for example $R^2$ or $R^3$, then when this substituent is taken as hydrogen, it is recognized that this is equivalent to said group being unsubstituted.

Unless otherwise indicated, a "ring" or "ring system" as a component of formula (I) is carbocyclic or heterocyclic. The term "ring system" denotes two or more fused rings. The term "heterocyclic ring" denotes a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. The term "heterocyclic ring system" denotes a ring system in which at least one ring of the ring system is a heterocyclic ring. Unless otherwise indicated, heterocyclic rings and ring systems can be attached through any available carbon or nitrogen by replacement of a hydrogen on said carbon or nitrogen.

As used herein, the following definitions shall apply unless otherwise indicated. The term "optionally substituted" is used interchangeably with the phrase "substituted or unsubstituted" or with the term "(un)substituted". The expression "optionally substituted with 1 to 4 substituents" means that no substituent is present (i.e. unsubstituted) or that 1, 2, 3 or 4 substituents are present (limited by the number of available bonding positions). Unless otherwise indicated, an optionally substituted group may have a substituent at each substitutable position of the group, and each substitution is independent of the other.

In another individual embodiment (embodiment 1-2), the structural elements in the compound of formula (I) are defined as follows:

$B^1$, $B^2$ are as defined in embodiment 1-1, n is as defined in embodiment 1-1, each X is as defined in embodiment 1-1, m is 0, 1, 2, 3, 4 or 5, and each Y is independently selected from the group consisting of hydrogen, halogen, nitro, cyano, hydroxy, amino, —SH, —SF$_5$, —CHO, —OCHO, —NHCHO, —COOH, —CONH$_2$, —CONH(OH), —OCONH$_2$, (hydroxyimino)-$C_1$-$C_8$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, wherein both alkyl residues may form a 4- to 7-membered heterocycle incorporating the nitrogen bonded to the phenyl system of the compound, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_8$-halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON(O$C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(O$C_1$-$C_8$-alkyl), —OCO(O$C_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, —CH$_2$—S—$C_1$-$C_8$-alkyl, —CH$_2$—S(O)—$C_1$-$C_8$-alkyl, —CH$_2$—S(O)$_2$—$C_1$-$C_8$-alkyl, ($C_1$-$C_6$-alkoxyimino)-$C_1$-$C_8$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)-$C_1$-$C_6$-alkyl, benzyloxy, —S-benzyl, benzylamino, phenoxy, —S-phenyl and phenylamino, or m is 2, 3, 4 or 5, and at least two substituents Y are vicinal and, together with the carbon atoms to which they are bonded, form an annellated 5- or 6-membered carbocycle or a 5- or 6-membered heterocycle with one or two heteroatoms selected from the group consisting of oxygen and nitrogen, whereat two oxygen atoms are not directly connected, the carbocycle or heterocycle being independently substituted by 0 to 4 halogen atoms, 0 to 2 oxo-groups, 0 to 8 $C_1$-$C_8$-alkyl, 0 to 8 $C_1$-$C_8$-alkoxy or 0 to 4 $C_1$-$C_8$-halogenoalkyl having 1 to 5 halogen atoms, and the remaining substituents Y are independently selected from the group consisting of hydrogen, halogen, nitro, cyano, hydroxy, amino, —SH, —SF$_5$, —CHO, —OCHO, —NHCHO, —COOH, —CONH$_2$, —CONH(OH), —OCONH$_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_8$-halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON(O$C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(O$C_1$-$C_8$-alkyl), —OCO(O$C_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, —CH$_2$—S—$C_1$-$C_8$-alkyl, —CH$_2$—S(O)—$C_1$-$C_8$-alkyl, —CH$_2$—S(O)$_2$—$C_1$-$C_8$-alkyl, ($C_1$-$C_6$-alkoxyimino)-$C_1$-$C_6$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)-$C_1$-$C_6$-alkyl, benzyloxy, —S-benzyl, benzylamino, phenoxy, —S-phenyl and phenylamino, $R^1$, $R^2$, $R^3$ and $R^4$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-$C_1$-$C_6$-alkyl group, $C_1$-$C_8$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_6$-alkyl), —CON(O$C_1$-$C_6$-alkyl) ($C_1$-$C_6$-alkyl), $C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$—$C_1$-$C_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino and phenyl, with the provisio that $R^1$ is fluorine and/or $R^2$ is fluorine, $R^5$ is as defined in embodiment 1-1, and A is as defined in embodiment 1-1.

In another individual aspect of embodiment 1-1, $R^1$ is fluorine. In another individual aspect of embodiment 1-1, $R^2$ is fluorine. In another individual aspect of embodiment 1-1, $R^1$ is fluorine and $R^2$ is fluorine. In another individual aspect of embodiment 1-1, the combination $R^1/R^2$ is fluorine/methyl. In another individual aspect of embodiment 1-2, $R^1$ is fluorine. In another individual aspect of embodiment 1-2, $R^2$ is fluorine. In another individual aspect of embodiment 1-2, $R^1$ is fluorine and $R^2$ is fluorine. In another individual aspect of embodiment 1-2, the combination $R^1/R^2$ is fluorine/methyl.

Preferred substituents or ranges of the structural elements mentioned in the compounds of formula (I) are explained below (embodiment 2-1):

$B^1$, $B^2$ represent C—X or N, wherein at least $B^1$ or $B^2$ is N, n is 1 or 2, limited by the number of available positions in the ring to which a substituent X can be connected, each X is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, —CH$_2$—S—$C_1$-$C_4$-alkyl, —CH$_2$—S(O)—$C_1$-$C_4$-alkyl, —CH$_2$—S(O)$_2$—$C_1$-$C_4$-alkyl, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino, or m is 2, 3 or 4 and at least two substituents Y are vicinal and, together with the carbon atoms to which they are bonded, form an annellated 5- or 6-membered carbocycle or a 5- or 6-membered heterocycle with one or two heteroatoms selected from the group consisting of oxygen and nitrogen, whereat two oxygen atoms are not directly connected, the carbocycle or heterocycle being independently substituted by 0 to 2 halogen atoms, 0 to 2 oxo-groups, 0 to 4 $C_1$-$C_4$-alkyl, 0 to 4 $C_1$-$C_4$-alkoxy or 0 to 2 $C_1$-$C_4$-halogenoalkyl having 1 to 5 halogen atoms, and the remaining substituents Y are independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, —CH$_2$—S—$C_1$-$C_4$-alkyl, —CH$_2$—S(O)—$C_1$-$C_4$-alkyl, —CH$_2$—S(O)$_2$—$C_1$-$C_4$-alkyl, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino, $R^1$, $R^2$, $R^3$ and $R^4$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^1$ and $R^2$ together with the carbon atom to which they are bonded form a 4- or 5-membered carbocycle and $R^3$ and $R^4$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^3$ and $R^4$ together with the carbon atom to which they are bonded form a 3-, 4- or 5-membered carbocycle and $R^1$ and $R^2$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^2$ and $R^4$ together with the carbon atoms to which they are bonded form a 4- or 5-membered non-aromatic carbocycle optionally substituted by substituents selected from the group consisting of one to four $C_1$-$C_4$-alkyl groups and one to four halogen atoms, and $R^1$ and $R^3$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH ($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, or $R^1$ and $R^3$ together with the carbon atoms to which they are bonded form a 4- or 5-membered non-aromatic carbocycle optionally substituted by substituents selected from the group consisting of one to four $C_1$-$C_4$-alkyl groups and one to four halogen atoms, and $R^2$ and $R^4$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino, 2,6-dichlorophenyl-carbonylamino, 2-chlorophenyl-carbonylamino and phenyl, $R^5$ is selected from the group consisting of hydrogen, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_2$-$C_4$-alkenyl, $C_2$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, amino-$C_1$-$C_4$-alkyl, $C_1$-$C_4$-alkylamino-$C_1$-$C_4$-alkyl, di-($C_1$-$C_4$-alkyl)amino-$C_1$-$C_4$-alkyl, $C_1$-$C_4$-alkylcarbonyl, $C_1$-$C_4$-halogenoalkylcarbonyl having 1 to 5 halogen atoms, $C_1$-$C_4$-alkoxycarbonyl, benzyloxycarbonyl, $C_1$-$C_4$-alkoxy-$C_1$-$C_4$-alkylcarbonyl, —S(O)$_2$—$C_1$-$C_4$-alkyl, and S(O)$_2$—$C_1$-$C_4$-halogenoalkyl having 1 to 5 halogen atoms, A represents a phenyl group of formula (A1)

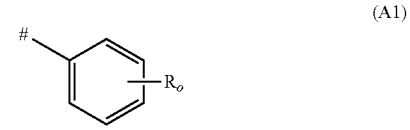

wherein o is 0, 1 or 2, and each R is independently selected from the group consisting of halogen, nitro, —OH, CHO, OCHO, NHCHO cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_3$-$C_6$-cycloalkyl, —S—$C_1$-$C_4$-alkyl, —S—$C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-alkoxy-$C_2$-$C_4$-alkenyl, $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, $C_1$-$C_4$-alkylsulfonamide, —NH($C_1$-$C_4$-alkyl), N($C_1$-$C_4$-alkyl)$_2$, phenyl (optionally substituted by $C_1$-$C_4$-alkoxy) and phenoxy, or two R bonded to adjacent carbon atoms together represent —O(CH$_2$)$_p$O—, wherein p represents 1 or 2, or A represents a heterocycle of the formula (Het-1)

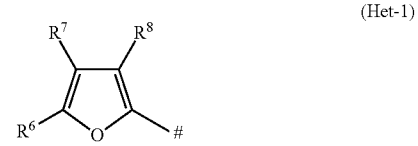

in which $R^6$ and $R^7$ may be the same or different and are selected from the group consisting of hydrogen, halogen, nitro, $C_1$-$C_4$-alkyl and $C_1$-$C_4$-halogenoalkyl having 1 to 5 halogen atoms, and $R^8$ is selected from the group consisting of hydrogen, halogen, $C_1$-$C_4$-alkyl and $C_1$-$C_4$-halogenoalkyl having 1 to 5 halogen atoms, or A represents a heterocycle of the formula (Het-2)

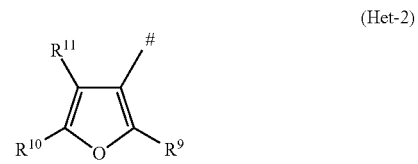

in which $R^9$ is selected from the group consisting of hydrogen, halogen, $C_1$-$C_4$-alkyl and $C_1$-$C_4$-halogenoalkyl having 1 to 5 halogen atoms, and $R^{10}$ and $R^{11}$ may be the same or different and are selected from the group consisting of hydrogen, halogen, $C_1$-$C_4$-alkyl and $C_1$-$C_4$-halogenoalkyl having 1 to 5 halogen atoms, phenyl optionally substituted by halogen or $C_1$-$C_4$-alkyl), or A represents a heterocycle of the formula (Het-4)

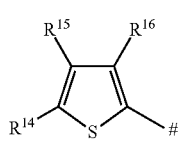
(Het-4)

in which

R$^{14}$ and R$^{15}$ may be the same or different and are selected from the group consisting of hydrogen, halogen, C$_1$-C$_4$-alkyl, C$_1$-C$_4$-halogenoalkyl having 1 to 5 halogen atoms, —S—C$_1$-C$_4$-alkyl, —S(O)$_2$—C$_1$-C$_4$-alkyl, phenyl (optionally substituted by halogen or C$_1$-C$_4$-alkyl) and pyridyl (optionally substituted by halogen or C$_1$-C$_4$-alkyl), and R$^{16}$ is selected from the group consisting of hydrogen, halogen, cyano, C$_1$-C$_4$-alkyl, C$_1$-C$_4$-halogenoalkyl having 1 to 5 halogen atoms and C$_1$-C$_4$-halogenoalkoxy having 1 to 5 halogen atoms, or A represents a heterocycle of the formula (Het-5)

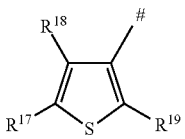
(Het-5)

in which

R$^{17}$ and R$^{18}$ may be the same or different and are selected from the group consisting of hydrogen, halogen, C$_1$-C$_4$-alkyl, C$_1$-C$_4$-alkyloxy and C$_1$-C$_4$-halogenoalkyl having 1 to 5 halogen atoms, and R$^{19}$ is selected from the group consisting of hydrogen, halogen, C$_1$-C$_4$-alkyl and C$_1$-C$_4$-halogenoalkyl having 1 to 5 atoms, or A represents a heterocycle of the formula (Het-6)

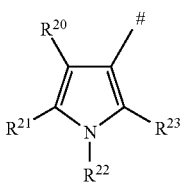
(Het-6)

in which

R$^{20}$ is selected from the group consisting of hydrogen, halogen, cyano, C$_1$-C$_4$-alkyl and C$_1$-C$_4$-halogenoalkyl having 1 to 5 halogen atoms, and R$^{21}$ and R$^{23}$ may be the same or different and are selected from the group consisting of hydrogen, halogen, C$_1$-C$_4$-alkyl and C$_1$-C$_4$-halogenoalky having 1 to 5 halogen atoms, and R$^{22}$ is selected from the group consisting of hydrogen, cyano, C$_1$-C$_4$-alkyl, C$_1$-C$_4$-halogenoalkyl having 1 to 5 halogen atoms, C$_1$-C$_4$-alkoxy-C$_1$-C$_4$-alkyl, or A represents a heterocycle of the formula (Het-7)

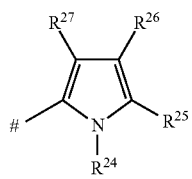
(Het-7)

in which

R$^{24}$ is selected from the group consisting of hydrogen, cyano, C$_1$-C$_4$-alkyl, C$_1$-C$_4$-halogenoalkyl having 1 to 5 halogen atoms, C$_1$-C$_4$-alkoxy-C$_1$-C$_4$-alkyl, C$_1$-C$_8$-alkylcarbonyl, or benzoyl (optionally substituted by halogen or a C$_1$-C$_4$-alkyl), and R$^{25}$, R$^{26}$ and R$^{27}$ may be the same or different and are selected from the group consisting of hydrogen, halogen, cyano, C$_1$-C$_4$-alkyl, C$_1$-C$_4$-halogenalkyl having 1 to 5 halogen atoms and C$_1$-C$_4$-alkylcarbonyl, or A represents a heterocycle of the formula (Het-9)

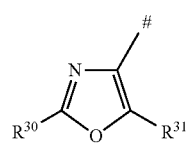
(Het-9)

in which

R$^{30}$ is selected from the group consisting of hydrogen and C$_1$-C$_4$-alkyl, and R$^{31}$ is selected from the group consisting of halogen, C$_1$-C$_4$-alkyl, C$_1$-C$_4$-halogenoalkyl having 1 to 5 halogen atoms and phenyl (optionally substituted by halogen or C$_1$-C$_4$-alkyl), or A represents a heterocycle of the formula (Het-10)

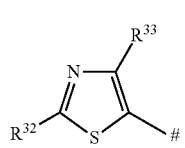
(Het-10)

in which

R$^{32}$ is selected from the group consisting of hydrogen, halogen, amino, cyano, C$_1$-C$_4$-alkylamino, di-(C$_1$-C$_4$-alkyl)amino, C$_1$-C$_4$-alkyl, C$_1$-C$_4$-halogenoalkyl having 1 to 5 halogen atoms and phenyl (optionally substituted by halogen or C$_1$-C$_4$-alkyl), and R$^{33}$ is selected from the group consisting of halogen, C$_1$-C$_4$-alkyl and C$_1$-C$_4$-halogenoalkyl having 1 to 5 halogen atoms, C$_1$-C$_5$-halogenoalkoxy comprising 1 to 9 halogen atoms, amino, substituted or unsubstituted C$_1$-C$_5$-alkylamino or substituted or unsubstituted di-(C$_1$-C$_5$-alkyl)-amino, or A represents a heterocycle of the formula (Het-11)

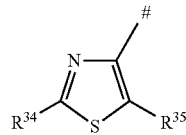

in which
R³⁴ is selected from the group consisting of hydrogen, halogen, $C_1$-$C_4$-alkylamino, di-($C_1$-$C_4$-alkyl)amino, $C_1$-$C_4$-alkyl and $C_1$-$C_4$-halogenoalkyl having 1 to 5 halogen atoms, and
R³⁵ is selected from the group consisting of halogen, $C_1$-$C_4$-alkyl and $C_1$-$C_4$-halogenoalkyl having 1 to 5 halogen atoms, or
A represents a heterocycle of the formula (Het-12)

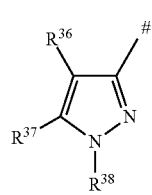

in which
R³⁶ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, —S(O)$_2$—$C_1$-$C_4$-alkyl and —S—$C_1$-$C_4$-halogenoalkyl having 1 to 5 halogen atoms, and
R³⁷ is selected from the group consisting of hydrogen, halogen, cyano, nitro, $C_1$-$C_4$-alkyl, $C_1$-$C_4$-alkoxy and —S—$C_1$-$C_4$-alkyl, —S(O)—$C_1$-$C_4$-alkyl, —S(O)$_2$—$C_1$-$C_4$-alkyl, and
R³⁸ is selected from the group consisting of phenyl, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl and $C_1$-$C_4$-halogenoalkoxy-$C_1$-$C_4$-alkyl having 1 to 5 halogen atoms, or
A represents a heterocycle of the formula (Het-13)

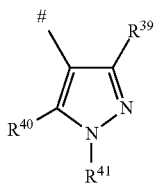

in which
R³⁹ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 atoms, aminocarbonyl and aminocarbonyl-$C_1$-$C_4$-alkyl, and
R⁴⁰ is selected from the group consisting of hydrogen, halogen, cyano, $C_1$-$C_4$-alkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, and —S(O)$_2$—$C_1$-$C_4$-alkyl, and
R⁴¹ is selected from the group consisting of hydrogen, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl, $C_1$-$C_4$-halogenoalkoxy-$C_1$-$C_4$-alkyl having 1 to 5 halogen atoms and phenyl optionally substituted by halogen, $C_1$-$C_4$-alkyl, $C_1$-$C_4$-alkoxy-$C_1$-$C_4$-alkyl or nitro, or
A represents a heterocycle of the formula (Het-14)

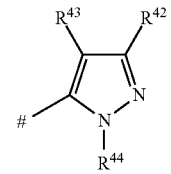

in which
R⁴² is selected from the group consisting of hydrogen, halogen, cyano, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, and —S(O)$_2$—$C_1$-$C_4$-alkyl, —S—$C_1$-$C_4$-halogenoalkyl having 1 to 5 halogen atoms, aminocarbonyl and aminocarbonyl-$C_1$-$C_4$-alkyl, and
R⁴³ is selected from the group consisting of hydrogen, halogen, cyano, $C_1$-$C_4$-alkyl, $C_1$-$C_4$-alkoxy, —S—$C_1$-$C_4$-alkyl, —S(O)—$C_1$-$C_4$-alkyl, and —S(O)$_2$—$C_1$-$C_4$-alkyl, and $C_1$-$C_4$-halogenoalkyl having 1 to 5 halogen atoms, and
R⁴⁴ is selected from the group consisting of phenyl, benzyl, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl and $C_1$-$C_4$-halogenoalkoxy-$C_1$-$C_4$-alkyl having 1 to 5 halogen atoms, or
A represents a heterocycle of the formula (Het-15)

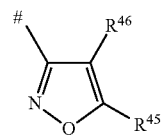

in which
R⁴⁵ and R⁴⁶ may be the same or different and are selected from the group consisting of hydrogen, halogen, $C_1$-$C_4$-alkyl and $C_1$-$C_4$-halogenoalkyl having 1 to 5 halogen atoms, or A represents a heterocycle of the formula (Het-16)

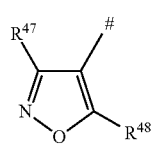
(Het-16)

in which
R$^{47}$ and R$^{48}$ may be the same or different and are selected from the group consisting of hydrogen, halogen, C$_1$-C$_4$-alkyl, C$_1$-C$_4$-halogenoalkyl having 1 to 5 halogen atoms, phenyl (optionally substituted by halogen or a C$_1$-C$_4$-alkyl), or heterocyclyl like pyridyl, pyrimidinyl and thiadiazolyl (optionally substituted by halogen or C$_1$-C$_4$-alkyl), or A represents a heterocycle of the formula (Het-17)

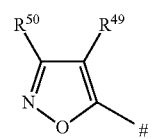
(Het-17)

in which
R$^{49}$ and R$^{50}$ may be the same or different and are selected from the group consisting of hydrogen, halogen, C$_1$-C$_4$-alkyl and C$_1$-C$_4$-halogenoalkyl having 1 to 5 halogen atoms, or A represents a heterocycle of the formula (Het-19)

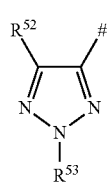
(Het-19)

in which
R$^{52}$ is selected from the group consisting of halogen, C$_1$-C$_4$-alkyl and C$_1$-C$_4$-halogenoalkyl having 1 to 5 halogen atoms, and
R$^{53}$ is selected from the group consisting of C$_1$-C$_4$-alkyl, C$_1$-C$_4$-halogenoalkyl having 1 to 5 halogen atoms and phenyl (optionally substituted by halogen or C$_1$-C$_4$-alkyl), or A represents a heterocycle of the formula (Het-20)

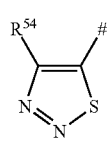
(Het-20)

in which
R$^{54}$ is selected from the group consisting of halogen, C$_1$-C$_4$-alkyl and C$_1$-C$_4$-halogenoalkyl having 1 to 5 halogen atoms, or A represents a heterocycle of the formula (Het-21)

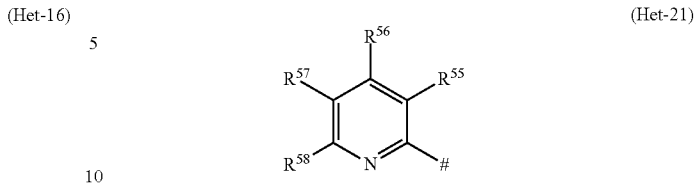
(Het-21)

in which
R$^{55}$ is selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, —S(O)—C$_1$-C$_4$-alkyl, —S(O)$_2$—C$_1$-C$_4$-alkyl, —S—C$_1$-C$_4$-halogenoalkyl having 1 to 5 halogen atoms and C$_1$-C$_4$-halogenoalkoxy having 1 to 5 halogen atoms, and
R$^{56}$, R$^{57}$ and R$^{58}$, which may be the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, —S(O)—C$_1$-C$_4$-alkyl, —S(O)$_2$—C$_1$-C$_4$-alkyl, C$_1$-C$_4$-halogenoalkoxy having 1 to 5 halogen atoms, —S(O)—C$_1$-C$_4$-alkyl and S(O)$_2$—C$_1$-C$_4$-alkyl, or A represents a heterocycle of the formula (Het-22)

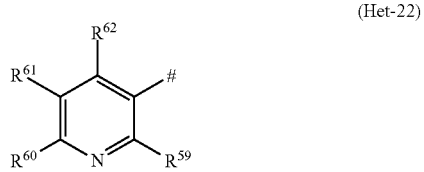
(Het-22)

in which
R$^{59}$ is selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$ alkoxy, —S—C$_1$-C$_8$-alkyl, —S(O)—C$_1$-C$_4$-alkyl, —S(O)$_2$—C$_1$-C$_4$-alkyl, —S—C$_2$-C$_8$-alkenyl, —S—C$_1$-C$_4$-halogenoalkyl having 1 to 5 halogen atoms, C$_1$-C$_4$-halogenoalkoxy having 1 to 5 halogen atoms, phenyloxy (optionally substituted by halogen or C$_1$-C$_4$-alkyl) and S-phenyl (optionally substituted by halogen or C$_1$-C$_4$-alkyl), and
R$^{60}$, R$^{61}$ and R$^{62}$, which may the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, C$_1$-C$_4$-halogenoalkoxy having 1 to 5 halogen atoms, —S(O)—C$_1$-C$_4$-alkyl, —S(O)$_2$—C$_1$-C$_4$-alkyl, N-morpholine (optionally substituted by halogen or C$_1$-C$_4$-alkyl) and thienyl (optionally substituted by halogen or a C$_1$-C$_4$-alkyl), or A represents a heterocycle of the formula (Het-23)

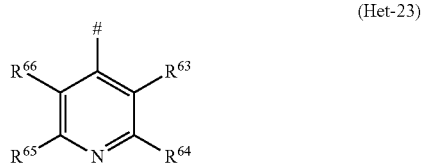
(Het-23)

in which
R$^{63}$, R$^{64}$, R$^{65}$ and R$^{66}$, which may be the same or different, are selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S—$C_1$-$C_4$-halogenoalkyl having 1 to 5 halogen atoms, $C_1$-$C_4$-halogenoalkoxy having 1 to 5 halogen atoms, —S(O)—$C_1$-$C_4$-alkyl and $S(O)_2$—$C_1$-$C_4$-alkyl, or A represents a heterocycle of the formula (Het-24)

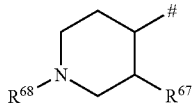

(Het-24)

in which $R^{67}$ is selected from the group consisting of hydrogen, halogen, $C_1$-$C_4$-alkyl and $C_1$-$C_4$-halogenoalkyl having 1 to 5 halogen atoms, and $R^{68}$ is selected from the group consisting of $C_1$-$C_4$-alkyl, $C_1$-$C_4$-halogenoalkyl having 1 to 5 halogen atoms, $C_1$-$C_6$-alkoxycarbonyl, benzyl (optionally substituted by 1 to 3 halogen atoms), benzyloxycarbonyl (optionally substituted by 1 to 3 halogen atoms) and heterocyclyl like pyrimidinyl, (optionally substituted by halogen, $C_1$-$C_4$-alkyl, $C_1$-$C_4$-halogenoalkyl having 1 to 5 halogen atoms), or A represents a heterocycle of the formula (Het-25)

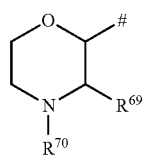

(Het-25)

in which $R^{69}$ is selected from the group consisting of hydrogen, $C_1$-$C_4$-alkyl and $C_1$-$C_4$-halogenoalkyl having 1 to 5 halogen atoms, and $R^{70}$ is selected from the group consisting of hydrogen, $C_1$-$C_4$-alkyl, $C_1$-$C_4$-halogenoalkyl having 1 to S halogen atoms and benzyl, or A represents a heterocycle of the formula (Het-26)

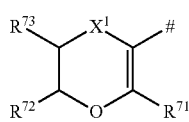

(Het-26)

in which $X^1$ is selected from the group consisting of sulphur, —SO—, or —$SO_2$—, and $R^{71}$ is selected from the group consisting of $C_1$-$C_4$-alkyl and $C_1$-$C_4$-halogenoalkyl having 1 to 5 halogen atoms, and $R^{72}$ and $R^{73}$ may be the same or different and are selected from the group consisting of hydrogen and $C_1$-$C_4$-alkyl, or A represents a heterocycle of the formula (Het-29)

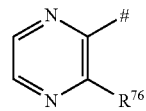

(Het-29)

in which $R^{76}$ is selected from the group consisting of hydrogen, halogen, $C_1$-$C_4$-alkyl and $C_1$-$C_4$-halogenoalkyl having 1 to 5 halogen atoms.

In another individual embodiment (embodiment 2-2), the structural elements in the compound of formula (I) are preferably defined as follows:

$B^1$, $B^2$ are as defined in embodiment 2-1, n is as defined in embodiment 2-1, each X is as defined in embodiment 2-1, m is 0, 1, 2, 3 or 4 and each Y is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, wherein both alkyl residues may form a 4- to 7-membered heterocycle incorporating the nitrogen bonded to the phenyl system of the compound, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, —$CH_2$—S—$C_1$-$C_4$-alkyl, —$CH_2$—S(O)—$C_1$-$C_4$-alkyl, —$CH_2$—S(O)$_2$—$C_1$-$C_4$-alkyl, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino, or m is 2, 3 or 4 and at least two substituents Y are vicinal and, together with the carbon atoms to which they are bonded, form an annellated 5- or 6-membered carbocycle or a 5- or 6-membered heterocycle with one or two heteroatoms selected from the group consisting of oxygen and nitrogen, whereat two oxygen atoms are not directly connected, the carbocycle or heterocycle being independently substituted by 0 to 2 halogen atoms, 0 to 2 oxo-groups, 0 to 4 $C_1$-$C_4$-alkyl, 0 to 4 $C_1$-$C_4$-alkoxy or 0 to 2 $C_1$-$C_4$-halogenoalkyl having 1 to 5 halogen atoms, and the remaining substituents Y are independently selected from the group consisting of hydrogen, halogen, nitro, cyano, C₁-C₄-alkyl, C₁-C₄-halogenoalkyl having 1 to 5 halogen atoms, C₂-C₄-alkenyl, C₂-C₄-alkynyl, C₁-C₄-alkylamino, di-(C₁-C₄-alkyl)amino, C₁-C₄-alkoxy, C₁-C₄-halogenoalkoxy having 1 to 5 halogen atoms, C₂-C₄-alkenyloxy, C₂-C₄-halogenoalkenyloxy having 1 to 5 halogen atoms, C₃-C₄-alkynyloxy, C₃-C₄-halogenoalkynyloxy having 1 to 5 halogen atoms, C₃-C₆-cycloalkyl, C₃-C₆-halogenocycloalkyl having 1 to 5 halogen atoms, C₁-C₄-alkylcarbonyl, C₁-C₄-halogenoalkylcarbonyl having 1 to 5 halogen atoms, —CONH(C₁-C₄-alkyl), —CON(C₁-C₄-alkyl)₂, —CONH(OC₁-C₄-alkyl), —CON(OC₁-C₄-alkyl)(C₁-C₄-alkyl), C₁-C₄-alkoxycarbonyl, C₁-C₄-halogenoalkoxycarbonyl having 1 to 5 halogen atoms, C₁-C₄-alkylcarbonyloxy, C₁-C₄-halogenoalkylcarbonyloxy having 1 to 5 halogen atoms, C₁-C₄-alkylcarbonylamino, C₁-C₄-halogenoalkylcarbonylamino having 1 to 5 halogen atoms, —OCONH(C₁-C₄-alkyl), —OCON(C₁-C₄-alkyl)₂, —OCONH(OC₁-C₄-alkyl), —OCO(OC₁-C₄-alkyl), —S—C₁-C₄-alkyl, —S—C₁-C₄-halogenoalkyl having 1 to 5 halogen atoms, —S(O)—C₁-C₄-alkyl, —S(O)—C₁-C₄-halogenoalkyl having 1 to 5 halogen atoms, —S(O)₂—C₁-C₄-alkyl, —S(O)₂—C₁-C₄-halogenoalkyl having 1 to 5 halogen atoms, —CH₂—S—C₁-C₄-alkyl, —CH₂—S(O)—C₁-C₄-alkyl, —CH₂—S(O)₂—C₁-C₄-alkyl, (C₁-C₄-alkoxyimino)-C₁-C₄-alkyl, (C₂-C₆-alkenyloxyimino)-C₁-C₄-alkyl, (C₃-C₆-alkynyloxyimino)-C₁-C₄-alkyl, (benzyloxyimino)-C₁-C₆-alkyl, benzyloxy, —S-benzyl, benzylamino, phenoxy, —S-phenyl and phenylamino, R¹, R², R³ and R⁴ are the same or different and are selected from the group consisting of hydrogen, halogen, cyano, hydroxy, amino, —CHO, —COOH, —CONH₂, C₁-C₄-alkyl, C₂-C₄-alkenyl, C₂-C₄-alkynyl, C₁-C₄-alkylamino, di-(C₁-C₄-alkyl)amino, C₁-C₄-alkoxy, C₁-C₄-halogenoalkyl having 1 to 5 halogen atoms, C₁-C₄-halogenoalkoxy having 1 to 5 halogen atoms, C₂-C₄-alkenyloxy, C₂-C₄-halogenoalkenyloxy having 1 to 5 halogen atoms, C₃-C₄-alkynyloxy, C₃-C₄-halogenoalkynyloxy having 1 to 5 halogen atoms, C₃-C₆-cycloalkyl, C₃-C₆-halogenocycloalkyl having 1 to 5 halogen atoms, C₃-C₆-cycloalkyl-C₁-C₃-alkyl, C₃-C₆-halogenocycloalkyl-C₁-C₃-alkyl having 1 to 5 halogen atoms, C₁-C₄-alkylcarbonyl, C₁-C₄-halogenoalkylcarbonyl having 1 to 5 halogen atoms, —CONH(C₁-C₄-alkyl), —CON(C₁-C₄-alkyl)₂, —CONH(OC₁-C₄-alkyl), —CON(C₁-C₄-alkyl)(C₁-C₄-alkyl), C₁-C₄-alkoxycarbonyl, C₁-C₄-halogenoalkoxycarbonyl having 1 to 5 halogen atoms, —OC(O)—C₁-C₄-alkyl, —OC(O)—C₁-C₄-halogenoalkyl having 1 to 5 halogen atoms, —NHC(O)—C₁-C₄-alkyl, —NHC(O)—C₁-C₄-halogenoalkyl having 1 to 5 halogen atoms, —OCONH(C₁-C₄-alkyl), —OCON(C₁-C₄-alkyl)₂, —OCONH(OC₁-C₄-alkyl), OCO(OC₁-C₄-alkyl), —S—C₁-C₄-alkyl, —S—C₁-C₄-halogenoalkyl having 1 to 5 halogen atoms, —S(O)—C₁-C₄-alkyl, —S(O)—C₁-C₄-halogenoalkyl having 1 to 5 halogen atoms, —S(O)₂—C₁-C₄-alkyl, —S(O)₂—C₁-C₄-halogenoalkyl having 1 to 5 halogen atoms, benzyl, benzyloxy, —S-benzyl, —S(O)-benzyl, —S(O)₂-benzyl, benzylamino, phenoxy, —S-phenyl, —S(O)-phenyl, —S(O)₂-phenyl, phenylamino, phenylcarbonylamino and phenyl, with the provisio that R¹ is fluorine and/or R² is fluorine, R⁵ is as defined in embodiment 2-1, and A is as defined in embodiment 2-1.

In another individual aspect of embodiment 2-1, R¹ is fluorine. In another individual aspect of embodiment 2-1, R² is fluorine. In another individual aspect of embodiment 2-1, R¹ is fluorine and R² is fluorine. In another individual aspect of embodiment 2-1, the combination R¹/R² is fluorine/methyl.

In another individual aspect of embodiment 2-2, R¹ is fluorine. In another individual aspect of embodiment 2-2, R² is fluorine. In another individual aspect of embodiment 2-2, R¹ is fluorine and R² is fluorine. In another individual aspect of embodiment 2-2, the combination R¹/R² is fluorine/methyl.

More preferred substituents or ranges of the structural elements mentioned in the compounds of formula (I) are explained below (embodiment 3-1):

B¹, B² represent C—X or N, wherein at least B¹ or B² is N, n is 1,

X is selected from the group consisting of hydrogen, halogen, nitro, cyano, C₁-C₄-alkyl, C₁-C₄-halogenoalkyl having 1 to 5 halogen atoms, C₁-C₄-alkoxy, C₁-C₄-halogenoalkoxy having 1 to 5 halogen atoms, m is 0, 1, 2 or 3 and each Y is independently selected from the group consisting of hydrogen, halogen, nitro, cyano, C₁-C₄-alkyl, C₁-C₄-halogenoalkyl having 1 to 5 halogen atoms, C₁-C₄-alkoxy, C₁-C₄-halogenoalkoxy having 1 to 5 halogen atoms, or m is 2 or 3 and at least two substituents Y are vicinal and, together with the phenyl ring to which they are bonded, form a structure which is selected from:

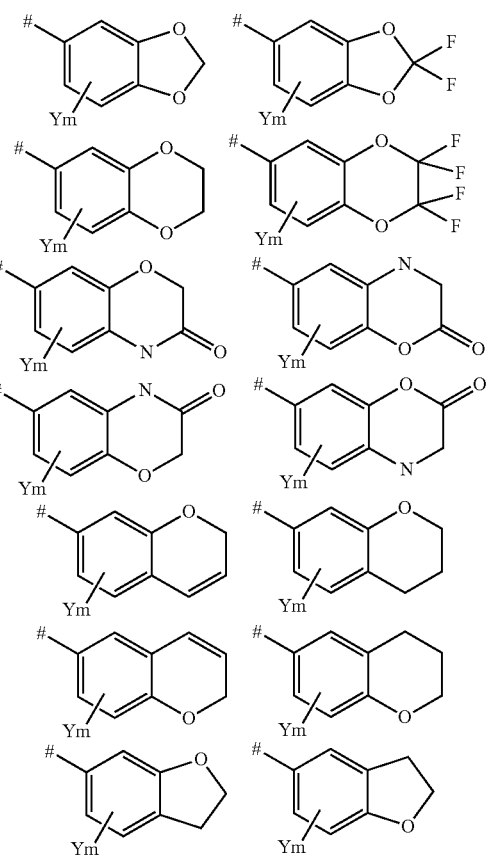

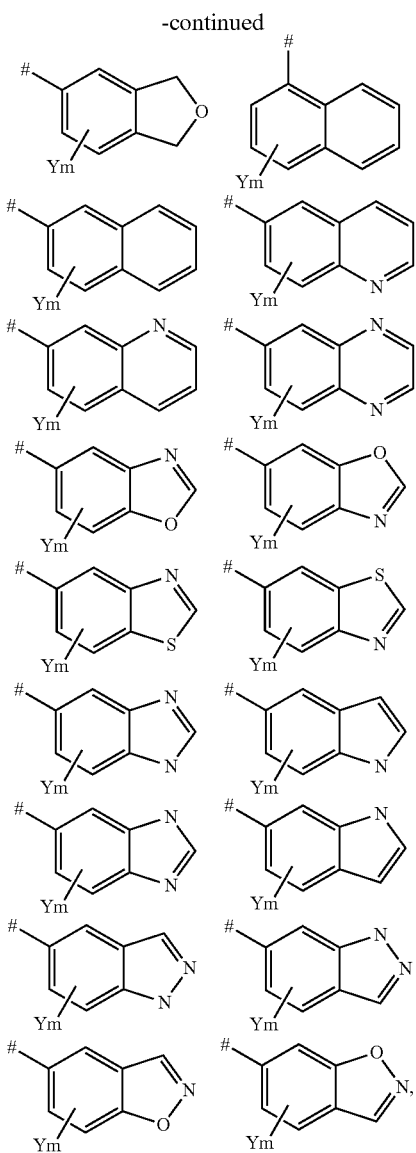

and
the remaining substituent Y is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^1$ and $R^2$ are the same or different and are selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_8$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, $R^3$ and $R^4$ are the same or different and are selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, or $R^1$ and $R^2$ together with the carbon atom to which they are bonded form a 4- or 5-membered carbocycle, and $R^3$ and $R^4$ are the same or different and are selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, preferably $R^1$ and $R^2$ together with the carbon atom to which they are bonded form a cyclobutyl or a cyclopentyl, or $R^3$ and $R^4$ together with the carbon atom to which they are bonded form a 3-, 4- or 5-membered carbocycle, and $R^1$ and $R^2$ are the same or different and are selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, preferably $R^3$ and $R^4$ together with the carbon atom to which they are bonded form a cyclopropyl or a cyclobutyl, or $R^2$ and $R^4$ together with the carbon atoms to which they are bonded form a 4- or 5-membered non-aromatic carbocycle optionally substituted by substituents selected from the group consisting of one to four $C_1$-$C_3$-alkyl groups and one to two halogen atoms, and $R^1$ is selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, and $R^3$ is selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, preferably $R^2$ and $R^4$ together with the carbon atoms to which they are bonded form a cyclobutyl or cyclopentyl, or $R^1$ and $R^3$ together with the carbon atoms to which they are bonded form a 4- or 5-membered non-aromatic carbocycle optionally substituted by substituents selected from the group consisting of one to four $C_1$-$C_3$-alkyl groups and one to two halogen atoms, preferably cyclopropyl, cyclobutyl or cyclopentyl, and $R^2$ is selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, 2,6-dichlorophenyl-carbonylamino, 2-chlorophenyl-carbonylamino and phenyl, and $R^4$ is selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, preferably $R^1$ and $R^3$ together with the carbon atoms to which they are bonded form a cyclobutyl or cyclopentyl, $R^5$ is selected from the group consisting of hydrogen, $C_3$-$C_6$-cycloalkyl, $C_1$-$C_4$-alkylcarbonyl, $C_1$-$C_4$-alkoxycarbonyl, A represents a phenyl group of formula (A1)

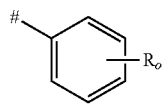

(A1)

wherein
o is 0, 1 or 2, and
each R is independently selected from the group consisting of halogen, nitro, —OH, cyano, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1C_1$-$C_4$-alkoxycarbonyl, —NH($C_1$-$C_4$-alkyl), phenyl (optionally substituted by $C_1$-$C_4$-alkoxy) and phenoxy, or A represents a heterocycle of the formula (Het-1)

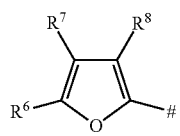

(Het-1)

in which
$R^6$ and $R^7$ may be the same or different and are selected from the group consisting of hydrogen, halogen, nitro, $C_1$-$C_4$-alkyl and $C_1$-$C_4$-halogenoalkyl having 1 to 5 halogen atoms, and
$R^8$ is selected from the group consisting of hydrogen, halogen, $C_1$-$C_4$-alkyl and $C_1$-$C_4$-halogenoalkyl having 1 to 5 halogen atoms, or A represents a heterocycle of the formula (Het-2)

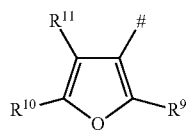

(Het-2)

in which
$R^9$ is selected from the group consisting of hydrogen, halogen, $C_1$-$C_4$-alkyl and $C_1$-$C_4$-halogenoalkyl having 1 to 5 halogen atoms, and
$R^{10}$ and $R^{11}$ may be the same or different and are selected from the group consisting of hydrogen, halogen, $C_1$-$C_4$-alkyl and $C_1$-$C_4$-halogenoalkyl having 1 to 5 halogen atoms, phenyl optionally substituted by halogen or $C_1$-$C_4$-alkyl), or A represents a heterocycle of the formula (Het-4)

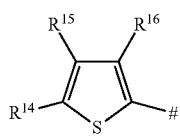

(Het-4)

in which
$R^{14}$ and $R^{15}$ may be the same or different and are selected from the group consisting of hydrogen, halogen, $C_1$-$C_4$-alkyl, $C_1$-$C_4$-halogenoalkyl having 1 to 5 halogen atoms, —S—$C_1$-$C_4$-alkyl, —S(O)$_2$—$C_1$-$C_4$-alkyl, phenyl (optionally substituted by halogen or $C_1$-$C_4$-alkyl) and pyridyl (optionally substituted by halogen or $C_1$-$C_4$-alkyl), and
$R^{16}$ is selected from the group consisting of hydrogen, halogen, cyano, $C_1$-$C_4$-alkyl, $C_1$-$C_4$-halogenoalkyl having 1 to 5 halogen atoms and $C_1$-$C_4$-halogenoalkoxy having 1 to 5 halogen atoms, or A represents a heterocycle of the formula (Het-5)

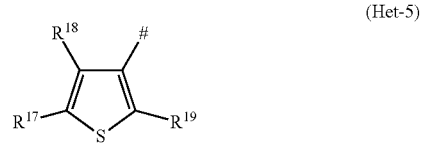

(Het-5)

in which
$R^{17}$ and $R^{18}$ may be the same or different and are selected from the group consisting of hydrogen, halogen, $C_1$-$C_4$-alkyl, $C_1$-$C_4$-alkyloxy and $C_1$-$C_4$-halogenoalkyl having 1 to 5 halogen atoms, and
$R^{19}$ is selected from the group consisting of hydrogen, halogen, $C_1$-$C_4$-alkyl and $C_1$-$C_4$-halogenoalkyl having 1 to 5 atoms, or A represents a heterocycle of the formula (Het-6)

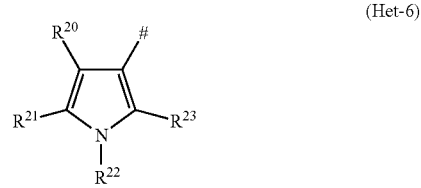

(Het-6)

in which
$R^{20}$ is selected from the group consisting of hydrogen, halogen, cyano, $C_1$-$C_4$-alkyl and $C_1$-$C_4$-halogenoalkyl having 1 to 5 halogen atoms, and
$R^{21}$ and $R^{23}$ may be the same or different and are selected from the group consisting of hydrogen, halogen, $C_1$-$C_4$-alkyl and $C_1$-$C_4$-halogenoalky having 1 to 5 halogen atoms, and
$R^{22}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, or A represents a heterocycle of the formula (Het-10)

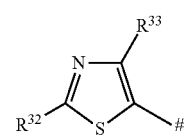

(Het-10)

in which
$R^{32}$ is selected from the group consisting of hydrogen, halogen, amino, cyano, $C_1$-$C_4$-alkylamino, di-($C_1$-$C_4$-alkyl)amino, $C_1$-$C_4$-alkyl, $C_1$-$C_4$-halogenoalkyl having 1 to 5 halogen atoms and phenyl (optionally substituted by halogen or $C_1$-$C_4$-alkyl), and $R^{33}$ is selected from the group consisting of halogen, $C_1$-$C_4$-alkyl and $C_1$-$C_4$-halogenoalkyl having 1 to 5 halogen atoms, $C_1$-$C_5$-halogenoalkoxy comprising 1 to 9 halogen atoms, amino, substituted or unsubstituted $C_1$-$C_5$-alkylamino or substituted or unsubstituted di-($C_1$-$C_5$-alkyl)-amino, or A represents a heterocycle of the formula (Het-21)

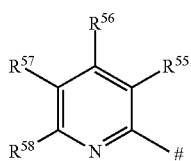

(Het-21)

in which $R^{55}$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 halogen atoms and $C_1$-$C_4$-halogenoalkoxy having 1 to 5 halogen atoms, and $R^{56}$, $R^{57}$ and $R^{58}$, which may be the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl and S(O)$_2$—$C_1$-$C_4$-alkyl, or A represents a heterocycle of the formula (Het-22)

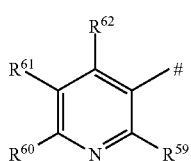

(Het-22)

in which $R^{59}$ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$ alkoxy, —S—$C_1$-$C_8$-alkyl, —S(O)—$C_1$-$C_4$-alkyl, —S(O)$_2$—$C_1$-$C_4$-alkyl, —S—$C_2$-$C_8$-alkenyl, —S—$C_1$-$C_4$-halogenoalkyl having 1 to 5 halogen atoms, $C_1$-$C_4$-halogenoalkoxy having 1 to 5 halogen atoms, phenyloxy (optionally substituted by halogen or $C_1$-$C_4$-alkyl) and S-phenyl (optionally substituted by halogen or $C_1$-$C_4$-alkyl), and $R^{60}$, $R^{61}$ and $R^{62}$, which may the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl, —S(O)$_2$—$C_1$-$C_4$-alkyl, N-morpholine (optionally substituted by halogen or $C_1$-$C_4$-alkyl) and thienyl (optionally substituted by halogen or a $C_1$-$C_4$-alkyl), or A represents a heterocycle of the formula (Het-29)

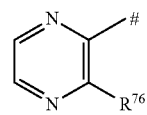

(Het-29)

in which $R^{76}$ is selected from the group consisting of hydrogen, halogen, $C_1$-$C_4$-alkyl and $C_1$-$C_4$-halogenoalkyl having 1 to 5 halogen atoms.

In another individual embodiment (embodiment 3-2), the structural elements in the compound of formula (I) are more preferably defined as follows:

$B^1$, $B^2$ are as defined in embodiment 3-1, n is as defined in embodiment 3-1, each X is as defined in embodiment 3-1, m is 0, 1, 2 or 3 and each Y is independently selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-alkylamino, di-($C_1$-$C_4$-alkyl)amino, wherein both alkyl residues may form a 4- to 7-membered heterocycle incorporating the nitrogen bonded to the phenyl system of the compound, $C_1$-$C_4$-alkylcarbonylamino, —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, or m is 2 or 3 and at least two substituents Y are vicinal and, together with the phenyl ring to which they are bonded, form a structure which is selected from:

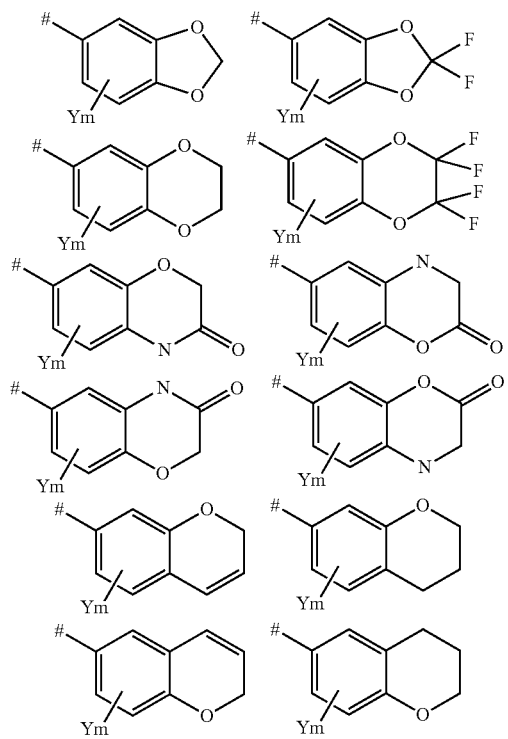

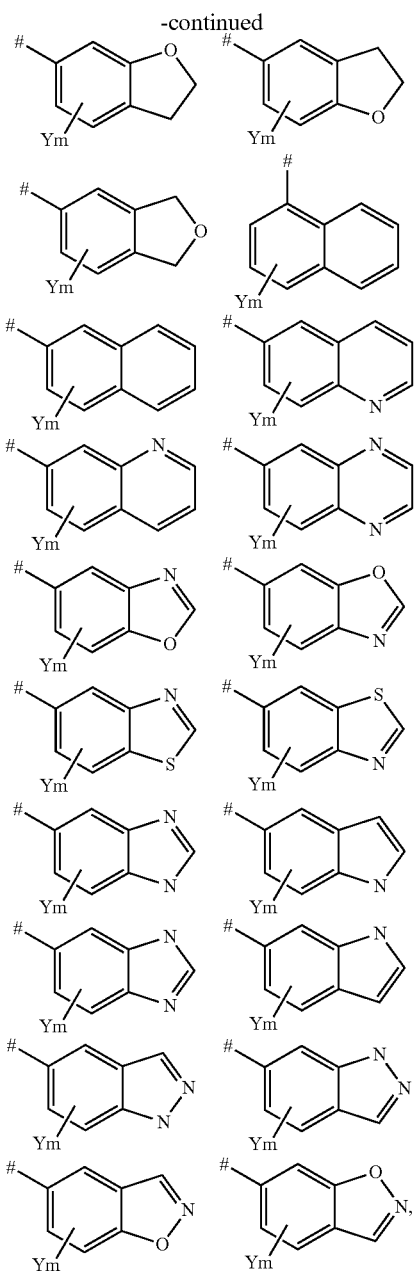

and the remaining substituent Y is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $R^1$ and $R^2$ are the same or different and are selected from the group consisting of hydrogen, halogen, cyano, hydroxy, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, and phenyl, with the provisio that $R^1$ is fluorine and/or $R^2$ is fluorine, $R^3$ and $R^4$ are the same or different and are selected from the group consisting of hydrogen, —COOH, $C_1$-$C_4$-alkyl, $C_1$-$C_4$-halogenoalkyl $C_1$-$C_4$-alkoxy, hydroxy-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, $R^5$ is as defined in embodiment 3-1, and A is as defined in embodiment 3-1.

In another individual aspect of embodiment 3-1, $R^1$ is fluorine. In another individual aspect of embodiment 3-1, $R^2$ is fluorine. In another individual aspect of embodiment 3-1, $R^1$ is fluorine and $R^2$ is fluorine. In another individual aspect of embodiment 3-1, the combination $R^1/R^2$ is fluorine/methyl.

In another individual aspect of embodiment 3-2, $R^1$ is fluorine. In another individual aspect of embodiment 3-2, $R^2$ is fluorine. In another individual aspect of embodiment 3-2, $R^1$ is fluorine and $R^2$ is fluorine. In another individual aspect of embodiment 3-2, the combination $R^1/R^2$ is fluorine/methyl.

Especially preferred substituents or ranges of the structural elements mentioned in the compounds of formula (I) are explained below (embodiment 4-1):

$B^1$ represents N, $B^2$ represents CH, n is 1,

X is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, m is 0, 1 or 2 and each Y is independently selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, or m is 2 or 3 and at least two substituents Y are vicinal and, together with the phenyl ring to which they are bonded, form a structure which is selected from:

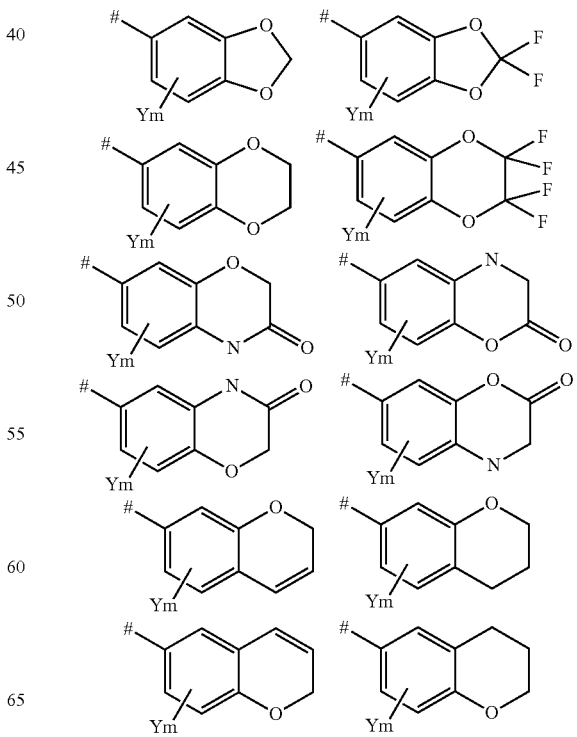

-continued

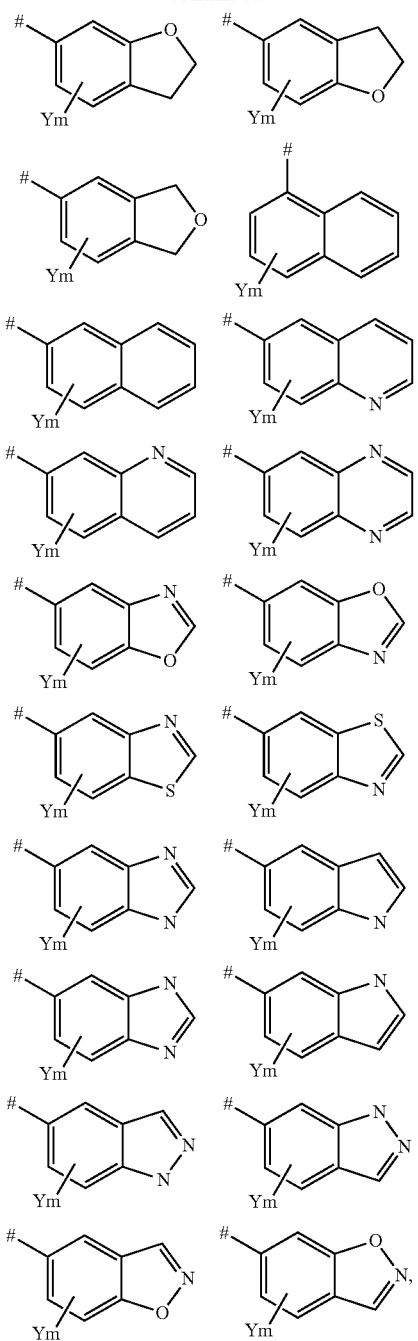

A is selected from:

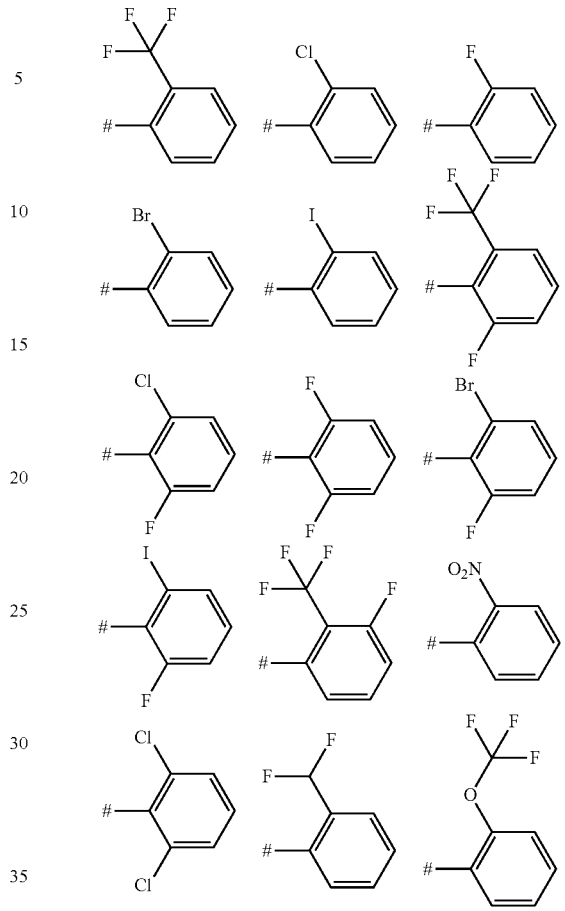

or
A is selected from:

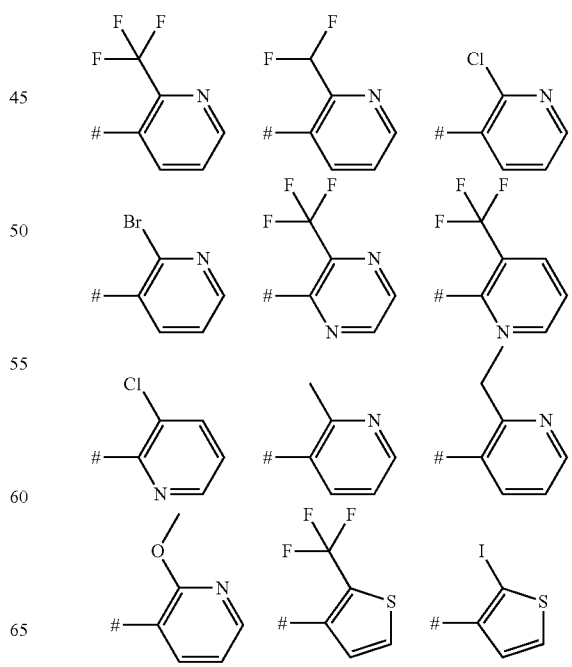

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl or difluoromethyl, $R^1$ and $R^2$ are the same or different and are selected from the group consisting of hydrogen, methyl, ethyl, methoxy, ethoxy or fluorine, $R^3$ and $R^4$ are the same or different and are selected from the group consisting of hydrogen, methyl or ethyl, $R^5$ is hydrogen,

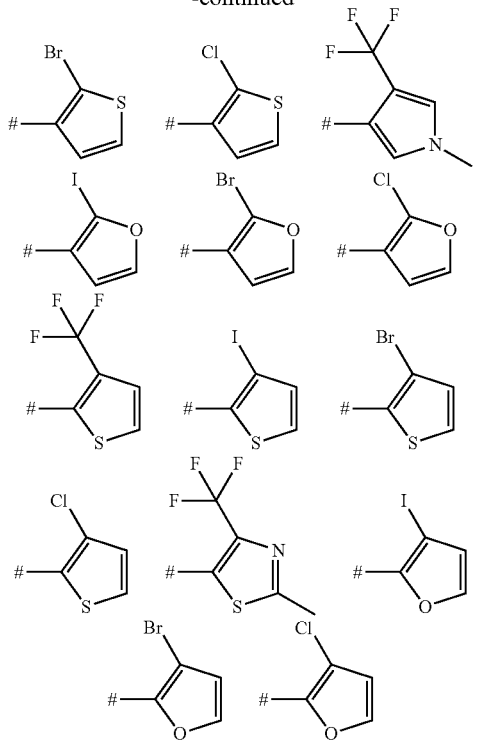

In another individual embodiment (embodiment 4-2), the structural elements in the compound of formula (I) are especially preferably defined as follows:

$B^1$ is as defined in embodiment 4-1,
$B^2$ is as defined in embodiment 4-1,
n is as defined in embodiment 4-1,
each X is as defined in embodiment 4-1,
m is 0, 1 or 2 and
each Y is independently selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-alkylamino, di-($C_1$-$C_4$-alkyl)amino, wherein both alkyl residues may form a 4- to 7-membered heterocycle incorporating the nitrogen bonded to the phenyl system of the compound, $C_1$-$C_4$-alkylcarbonylamino, —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, or
m is 2 or 3 and
at least two substituents Y are vicinal and, together with the phenyl ring to which they are bonded, form a structure which is selected from:

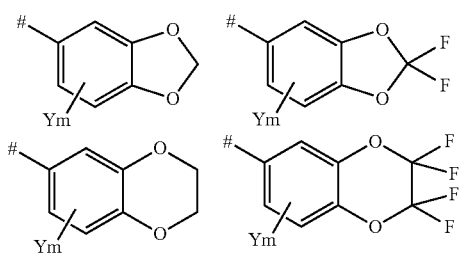

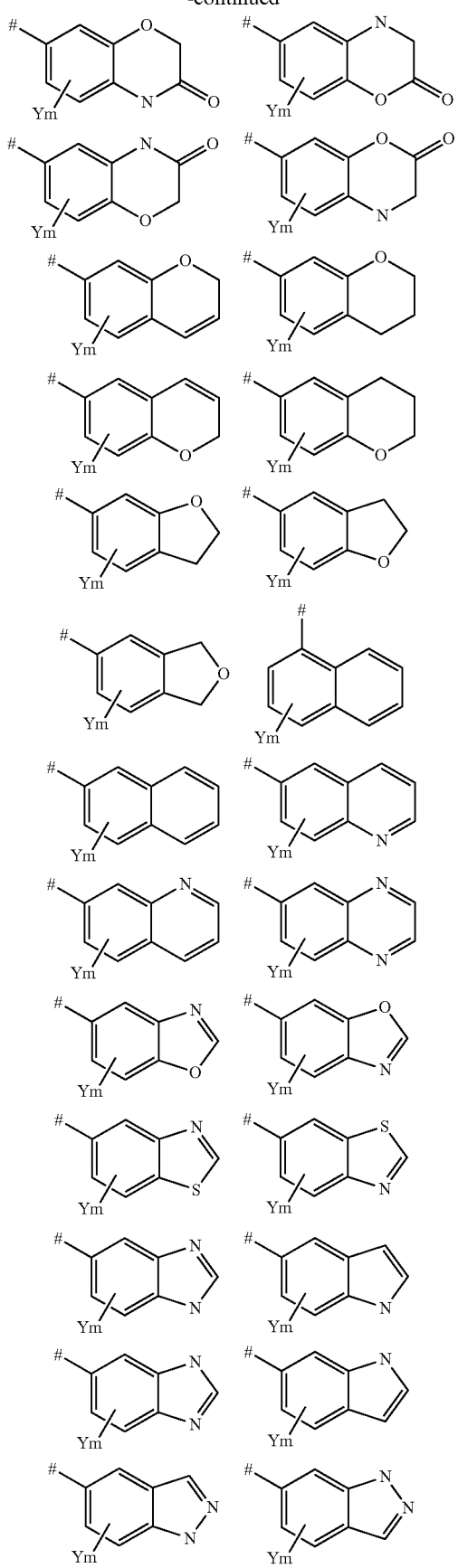

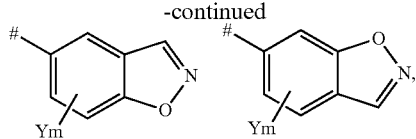

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl or difluoromethyl, $R^1$ and $R^2$ are the same or different and are selected from the group consisting of hydrogen, methyl, ethyl, methoxy, ethoxy or fluorine,
with the provisio that $R^1$ is fluorine and/or $R^2$ is fluorine, $R^3$ and $R^4$ are the same or different and are selected from the group consisting of hydrogen, methyl or ethyl, $R^5$ is as defined in embodiment 4-1, and A is as defined in embodiment 4-1.

In another individual aspect of embodiment 4-1, $R^1$ is fluorine. In another individual aspect of embodiment 4-1, $R^2$ is fluorine. In another individual aspect of embodiment 4-1, $R^1$ is fluorine and $R^2$ is fluorine. In another individual aspect of embodiment 4-1, the combination $R^1/R^2$ is fluorine/methyl.

In another individual aspect of embodiment 4-2, $R^1$ is fluorine. In another individual aspect of embodiment 4-2, $R^2$ is fluorine. In another individual aspect of embodiment 4-2, $R^1$ is fluorine and $R^2$ is fluorine. In another individual aspect of embodiment 4-2, the combination $R^1/R^2$ is fluorine/methyl.

In another individual embodiment (embodiment 4-3), especially preferred substituents or ranges of the structural elements mentioned in the compounds of formula (I) are explained below:

$B^1$ represents N,
$B^2$ represents CH,
n is 1,
X is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms,
m is 0, 1 or 2 and
each Y is independently selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, or
m is 2 or 3 and
at least two substituents Y are vicinal and, together with the phenyl ring to which they are bonded, form a structure which is selected from:

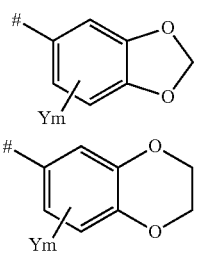

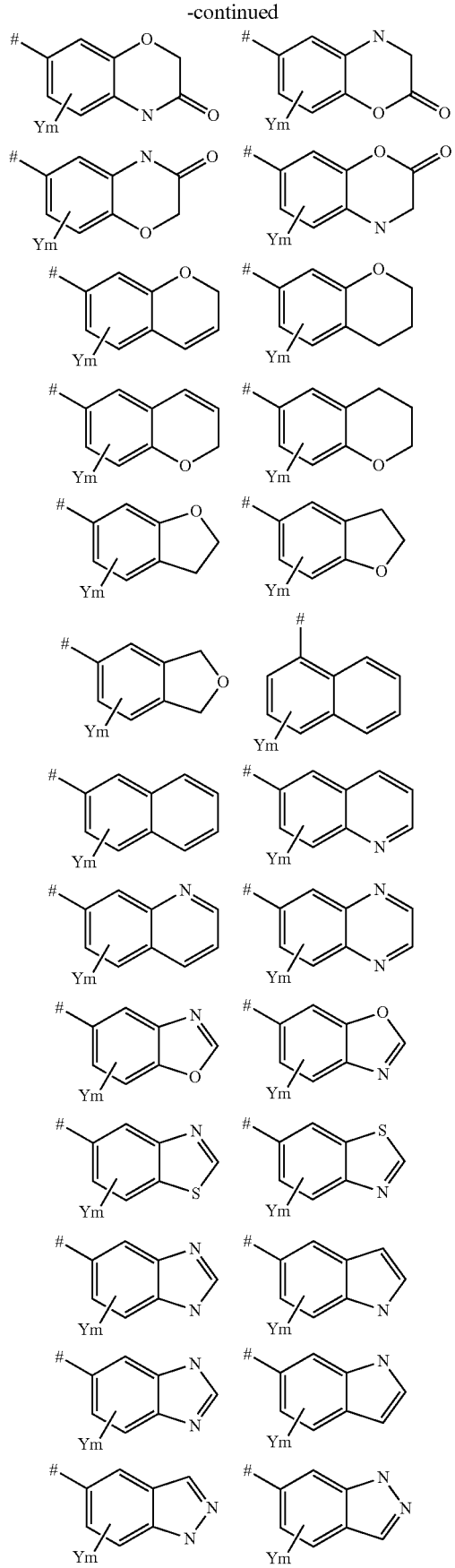

-continued

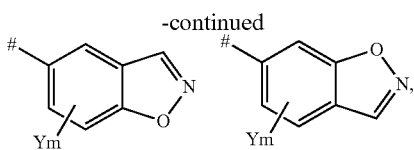

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, iso-propoxy, n-propoxy, trifluoromethyl or difluoromethyl,
$R^1$ is selected from the group consisting of hydrogen, methyl, ethyl, methoxy, ethoxy or fluorine,
$R^3$ is selected from the group consisting of hydrogen, methyl or ethyl,
$R^2$ and $R^4$ together with the carbon atoms to which they are bonded form a cyclobutane,
$R^5$ is hydrogen,
A is selected from:

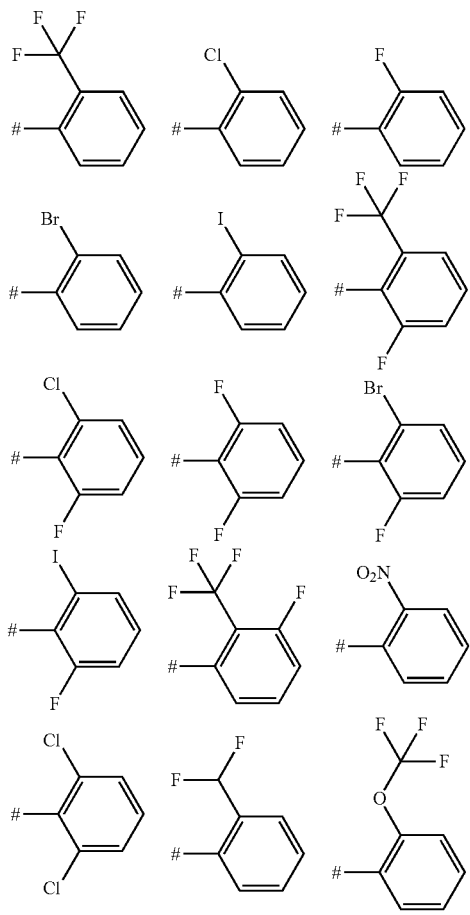

or
A is selected from:

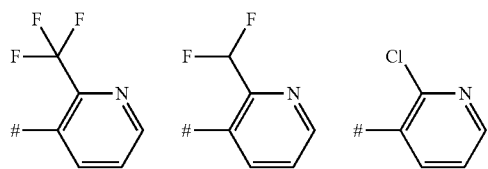

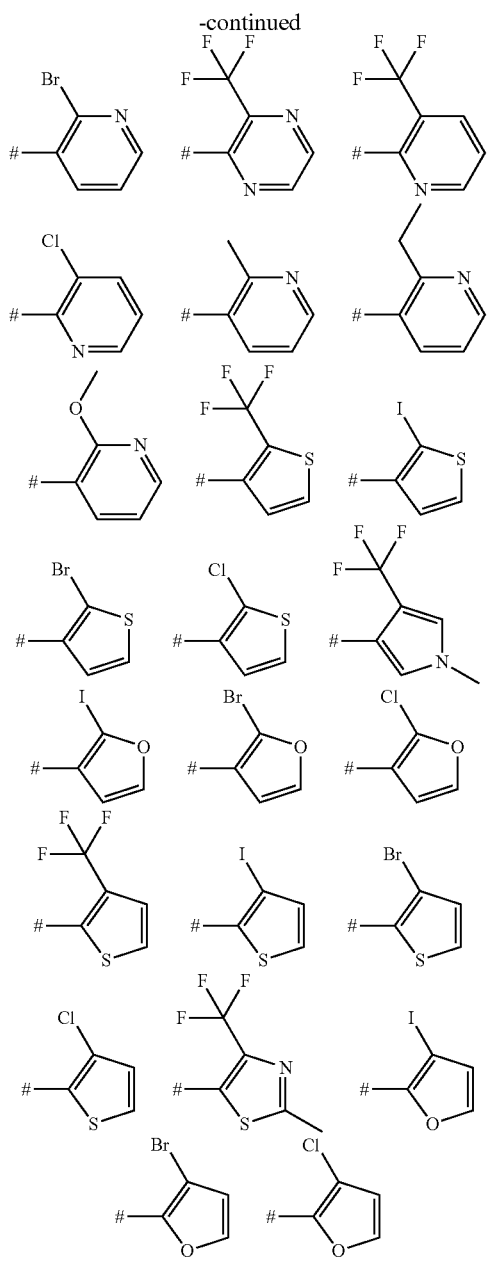

In another individual embodiment (embodiment 4-4), the structural elements in the compound of formula (I) are especially preferably defined as follows:
$B^1$ is as defined in embodiment 4-3,
$B^2$ is as defined in embodiment 4-3,
n is as defined in embodiment 4-3,
each X is as defined in embodiment 4-3,
m is 0, 1 or 2 and
each Y is independently selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-alkylamino, di-($C_1$-$C_4$-alkyl)amino, wherein both alkyl residues may form a 4- to 7-membered heterocycle incorporating the nitrogen bonded to the phenyl system of the compound, $C_1$-$C_4$-alkylcarbonylamino, —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, or m is 2 or 3 and at least two substituents Y are vicinal and, together with the phenyl ring to which they are bonded, form a structure which is selected from:

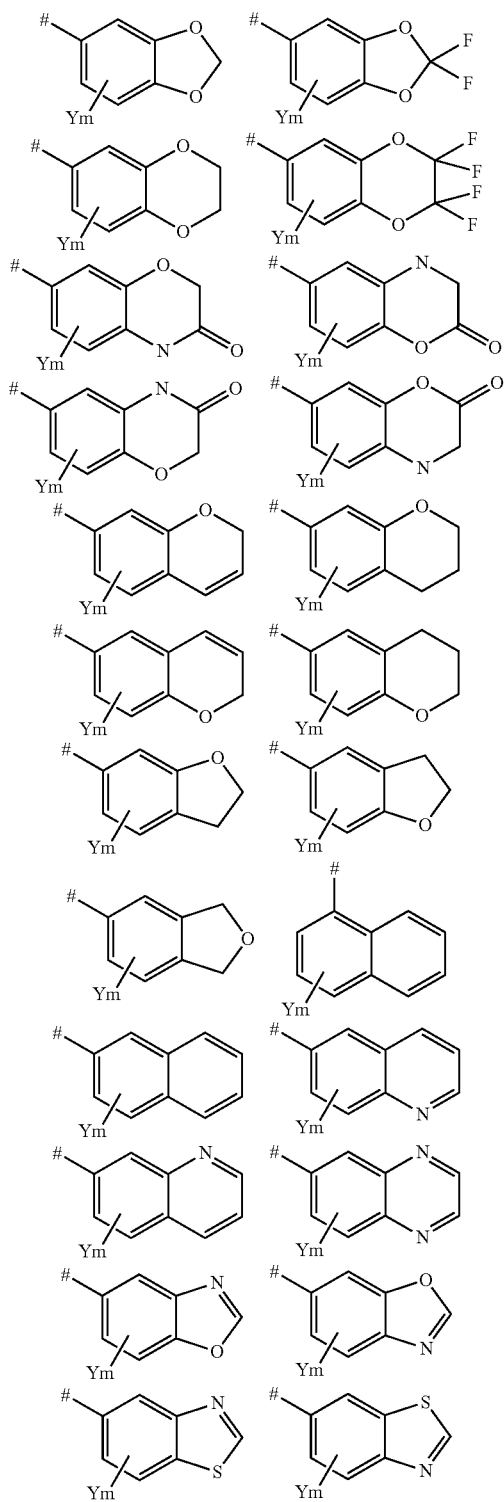

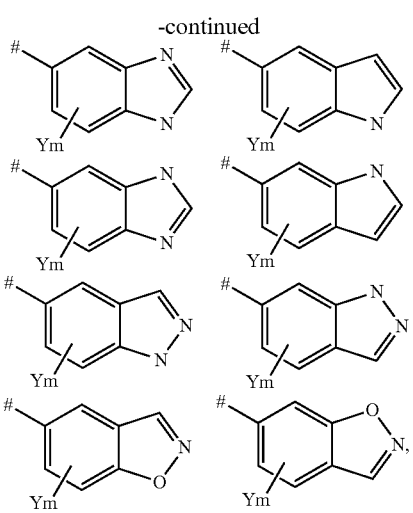

and the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl or difluoromethyl, $R^1$ is selected from the group consisting of hydrogen, methyl, ethyl, methoxy, ethoxy or fluorine, $R^3$ is selected from the group consisting of hydrogen, methyl or ethyl, $R^2$ and $R^4$ together with the carbon atoms to which they are bonded form a cyclobutane, $R^5$ is as defined in embodiment 4-3, and A is as defined in embodiment 4-3.

In another individual aspect of embodiment 4-3, $R^1$ is fluorine.

In another individual aspect of embodiment 4-4, $R^1$ is fluorine.

In a very specific aspect (embodiment 5-1) of the especially preferred substituents or ranges of the structural elements mentioned in the compounds of formula (I), $B^1$ represents N, $B^2$ represents CH, n is 1, X is selected from the group consisting of hydrogen or chlorine, m is 0, 1 or 2 and each Y is independently selected from hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy or difluoromethoxy, or m is 2 or 3 and at least two substituents Y are vicinal and, together with the phenyl ring to which they are bonded, form a structure which is selected from:

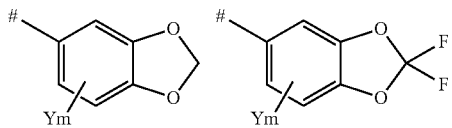

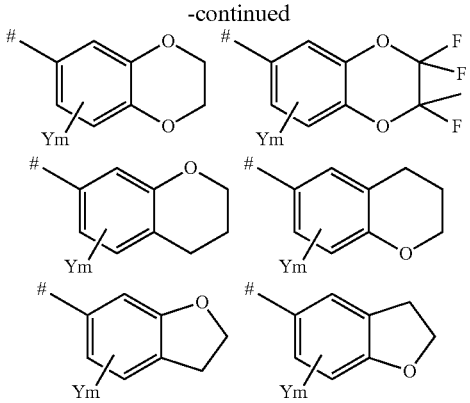

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, iso-propoxy, n-propoxy, trifluoromethyl or difluoromethyl,
$R^1$ and $R^2$ are independently hydrogen or fluorine,
$R^3$, $R^4$ and $R^5$ are hydrogen,
A is

or

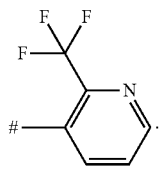

In another very specific aspect (embodiment 5-2) of the especially preferred substituents or ranges of the structural elements mentioned in the compounds of formula (I),
$B^1$ represents N,
$B^2$ represents CH,
n is 1,
X is selected from the group consisting of hydrogen or chlorine,
m is 0, 1 or 2 and
each Y is independently selected from hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, iso-propoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluormethylsulfonyl, trifluormethylsulfinyl or trifluormethylsulfanyl, or
m is 2 or 3 and
at least two substituents Y are vicinal and, together with the phenyl ring to which they are bonded, form a structure which is selected from:

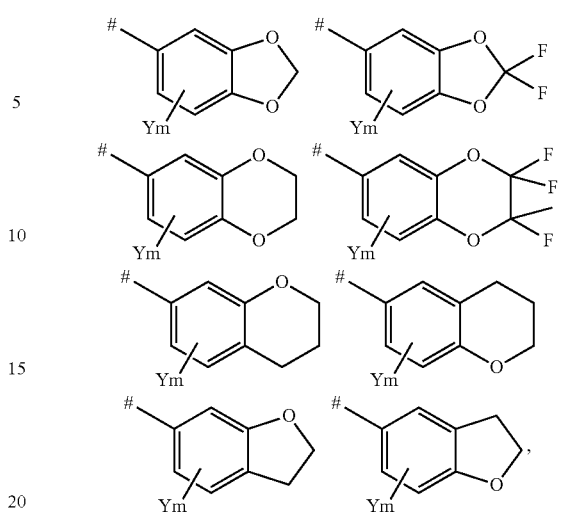

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, iso-propoxy, n-propoxy, trifluoromethyl or difluoromethyl,
$R^1$ and $R^2$ are independently hydrogen, methyl or fluorine,
with the provisio that $R^1$ is fluorine and/or $R^2$ is fluorine,
$R^3$, $R^4$ and $R^5$ are hydrogen,
A is

or

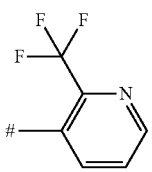

or

In another very specific aspect (embodiment 5-3) of the especially preferred substituents or ranges of the structural elements mentioned in the compounds of formula (I), B¹ represents N,
B² represents CH,
n is 1,
X is selected from the group consisting of hydrogen or chlorine,
m is 0, 1 or 2 and
each Y is independently selected from hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluormethylsulfonyl, trifluormethylsulfinyl or trifluormethylsulfanyl, or
m is 2 or 3 and
at least two substituents Y are vicinal and, together with the phenyl ring to which they are bonded, form a structure which is selected from:

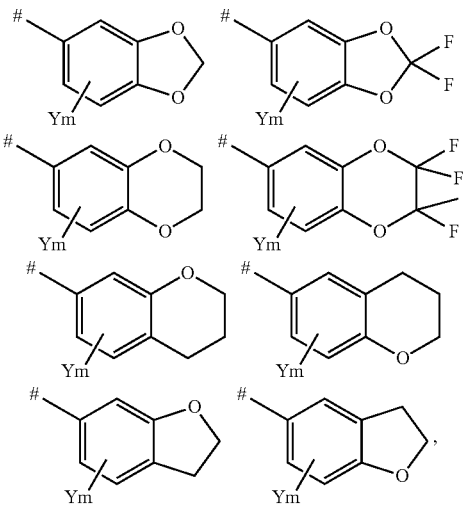

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl or difluoromethyl,
R¹ and R² are independently methyl or fluorine,
with the proviso that R¹ is fluorine and/or R² is fluorine,
R³, R⁴ and R⁵ are hydrogen,
A is

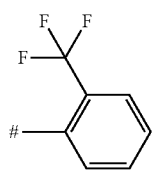

or

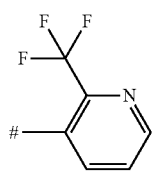

or

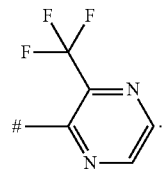

In another very specific aspect (embodiment 5-4) of the especially preferred substituents or ranges of the structural elements mentioned in the compounds of formula (I),
B¹ represents N,
B² represents CH,
n is 1,
X is selected from the group consisting of hydrogen or chlorine;
m is 0, 1 or 2 and
each Y is independently selected from the group hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy or difluoromethoxy, or
m is 2 or 3 and
at least two substituents Y are vicinal and, together with the phenyl ring to which they are bonded, form a structure which is selected from:

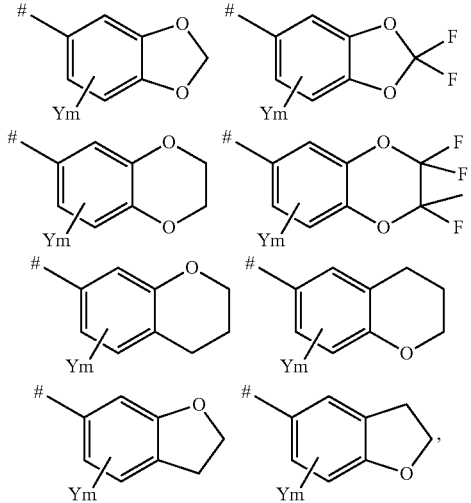

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl or difluoromethyl,
R¹ is hydrogen or fluorine,
R³ and R⁵ are hydrogen,
R² and R⁴ together with the carbon atoms to which they are bonded form a cyclobutane, A is

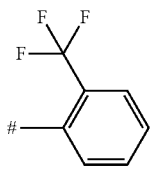

or

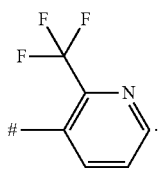

In another very specific aspect (embodiment 5-5) of the especially preferred substituents or ranges of the structural elements mentioned in the compounds of formula (I),
$B^1$ represents N,
$B^2$ represents CH,
n is 1,
X is selected from the group consisting of hydrogen or chlorine;
m is 0, 1 or 2 and
each Y is independently selected from the group hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, iso-propoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluormethylsulfonyl, trifluormethylsulfinyl or trifluormethylsulfanyl, or
m is 2 or 3 and
at least two substituents Y are vicinal and, together with the phenyl ring to which they are bonded, form a structure which is selected from:

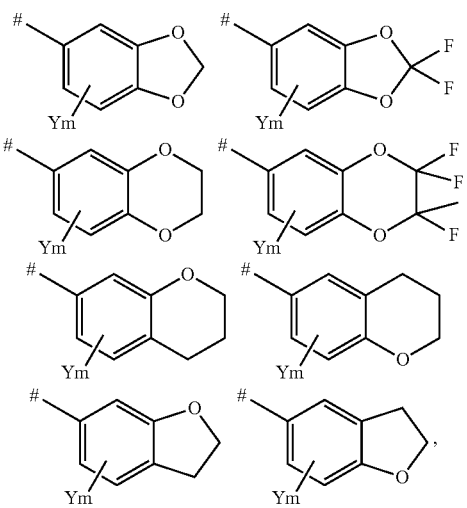

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, iso-propoxy, n-propoxy, trifluoromethyl or difluoromethyl,
$R^1$ is hydrogen or fluorine,
$R^3$ and $R^5$ are hydrogen,
$R^2$ and $R^4$ together with the carbon atoms to which they are bonded form a cyclobutane,
A is

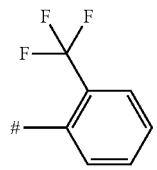

or

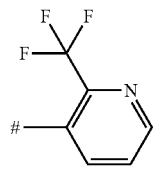

or

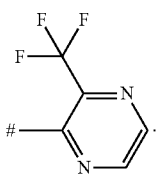

In another individual aspect of embodiment 5-1, $R^1$ is fluorine. In another individual aspect of embodiment 5-1, $R^2$ is fluorine. In another individual aspect of embodiment 5-1, $R^1$ is fluorine and $R^2$ is fluorine.

In another individual aspect of embodiment 5-2, $R^1$ is fluorine. In another individual aspect of embodiment 5-2, $R^2$ is fluorine. In another individual aspect of embodiment 5-2, $R^1$ is fluorine and $R^2$ is fluorine. In another individual aspect of embodiment 5-2, the combination $R^1/R^2$ is fluorine/methyl.

In another individual aspect of embodiment 5-3, $R^1$ is fluorine. In another individual aspect of embodiment 5-3, $R^2$ is fluorine. In another individual aspect of embodiment 5-3, $R^1$ is fluorine and $R^2$ is fluorine. In another individual aspect of embodiment 5-3, the combination $R^1/R^2$ is fluorine/methyl.

In another individual aspect of embodiment 5-4, $R^1$ is fluorine.

In another individual aspect of embodiment 5-5, $R^1$ is fluorine.

The definitions of radicals, and explanations, that are given above in general or in ranges of preference may be combined arbitrarily with one another, thus including combinations between the respective ranges and ranges of preference. The definitions and explanations apply to the end products and also to the precursors and intermediates accordingly.

Preferred in accordance with the invention are the compounds of the formula (I) in which there is a combination of the definitions given above as being preferred (preferably), wherein each embodiment described above as being preferred constitutes an individual combination.

More preferred in accordance with the invention are the compounds of the formula (I) in which there is a combination of the definitions given above as being more preferred (more preferably), wherein each embodiment described above as being more preferred constitutes an individual combination.

Especially preferred in accordance with the invention are the compounds of the formula (I) in which there is a combination of the definitions given above as being especially preferred (especially preferably), wherein each embodiment described above as being especially preferred constitutes an individual combination.

A very specific aspect in accordance with the invention are the compounds of the formula (I) in which there is a combination of the definitions given above as being a first very specific aspect (embodiment 5-1) of the especially preferred substituents or ranges of the structural elements.

Another very specific aspect in accordance with the invention are the compounds of the formula (I) in which there is a combination of the definitions given above as being a second very specific aspect (embodiment 5-2) of the especially preferred substituents or ranges of the structural elements.

Another very specific aspect in accordance with the invention are the compounds of the formula (I) in which there is a combination of the definitions given above as being a third very specific aspect (embodiment 5-3) of the especially preferred substituents or ranges of the structural elements.

Another very specific aspect in accordance with the invention are the compounds of the formula (I) in which there is a combination of the definitions given above as being a fourth very specific aspect (embodiment 5-4) of the especially preferred substituents or ranges of the structural elements.

Another very specific aspect in accordance with the invention are the compounds of the formula (I) in which there is a combination of the definitions given above as being a fifth very specific aspect (embodiment 5-5) of the especially preferred substituents or ranges of the structural elements.

Saturated or unsaturated hydrocarbon radicals such as alkyl, alkanediyl or alkenyl may in each case, both alone and in conjunction with heteroatoms, as in alkoxy, for example, be—where possible—either straight-chain or branched.

Any substituted radicals may, unless indicated otherwise, be substituted one or more times, and the substituents in the case of multiple substitutions may be alike or different.

In the definitions of radicals that are stated as being preferred, halogen (halo) is fluoro, chloro, bromo and iodo, very preferably fluoro, chloro and bromo, and especially preferably fluoro and chloro.

Further specific embodiments of the invention are described hereafter.

A specific embodiment (embodiment 6-1) of the invention is a compound of the formula (I-1)

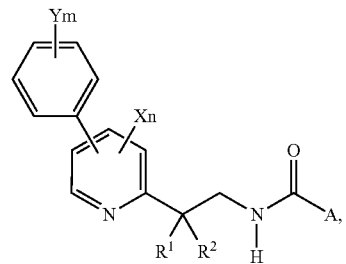

(I-1)

in which $R^1$, $R^2$, X, Y, n, m and A are as defined above in embodiment 1-1.

Another specific embodiment (embodiment 6-2) of the invention is a compound of the formula (I-1)

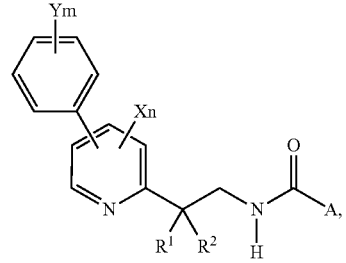

(I-1)

in which $R^1$, $R^2$, X, Y, n, m and A are as defined above in embodiment 1-2.

Another specific embodiment (embodiment 7-1) of the invention is a compound of the formula (I-1)

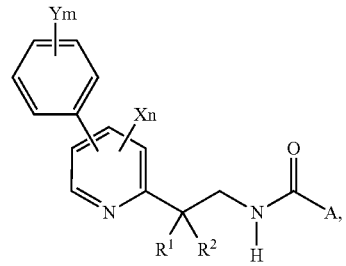

(I-1)

in which $R^1$, $R^2$, X, Y, n, m and A are as defined above in embodiment 2-1.

Another specific embodiment (embodiment 7-2) of the invention is a compound of the formula (I-1)

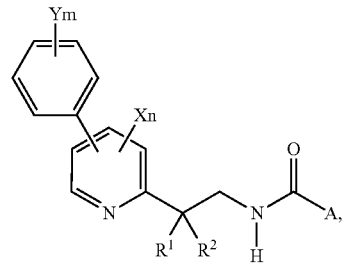

(I-1)

in which $R^1$, $R^2$, X, Y, n, m and A are as defined above in embodiment 2-2.

Another specific embodiment (embodiment 8-1) of the invention is a compound of the formula (I-1)

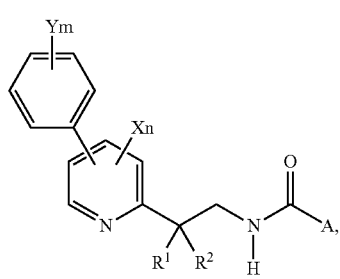

(I-1)

in which $R^1$, $R^2$, X, Y, n, m and A are as defined above in embodiment 3-1.

Another specific embodiment (embodiment 8-2) of the invention is a compound of the formula (I-1)

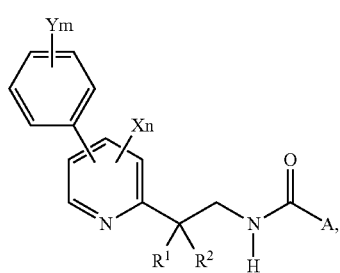

(I-1)

in which $R^1$, $R^2$, X, Y, n, m and A are as defined above in embodiment 3-2.

Another specific embodiment (embodiment 9-1) of the invention is a compound of the formula (I-1)

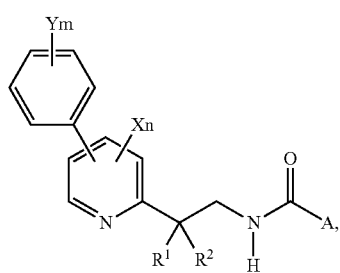

(I-1)

in which $R^1$, $R^2$, X, Y, n, m and A are as defined above in embodiment 4-1.

Another specific embodiment (embodiment 9-2) of the invention is a compound of the formula (I-1)

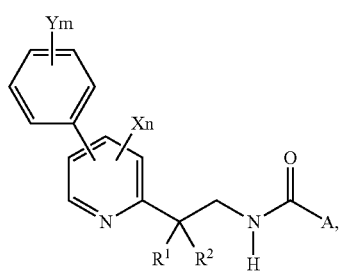

(I-1)

in which $R^1$, $R^2$, X, Y, n, m and A are as defined above in embodiment 4-2.

Another specific embodiment (embodiment 9-3) of the invention is a compound of the formula (I-1)

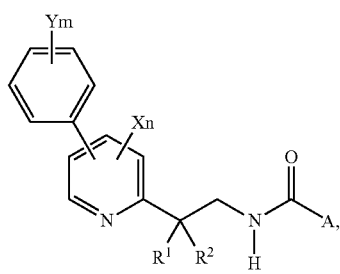

(I-1)

in which $R^1$, $R^2$, X, Y, n, m and A are as defined above in embodiment 4-3.

Another specific embodiment (embodiment 9-4) of the invention is a compound of the formula (I-1)

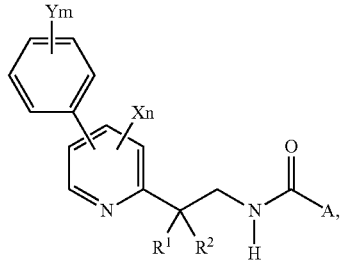

(I-1)

in which $R^1$, $R^2$, X, Y, n, m and A are as defined above in embodiment 4-4.

Another specific embodiment (embodiment 10-1) of the invention is a compound of the formula (I-1)

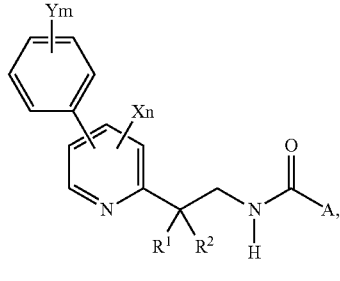

(I-1)

in which $R^1$, $R^2$, X, Y, n, m and A are as defined above in embodiment 5-1.

Another specific embodiment (embodiment 10-2) of the invention is a compound of the formula (I-1)

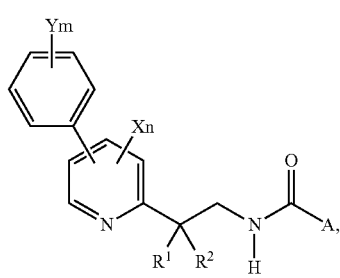

(I-1)

in which $R^1$, $R^2$, X, Y, n, m and A are as defined above in embodiment 5-2.

Another specific embodiment (embodiment 10-3) of the invention is a compound of the formula (I-1)

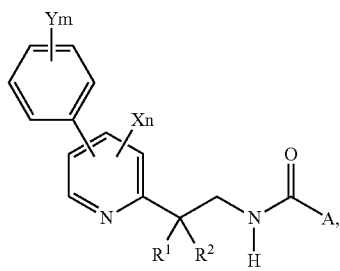

in which $R^1$, $R^2$, X, Y, n, m and A are as defined above in embodiment 5-3.

Another specific embodiment (embodiment 10-4) of the invention is a compound of the formula (I-1)

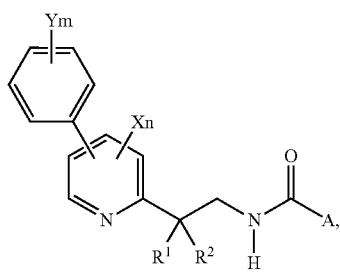

in which $R^1$, $R^2$, X, Y, n, m and A are as defined above in embodiment 5-4.

Another specific embodiment (embodiment 10-5) of the invention is a compound of the formula (I-1)

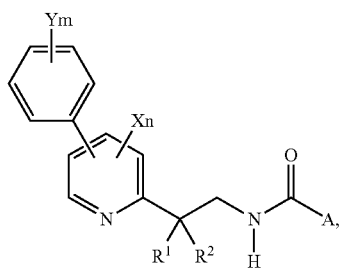

in which $R^1$, $R^2$, X, Y, n, m and A are as defined above in embodiment 5-5.

Further specific embodiments of the invention are compounds of the formula (I-1) in which $R^1$, $R^2$, X, Y, n, m and A are as defined above as being a specific or a very specific embodiment or aspect within the general, preferred, more preferred or especially preferred definitions given herein.

Another specific embodiment (embodiment 11-1) of the invention is a compound of the formula (I) in which
$B^1$ represents N,
$B^2$ represents CH,
n is 1,
X is chlorine,
m is 1 and
Y is chlorine, hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluormethylsulfonyl, trifluormethylsulfinyl or trifluormethylsulfanyl, or
m is 2 or 3 and
at least two substituents Y are vicinal and, together with the phenyl ring to which they are bonded, form a structure which is selected from:

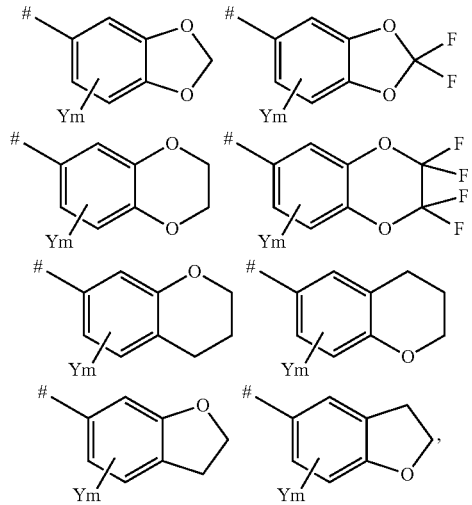

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl or difluoromethyl,
$R^1$ and $R^2$ both are hydrogen or both are fluorine,
$R^3$, $R^4$ and $R^5$ are hydrogen,
A is

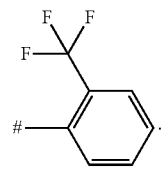

Another specific embodiment (embodiment 11-2) of the invention is a compound of the formula (I) in which
$B^1$ represents N,
$B^2$ represents CH,
n is 1,
X is chlorine,
m is 1 and
Y is chlorine, hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluormethylsulfonyl, trifluormethylsulfinyl or trifluormethylsulfanyl, or
m is 2 or 3 and
at least two substituents Y are vicinal and, together with the phenyl ring to which they are bonded, form a structure which is selected from:

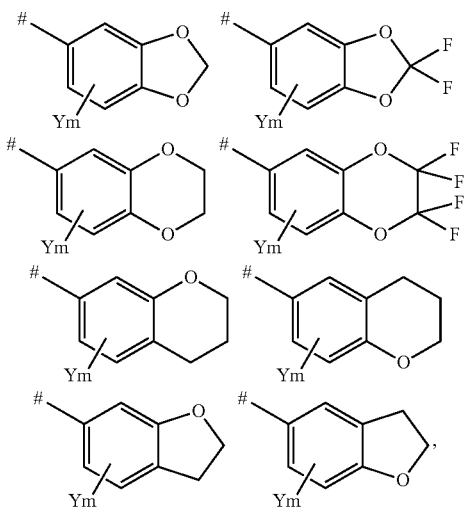

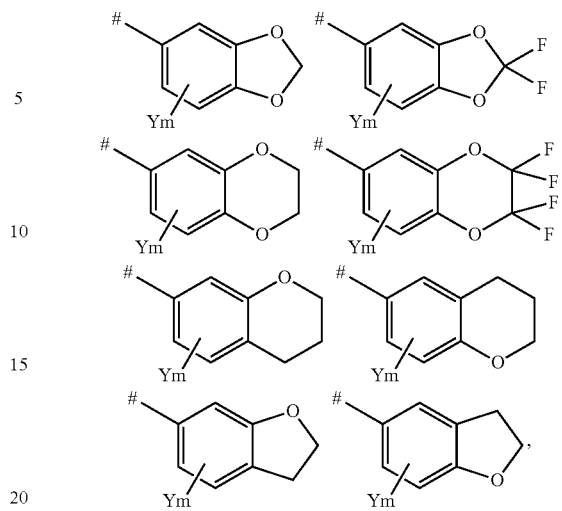

and the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl or difluoromethyl, $R^1$ is methyl, $R^2$ is fluorine, $R^3$, $R^4$ and $R^5$ are hydrogen, A is

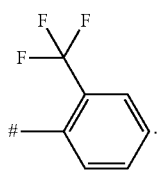

Another specific embodiment (embodiment 11-3) of the invention is a compound of the formula (I) in which $B^1$ represents N, $B^2$ represents CH, n is 1, X is chlorine, m is 1 and Y is chlorine, hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluoromethylsulfonyl, trifluormethylsulfinyl or trifluormethylsulfanyl, or m is 2 or 3 and at least two substituents Y are vicinal and, together with the phenyl ring to which they are bonded, form a structure which is selected from:

and the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl or difluoromethyl, $R^1$ is hydrogen, $R^2$ is fluorine, $R^3$, $R^4$ and $R^5$ are hydrogen, A is

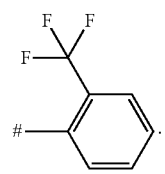

Another specific embodiment (embodiment 11-4) of the invention is a compound of the formula (I) in which $B^1$ represents N, $B^2$ represents CH, n is 1, X is chlorine, m is 1 and Y is chlorine, hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluoromethylsulfonyl, trifluormethylsulfinyl or trifluormethylsulfanyl, or m is 2 or 3 and at least two substituents Y are vicinal and, together with the phenyl ring to which they are bonded, form a structure which is selected from:

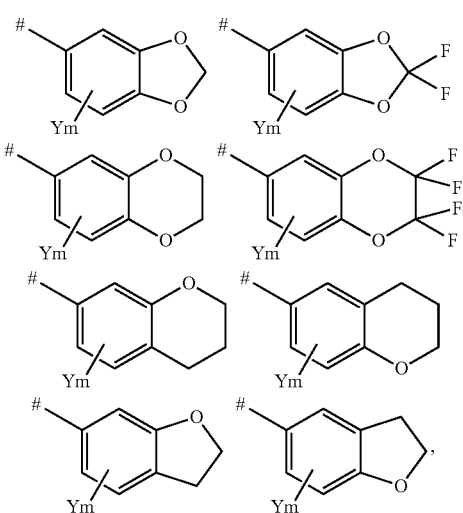

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, iso-propoxy, n-propoxy, trifluoromethyl or difluoromethyl,
$R^1$ and $R^2$ both are hydrogen or both are fluorine,
$R^3$, $R^4$ and $R^5$ are hydrogen,
A is

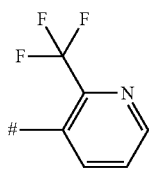

Another specific embodiment (embodiment 11-5) of the invention is a compound of the formula (I) in which
$B^1$ represents N,
$B^2$ represents CH,
n is 1,
X is chlorine,
m is 1 and
Y is chlorine, hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluormethylsulfonyl, trifluormethylsulfinyl or trifluormethylsulfonyl, or
m is 2 or 3 and
at least two substituents Y are vicinal and, together with the phenyl ring to which they are bonded, form a structure which is selected from:

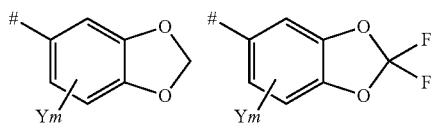

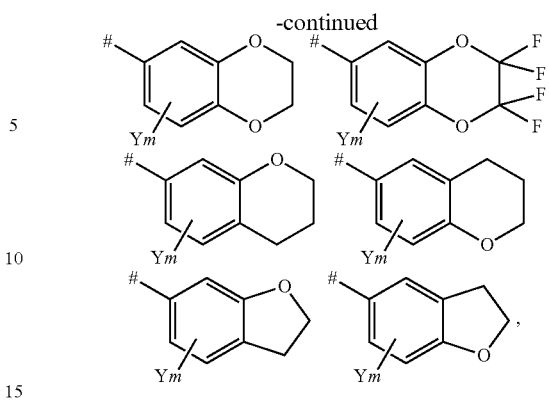

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl or difluoromethyl,
$R^1$ is methyl,
$R^2$ is fluorine,
$R^3$, $R^4$ and $R^5$ are hydrogen,
A is

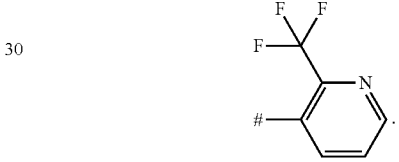

Another specific embodiment (embodiment 11-6) of the invention is a compound of the formula (I) in which
$B^1$ represents N,
$B^2$ represents CH,
n is 1,
X is chlorine,
m is 1 and
Y is chlorine, hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluormethylsulfonyl, trifluormethylsulfinyl or trifluormethylsulfanyl, or
m is 2 or 3 and
at least two substituents Y are vicinal and, together with the phenyl ring to which they are bonded, form a structure which is selected from:

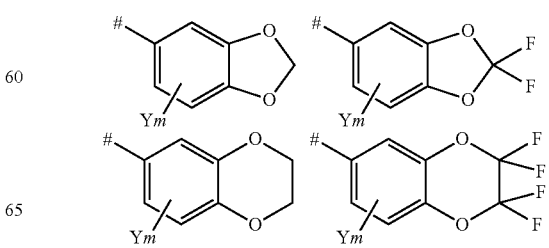

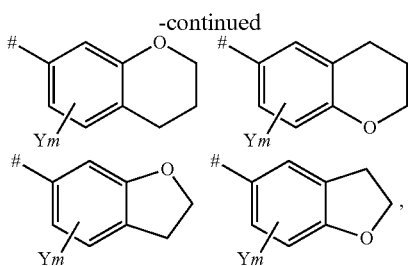

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, iso-propoxy, n-propoxy, trifluoromethyl or difluoromethyl,
$R^1$ is hydrogen,
$R^2$ is fluorine,
$R^3$, $R^4$ and $R^5$ are hydrogen,
A is

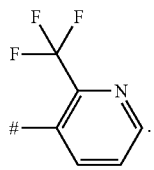

Another specific embodiment (embodiment 11-7) of the invention is a compound of the formula (I) in which
$B^1$ represents N,
$B^2$ represents CH,
n is 1,
X is chlorine,
m is 1 and
Y is chlorine, hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluormethylsulfonyl, trifluormethylsulfinyl or trifluormethylsulfanyl, or
m is 2 or 3 and
at least two substituents Y are vicinal and, together with the phenyl ring to which they are bonded, form a structure which is selected from:

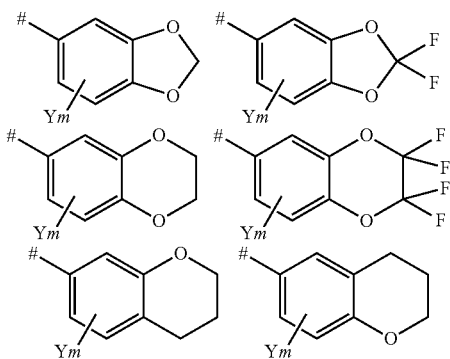

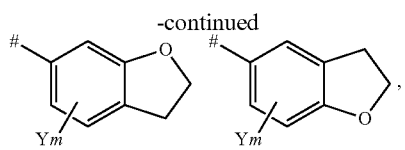

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, iso-propoxy, n-propoxy, trifluoromethyl or difluoromethyl,
$R^1$ and $R^2$ both are hydrogen or both are fluorine,
$R^3$, $R^4$ and $R^5$ are hydrogen,
A is

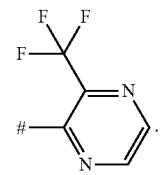

Another specific embodiment (embodiment 11-8) of the invention is a compound of the formula (I) in which
$B^1$ represents N,
$B^2$ represents CH,
n is 1,
X is chlorine,
m is 1 and
Y is chlorine, hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluormethylsulfonyl, trifluormethylsulfinyl or trifluormethylsulfanyl, or
m is 2 or 3 and
at least two substituents Y are vicinal and, together with the phenyl ring to which they are bonded, form a structure which is selected from:

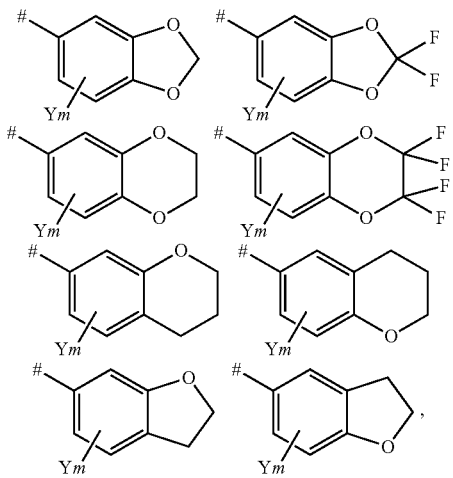

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl or difluoromethyl,
$R^1$ is methyl,
$R^2$ is fluorine,
$R^3$, $R^4$ and $R^5$ are hydrogen,
A is

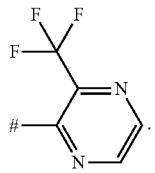

Another specific embodiment (embodiment 11-9) of the invention is a compound of the formula (I) in which
$B^1$ represents N,
$B^2$ represents CH,
n is 1,
X is chlorine,
m is 1 and
Y is chlorine, hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluoromethylsulfonyl, trifluormethylsulfinyl or trifluormethylsulfanyl, or
m is 2 or 3 and
at least two substituents Y are vicinal and, together with the phenyl ring to which they are bonded, form a structure which is selected from:

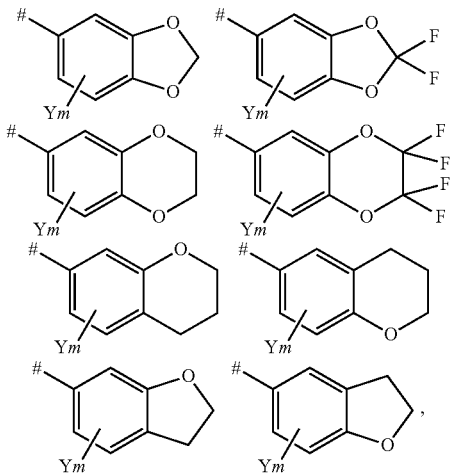

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl or difluoromethyl,
$R^1$ is hydrogen,
$R^2$ is fluorine,
$R^3$, $R^4$ and $R^5$ are hydrogen,
A is

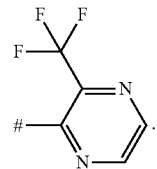

In embodiment 1-1 as well as in each individual aspect of said embodiment, the phenyl ring bearing the substituent Ym preferably is in para-position.

In embodiment 1-2 as well as in each individual aspect of said embodiment, the phenyl ring bearing the substituent Ym preferably is in para-position.

In embodiment 2-1 as well as in each individual aspect of said embodiment, the phenyl ring bearing the substituent Ym preferably is in para-position.

In embodiment 2-2 as well as in each individual aspect of said embodiment, the phenyl ring bearing the substituent Ym preferably is in para-position.

In embodiment 3-1 as well as in each individual aspect of said embodiment, the phenyl ring bearing the substituent Ym preferably is in para-position.

In embodiment 3-2 as well as in each individual aspect of said embodiment, the phenyl ring bearing the substituent Ym preferably is in para-position.

In embodiment 4-1 as well as in each individual aspect of said embodiment, the phenyl ring bearing the substituent Ym preferably is in para-position.

In embodiment 4-2 as well as in each individual aspect of said embodiment, the phenyl ring bearing the substituent Ym preferably is in para-position.

In embodiment 4-3 as well as in each individual aspect of said embodiment, the phenyl ring bearing the substituent Ym preferably is in para-position.

In embodiment 4-4 as well as in each individual aspect of said embodiment, the phenyl ring bearing the substituent Ym preferably is in para-position.

In embodiment 5-1 as well as in each individual aspect of said embodiment, the phenyl ring bearing the substituent Ym preferably is in para-position.

In embodiment 5-2 as well as in each individual aspect of said embodiment, the phenyl ring bearing the substituent Ym preferably is in para-position.

In embodiment 5-3 as well as in each individual aspect of said embodiment, the phenyl ring bearing the substituent Ym preferably is in para-position.

In embodiment 5-4 as well as in each individual aspect of said embodiment, the phenyl ring bearing the substituent Ym preferably is in para-position.

In embodiment 5-5 as well as in each individual aspect of said embodiment, the phenyl ring bearing the substituent Ym preferably is in para-position.

In embodiment 6-1 as well as in each individual aspect of said embodiment, the phenyl ring bearing the substituent Ym preferably is in para-position.

In embodiment 6-2 as well as in each individual aspect of said embodiment, the phenyl ring bearing the substituent Ym preferably is in para-position.

In embodiment 7-1 as well as in each individual aspect of said embodiment, the phenyl ring bearing the substituent Ym preferably is in para-position.

In embodiment 7-2 as well as in each individual aspect of said embodiment, the phenyl ring bearing the substituent Ym preferably is in para-position.

In embodiment 8-1 as well as in each individual aspect of said embodiment, the phenyl ring bearing the substituent Ym preferably is in para-position.

In embodiment 8-2 as well as in each individual aspect of said embodiment, the phenyl ring bearing the substituent Ym preferably is in para-position.

In embodiment 9-1 as well as in each individual aspect of said embodiment, the phenyl ring bearing the substituent Ym preferably is in para-position.

In embodiment 9-2 as well as in each individual aspect of said embodiment, the phenyl ring bearing the substituent Ym preferably is in para-position.

In embodiment 9-3 as well as in each individual aspect of said embodiment, the phenyl ring bearing the substituent Ym preferably is in para-position.

In embodiment 9-4 as well as in each individual aspect of said embodiment, the phenyl ring bearing the substituent Ym preferably is in para-position.

In embodiment 10-1 as well as in each individual aspect of said embodiment, the phenyl ring bearing the substituent Ym preferably is in para-position.

In embodiment 10-2 as well as in each individual aspect of said embodiment, the phenyl ring bearing the substituent Ym preferably is in para-position.

In embodiment 10-3 as well as in each individual aspect of said embodiment, the phenyl ring bearing the substituent Ym preferably is in para-position.

In embodiment 10-4 as well as in each individual aspect of said embodiment, the phenyl ring bearing the substituent Ym preferably is in para-position.

In embodiment 10-5 as well as in each individual aspect of said embodiment, the phenyl ring bearing the substituent Ym preferably is in para-position.

In embodiment 11-1 as well as in each individual aspect of said embodiment, the phenyl ring bearing the substituent Ym preferably is in para-position.

In embodiment 11-2 as well as in each individual aspect of said embodiment, the phenyl ring bearing the substituent Ym preferably is in para-position.

In embodiment 11-3 as well as in each individual aspect of said embodiment, the phenyl ring bearing the substituent Ym preferably is in para-position.

In embodiment 11-4 as well as in each individual aspect of said embodiment, the phenyl ring bearing the substituent Ym preferably is in para-position.

In embodiment 11-5 as well as in each individual aspect of said embodiment, the phenyl ring bearing the substituent Ym preferably is in para-position.

In embodiment 11-6 as well as in each individual aspect of said embodiment, the phenyl ring bearing the substituent Ym preferably is in para-position.

In embodiment 11-7 as well as in each individual aspect of said embodiment, the phenyl ring bearing the substituent Ym preferably is in para-position.

In embodiment 11-8 as well as in each individual aspect of said embodiment, the phenyl ring bearing the substituent Ym preferably is in para-position.

In embodiment 11-9 as well as in each individual aspect of said embodiment, the phenyl ring bearing the substituent Ym preferably is in para-position.

Procedures and Methods

The synthesis of the compounds of the formula (I) can be performed according to or in analogy to scheme 1-4. The required starting materials are known or accessible via generally known procedures which are described in more detail in WO 2001/011965 A1 (P1), WO 2005/058828 A1 (P2), WO2005/014545 A2 (P3), WO 2005/103004 A1 (P4), WO 2006/122952 A1 (P5), EP 2 289 880 A1 (P6), WO 2006/008191 A1 (P7), WO 2006/008192 A1 (P8), WO 2004/074280 A1 (P9), WO 2005/058833 A2 (P10), WO 2005/085238 A1 (P11), WO 2005/103006 A1 (P12), WO 2006/122955 A1 (P13), WO 2006/008194 A1 (P14), WO 2006/008193 A1 (P15), WO 2006/067103 A2 (P16) and in case of $R^1=R^2=$fluorine WO 2013/064460.

Dichlorobromopyridine (VI) is synthesized from 2-hydroxy-5-nitroaniline (II) using the procedure described in US2004/242644 A and Synthesis 1990, 499. The synthesis of the nitrile (VIII) is performed as described in EP1674455 A1 or EP1548007 A1, followed by reduction to the BOC-protected amine (IX) with sodium borohydride in the presence of nickel chloride and BOCanhydride. (IX) is then cleaved with hydrogen chloride in methanol to the amine-hydrochloride (X).

The synthesis of the amine (XIX) is performed in analogy to the procedure described in WO 2013/064460 A1 (referred as intermediates IIa-14 and IIa-15). Amine-hydrochloride intermediate of formula (XXIV) can be obtained from intermediate (XXII) in 2 steps: (i) by fluorination with an agent such as NFSI [with an analogous procedure to the one described in U.S. Pat. No. 6,034,106 A1] followed by (ii) nitrite reduction with a reducing agent such as LiAlH$_4$ [with an analogous procedure to the one described in WO2008/124757 A1]. Pyridyl halide intermediate of formula (XXII) can be obtained from the pyridyl amine (XXI-d) by Sandmeyer reaction according to U.S. Pat. No. 4,885,026 A1. Intermediate of formula (XXI-d) can be obtained in 3 steps from reagent (XXI-a) by: (i) nucleophilic substitution reaction using alkyl 2-cyanopropanoate in the presence of a base such as potassium carbonate [with an analogous procedure to the one described in Pharmaceutical Chemistry Journal, 1996, p. 757-759], (ii) decarboxylation under heating conditions using a chloride salt such as LiCl in DMSO/water, [with an analogous procedure to the one described in WO2005/58828 A1], (iii) reduction of the nitro function to the amine function using for example Fe/NH$_4$Cl/HCl with heating [with an analogous procedure to the one described in EP1171440 B1].

The amine-hydrochloride (X) or the amines (XVII) and (XXIV) are then coupled with the appropriate acid or acid chloride (XI, A is as defined before) and a coupling reagent such as HOBT-EDC or a base such as triethylamine to yield for example the intermediate amides (XII), (XX) or (XXV) wherein A is as defined before. The compounds of the formula (I-a), (I-b) or (I-c) are then synthesized by a Suzuki-type coupling reaction with the appropriate boronic acid or ester (XIII, Y and m are as defined before) in the presence of a palladium catalyst and a base.

According to scheme 4, (I-b) or (I-c) can be alternatively synthesized from intermediate amines (XIX) or (XIV) which are coupled by a Suzuki-type coupling reaction with the appropriate boronic acid or esters (XIII, Y and m are as defined before) to yield intermediate amides (XXVI) followed by an amid coupling with the appropriate acid or acid chloride (XI, A is as defined before) and a coupling reagent such as HOBT-EDC or a base such as triethylamine.

Scheme 1:
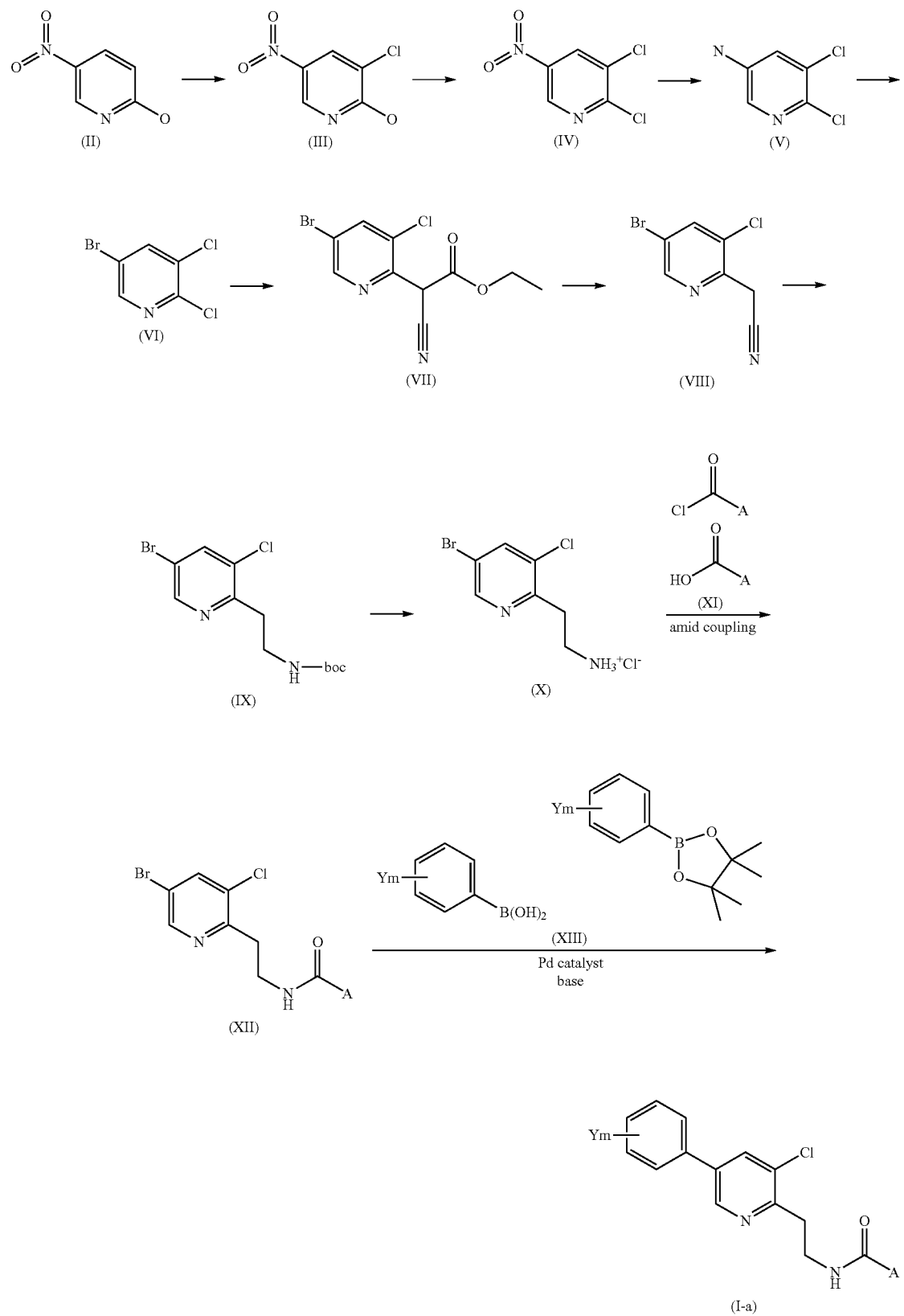

Scheme 2:
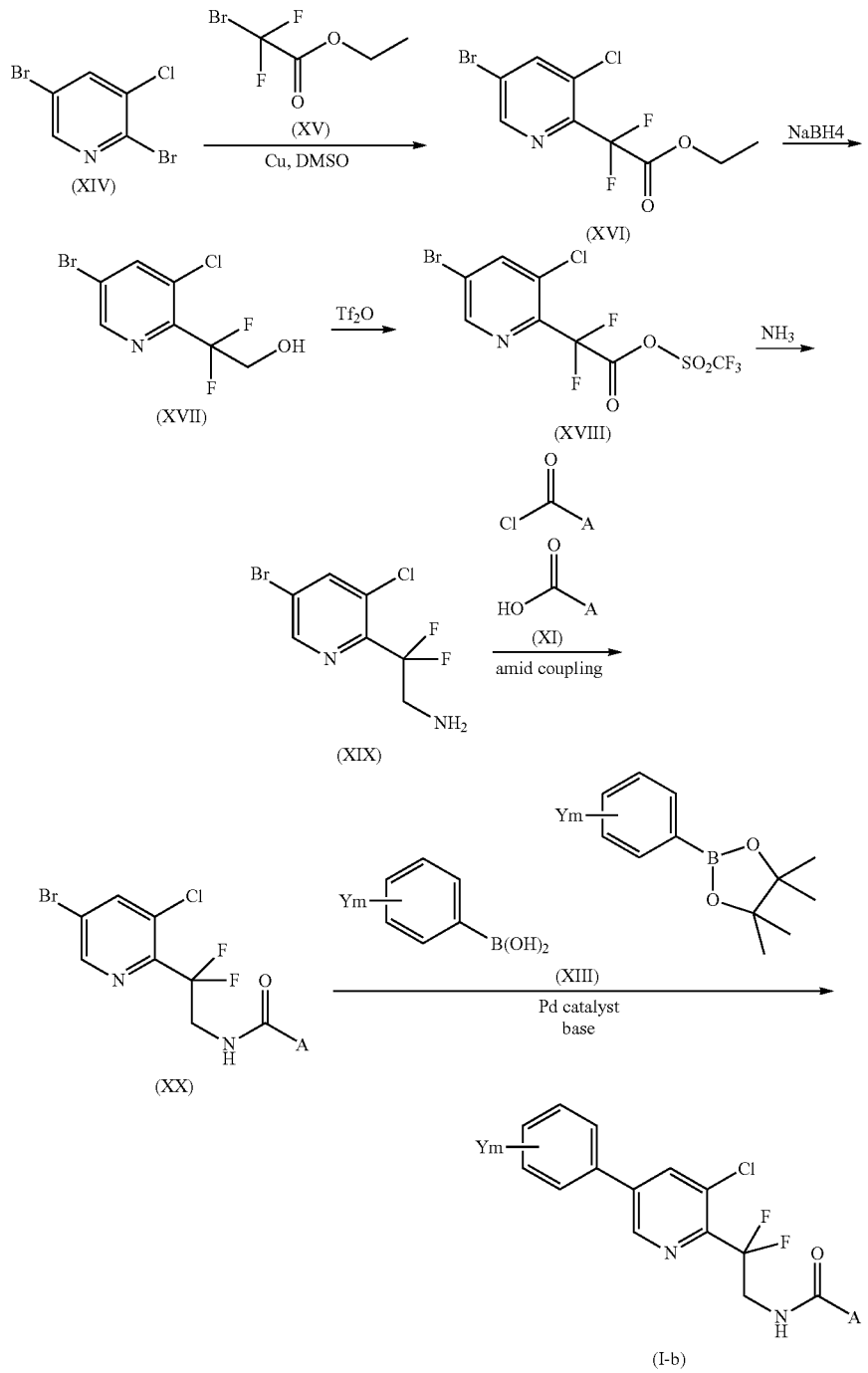
Scheme 3:
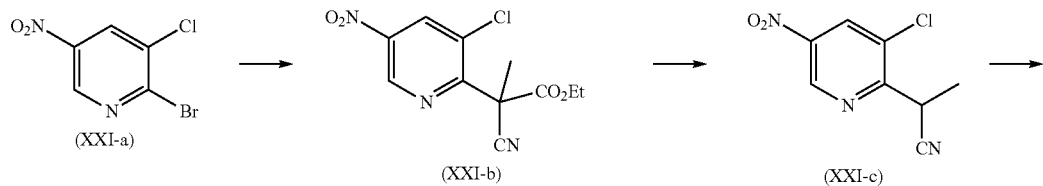

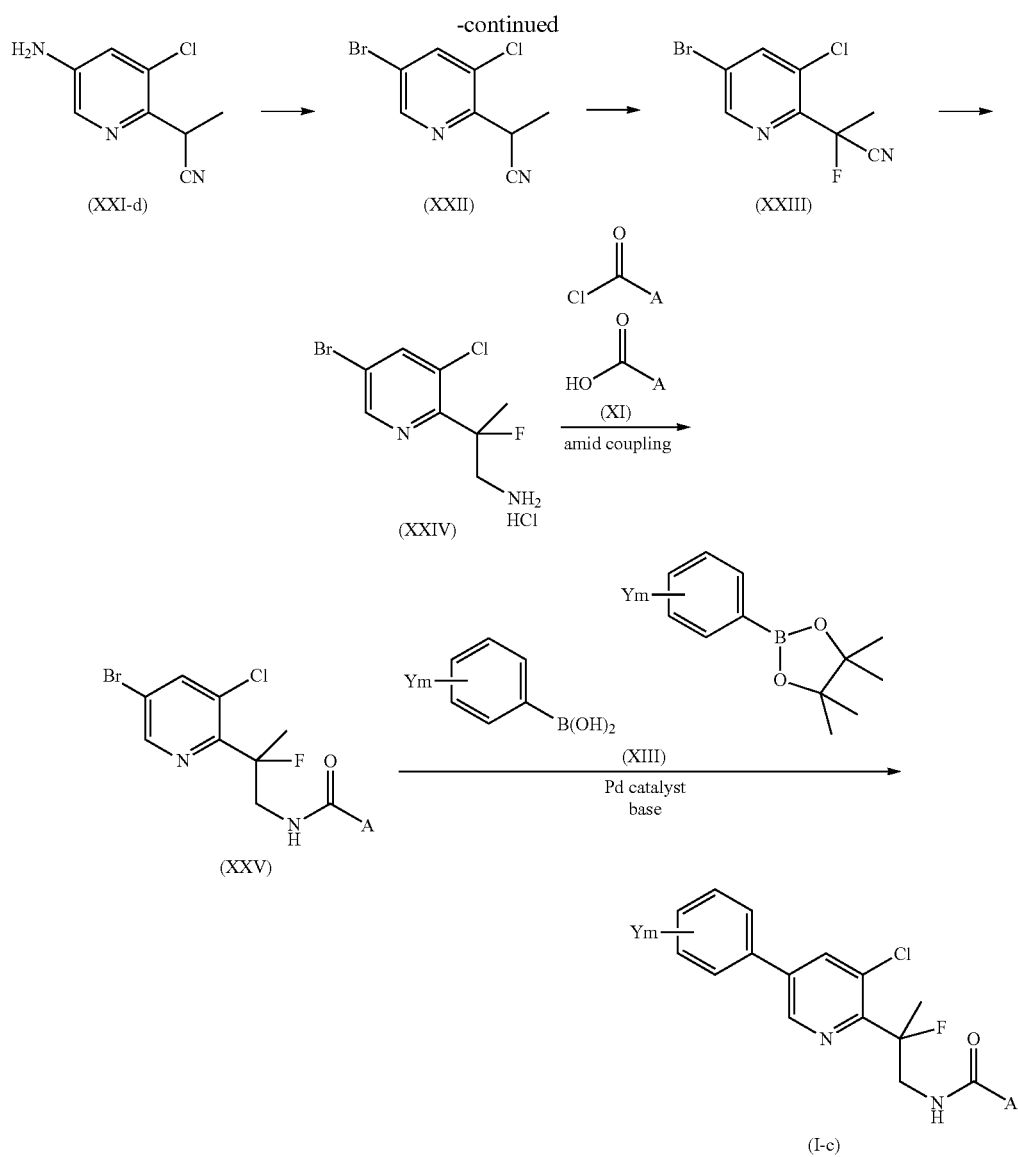
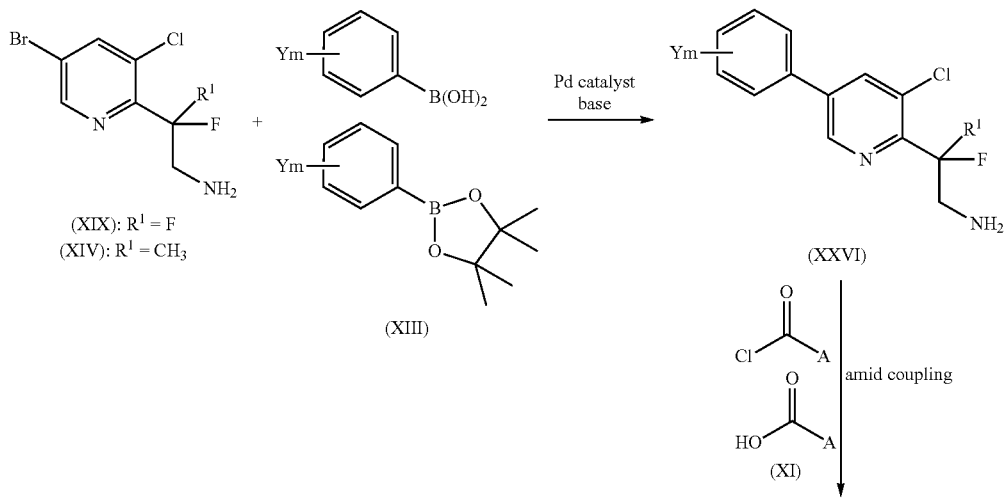
Scheme 4:

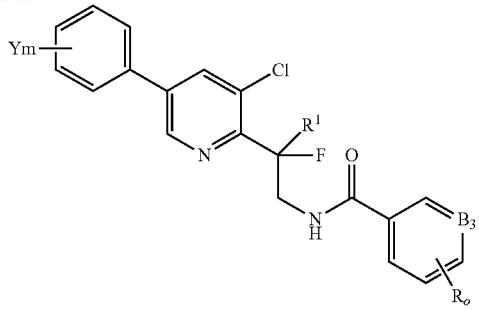

(I-b): R¹ = F
(I-c): R1 = CH₃

Of particular interest are intermediates of the procedures and methods described herein. These intermediates are further individual embodiments of the invention. In addition to the intermediates described above, further intermediates are described in the following.

Another embodiment of the invention is a compound of formula (INT-a)

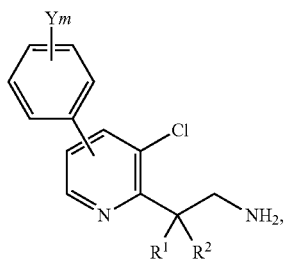

(INT-a)

wherein $R^1$, $R^2$, Y and m are as defined above. In an individual aspect, $R^1$, $R^2$, Y and m in a compound of formula (INT-a) are as defined in embodiment 1-1. In another individual aspect, $R^1$, $R^2$, Y and m in a compound of formula (INT-a) are as defined in embodiment 1-2. In another individual aspect, $R^1$, $R^2$, Y and m in a compound of formula (INT-a) are as defined in embodiment 2-1. In another individual aspect, $R^1$, $R^2$, Y and m in a compound of formula (INT-a) are as defined in embodiment 2-2. In another individual aspect, $R^1$, $R^2$, Y and m in a compound of formula (INT-a) are as defined in embodiment 3-1. In another individual aspect, $R^1$, $R^2$, Y and m in a compound of formula (INT-a) are as defined in embodiment 3-2. In another individual aspect, $R^1$, $R^2$, Y and m in a compound of formula (INT-a) are as defined in embodiment 4-1. In another individual aspect, $R^1$, $R^2$, Y and m in a compound of formula (INT-a) are as defined in embodiment 4-2. In another individual aspect, $R^1$, $R^2$, Y and m in a compound of formula (INT-a) are as defined in embodiment 4-3. In another individual aspect, $R^1$, $R^2$, Y and m in a compound of formula (INT-a) are as defined in embodiment 4-4. In another individual aspect, $R^1$, $R^2$, Y and m in a compound of formula (INT-a) are as defined in embodiment 5-1. In another individual aspect, $R^1$, $R^2$, Y and m in a compound of formula (INT-a) are as defined in embodiment 5-2. In another individual aspect, $R^1$, $R^2$, Y and m in a compound of formula (INT-a) are as defined in embodiment 5-3. In another individual aspect, $R^1$, $R^2$, Y and m in a compound of formula (INT-a) are as defined in embodiment 5-4. In another individual aspect, $R^1$, $R^2$, Y and m in a compound of formula (INT-a) are as defined in embodiment 5-5. In another individual aspect, $R^1$, $R^2$, Y and m in a compound of formula (INT-a) are as defined in embodiment 6-1. In another individual aspect, $R^1$, $R^2$, Y and m in a compound of formula (INT-a) are as defined in embodiment 6-2. In another individual aspect, $R^1$, $R^2$, Y and m in a compound of formula (INT-a) are as defined in embodiment 7-1. In another individual aspect, $R^1$, $R^2$, Y and m in a compound of formula (INT-a) are as defined in embodiment 7-2. In another individual aspect, $R^1$, $R^2$, Y and m in a compound of formula (INT-a) are as defined in embodiment 8-1. In another individual aspect, $R^1$, $R^2$, Y and m in a compound of formula (INT-a) are as defined in embodiment 8-2. In another individual aspect, $R^1$, $R^2$, Y and m in a compound of formula (INT-a) are as defined in embodiment 9-1. In another individual aspect, $R^1$, $R^2$, Y and m in a compound of formula (INT-a) are as defined in embodiment 9-2. In another individual aspect, $R^1$, $R^2$, Y and m in a compound of formula (INT-a) are as defined in embodiment 9-3. In another individual aspect, $R^1$, $R^2$, Y and m in a compound of formula (INT-a) are as defined in embodiment 9-4. In another individual aspect, $R^1$, $R^2$, Y and m in a compound of formula (INT-a) are as defined in embodiment 10-1. In another individual aspect, $R^1$, $R^2$, Y and m in a compound of formula (INT-a) are as defined in embodiment 10-2. In another individual aspect, $R^1$, $R^2$, Y and m in a compound of formula (INT-a) are as defined in embodiment 10-3. In another individual aspect, $R^1$, $R^2$, Y and m in a compound of formula (INT-a) are as defined in embodiment 10-4. In another individual aspect, $R^1$, $R^2$, Y and m in a compound of formula (INT-a) are as defined in embodiment 10-5. In another individual aspect, $R^1$, $R^2$, Y and m in a compound of formula (INT-a) are as defined in embodiment 11-1. In another individual aspect, $R^1$, $R^2$, Y and m in a compound of formula (INT-a) are as defined in embodiment 11-2. In another individual aspect, $R^1$, $R^2$, Y and m in a compound of formula (INT-a) are as defined in embodiment 11-3. In another individual aspect, $R^1$, $R^2$, Y and m in a compound of formula (INT-a) are as defined in embodiment 11-4. In another individual aspect, $R^1$, $R^2$, Y and m in a compound of formula (INT-a) are as defined in embodiment 11-5. In another individual aspect, $R^1$, $R^2$, Y and m in a compound of formula (INT-a) are as defined in embodiment 11-6. In another individual aspect, $R^1$, $R^2$, Y and m in a compound of formula (INT-a) are as defined in embodiment 11-7. In another individual aspect, $R^1$, $R^2$, Y and m in a compound of formula (INT-a) are as defined in embodiment 11-8. In another individual aspect, $R^1$, $R^2$, Y and m in a compound of formula (INT-a) are as defined in embodiment 11-9.

In such a compound of formula (INT-a), the phenyl ring bearing the substituent Ym preferably is in para-position.

An example of a preferred compound of formula (INT-a) is a compound which is represented by formula (INT-1)

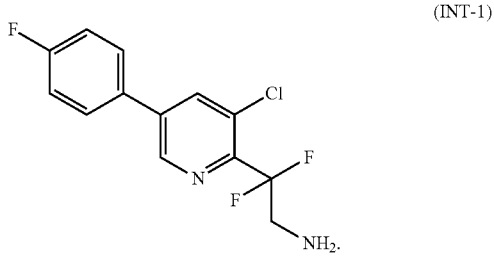 [SMILES: NCC(F)(F)c1ncc(-c2ccc(F)cc2)cc1Cl]

(INT-1)

The compounds according to the present invention can be prepared according to the processes described above. It will nevertheless be understood that, on the basis of his general knowledge and of available publications, the skilled worker will be able to adapt this method according to the specifics of each of the compounds, which is desired to synthesize.

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixture of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. Preferably excluded herefrom are methods for the surgical or therapeutic treatment of the human or animal body and diagnostic methods carried out on the human or animal body.

The invention furthermore relates to the use of the compounds of the formula (I) as pesticides, in particular crop protection agents.

In the context of the present application, the term "pesticide" in each case also always comprises the term "crop protection agent".

The compounds of the formula (I), having good plant tolerance, favourable homeotherm toxicity and good environmental compatibility, are suitable for protecting plants and plant organs against biotic and abiotic stressors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are active against normally sensitive and resistant species and against all or some stages of development. The abovementioned pests include: pests from the phylum of the Arthropoda, in particular from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermacentor* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Haemaphysalis* spp., *Hemitarsonemus* spp., for example *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., for example *Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri* (=*Metatetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici*;

from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Panchlora* spp., *Parcoblatta* spp., *Periplaneta* spp., for example *Periplaneta americana, Periplaneta australasiae, Supella longipalpa;* from the order of the Coleoptera, for example *Acalymma vittatum, Acanthoscelides obtectus, Adoretus* spp., *Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa*

*armigera, Diloboderus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides*;

from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula* simplex;

from the order of the Hemiptera, for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis glycines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenarytaina* spp., *Dalbulus* spp., *Dialeurodes citri, Diaphorina citri, Diaspis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni* (=*Parthenolecanium corni*), *Lepidosaphes* spp., for example *Lepidosaphes ulmi, Lipaphis erysimi, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Nephotettix* spp., for example *Nephotettix cincticeps Nephotettix nigropictus, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Phenacoccus* spp., for example *Phenacoccus madeirensis,*

*Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.;

from the suborder of the Heteroptera, for example *Anasa tristis, Antestiopsis* spp., *Boisea* spp., *Blissus* spp., *Calocoris* spp., *Campylomma livida, Cavelerius* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Monalonion atratum, Nezara* spp., for example *Nezara viridula, Oebalus* spp., *Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Diprion* spp., for example *Diprion similis, Hoplocampa* spp., for example *Hoplocampa cookei, Hoplocampa testudinea, Lasius* spp., *Monomorium pharaonis, Sirex* spp., *Solenopsis invicta, Tapinoma* spp., *Urocerus* spp., *Vespa* spp., for example *Vespa crabro, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Microtermes obesi, Odontotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choristoneura* spp., *Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diatraea saccharalis, Earias* spp., *Ecdytolopha aurantium, Elasmopalpus lignosellus, Eldana saccharina, Ephestia* spp., for example *Ephestia elutella, Ephestia kuehniella, Epinotia* spp., *Epiphyas postvittana, Etiella* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens Hofmannophila pseudospretella, Homoeosoma* spp., *Homona* spp., *Hyponomeuta padella, Kakivoria flavofasciata, Laphygma* spp., *Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Oria* spp., *Orthaga* spp., *Ostrinia* spp., for example *Ostrinia nubilalis, Oulema melanopus, Oulema oryzae, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stomopteryx subsecivella, Synanthedon* spp., *Tecia solanivora, Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example, *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Drepanothrips reu-* teri, *Enneothrips flavens*, *Frankliniella* spp., for example *Frankliniella fusca*, *Frankliniella occidentalis*, *Frankliniella schultzei*, *Frankliniella tritici*, *Frankliniella vaccinii*, *Frankliniella williamsi*, *Heliothrips* spp., *Hercinothrips femoralis*, *Rhipiphorothrips cruentatus*, *Scirtothrips* spp., *Taeniothrips cardamomi*, *Thrips* spp., for example *Thrips palmi*, *Thrips tabaci*;

from the order of the Zygentoma (=Thysanura), for example *Ctenolepisma* spp., *Lepisma saccharina*, *Lepismodes inquilinus*, *Thermobia domestica*;

from the class of the Symphyla, for example *Scutigerella* spp., for example *Scutigerella immaculata*;

pests from the phylum of the Mollusca, for example from the class of the Bivalvia, for example *Dreissena* spp., and also from the class of the Gastropoda, for example *Arlon* spp., for example *Arlon ater rufus*, *Biomphalaria* spp., *Bulinus* spp., *Deroceras* spp., for example *Deroceras laeve*, *Galba* spp., *Lymnaea* spp., *Oncomelania* spp., *Pomacea* spp., *Succinea* spp.;

from the pathogenic endoparasites of humans and animals, which are helminths, including platyhelmintha (e.g. monogenea, cestodes and trematodes), nematodes, acanthocephala, and pentastoma.

Additional exemplary helminths include—, without any limitation:

Monogenea: e.g.: *Gyrodactylus* spp., *Dactylogyrus* spp., *Polystoma* spp.;

cestodes: from the order of the Pseudophyllidea for example: *Diphyllobothrium* spp., *Spirometra* spp., *Schistocephalus* spp., *Ligula* spp., *Bothridium* spp., *Diplogonoporus* spp.;

from the order of the Cyclophyllida for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

trematodes: from the class of the Digenea for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp. *Metorchis* spp., *Heterophyes* spp., *Metagonimus* spp.;

nematodes: Trichinellida for example: *Trichuris* spp., *Capillaria* spp., *Paracapillaria* spp., *Trichomosoides* spp., *Trichinella* spp., *Eucoleus* spp.;

from the order of the Tylenchida for example: *Micronema* spp., *Strongyloides* spp.;

from the order of the Rhabditina for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Necator* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Oslerus* spp., *Trichostrongylus* spp., *Haemonchus* spp., *Ostertagia* spp., *Teladorsagia* spp., *Marshallagia* spp., *Cooperia* spp., *Nematodirus* spp., *Hyostrongylus* spp., *Obeliscoides* spp., *Amidostomum* spp., *Ollulanus* spp.; *Heligmosomoides* spp., *Nippostrongylus* spp.;

from the order of the Spirurida for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acantocephala: from the order of the Oligacanthorhynchid, for example: *Macracanthorhynchus* spp., *Prosthenorchis* spp.; from the order of the Polymorphida for example: *Filicollis* spp.; from the order of the Moniliformida for example: *Moniliformis* spp.;

from the order of the Echinorhynchida, for example: *Acanthocephalus* spp., *Echinorhynchus* spp., *Leptorhynchoides* spp.;

Pentastoma: from the order of the Porocephalida for example *Linguatula* spp.

Plant pests from the phylum of the Nematoda, i.e. phytoparasitic nematodes, in particular *Aglenchus* spp., for example *Aglenchus agricola*, *Anguina* spp., for example *Anguina tritici*, *Aphelenchoides* spp., for example *Aphelenchoides arachidis*, *Aphelenchoides fragariae*, *Belonolaimus* spp., for example *Belonolaimus gracilis*, *Belonolaimus longicaudatus*, *Belonolaimus nortoni*, *Bursaphelenchus* spp., for example *Bursaphelenchus cocophilus*, *Bursaphelenchus eremus*, *Bursaphelenchus xylophilus*, *Cacopaurus* spp., for example *Cacopaurus pestis*, *Criconemella* spp., for example *Criconemella curvata*, *Criconemella onoensis*, *Criconemella ornata*, *Criconemella rusium*, *Criconemella xenoplax* (=*Mesocriconema xenoplax*), *Criconemoides* spp., for example *Criconemoides ferniae*, *Criconemoides onoense*, *Criconemoides ornatum*, *Ditylenchus* spp., for example *Ditylenchus dipsaci*, *Dolichodorus* spp., *Globodera* spp., for example *Globodera pallida*, *Globodera rostochiensis*, *Helicotylenchus* spp., for example *Helicotylenchus dihystera*, *Hemicriconemoides* spp., *Hemicycliophora* spp., *Heterodera* spp., for example *Heterodera avenae*, *Heterodera glycines*, *Heterodera schachtii*, *Hoplolaimus* spp., *Longidorus* spp., for example *Longidorus africanus*, *Meloidogyne* spp., for example *Meloidogyne chitwoodi*, *Meloidogyne fallax*, *Meloidogyne hapla*, *Meloidogyne incognita*, *Meloinema* spp., *Nacobbus* spp., *Neotylenchus* spp., *Paraphelenchus* spp., *Paratrichodorus* spp., for example *Paratrichodorus minor*, *Pratylenchus* spp., for example *Pratylenchus penetrans*, *Pseudohalenchus* spp., *Psilenchus* spp., *Punctodera* spp., *Quinisulcius* spp., *Radopholus* spp., for example *Radopholus citrophilus*, *Radopholus similis*, *Rotylenchulus* spp., *Rotylenchus* spp., *Scutellonema* spp., *Subanguina* spp., *Trichodorus* spp., for example *Trichodorus obtusus*, *Trichodorus primitivus*, *Tylenchorhynchus* spp., for example *Tylenchorhynchus annulatus*, *Tylenchulus* spp., for example *Tylenchulus semipenetrans*, *Xiphinema* spp., for example *Xiphinema index*.

Furthermore, it is possible to control, from the subkingdom of the Protozoa, the order of the Coccidia, for example *Eimeria* spp.

Nematodes

In the present context, the term "nematodes" comprises all species of the phylum Nematoda and here in particular species acting as parasites on plants or fungi (for example species of the order Aphelenchida, *Meloidogyne*, Tylenchida and others) or else on humans and animals (for example species of the orders Trichinellida, Tylenchida, Rhabditina and Spirurida) and causing damage in or on these living organisms, and also other parasitic helminths.

A nematicide in crop protection, as described herein, is capable of controlling nematodes.

The term "controlling nematodes" means killing the nematodes or preventing or impeding their development or their growth or preventing or impeding their penetration into or their sucking on plant tissue.

Here, the efficacy of the compounds is determined by comparing mortalities, gall formation, cyst formation, nematode density per volume of soil, nematode density per root, number of nematode eggs per soil volume, mobility of the nematodes between a plant or plant part treated with the compound of the formula (I) or the treated soil and an untreated plant or plant part or the untreated soil (100%). Preferably, the reduction achieved is 25-50% in comparison to an untreated plant, plant part or the untreated soil, particularly preferably 51-79% and very particularly preferably the complete kill or the complete prevention of development and growth of the nematodes by a reduction of 80 to 100%. The control of nematodes as described herein also comprises the control of proliferation of the nematodes (development of cysts and/or eggs). Compounds of the formula (I) can also be used to keep the plants or animals healthy, and they can be employed curatively, preventatively or systemically for the control of nematodes.

The person skilled in the art knows methods for determining mortalities, gall formation, cyst formation, nematode density per volume of soil, nematode density per root, number of nematode eggs per volume of soil, mobility of the nematodes.

The use of a compound of the formula (I) may keep the plant healthy and also comprises a reduction of the damage caused by nematodes and an increase of the harvest yield.

In the present context, the term "nematodes" refers to plant nematodes which comprise all nematodes which damage plants. Plant nematodes comprise phytoparasitic nematodes and soil-borne nematodes. The phytoparasitic nematodes include ectoparasites such as *Xiphinema* spp., *Longidorus* spp. and *Trichodorus* spp.; semiparasites such as *Tylenchulus* spp.; migratory endoparasites such as *Pratylenchus* spp., *Radopholus* spp. and *Scutellonema* spp.; non-migratory parasites such as *Heterodera* spp., *Globodera* spp. and *Meloidogyne* spp., and also stem and leaf endoparasites such as *Ditylenchus* spp., *Aphelenchoides* spp. and *Hirschmaniella* spp. Particularly damaging root-parasitic soil nematodes are, for example, cyst-forming nematodes of the genera *Heterodera* or *Globodera*, and/or root gall nematodes of the genus *Meloidogyne*. Damaging species of these genera are, for example, *Meloidogyne incognita*, *Heterodera glycines* (soya bean cyst nematode), *Globodera pallida* and *Globodera rostochiensis* (yellow potato cyst nematode), these species being controlled effectively by the compounds described in the present text. However, the use of the compounds described in the present text is by no means restricted to these genera or species, but also extends in the same manner to other nematodes.

The plant nematodes include, for example, *Aglenchus agricola*, *Anguina tritici*, *Aphelenchoides arachidis*, *Aphelenchoides fragaria*, and the stem and leaf endoparasites *Aphelenchoides* spp., *Belonolaimus gracilis*, *Belonolaimus longicaudatus*, *Belonolaimus nortoni*, *Bursaphelenchus cocophilus*, *Bursaphelenchus eremus*, *Bursaphelenchus xylophilus* and *Bursaphelenchus* spp., *Cacopaurus pestis*, *Criconemella curvata*, *Criconemella onoensis*, *Criconemella ornata*, *Criconemella rusium*, *Criconemella xenoplax* (=*Mesocriconema xenoplax*) and *Criconemella* spp.,

*Criconemoides ferniae*, *Criconemoides onoense*, *Criconemoides ornatum* and *Criconemoides* spp., *Ditylenchus destructor*, *Ditylenchus dipsaci*, *Ditylenchus myceliophagus* and also the stem and leaf endoparasites *Ditylenchus* spp., *Dolichodorus heterocephalus*, *Globodera pallida* (=*Heterodera pallida*), *Globodera rostochiensis* (yellow potato cyst nematode), *Globodera solanacearum*, *Globodera tabacum*, *Globodera virginia* and the non-migratory cyst-forming parasites *Globodera* spp., *Helicotylenchus digonicus*, *Helicotylenchus dihystera*, *Helicotylenchus erythrine*, *Helicotylenchus multicinctus*, *Helicotylenchus nannus*, *Helicotylenchus pseudorobustus* and *Helicotylenchus* spp., *Hemicriconemoides*, *Hemicycliophora arenaria*, *Hemicycliophora nudata*, *Hemicycliophora parvana*, *Heterodera avenae*, *Heterodera cruciferae*, *Heterodera glycines* (soya bean cyst nematode), *Heterodera oryzae*, *Heterodera schachtii*, *Heterodera zeae* and the non-migratory cyst-forming parasites *Heterodera* spp., *Hirschmaniella gracilis*, *Hirschmaniella oryzae*, *Hirschmaniella spinicaudata* and the stem and leaf endoparasites *Hirschmaniella* spp., *Hoplolaimus aegyptii*, *Hoplolaimus californicus*, *Hoplolaimus columbus*, *Hoplolaimus galeatus*, *Hoplolaimus indicus*, *Hoplolaimus magnistylus*, *Hoplolaimus pararobustus*, *Longidorus africanus*, *Longidorus breviannulatus*, *Longidorus elongatus*, *Longidorus laevicapitatus*, *Longidorus vineacola* and the ectoparasites *Longidorus* spp., *Meloidogyne acronea*, *Meloidogyne africana*, *Meloidogyne arenaria*, *Meloidogyne arenaria thamesi*, *Meloidogyne artiella*, *Meloidogyne chitwoodi*, *Meloidogyne coffeicola*, *Meloidogyne ethiopica*, *Meloidogyne exigua*, *Meloidogyne fallax*, *Meloidogyne graminicola*, *Meloidogyne graminis*, *Meloidogyne hapla*, *Meloidogyne incognita*, *Meloidogyne incognita acrita*, *Meloidogyne javanica*, *Meloidogyne kikuyensis*, *Meloidogyne minor*, *Meloidogyne naasi*, *Meloidogyne paranaensis*, *Meloidogyne thamesi* and the non-migratory parasites *Meloidogyne* spp., *Meloinema* spp., *Nacobbus aberrans*, *Neotylenchus vigissi*, *Paraphelenchus pseudoparietinus*, *Paratrichodorus allius*, *Paratrichodorus lobatus*, *Paratrichodorus minor*, *Paratrichodorus nanus*, *Paratrichodorus porosus*, *Paratrichodorus teres* and *Paratrichodorus* spp., *Paratylenchus hamatus*, *Paratylenchus minutus*, *Paratylenchus projectus* and *Paratylenchus* spp., *Pratylenchus agilis*, *Pratylenchus alleni*, *Pratylenchus andinus*, *Pratylenchus brachyurus*, *Pratylenchus cerealis*, *Pratylenchus coffeae*, *Pratylenchus crenatus*, *Pratylenchus delattrei*, *Pratylenchus giibbicaudatus*, *Pratylenchus goodeyi*, *Pratylenchus hamatus*, *Pratylenchus hexincisus*, *Pratylenchus loosi*, *Pratylenchus neglectus*, *Pratylenchus penetrans*, *Pratylenchus pratensis*, *Pratylenchus scribneri*, *Pratylenchus teres*, *Pratylenchus thornei*, *Pratylenchus vulnus*, *Pratylenchus zeae* and the migratory endoparasites *Pratylenchus* spp., *Pseudohalenchus minutus*, *Psilenchus magnidens*, *Psilenchus tumidus*, *Punctodera chalcoensis*, *Quinisulcius acutus*, *Radopholus citrophilus*, *Radopholus similis*, the migratory endoparasites *Radopholus* spp., *Rotylenchulus borealis*, *Rotylenchulus parvus*, *Rotylenchulus reniformis* and *Rotylenchulus* spp., *Rotylenchus laurentinus*,

*Rotylenchus macrodoratus, Rotylenchus robustus, Rotylenchus uniformis* and *Rotylenchus* spp., *Scutellonema brachyurum, Scutellonema bradys, Scutellonema clathricaudatum* and the migratory endoparasites *Scutellonema* spp., *Subanguina radiciola, Tetylenchus nicotianae, Trichodorus cylindricus, Trichodorus minor, Trichodorus primitivus, Trichodorus proximus, Trichodorus similis, Trichodorus sparsus* and the ectoparasites *Trichodorus* spp., *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp., *Tylenchulus semipenetrans* and the semiparasites *Tylenchulus* spp., *Xiphinema americanum, Xiphinema brevicolle, Xiphinema dimorphicaudatum, Xiphinema index* and the ectoparasites *Xiphinema* spp.

Nematodes for the control of which a compound of the formula (I) may be used include nematodes of the genus *Meloidogyne* such as the Southern root-knot nematode (*Meloidogyne incognita*), the Javanese root-knot nematode (*Meloidogyne javanica*), the Northern root-knot nematode (*Meloidogyne hapla*) and the peanut root-knot nematode (*Meloidogyne arenaria*); nematodes of the genus *Ditylenchus* such as the potato rot nematode (*Ditylenchus destructor*) and stem and bulb eelworm (*Ditylenchus dipsaci*); nematodes of the genus *Pratylenchus* such as the cob root-lesion nematode (*Pratylenchus penetrans*), the chrysanthemum root-lesion nematode (*Pratylenchus fallax*), the coffee root nematode (*Pratylenchus coffeae*), the tea root nematode (*Pratylenchus loosi*) and the walnut root-lesion nematode (*Pratylenchus vulnus*); nematodes of the genus *Globodera* such as the yellow potato cyst nematode (*Globodera rostochiensis*) and the white potato cyst nematode (*Globodera pallida*); nematodes of the genus *Heterodera* such as the soya bean cyst nematode (*Heterodera glycines*) and beet cyst eelworm (*Heterodera schachtii*); nematodes of the genus *Aphelenchoides* such as the rice white-tip nematode (*Aphelenchoides besseyi*), the chrysanthemum nematode (*Aphelenchoides ritzemabosi*) and the strawberry nematode (*Aphelenchoides fragariae*); nematodes of the genus *Aphelenchus* such as the fungivorous nematode (*Aphelenchus avenae*); nematodes of the genus *Radopholus*, such as the burrowing nematode (*Radopholus similis*); nematodes of the genus *Tylenchulus* such as the citrus root nematode (*Tylenchulus semipenetrans*); nematodes of the genus *Rotylenchulus* such as the reniform nematode (*Rotylenchulus reniformis*); tree-dwelling nematodes such as the pine wood nematode (*Bursaphelenchus xylophilus*) and the red ring nematode (*Bursaphelenchus cocophilus*) and the like.

Plants for the protection of which a compound of the formula (I) can be used include plants such as cereals (for example rice, barley, wheat, rye, oats, maize and the like), beans (soya bean, aduki bean, bean, broadbean, peas, peanuts and the like), fruit trees/fruits (apples, citrus species, pears, grapevines, peaches, Japanese apricots, cherries, walnuts, almonds, bananas, strawberries and the like), vegetable species (cabbage, tomato, spinach, broccoli, lettuce, onions, spring onion, pepper and the like), root crops (carrot, potato, sweet potato, radish, lotus root, turnip and the like), plant for industrial raw materials (cotton, hemp, paper mulberry, mitsumata, rape, beet, hops, sugar cane, sugar beet, olive, rubber, palm trees, coffee, tobacco, tea and the like), cucurbits (pumpkin, cucumber, water melon, melon and the like), meadow plants (cocksfoot, sorghum, timothy-grass, clover, alfalfa and the like), lawn grasses (mascarene grass, bentgrass and the like), spice plants etc. (lavender, rosemary, thyme, parsley, pepper, ginger and the like) and flowers (chrysanthemums, rose, orchid and the like).

The compounds of the formula (I) are particularly suitable for controlling coffee nematodes, in particular *Pratylenchus brachyurus, Pratylenchus coffeae, Meloidogyne exigua, Meloidogyne incognita, Meloidogyne coffeicola, Helicotylenchus* spp. and also *Meloidogyne paranaensis, Rotylenchus* spp., *Xiphinema* spp., *Tylenchorhynchus* spp. and *Scutellonema* spp.

The compounds of the formula (I) are particularly suitable for controlling potato nematodes, in particular *Pratylenchus brachyurus, Pratylenchus pratensis, Pratylenchus scribneri, Pratylenchus penetrans, Pratylenchus coffeae, Ditylenchus dipsaci* and of *Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne fallax, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae* and *Meloinema* spp.

The compounds of the formula (I) are particularly suitable for controlling tomato nematodes, in particular *Meloidogyne arenaria, Meloidogyne hapla, Meloidogyne javanica, Meloidogyne incognita, Pratylenchus penetrans* and also *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus* and *Rotylenchulus reniformis*.

The compounds of the formula (I) are particularly suitable for controlling cucumber plant nematodes, in particular *Meloidogyne arenaria, Meloidogyne hapla, Meloidogyne javanica, Meloidogyne incognita, Rotylenchulus reniformis* and *Pratylenchus thornei*.

The compounds of the formula (I) are particularly suitable for controlling cotton nematodes, in particular *Belonolaimus longicaudatus, Meloidogyne incognita, Hoplolaimus columbus, Hoplolaimus galeatus* and *Rotylenchulus reniformis*.

The compounds of the formula (I) are particularly suitable for controlling maize nematodes, in particular *Belonolaimus longicaudatus, Paratrichodorus minor* and also *Pratylenchus brachyurus, Pratylenchus delattrei, Pratylenchus hexincisus, Pratylenchus penetrans, Pratylenchus zeae,* (*Belonolaimus gracilis*), *Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Qui-* nisulcius acutus, Paratylenchus minutus, Hemicycliophora parvana, Aglenchus agricola, Anguina tritici, Aphelenchoides arachidis, Scutellonema brachyurum and Subanguina radiciola.

The compounds of the formula (I) are particularly suitable for controlling soya bean nematodes, in particular *Pratylenchus brachyurus, Pratylenchus pratensis, Pratylenchus penetrans, Pratylenchus scribneri, Belonolaimus longicaudatus, Heterodera glycines, Hoplolaimus columbus* and also *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus, (Belonolaimus gracilis), Meloidogyne arenaria, Meloidogyne incognita, Meloidogyne javanica, Meloidogyne hapla, Hoplolaimus columbus, Hoplolaimus galeatus* and *Rotylenchulus reniformis.*

The compounds of the formula (I) are particularly suitable for controlling tobacco nematodes, in particular *Meloidogyne incognita, Meloidogyne javanica* and also *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp. and *Tetylenchus nicotianae.*

The compounds of the formula (I) are particularly suitable for controlling citrus nematodes, in particular *Pratylenchus coffeae* and also *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americanum, Xiphinema brevicolle, Xiphinema index, Criconemella* spp., *Hemicriconemoides, Radopholus similis* and *Radopholus citrophilus, Hemicycliophora arenaria, Hemicycliophora nudata* and *Tylenchulus semipenetrans.*

The compounds of the formula (I) are particularly suitable for controlling banana nematodes, in particular *Pratylenchus coffeae, Radopholus similis* and also *Pratylenchus giibbicaudatus, Pratylenchus loosi, Meloidogyne* spp., *Helicotylenchus multicinctus, Helicotylenchus dihystera* and *Rotylenchulus* spp.

The compounds of the formula (I) are particularly suitable for controlling pineapple nematodes, in particular *Pratylenchus zeae, Pratylenchus pratensis, Pratylenchus brachyurus, Pratylenchus goodeyi., Meloidogyne* spp., *Rotylenchulus reniformis* and also *Longidorus elongatus, Longidorus laevicapitatus, Trichodorus primitivus, Trichodorus minor, Heterodera* spp., *Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides ferniae, Criconemoides onoense* and *Criconemoides ornatum.*

The compounds of the formula (I) are particularly suitable for controlling grapevine nematodes, in particular *Pratylenchus vulnus, Meloidogyne arenaria, Meloidogyne incognita, Meloidogyne javanica, Xiphinema americanum, Xiphinema index* and also *Pratylenchus pratensis, Pratylenchus scribneri, Pratylenchus neglectus, Pratylenchus brachyurus, Pratylenchus thornei* and *Tylenchulus semipenetrans.*

The compounds of the formula (I) are particularly suitable for controlling nematodes in tree crops-pome fruit, in particular *Pratylenchus penetrans* and also *Pratylenchus vulnus, Longidorus elongatus, Meloidogyne incognita* and *Meloidogyne hapla.*

The compounds of the formula (I) are particularly suitable for controlling nematodes in tree crops-stone fruit, in particular *Pratylenchus penetrans, Pratylenchus vulnus, Meloidogyne arenaria, Meloidogyne hapla, Meloidogyne javanica, Meloidogyne incognita, Criconemella xenoplax* and of *Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum* and *Hoplolaimus galeatus.*

The compounds of the formula (I) are particularly suitable for controlling nematodes in tree crops, sugar cane and rice, in particular *Trichodorus* spp., *Criconemella* spp. and also *Pratylenchus* spp., *Paratrichodorus* spp., *Meloidogyne* spp., *Helicotylenchus* spp., *Tylenchorhynchus* spp., *Aphelenchoides* spp., *Heterodera* spp, *Xiphinema* spp. and *Cacopaurus pestis.*

In the present context, the term "nematodes" also refers to nematodes damaging humans or animals.

Specific nematode species harmful to humans or to animals are:

Trichinellida, for example: *Trichuris* spp., *Capillaria* spp *Paracapillaria* spp., *Trichomosoides* spp., *Trichinella* spp., *Eucoleus* spp.;

from the order of the Tylenchida, for example: *Micronema* spp., *Strongyloides* spp.;

From the order of the Rhabditina, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Necator* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Oslerus* spp., *Trichostrongylus* spp., *Haemonchus* spp., *Ostertagia* spp., *Teladorsagia* spp., *Marshallagia* spp., *Cooperia* spp., *Nematodirus* spp., *Hyostrongylus* spp., *Obeliscoides* spp., *Amidostomum* spp., *Ollulanus* spp., *Heligmosomoides* spp., *Nippostrongylus* spp.;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp.;

*Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.

Many known nematicides also act against other parasitic helminths and are therefore used for controlling worms—not necessarily belonging to the group Nematoda—which are parasites in humans and animals. The present invention also relates to the use of the compounds of the formula (I) as anthelmintic medicaments. The pathogenic endoparasitic helminths include Platyhelminthes (e.g. Monogenea, cestodes and trematodes), Acanthocephala and Pentastoma. The following helminths may be mentioned as being preferred:

Monogenea: e.g.: *Gyrodactylus* spp., *Dactylogyrus* spp., *Polystoma* spp.;

cestodes: from the order of the Pseudophyllidea, for example: *Diphyllobothrium* spp., *Spirometra* spp., *Schistocephalus* spp., *Ligula* spp., *Bothridium* spp., *Diplogonoporus* spp.;

from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.;

from the order of the Echinorhynchida, for example, *Acanthocephalus* spp., *Echinorhynchus* spp., *Leptorhynchoides* spp.;

Pentastoma: from the order of the Porocephalida, for example, *Linguatula* spp.

In the veterinary field and in animal keeping, the administration of the compounds of the formula (I) is carried out by methods generally known in the art, directly or enterally, parenterally, dermally or nasally in the form of suitable preparations. Administration can be carried out prophylactically or therapeutically.

The compounds of the formula (I) can optionally, at certain concentrations or application rates, also be used as herbicides, safeners, growth regulators or agents to improve plant properties, as microbicides or gametocides, for example as fungicides, antimycotics, bactericides, viricides (including agents against viroids) or as agents against MLO (*mycoplasma*-like organisms) and RLO (*rickettsia*-like organisms). If appropriate, they can also be used as intermediates or precursors for the synthesis of other active compounds.

Formulations

The present invention further relates to formulations and use forms prepared therefrom as pesticides, for example drench, drip and spray liquors, comprising at least one compound of the formula (I). In some cases, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropyl guar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers 173, prepared by the FAO/WHO Joint Meeting on Pesticide Specifications, 2004, ISBN: 9251048576. The formulations, in addition to one or more compounds of the formula (I), optionally comprise further agrochemically active compounds.

These are preferably formulations or use forms which comprise auxiliaries, for example extenders, solvents, spontaneity promoters, carriers, emulsifiers, dispersants, frost protectants, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are prepared either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

In principle, it is possible to use all suitable solvents. Examples of suitable solvents are aromatic hydrocarbons, such as xylene, toluene or alkylnaphthalenes, chlorinated aromatic or chlorinated aliphatic hydrocarbons, such as chlorobenzene, chloroethylene or methylene chloride, aliphatic hydrocarbons, such as cyclohexane, paraffins, petroleum fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers include especially: for example ammonium salts and ground natural minerals such as kaolins, clays, talc, chalk, quartz, attapulgite, montmorillonite or diatomaceous earth, and ground synthetic materials such as finely divided silica, alumina and natural or synthetic silicates, resins, waxes and/or solid fertilizers. Mixtures of such carriers can likewise be used. Useful carriers for granules include: for example crushed and fractionated natural rocks such as calcite, marble, pumice, sepiolite, dolomite, and synthetic granules of inorganic and organic meals, and also granules of organic material such as sawdust, paper, coconut shells, corn cobs and tobacco stalks.

Liquefied gaseous extenders or solvents can also be used. Particularly suitable extenders or carriers are those which are gaseous at ambient temperature and under atmospheric pressure, for example aerosol propellant gases, such as halohydrocarbons, and also butane, propane, nitrogen and carbon dioxide.

Examples of emulsifiers and/or foam-formers, dispersants or wetting agents with ionic or nonionic properties, or mixtures of these surfactants, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and when the application takes place in water.

It is possible to use colorants such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc as further auxiliaries in the formulations and the use forms derived therefrom.

Additional components may be stabilizers, such as low-temperature stabilizers, preservatives, antioxidants, light stabilizers or other agents which improve chemical and/or physical stability. Foam formers or antifoams may also be present.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids may also be present as additional auxiliaries in the formulations and the use forms derived therefrom. Further possible auxiliaries are mineral and vegetable oils.

Optionally, further auxiliaries may be present in the formulations and the use forms derived therefrom. Examples of such additives include fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce the dynamic surface tension, for example dioctyl sulphosuccinate, or increase the viscoelasticity, for example hydroxypropylguar polymers.

Suitable penetrants in the present context are all those substances which are usually used for improving the penetration of agrochemical active compounds into plants. Penetrants are defined in this context by their ability to penetrate from the (generally aqueous) application liquor and/or from the spray coating into the cuticle of the plant and thereby increase the mobility of active compounds in the cuticle. The method described in the literature (Baur et al., 1997, Pesticide Science 51, 131-152) can be used to determine this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001 and 98% by weight of the compound of the formula (I) or, with particular preference, between 0.01% and 95% by weight of the compound of the formula (I), more preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms is usually between 0.00000001 and 95% by weight of the compound of the formula (I), preferably between 0.00001 and 1% by weight, based on the weight of the use form. The compounds are employed in a customary manner appropriate for the use forms.

Mixtures

The compounds of the formula (I) may also be employed as a mixture with one or more suitable fungicides, bactericides, acaricides, molluscicides, nematicides, insecticides, microbiologicals, beneficial species, herbicides, fertilizers, bird repellents, phytotonics, sterilants, safeners, semiochemicals and/or plant growth regulators, in order thus, for example, to broaden the spectrum of action, to prolong the duration of action, to increase the rate of action, to prevent repulsion or prevent evolution of resistance. In addition, such active compound combinations may improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

Furthermore, the compounds of the formula (I) can be present in a mixture with other active compounds or semiochemicals such as attractants and/or bird repellants and/or plant activators and/or growth regulators and/or fertilizers. Likewise, the compounds of the formula (I) can be used to improve plant properties such as, for example, growth, yield and quality of the harvested material.

In a particular embodiment according to the invention, the compounds of the formula (I) are present in formulations or the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active compounds identified here by their common names are known and are described, for example, in the pesticide handbook ("The Pesticide Manual" 16th Ed., British Crop Protection Council 2012) or can be found on the Internet (e.g. http://www.alanwood.net/pesticides).

(1) Acetylcholinesterase (AChE) inhibitors, such as, for example, carbamates, for example alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, for example acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, such as, for example, cyclodiene-organochlorines, for example chlordane and endosulfan or phenylpyrazoles (fiproles), for example ethiprole and fipronil.

(3) Sodium channel modulators/voltage-gated sodium channel blockers such as, for example, pyrethroids, e.g. acrinathrin, allethrin, d-cis-trans allethrin, d-trans allethrin, bifenthrin, bioallethrin, bioallethrin s-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans-isomer], deltamethrin, empenthrin [(EZ)-(1R)-isomer], esfenvalerate, etofenprox, fenpropathrin, fenvalerate, flucythrinate, flumethrin, tau-fluvalinate, halfenprox, imiprothrin, kadethrin, permethrin, phenothrin [(1R)-trans-isomer], prallethrin, pyrethrins (pyrethrum), resmethrin, silafluofen, tefluthrin, tetramethrin, tetramethrin [(1R)-isomer)], tralomethrin and transfluthrin or DDT or methoxychlor.

(4) Nicotinergic acetylcholine receptor (nAChR) agonists, such as, for example, neonicotinoids, e.g. acetamiprid, clothianidin, dinotefuran, imidacloprid, nitenpyram, thiacloprid and thiamethoxam or nicotine or sulfoxaflor.

(5) Allosteric activators of the nicotinergic acetylcholine receptor (nAChR) such as, for example, spinosyns, e.g. spinetoram and spinosad.

(6) Chloride channel activators, such as, for example, avermectins/milbemycins, for example abamectin, emamectin benzoate, lepimectin and milbemectin.

(7) Juvenile hormone imitators such as, for example, juvenile hormone analogues, e.g. hydroprene, kinoprene and methoprene or fenoxycarb or pyriproxyfen.

(8) Active compounds with unknown or nonspecific mechanisms of action such as, for example, alkyl halides, e.g. methyl bromide and other alkyl halides; or chloropicrine or sulphuryl fluoride or borax or tartar emetic.

(9) Selective antifeedants, for example pymetrozine or flonicamid.

(10) Mite growth inhibitors, for example clofentezine, hexythiazox and diflovidazin or etoxazole.

(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors such as, for example, diafenthiuron or organotin compounds, for example azocyclotin, cyhexatin and fenbutatin oxide or propargite or tetradifon;

(13) Oxidative phosphorylation decouplers acting by interrupting the H proton gradient such as, for example, chlorfenapyr, DNOC and sulfluramid.

(14) Nicotinergic acetylcholine receptor antagonists such as, for example, bensultap, cartap hydrochloride, thiocylam, and thiosultap-sodium.

(15) Chitin biosynthesis inhibitors, type 0, such as, for example, bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting inhibitors (in particular for Diptera, i.e. dipterans) such as, for example, cyromazine.

(18) Ecdysone receptor agonists such as, for example, chromafenozide, halofenozide, methoxyfenozide and tebufenozide.

(19) Octopaminergic agonists such as, for example, amitraz.

(20) Complex-III electron transport inhibitors such as, for example, hydramethylnone or acequinocyl or fluacrypyrim.

(21) Complex-I electron transport inhibitors, for example from the group of the METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase such as, for example, tetronic and tetramic acid derivatives, e.g. spirodiclofen, spiromesifen and spirotetramat.

(24) Complex-IV electron transport inhibitors, such as, for example, phosphines, e.g. aluminium phosphide, calcium phosphide, phosphine and zinc phosphide or cyanide.

(25) Complex II electron transport inhibitors, such as, for example, cyenopyrafen and cyflumetofen.

(28) Ryanodine receptor effectors, such as, for example, diamides, e.g. chlorantraniliprole, cyantraniliprole and flubendiamide, further active compounds such as, for example, afidopyropen, azadirachtin, benclothiaz, benzoximate, bifenazate, bromopropylate, chinomethionat, cryolite, dicofol, diflovidazin, fluensulfone, flometoquin, flufenerim, flufenoxystrobin, flufiprole, fluopyram, flupyradifurone, fufenozide, heptafluthrin, imidaclothiz, iprodione, meperfluthrin, paichongding, pyflubumide, pyrifluquinazon, pyriminostrobin, tetramethylfluthrin and iodomethane; furthermore preparations based on *Bacillus firmus* (I-1582, BioNeem, Votivo), and also the following compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) and 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl-ethylcarbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethylamino]ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethylamino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazineearboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), 1-(3-chloropyridin-2-yl)-N-[4-cyano-2-methyl-6-(methylcarbamoyflphenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl)sulphonyl]-6-(trifluoromethyflimidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), 4-[5-(3,5-diehlorophenyl)-5-(trifluoromethyl)-4,5-dihydro-1,2-oxazol-3-yl]-2-methyl-N-(1-oxidothietan-3-yl)benzamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl)methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N'-nitro-2-pentylidenehydrazinecarboximidamide (known from WO2010/060231), 4-(3-{2,6-dichloro-4-[(3,3-diehloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Fungicides

The active compounds specified herein by their common name are known and described, for example, in "Pesticide Manual" or on the Internet (for example: http://www.alanwood.net/pesticides).

(1) Inhibitors of ergosterol biosynthesis such as, for example, (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafole, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifin, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-P, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]-1H-imidazole-1-carbothioate, (1.65) pyrisoxazole.

(2) Respiration inhibitors (respiratory chain inhibitors) such as, for example, (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam mixture of the syn-epimeric racemate 1RS,4SR,9RS and the anti-empimeric racemate 1RS,4SR,9SR, (2.12) isopyrazam (anti-epimeric racemate), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS, 4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28), 5,8-difluoro-N-[2-(2-fluoro-4-{[4-(trifluoromethyl)pyridin-2-yl]oxy}phenyl)ethyl]quinazoline-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid (3) Respiration inhibitors (respiratory chain inhibitors) acting on complex III of the respiratory chain such as, for example, (3.1) ametoctradin, (3.2) amisulbrom, (3.3) azoxystrobin, (3.4) cyazofamid, (3.5) coumethoxystrobin, (3.6) coumoxystrobin, (3.5) dimoxystrobin, (3.8) enestroburin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxylmino)-N-methylethanamide, (3.24) (2E)-2-(methoxyimino)-N-methyl-2-(2-{[({(1E)-1-[3-(trifluoromethyl)phenyl]ethylidene}amino)oxy]methyl}phenypethanamide, (3.25) (2E)-2-(methoxyimino)-N-methyl-2-{2-[(E)-({1-[3-(trifluoromethyl)phenyl]ethoxy}imino)methyl]phenyl}ethanamide, (3.26) (2E)-2-{2-[({[(1E)-1-(3-{[(E)-1-fluoro-2-phenylethenyl]oxy}phenyethylidene]amino}oxy)methyl]phenyl}-2-(methoxyimino)-N-methylethanamide, (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide, (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulphanyl)methyl]phenyl}-3-methoxyprop-2-enoate, (3.31) N-(3-ethyl-3,5,5-trimethylcyclohexyl)-3-(formylamino)-2-hydroxybenzamide, (3.32) 2-{2-[(2,5-dimethylphenoxy)methyl]phenyl}-2-methoxy-N-methylacetamide, (4) inhibitors of mitosis and cell division such as, for example, (4.1) benomyl, (4.2) carbendazim, (4.3) chlorfenazole, (4.4) diethofencarb, (4.5) ethaboxam, (4.6) fluopicolid, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine and (4.14) 3-chloro-5-(6-chloropyridin-3-yl)-6-methyl-4-(2,4,6-trifluorophenyl)pyridazine.

(5) Compounds having multisite activity such as, for example, (5.1) Bordeaux mixture, (5.2) captafol, (5.3) captan, (5.4) chlorothalonil, (5.5) copper preparations such as copper hydroxide, (5.6) copper naphthenate, (5.7) copper oxide, (5.8) copper oxychloride, (5.9) copper sulphate, (5.10) dichlofluanid, (5.11) dithianon, (5.12) dodine, (5.13) dodine free base, (5.14) ferbam, (5.15) fluorfolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) zinc metiram, (5.27) copperoxine, (5.28) propamidine, (5.29) propineb, (5.30) sulphur and sulphur preparations such as, for example calcium polysulphide, (5.31) thiram, (5.32) tolylfluanid, (5.33) zineb, (5.34) ziram and (5.35) anilazine.

(6) Resistance inducers such as, for example, (6.1) acibenzolar-S-methyl, (6.2) isotianil, (6.3) probenazole, (6.4) tiadinil and (6.5) laminarin.

(7) Inhibitors of amino acid and protein biosynthesis such as, for example, (7.1), (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline and (7.9) oxytetracycline and (7.10) streptomycin.

(8) ATP production inhibitors such as, for example, (8.1) fentin acetate, (8.2) fentin chloride, (8.3) fentin hydroxide and (8.4) silthiofam.

(9) Inhibitors of cell wall synthesis such as, for example, (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate and (9.10) polyoxin B.

(10) Inhibitors of lipid and membrane synthesis such as, for example, (10.1) biphenyl, (10.2) chlorneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb (10.12) pyrazophos, (10.13) quintozene, (10.14) tecnazene and (10.15) tolclofos-methyl.

(11) Melanin biosynthesis inhibitors, for example (11.1) carpropamid, (11.2) diclocymet, (11.3) fenoxanil, (11.4) fthalide, (11.5) pyroquilon, (11.6) tricyclazole and (11.7) 2,2,2-trifluoroethyl {3-methyl-1-[(4-methylbenzoyl)amino]butan-2-yl}carbamate.

(12) Inhibitors of nucleic acid synthesis such as, for example, (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazole, (12.9) metalaxyl, (12.10) metalaxyl-M (mefenoxam), (12.11) ofurace, (12.12) oxadixyl, (12.13) oxolinic acid and (12.14) octhilinone.

(13) Signal transduction inhibitors such as, for example, (13.1) chlozolinate, (13.2) fenpiclonil, (13.3) fludioxonil, (13.4) iprodione, (13.5) procymidone, (13.6) quinoxyfen, (13.7) vinclozolin and (13.8) proquinazid.

(14) Decouplers such as, for example, (14.1) binapacryl, (14.2) dinocap, (14.3) ferimzone, (14.4) fluazinam and (14.5) meptyldinocap.

(15) Further compounds such as, for example, (15.1) benthiazole, (15.2) bethoxazine, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat methylsulphate, (15.17) diphenylamine, (15.18) EcoMate, (15.19) fenpyrazamine, (15.20) flumetover, (15.21) fluorimid, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.36) octhilinone, (15.37) oxamocarb, (15.38) oxyfenthiin, (15.39) pentachlorophenol and its salts, (15.40) phenothrin, (15.41) phosphoric acid and its salts, (15.42) propamocarb-fosetylate, (15.43) propanosine-sodium, (15.44) pyrimorph, (15.45) (2E)-3-(4-tert-butylphenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrin, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl) amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl] ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulphonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7 (2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl] pyridine, (15.67) 2-phenylphenol and salts, (15.68) 3-(4,4, 5-trifluoro-3,3-dimethyl-3,4-dihydroisoquinolin-1-yl) quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2, 6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulphonohydrazide, (15.74) 5-fluoro-2-[(4-fluorobenzyl)oxy]pyrimidine-4-amine, (15.75) 5-fluoro-2-[(4-methylbenzyl)oxy]pyrimidine-4-amine, (15.76) 5-methyl-6-octyl[1,2,4]triazolo[1,5-a]pyrimidine-7-amine, (15.77) ethyl (2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2, 4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N—{(Z)-[(cyclopropylmethoxy)imino][6-(difluoromethoxy)-2,3-difluorophenyl]methyl}-2-phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, (15.90) pentyl {6-[({[(1-methyl-1H-tetrazol-5-yl)(phenyl)methylene]amino}oxy)methyl]pyridin-2-yl}carbamate, (15.91) phenazine-1-carboxylic acid, (15.92) quinolin-8-ol, (15.93) quinolin-8-ol sulphate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl] nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl] nicotinamide, (15.115) (5-bromo-2-methoxy-4-methylpyridin-3-yl)(2,3,4-trimethoxy-6-methylphenyl) methanone, (15.116) N-[2-(4-{[3-(4-chlorophenyl)prop-2- yn-1-yl]oxy}-3-methoxyphenyl)ethyl]-N2-(methylsulphonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl) (phenyl)methylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulfanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel(2R,3S)-3-(2-chlorophenyl)-2-(2,4-difluorophenyoxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulphanyl)-1-{[rel(2R,3S)-3-(2-chlorophenyl)-2-(2,4-difluorophenyl)oxiran-2-yl]methyl}-1H-1,2,4-triazole, (15.136) 5-(allylsulphanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5 S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R, 5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5 S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2-methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazol-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-1H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide,
(15.182) N-(4-chloro-2,6-difluorophenyl)-4-(2-chloro-4-fluorophenyl)-1,3-dimethyl-1H-pyrazole-5-amine. All mixing components mentioned in classes (1) to (15) can, if they are capable on the basis of their functional groups, optionally form salts with suitable bases or acids.

Biological Pesticides as Mixing Components

The compounds of the formula (I) can be combined with biological pesticides.

Biological pesticides comprise in particular bacteria, fungi, yeasts, plant extracts and products formed by microorganisms, including proteins and secondary metabolites.

Biological pesticides comprise bacteria such as spore-forming bacteria, root-colonising bacteria and bacteria which act as biological insecticides, fungicides or nematicides.

Examples of such bacteria which are employed or can be used as biological pesticides are:

*Bacillus amyloliquefaciens*, strain FZB42 (DSM 231179), or *Bacillus cereus*, in particular *B. cereus* strain CNCM 1-1562 or *Bacillus firmus*, strain 1-1582 (Accession number CNCM 1-1582) or *Bacillus pumilus*, in particular strain GB34 (Accession No. ATCC 700814) and strain QST2808 (Accession No. NRRL B-30087), or *Bacillus subtilis*, in particular strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, in particular *B. thuringiensis* subspecies *israelensis* (serotype H-14), strain AM65-52 (Accession No. ATCC 1276), or *B. thuringiensis* subsp. *aizawai*, in particular strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans*, *Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Acession Number NRRL 30232).

Examples of fungi and yeasts which are employed or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (now: *Isaria fumosorosea*), in particular strain IFPC 200613, or strain Apopka 97 (Accesion No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39. (Accession Number CNCM 1-952).

Examples of viruses which are employed or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples which may be mentioned are:

*Agrobacterium* spp., *Azorhizobium caulinodans*, *Azospirillum* spp., *Azotobacter* spp., *Bradyrhizobium* spp., *Burkholderia* spp., in particular *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., in particular *Rhizobium trifolii*, *Rhizopogon* spp., *Scleroderma* spp., *Suillus* spp., *Streptomyces* spp.

Examples of plant extracts and products formed by microorganisms including proteins and secondary metabolites which are employed or can be used as biological pesticides are:

*Allium sativum*, *Artemisia absinthium*, azadirachtin, Biokeeper WP, *Cassia nigricans*, *Celastrus angulatus*, *Chenopodium anthelminticum*, chitin, Armour-Zen, *Dryopteris filix-mas*, *Equisetum arvense*, Fortune Aza, Fungastop, Heads Up (*Chenopodium quinoa* saponin extract), Pyrethrum/Pyrethrins, *Quassia amara*, *Quercus*, *Quillaja*, *Regalia*, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, Brassicaceae extract, in particular oilseed rape powder or mustard powder.

Safener as Mixing Components

The compounds of the formula (I) can be combined with safeners such as, for example, benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Here, plants are to be understood to mean all plants and plant parts such as wanted and unwanted wild plants or crop plants (including naturally occurring crop plants), for example cereals (wheat, rice, triticale, barley, rye, oats), maize, soya bean, potato, sugar beet, sugar cane, tomatoes, peas and other vegetable species, cotton, tobacco, oilseed rape, and also fruit plants (with the fruits apples, pears, citrus fruits and grapevines). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts should be understood to mean all parts and organs of the plants above and below ground, such as shoot, leaf, flower and root, examples given being leaves, needles, stalks, stems, flowers, fruit bodies, fruits and seeds, and also tubers, roots and rhizomes. Parts of plants also include harvested plants and vegetative and generative propagation material, for example seedlings, tubers, rhizomes, cuttings and seeds.

Treatment according to the invention of the plants and plant parts with the compounds of the formula (I) is carried out directly or by allowing the compounds to act on the surroundings, environment or storage space by the customary treatment methods, for example by immersion, spraying, evaporation, fogging, scattering, painting on, injection and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. The invention is used with particular preference to treat plants of the respective commercially customary cultivars or those that are in use. Plant cultivars are to be understood as meaning plants having new properties ("traits") and which have been obtained by conventional breeding, by mutagenesis or by recombinant DNA techniques. They can be cultivars, varieties, bio- or genotypes.

Transgenic Plant, Seed Treatment and Integration Events

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processability of the harvested products. Further and particularly emphasized examples of such properties are increased resistance of the plants against animal and microbial pests, such as against insects, arachnids, nematodes, mites, slugs and snails owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof), furthermore increased resistance of the plants against phytopathogenic fungi, bacteria and/or viruses owing, for example, to systemic acquired resistance (SAR), systemin, phytoalexins, elicitors and also resistance genes and correspondingly expressed proteins and toxins, and also increased tolerance of the plants to certain herbicidally active compounds, for example imidazolinones, sulphonylureas, glyphosate or phosphinothricin (for example the "PAT" gene). The genes which impart the desired traits in question may also be present in combinations with one another in the transgenic plants. Examples of transgenic plants which may be mentioned are the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), with particular emphasis being given to maize, soya beans, wheat, rice, potatoes, cotton, sugar cane, tobacco and oilseed rape. Traits which are particularly emphasized are the increased resistance of the plants to insects, arachnids, nematodes and slugs and snails.

Crop Protection—Types of Treatment

The treatment of the plants and plant parts with the compounds of the formula (I) is carried out directly or by action on their surroundings, habitat or storage space using customary treatment methods, for example by clipping, spraying, atomizing, irrigating, evaporating, dusting, fogging, broadcasting, foaming, painting, spreading-on, injecting, watering (drenching), drip irrigating and, in the case of propagation material, in particular in the case of seed, furthermore as a powder for dry seed treatment, a solution for liquid seed treatment, a water-soluble powder for slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. the compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This may be done, for example, by drenching, or by mixing into the soil or the nutrient solution, i.e. the locus of the plant (e.g. soil or hydroponic systems) is impregnated with a liquid form of the compounds of the formula (I), or by soil application, i.e. the compounds of the formula (I) according to the invention are introduced in solid form (e.g. in the form of granules) into the locus of the plants. In the case of paddy rice crops, this can also be done by metering the compound of the formula (I) in a solid application form (for example as granules) into a flooded paddy field.

Treatment of Seed

The control of animal pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is furthermore desirable to optimize the amount of active compound employed in such a way as to provide optimum protection for the seed and the germinating plant from attack by animal pests, but without damaging the plant itself by the active compound employed. In particular, methods for the treatment of seed should also take into consideration the intrinsic insecticidal or nematicidal properties of pest-resistant or -tolerant transgenic plants in order to achieve optimum protection of the seed and also the germinating plant with a minimum of pesticides being employed.

The present invention therefore in particular also relates to a method for the protection of seed and germinating plants, from attack by pests, by treating the seed with one of the compounds of the formula (I). The method according to the invention for protecting seed and germinating plants against attack by pests furthermore comprises a method where the seed is treated simultaneously in one operation or sequentially with a compound of the formula (I) and a mixing component. It also comprises a method where the seed is treated at different times with a compound of the formula (I) and a mixing component.

The invention likewise relates to the use of the compounds of the formula (I) for the treatment of seed for protecting the seed and the resulting plant from animal pests.

Furthermore, the invention relates to seed which has been treated with a compound of the formula (I) according to the invention so as to afford protection from animal pests. The invention also relates to seed which has been treated simultaneously with a compound of the formula (I) and a mixing component. The invention furthermore relates to seed which has been treated at different times with a compound of the formula (I) and a mixing component. In the case of seed which has been treated at different points in time with a compound of the formula (I) and a mixing component, the individual substances may be present on the seed in different layers. Here, the layers comprising a compound of the formula (I) and mixing components may optionally be separated by an intermediate layer. The invention also relates to seed where a compound of the formula (I) and a mixing component have been applied as component of a coating or as a further layer or further layers in addition to a coating.

Furthermore, the invention relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this manner, the immediate treatment of the crop at the time of sowing or shortly thereafter can be dispensed with.

It has to be considered a further advantage that by treatment of the seed with a compound of the formula (I), germination and emergence of the treated seed may be enhanced.

It is likewise to be considered advantageous that compounds of the formula (I) can be used in particular also for transgenic seed.

Furthermore, compounds of the formula (I) can be employed in combination with compositions or compounds of signalling technology, leading to better colonization by symbionts such as, for example, *rhizobia*, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. In particular, this takes the form of seed of cereals (for example wheat, barley, rye, millet and oats), corn, cotton, soya beans, rice, potatoes, sunflowers, coffee, tobacco, canola, oilseed rape, beets (for example sugarbeets and fodder beets), peanuts, vegetables (for example tomatoes, cucumbers, bean, cruciferous vegetables, onions and lettuce), fruit plants, lawns and ornamental plants. The treatment of the seed of cereals (such as wheat, barley, rye and oats), maize, soya beans, cotton, canola, oilseed rape and rice is of particular importance.

As already mentioned above, the treatment of transgenic seed with a compound of the formula (I) is also of particular importance. This takes the form of seed of plants which, as a rule, comprise at least one heterologous gene which governs the expression of a polypeptide with in particular insecticidal and/or nematicidal properties. The heterologous genes in transgenic seed can originate from microorganisms such as *Bacillus, Rhizobium, Pseudomonas, Serratia, Trichoderma, Clavibacter, Glomus* or *Gliocladium*. The present invention is particularly suitable for the treatment of transgenic seed which comprises at least one heterologous gene originating from *Bacillus* sp. It is particularly preferably a heterologous gene derived from *Bacillus thuringiensis*.

In the context of the present invention, the compound of the formula (I) is applied to the seed. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming.

When treating the seed, care must generally be taken that the amount of the compound of the formula (I) applied to the seed and/or the amount of further additives is chosen in such a way that the germination of the seed is not adversely affected, or that the resulting plant is not damaged. This must be ensured particularly in the case of active compounds which can exhibit phytotoxic effects at certain application rates.

In general, the compounds of the formula (I) are applied to the seed in a suitable formulation. Suitable formulations and processes for seed treatment are known to the person skilled in the art.

The compounds of the formula (I) can be converted to the customary seed dressing formulations, such as solutions, emulsions, suspensions, powders, foams, slurries or other coating compositions for seed, and also ULV formulations.

These formulations are prepared in a known manner, by mixing the compounds of the formula (I) with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of agrochemically active compounds. Preference is given to using alkylnaphthalenesulphonates, such as diisopropyl- or diisobutylnaphthalenesulphonates.

Useful dispersants and/or emulsifiers which may be present in the seed dressing formulations usable in accordance with the invention are all nonionic, anionic and cationic dispersants conventionally used for the formulation of active agrochemical ingredients. Preference is given to using nonionic or anionic dispersants or mixtures of nonionic or anionic dispersants. Suitable nonionic dispersants include in particular ethylene oxide/propylene oxide block polymers, alkylphenol polyglycol ethers and tristryrylphenol polyglycol ethers, and the phosphated or sulphated derivatives thereof. Suitable anionic dispersants are in particular lignosulphonates, polyacrylic acid salts and arylsulphonate/formaldehyde condensates.

Antifoams which may be present in the seed dressing formulations usable in accordance with the invention are all foam-inhibiting substances conventionally used for the formulation of active agrochemical ingredients. Preference is given to using silicone antifoams and magnesium stearate.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances which can be used for such purposes in agrochemical compositions. Cellulose derivatives, acrylic acid derivatives, xanthan, modified clays and finely divided silica are preferred.

Adhesives which may be present in the seed dressing formulations usable in accordance with the invention are all customary binders usable in seed dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel", vol. 2, Springer Verlag, 1970, pp. 401-412).

The seed dressing formulations usable in accordance with the invention can be used to treat a wide variety of different kinds of seed either directly or after prior dilution with water. For instance, the concentrates or the preparations obtainable therefrom by dilution with water can be used to dress the seed of cereals, such as wheat, barley, rye, oats, and triticale, and also the seed of maize, rice, oilseed rape, peas, beans, cotton, sunflowers, soya beans and beets, or else a wide variety of different vegetable seed. The seed dressing formulations usable in accordance with the invention, or the dilute use forms thereof, can also be used to dress seed of transgenic plants.

For treatment of seed with the seed dressing formulations usable in accordance with the invention, or the use forms prepared therefrom by adding water, all mixing units usable customarily for the seed dressing are useful. Specifically, the procedure in the seed dressing is to place the seed into a mixer, operated batch-wise or continuously, to add the particular desired amount of seed dressing formulations, either as such or after prior dilution with water, and to mix everything until the formulation is distributed homogeneously on the seed. If appropriate, this is followed by a drying operation.

The application rate of the seed dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. in the field of veterinary medicine, the compounds of the formula (I) are active against animal parasites, in particular ectoparasites or endoparasites. The term endoparasites includes in particular helminths and protozoans, such as coccidia. Ectoparasites are typically and preferably arthropods, in particular insects and acarids.

In the field of veterinary medicine the compounds of the formula (I) are suitable, with favourable homeotherm toxicity, for controlling parasites which occur in animal breeding and animal husbandry in livestock, breeding, zoo, laboratory, experimental and domestic animals. They are active against all or specific stages of development of the parasites.

Agricultural livestock include, for example, mammals, such as sheep, goats, horses, donkeys, camels, buffaloes, rabbits, reindeers, fallow deers, and in particular cattle and pigs; or poultry such as turkeys, ducks, geese, and in particular chickens; fish and crustaceans, for example in aquaculture; and also insects such as bees.

Domestic animals include, for example, mammals, such as hamsters, guinea pigs, rats, mice, chinchillas, ferrets and in particular dogs, cats, cage birds, reptiles, amphibians and aquarium fish.

According to a preferred embodiment, the compounds of the formula (I) are administered to mammals.

According to another preferred embodiment, the compounds of the formula (I) are administered to birds, namely cage birds and in particular poultry.

By using the compounds of the formula (I) to control animal parasites, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling" as used herein with regard to the animal health field, means that the compounds of the formula (I) are effective in reducing the incidence of the respective parasite in an animal infected with such parasites to innocuous levels. More specifically, "controlling", as used herein, means that the compound of the formula (I) is effective in killing the respective parasite, inhibiting its growth, or inhibiting its proliferation.

Arthropods include:

from the order of the Anoplurida, for example *Haematopinus* spp., *Linognathus* spp., *Pediculus* spp., *Phtirus* spp., *Solenopotes* spp.; *from the order of the Mallophagida and the suborders Amblycerina and Ischnocerina, for example Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.;

from the order of the Heteropterida, for example *Cimex* spp., *Triatoma* spp., *Rhodnius* spp., *Panstrongylus* spp.; as well as nuisance and hygiene pests from the order of the Blattarida.

Arthropods furthermore include:

from the subclass of the Acari (Acarina) and the order of the Metastigmata, for example from the family of argasidae like *Argas* spp., *Ornithodorus* spp., *Otobius* spp., from the family of Ixodidae like *Ixodes* spp., *Amblyomma* spp., *Rhipicephalus (Boophilus)* spp *Dermacentor* spp., *Haemophysalis* spp., *Hyalomma* spp., *Rhipicephalus* spp. (the original genus of multi-host ticks); from the order of mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Exemplary parasitic protozoa include, without any limitation:
Mastigophora (*Flagellata*) such as:
Metamonada: from the order Diplomonadida for example *Giardia* spp., *Spironucleus* spp.;
Parabasala: from the order Trichomonadida for example *Histomonas* spp., *Trichomonas* spp., *Tritrichomonas* spp., *Tetratrichomonas* spp., *Pentatrichomonas* spp.;
Euglenozoa: from the order Trypanosomatida for example *Leishmania* spp., *Trypanosoma* spp.;
Sarcomastigophora (Rhizopoda), such as Entamoebidae, for example, *Entamoeba* spp., Centramoebidae, for example, *Acanthamoeba* spp., Euamoebidae, e.g. *Hartmanella* spp.;
Alveolata such as Apicomplexa (Sporozoa): e.g. *Cryptosporidium* spp.; from the order Eimeriida, for example, *Eimeria* spp., *Besnoitia* spp., *Isospora* spp., *Cystoisospora* spp., *Toxoplasma* spp., *Neospora* spp., *Hammondia* spp., *Sarcocystis* spp.; from the order Adeleida e.g. *Hepatozoon* spp., *Klossiella* spp.; from the order Haemosporida e.g. *Plasmodium* spp., *Leucocytozoon* spp.; from the order Piroplasmida e.g. *Babesia* spp., *Echinozoon* spp., *Theileria* spp.; and Ciliophora: from the order Vesibuliferida e.g. *Balantidium* spp., *Buxtonella* spp.;
Microspora such as *Encephalitozoon* spp., *Enterocytozoon* spp., *Nosema* spp.; Myxozoa and furthermore, e.g. *Globidium* spp.

Pathogenic endoparasites, which are helminths, include Platyhelmintha (e.g. Monogenea, cestodes and trematodes), nematodes, Acanthocephala, and Pentastoma. Further helminths include:
Trichinellida, for example: *Trichuris* spp., *Capillaria* spp., *Paracapillaria* spp., *Trichomosoides* spp., *Trichinella* spp., *Eucoleus* spp.;
from the order of the Tylenchida, for example: *Micronema* spp., *Strongyloides* spp.;
from the order of the Rhabditina, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Necator* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Oslerus* spp., *Trichostrongylus* spp., *Haemonchus* spp., *Ostertagia* spp., *Teladorsagia* spp., *Marshallagia* spp., *Cooperia* spp., *Nematodirus* spp., *Hyostrongylus* spp., *Obeliscoides* spp., *Amidostomum* spp., *Ollulanus* spp., *Heligmosomoides* spp., *Nippostrongylus* spp.;

from the order of the Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.

Many known nematicides also act against other parasitic helminths and are therefore used for controlling worms—not necessarily belonging to the group Nematoda—which are parasites in humans and animals. The present invention also relates to the use of the compounds of the formula (I) as anthelmintic medicaments. The pathogenic endoparasitic helminths include Platyhelminthes (e.g. Monogenea, cestodes and trematodes), Acanthocephala and Pentastoma. The following helminths may be mentioned as being preferred:
Monogenea: e.g.: *Gyrodactylus* spp., *Dactylogyrus* spp., *Polystoma* spp.;
cestodes: from the order of the Pseudophyllidea, for example: *Diphyllobothrium* spp., *Spirometra* spp., *Schistocephalus* spp., *Ligula* spp., *Bothridium* spp., *Diplogonoporus* spp.;
from the order of the Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;
trematodes: from the class of the Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;
Acanthocephala: from the order of the Oligacanthorhynchida, for example: *Macracanthorhynchus* spp., *Prosthenorchis* spp.; from the order of the Polymorphida, for example: *Filicollis* spp.; from the order of the Moniliformida, for example: *Moniliformis* spp.;
from the order of the Echinorhynchida, for example, *Acanthocephalus* spp., *Echinorhynchus* spp., *Leptorhynchoides* spp.;
Pentastoma: from the order of the Porocephalida, for example, *Linguatula* spp.

In the veterinary field and in animal keeping, administration of the compounds of the formula (I) is carried out by methods generally known in the art, such as enterally, parenterally, dermally or nasally in the form of suitable preparations. Administration can be carried out prophylactically or therapeutically.

Thus, one embodiment of the present invention refers to the use of a compound of the formula (I) as medicament.

A further aspect refers to the use of a compound of the formula (I) as an antiendoparasitic agent, in particular an anthelmintic agent or antiprotozoic agent. Compounds of the formula (I) are suitable for use as an antiendoparasitic agent, in particular an anthelmintic agent or antiprotozoic agent, for example in animal husbandry, in animal breeding, in animal housing and in the hygiene sector.

A further aspect in turn relates to the use of a compound of the formula (I) as an antiectoparasitic, in particular an arthropodicide such as an insecticide or an acaricide. A further aspect relates to the use of a compound of the formula (I) as an antiectoparasitic, in particular an arthropodicide such as an insecticide or an acaricide, for example in animal husbandry, in animal breeding, in stables or in the hygiene sector.

Anthelmintic Mixing Components

The following anthelmintic mixing components may be mentioned by way of example:

Anthelmintically active compounds including trematicidally and cestocidally active compounds:

from the class of the macrocyclic lactones, for example: abamectin, doramectin, emamectin, eprinomectin, ivermectin, milbemycin, moxidectin, nemadectin, selamectin;

from the class of the benzimidazoles and probenzimidazoles, for example: albendazole, albendazole-sulphoxide, cambendazole, cyclobendazole, febantel, fenbendazole, flubendazole, mebendazole, netobimin, oxfendazole, oxibendazole, parbendazole, thiabendazole, thiophanate, triclabendazole;

from the class of the cyclooctadepsipeptides, for example: emodepside, PF1022;

from the class of the aminoacetonitrile derivatives, for example: monepantel;

from the class of the tetrahydropyrimidines, for example: morantel, pyrantel, oxantel;

from the class of the imidazothiazoles, for example: butamisole, levamisole, tetramisole;

from the class of the salicylanilides, for example: bromoxanide, brotianide, clioxanide, closantel, niclosamide, oxyclozanide, rafoxanide, tribromsalan;

from the class of the paraherquamides, for example: derquantel, paraherquamide;

from the class of the aminophenylamidines, for example: amidantel, deacylated amidantel (dAMD), tribendimidine;

from the class of the organophosphates, for example: coumaphos, crufomate, dichlorvos, haloxone, naphthalofos, trichlorfon;

from the class of the substituted phenols, for example: bithionol, disophenol, hexachlorophene, niclofolan, meniclopholan, nitroxynil;

from the class of the piperazinones, for example: praziquantel, epsiprantel;

from various other classes, for example: amoscanate, bephenium, bunamidine, clonazepam, clorsulon, diamfenetid, dichlorophen, diethylcarbamazine, emetine, hetolin, hycanthone, lucanthone, Miracil, mirasan, niclosamide, niridazole, nitroxynil, nitroscanate, oltipraz, omphalotin, oxamniquin, paromomycin, piperazine, resorantel.

All named mixing partners can, if their functional groups enable this, optionally form salts with suitable bases or acids.

In another particular embodiment, for the animal health field, mixtures with antiprotozoals are also provided.

Exemplary mixing partners include, without any limitation:

from the class of carbanilides, for example: imidocarb;
from the class of quinazolinone alkaloid, for example: halofuginon;
from the class of sulfonamides, for example: sulfaclozin;
from the class of triazines, for example: diclazuril, toltrazuril;

In another particular embodiment, for the animal health field, mixtures with ectoparasiticides are also provided.

Exemplary mixing partners include, without any limitation:

from the class of amidine derivatives, for example: amitraz, chlormebuform, cymiazole, demiditraz; from the class of arylisoxazolines, not excluding related classes with pyrroline or pyrrolidine moiety replacing the isoxazoline ring, for example: afoxolaner, fluralaner;

from the class of *bacillus thuringiensis* strains, for example: *bacillus thuringiensis* strains;

from the class of benzoylureas, for example: bistrifluron, chlofluazuron, chlorfluazuron, diflubenzuron, fluazuron, flucycloxuron, flufenoxuron, hexaflumuron, lufenuron, novaluron, noviflumuron, penfluron, teflubenzuron, triflumuron;

from the class of beta-ketonitrile derivatives, for example: cyenopyrafen, cyflumetofen;

from the class of carbamates, for example: alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, formparanate, furathiocarb, isoprocarb, metam-sodium, methiocarb, methomyl, metolcarb, oxamyl, pirimicarb, promecarb, propoxur, thiodicarb, thiofanox, triazamate, trimethacarb, xmc, xylylcarb;

from the class of chloronicotinyls, for example: acetamiprid, clothianidin, dinotefuran, flupyradifurone, imidacloprid, nicotine, nitenpyram, nithiazine, thiacloprid, thiamethoxam;

from the class of diacylhydrazines, for example: chromafenozide, halofenozide, methoxyfenozide, tebufenozide;

from the class of diamides, for example: chlorantraniliprole, cyantraniliprole;

from the class of dicarboxamides, for example: flubendiamide;

from the class of dinitrophenols, for example: binapacyrl, dinobuton, dinocap, dnoc;

from the class of feeding inhibitors, for example: cryolite, flonicamid, pymetrozine;

from the class of fumigants, for example: aluminium phosphide, methyl bromide, sulphuryl fluoride;

from the class of halogenated carbonhydrogen compounds (hch), for example: DDT, methoxychlor;

from the class of macrocyclic lactones, for example: moxidectin, emamectin benzoate, latidectin, lepimectin;

from the class of microorganisms, for example: *bacillus* spec., *beauveria* spec., *metarrhizium* spec., *paecilomyces* spec., *verticillium* spec.

from the class of mite growth inhibitors, for example: amidoflumet, benclothiaz, benzoximate, bifenazate, bromopropylate, chlordimeform, chlorobenzilate, chloropicrin, clofentezine, clothiazoben, cyclopene, dicyclanil, etoxazole, fenoxacrim, fentrifanil, flubenzimine, flufenerim, flutenzin, gossyplure, hexythiazox, hydramethylnone, japonilure, metoxadiazone, petroleum, potassium oleate, pyridalyl, quinomethionate, tetrasul, triarathene;

from the class of natural products, for example: codlemone, essential oils, thuringiensin;

from the class of neem components, for example: azadirachtin a;

from the class of nereistoxin analogues, for example: bensultap, cartap, sulfoxaflor, thiocyclam, thiocyclam hydrogen oxalate, thiosultap sodium, thiosultap-sodium;

from the class of organic acids, for example: formic acid, oxalic acid;

from the class of organochlorines, for example: camphechlor, chlordane, endosulfan, gamma-HCH, HCH, heptachlor, lindane;

from the class of organophosphates, for example: acephate, aromfenvinfos (-methyl), aromophos-ethyl, autathiofos, azamethiphos, azinphos (-methyl, -ethyl), cadusafos, carbophenothion, chlorethoxyfos, chlorfenvinphos, chlormephos, chlorpyrifos (-methyl/-ethyl), cyanofenphos, cyanophos, demeton-s-methyl, demeton-s-methylsulphone, dialifos, diazinon, dichlofenthion, dichlorvos/ddvp, dicrotophos, dimethoate, dimethylvinphos, dioxabenzofos, disulfoton, epn, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidone, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion;

from the class of organotin compounds, for example: azocyclotin, cyhexatin, fenbutatin-oxide;

from the class of other decouplers, for example: sulfluramid;

from the class of other inhibitors of cuticle development, for example: buprofezin, cyromazine;

from the class of other inhibitors of cuticle development, for example: buprofezin, cyromazine;

from the class of others, for example: chinomethionat, pyrifluquinazon;

from the class of oxadiazines, for example: indoxacarb;

from the class of phenylpyrazoles, for example: acetoprole, ethiprole, fipronil, pyrafluprole, pyriprole, vaniliprole;

from the class of pyrethroids, for example: acrinathrin, allethrin (d-cis-trans, d-trans-), beta-cyfluthrin, bifenthrin, bioallethrin, bioallethrin-s-cyclopentyl-isomer, bioethanomethrin, biopermethrin, bioresmethrin, chlovaporthrin, cis-cypermethrin, cis-permethrin, cis-resmethrin, clocythrin, cycloprothrin, cyfluthrin, cyhalothrin (lambda-), cypermethrin (alpha-, beta-, theta-, zeta-), cyphenothrin, deltamethrin, empenthrin (1r-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1r-trans isomer), prallethrin, profluthrin, protrifenbute, pyresmethrin, pyrethrins (pyrethrum), resmethrin, ru 15525, silafluofen, tau-fluvalinate, tefluthrin, terallethrin, tetramethrin (-1r-isomer), tralomethrin, transfluthrin, zxi 8901;

from the class of pyrroles, for example: chlorfenapyr;

from the class of quinones, for example: acequinocyl;

from the class of rotenone, for example: rotenone;

from the class of semicarbazones, for example: metaflumizone;

from the class of spinosynes, for example: spinetoram, spinosad;

from the class of tetronic and tetramic acids, for example: spirodiclofen, spiromesifen, spirotetramat;

from the class of nereistoxin analogues, for example: bensultap, cartap, sulfoxaflor, thiocyclam, thiocyclam hydrogen oxalate, thiosultap sodium, thiosultap-sodium.

Salts like hydrochlorides, tartrates, citrates, embonates/pamoates or benzoates are included.

Vector Control

The compounds of the formula (I) can also be used in vector control. For the purpose of the present invention, a vector is an arthropod, in particular an insect or arachnid, capable of transmitting pathogens such as, for example, viruses, worms, single-cell organisms and bacteria from a reservoir (plant, animal, human, etc.) to a host. The pathogens can be transmitted either mechanically (for example trachoma by non-stinging flies) to a host, or by injection (for example malaria parasites by mosquitoes) into a host.

Examples of vectors and the diseases or pathogens they transmit are:

1) Mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simuliidae: transmission of worms, in particular *Onchocerca volvulus*;
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia duttoni*, tick-borne encephalitis, Q fever (*Coxiella burnetii*), babesioses (*Babesia canis canis*).

Examples of vectors in the sense of the present invention are insects, for example aphids, flies, leafhoppers or *thrips*, which are capable of transmitting plant viruses to plants. Other vectors capable of transmitting plant viruses are spider mites, lice, beetles and nematodes.

Further examples of vectors in the sense of the present invention are insects and arachnids such as mosquitoes, in particular of the genera *Aedes, Anopheles*, for example *A. gambiae, A. arabiensis, A. funestus, A. dirus* (malaria) and *Culex*, lice, fleas, flies, mites and ticks capable of transmitting pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protecting wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. they can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. Likewise, the compounds of the formula (I), alone or in combinations with other active compounds, can be used as antifouling agents.

Control of Animal Pests in the Hygiene Sector

The compounds of the formula (I) are suitable for controlling animal pests in the hygiene sector. In particular, the invention can be applied in the domestic sector, in the hygiene sector and in the protection of stored products, especially for controlling insects, arachnids and mites encountered in enclosed spaces such as dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

They are used, for example, in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The various aspects of the invention will now be illustrated with reference to the following production and use examples in a non-limiting manner.

PREPARATION EXAMPLES $^1$H-NMR Data $^1$H-NMR-data were determined with a Bruker Avance 400 (Method M1) equipped with a flow cell (60 μl volume) or with a Bruker AVIII 400 equipped with 1.7 mm cryo-CPTCI probe head or with a Bruker AVII 600 (600.13 MHz) equipped with a 5 mm cyroTCI probe head or with a Bruker AVIII 600 (601.6 MHz) equipped with a 5 mm cryo CPMNP probe head with tetramethylsilane as reference (0.0) and the solvents $CD_3CN$, $CDCl_3$ or $D_6$-DMSO.

NMR-data of selected examples are listed in classic format (chemical shift S, multiplicity, number of hydrogen atoms) or as NMR-peak-lists.

The NMR spectra of steps 1 to 5 of preparation 1 have been measured on a Varian 400 MHz Mercury Plus.

Preparation 1:

Step 1:

Synthesis of ethyl (5-bromo-3-chloropyridin-2-yl)-(cyano)acetate

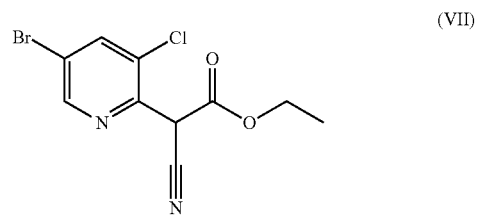 [SMILES: CCOC(=O)C(C#N)c1ncc(Br)cc1Cl]

(VII)

To a suspension of NaH (4.0 g, 1.5 eq.) in DMF (45 ml) at 0° C., ethyl cyanoacetate (10.6 ml, 1.5 eq.) was added and stirred at room temperature for 30 minutes. Then 5-bromo-2,3-dichloropyridine (15.0 g, 1.0 eq.) in DMF (30 ml) was added to the reaction mixture at room temperature and stirred at 80° C. for 4 hours. After completion of the reaction, the reaction mixture was diluted with water and extracted with ethyl acetate. The combined organic layers were washed with water, brine, dried over anhydrous sodium sulphate and the solvent was removed under reduced pressure. The crude product was purified over silica gel (100-200 mesh) column chromatography by eluting with 5% EtOAc/pet ether, this yielded 10.0 g (49.8%).

$^1$H-NMR (400 MHz, $CDCl_3$); δ 1.3 (t, 3H), 4.3 (q, 2H), 5.3 (s, 1H), 8.0 (s, 1H), 8.6 (s, 1H).

Step 2:

Synthesis of (5-bromo-3-chloropyridin-2-yl)acetonitrile

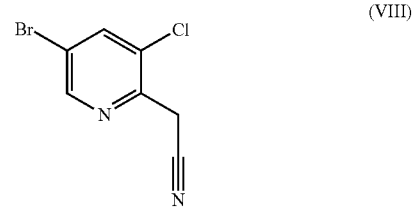 [SMILES: N#CCc1ncc(Br)cc1Cl]

(VIII)

To a solution of ethyl (5-bromo-3-chloropyridin-2-yl)(cyano)acetate (10.0 g, 1.0 eq.) in DMSO (30 ml) and water (5 ml) at room temperature, NaCl (636 mg, 0.33 eq) was added and the reaction mixture was stirred at 170° C. for one hour. After completion of reaction, the reaction mixture was diluted with water and extracted with ethyl acetate. The combined organic layers were washed with water, brine, dried over anhydrous sodium sulphate and the solvent was removed under reduced pressure. The crude product was purified over silica gel (100-200 mesh) column chromatography by eluting with 3% EtOAc/pet ether to yield 7.0 g (91.8%).

$^1$H-NMR (400 MHz, $CDCl_3$); δ 4 (s, 2H) 7.9 (s, 1H), 8.6 (s, 1H).

Step 3:

Synthesis of tert-butyl [2-(5-bromo-3-chloropyridin-2-yl)ethyl]carbamate

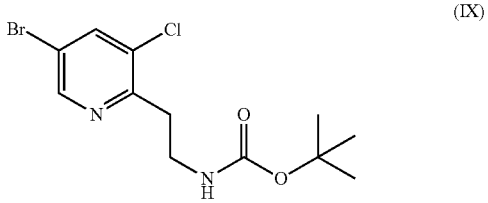 [SMILES: CC(C)(C)OC(=O)NCCc1ncc(Br)cc1Cl]

(IX)

The solution of (5-bromo-3-chloropyridin-2-yl)acetonitrile (2×3.5 g, 1.0 eq.) in methanol (2×28 ml) at 0° C., BOC anhydride (2×3.5 ml, 1.1 eq.), NiCl$_2$.6H$_2$O (2×1.08 g, 0.3 eq.), NaBH$_4$ (2×1.72 g, 3.0 eq.) were added and the reaction mixture was stirred at room temperature for 30 minutes. After completion of reaction the reaction mixture was concentrated under reduced pressure, the residue was diluted with water and extracted with ethyl acetate. The combined organic layers were washed with water, brine, dried over anhydrous sodium sulphate and the solvent was removed under reduced pressure. The crude product was purified over silica gel (100-200 mesh) column chromatography by eluting with 10% EtOAc/pet ether to to yield 5.0 g (49.2%).

$^1$H-NMR (400 MHz, CDCl$_3$); δ 1.4 (s, 9H), 3.1 (m, 2H), 3.6 (m, 2H), 5.1 (br, 1H), 7.8 (s, 1H), 8.5 (s, 1H).

Step 4:

Synthesis of 2-(5-bromo-3-chloropyridin-2-yl)ethanamine hydrochloride

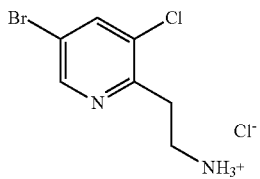

(X)

The solution of tert-butyl [2-(5-bromo-3-chloropyridin-2-yl)ethyl]carbamate (5.0 g, 1.0 eq.) in methanol (30 ml) at room temperature, methanolic HCl (50 ml) was added and the reaction mixture was stirred at 70° C. for one hour. After completion of reaction, the reaction mixture was concentrated under reduced pressure. The crude product was purified by ethyl acetate washings to yield 3.0 g (74%).

$^1$H-NMR (400 MHz, D$_6$-DMSO); δ: 3.2 (m, 4H), 8.2 (br, 2H), 8.4 (s, 1H), 8.6 (s, 1H).

Step 5:

Synthesis of N-[2-(5-bromo-3-chloropyridin-2-yl)ethyl]-2-(trifluoromethyl)benzamide

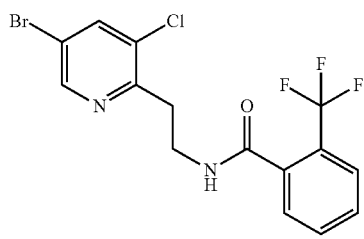 [SMILES: O=C(NCCc1ncc(Br)cc1Cl)c1ccccc1C(F)(F)F]

To a solution of 2-(5-bromo-3-chloropyridin-2-yl)ethanamine hydrochloride (3.0 g, 1.0 eq.) in THF (30 ml) at room temperature, TEA (4.6 ml, 3.0 eq.), 2-trifluoromethyl benzoic acid (2.3 g, 1.1 eq.), EDC.HCl (3.16 g, 1.5 eq.) were added and stirred for 15 minutes. Then HOBT (2.23 g, 1.5 eq.) was added to the reaction mixture and continued the reaction at same temperature for four hours. After completion of reaction, the reaction mixture was diluted with 2N HCl and extracted with ethyl acetate. The combined organic layers were washed with Na$_2$CO$_3$ solution, brine, dried over anhydrous sodium sulphate and the solvent was removed under reduced pressure to yield 3.0 g, (68.2%).

$^1$H-NMR (400 MHz, CDCl$_3$); δ 3.2 (m, 2H), 4 (m, 2H), 6.6 (br, 1H), 7.5-7.6 (m, 3H), 7.7 (m, 1H), 7.8 (s, 1H), 8.4 (s, 1H).

Step 6:

Synthesis of N-{2-[3-chloro-5-(4-chlorophenyl)pyridin-2-yl]ethyl}-2-(trifluoromethyl)benzamide (expl. 1)

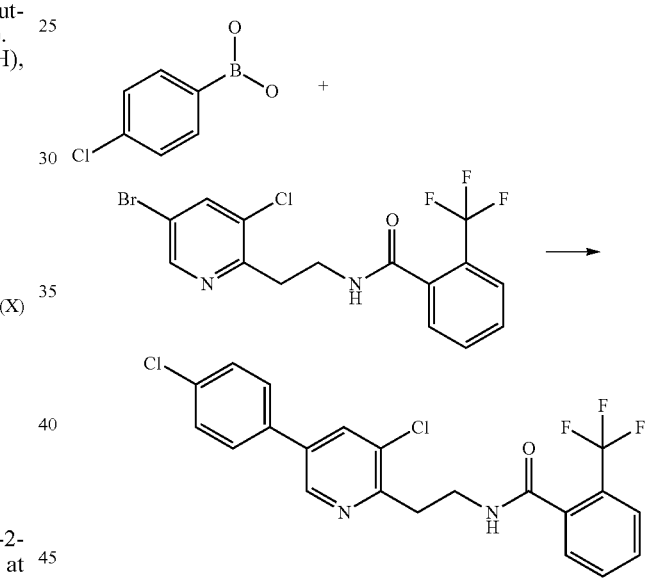

114 mg (0.28 mmol) N-[2-(5-bromo-3-chloropyridin-2-yl)ethyl]-2-(trifluoromethyl)benzamide (from step 5) and 43.8 mg (0.28 mmol) (4-chlorophenyl)boronic acid were dissolved in 3 mL dioxane. Thereafter, 20.7 mg (0.02 mmol) dichloro-bis(tricyclohexylphosphine) palladium-(II) and 182.5 mg (0.56 mmol) cesium carbonate in 0.5 mL water were added and treated in a sealed microwave vial in a Biotage microwave oven (Initiator) at 100° C. for 20 minutes. The reaction mixture was filtered over a silica gel sodium sulfate cartridge, the solvents were evaporated and the crude product was purified by silica gel chromatography (cyclohexane/ethyl acetate gradient) to afford 103 mg (79.9%) of the title compound as off-white solid.

LC-MS (M+H)$^+$=439.0

$^1$H-NMR (400 MHz, d6-DMSO); δ 8.85 (d, 1H), 8.63 (t, NH), 8.25 (d, 1H), 7.84 (d, 2H), 7.77-7.61 (m, 3H), 7.58 (d, 2H), 7.53 (d, 1H), 3.69-3.64 (qu, 2H), 3.19-3.15 (t, 2H).

Preparation 2:
Step 1:

Synthesis of 2-(5-bromo-3-chloropyridin-2-yl)-2,2-difluoroethanamine was performed in analogy to WO 2013/064460 A1 (referred as intermediate IIa-14 and IIa-151

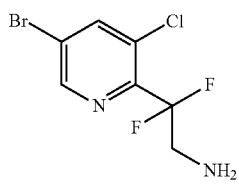

(XVII)

¹H-NMR (400 MHz, d6-DMSO); δ 8.78 (d, J=1.6 Hz, 1H), 8.52 (d, J=2.0 Hz, 1H), 3.37 (t, J=14.8 Hz, 2H), 1.72 (s, 2H).
Step 2a:

Synthesis of N-[2-(5-bromo-3-chloropyridin-2-yl)-2,2-difluoroethyl]-2-(trifluoromethyl)benzamide

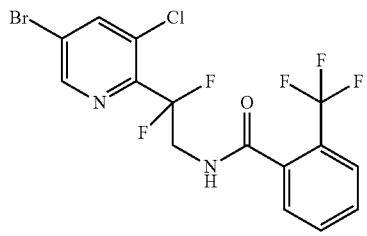 [SMILES: O=C(NCC(F)(F)c1ncc(Br)cc1Cl)c1ccccc1C(F)(F)F]

To a solution of 2-(5-bromo-3-chloropyridin-2-yl)-2,2-difluoroethanamine (2.56 g, 1.03 eq.) in dichloromethane (50 ml) at room temperature, TEA (3.38 ml, 3.0 eq.) and 2-trifluoromethyl benzoic acid chloride (1.68 g, 1.0 eq.) were added and stirred overnight. After completion of reaction, the reaction mixture was diluted with water and extracted with dichloromethane. The solvent of the combined organic layers was evaporated under reduced pressure. The residue was purified by silica gel chromatography (cyclohexane/ethyl acetate) to yield 2.86 g (68.5%) as off-white solid.
LC-MS (M+H)⁺=442.9; 444.9
¹H-NMR (400 MHz, d6-DMSO); δ 8.97 (t, 1H, NH), 8.80 (d, 1H), 8.56 (d, 1H), 7.77-7.63 (m, 3H), 7.45 (d, 1H), 4.28-4.19 (m, 2H).
Step 2b:

Synthesis of 2-[3-chloro-5-(4-fluorophenyl)-2-pyridyl]-2,2-difluoro-ethanamine (expl. INT-1)

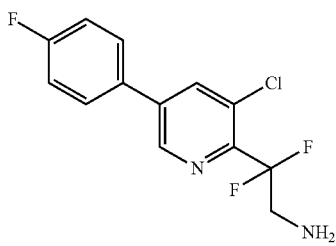 [SMILES: NCC(F)(F)c1ncc(-c2ccc(F)cc2)cc1Cl]

42 mg (0.3 mmol) (4-fluorophenyl)boronic acid and 100 mg (0.3 mmol) 2-(5-bromo-3-chloro-2-pyridyl)-2,2-difluoro-ethanamine from step 1 were dissolved in 4.6 mL dioxane followed by addition of 195.5 mg (0.6 mmol) cesium carbonate in 0.58 mL water and 22.14 mg (0.03 mmol) dichloro-bis(tricyclohexylphosphine)-palladium-(II) catalyst. The reaction mixture was kept under stirring in a closed vial for 16 h at 100° C. The reaction mixture was filtered via a silica gel/sodium sulfate cartridge, solvents have been evaporated under reduced pressure and the remaining yellow-coloured solid was purified by MPLC on silicagel (solvent gradient cyclohexane/ethylacetate) to afford 69 mg the title compound as colorless crystalline solid (yield: 77%).
LC-MS (M+H)⁺=287.0
¹H-NMR (400 MHz, d6-DMSO); δ 8.93 (s, 1H), 8.41 (s, 1H), 7.94-7.90 (dd, 2H), 7.39 (t, 2H), 3.45-3.37 (dd, 2H), 3.33 (m, 2H, NH₂).
Step 3:

Synthesis of N-{2-[3-chloro-5-(4-chlorophenyl)pyridin-2-yl]-2,2-difluoroethyl}-2-(trifluoromethyl)-benzamide (expl. 2)

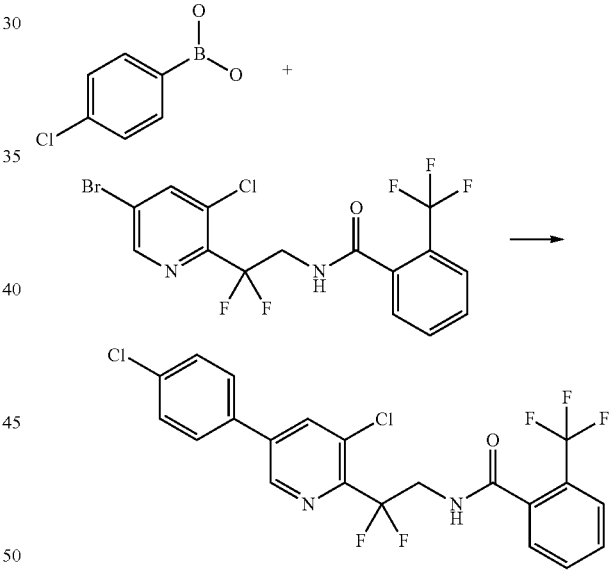

100 mg (0.22 mmol) N-[2-(5-bromo-3-chloropyridin-2-yl)-2,2-difluoroethy]-2-(trifluoromethyl)-benzamide (from step 2a) and 35.2 mg (0.22 mmol) (4-chlorophenyl)boronic acid were dissolved in 3 mL dioxane. Thereafter, 16.6 mg (0.02 mmol) dichlorobis(tricyclohexylphosphine) palladium (II) and 146.6 mg (0.45 mmol) cesium carbonate in 0.44 mL water were added and treated in a sealed microwave vial in a Biotage microwave oven (Initiator) at 100° C. for 20 minutes. The reaction mixture was filtered over a silica gel sodium sulfate cartridge, the solvents were evaporated and the crude product was purified by preparative HPLC to afford 35 mg (32%) of the title compound as off-white solid.
For LC-MS (M+H)⁺ and ¹H-NMR see example table (example 2).

Preparation 3:
Step 1:

Synthesis of ethyl 2-(3-chloro-5-nitropyridin-2-yl)-2-cyanopropanoate

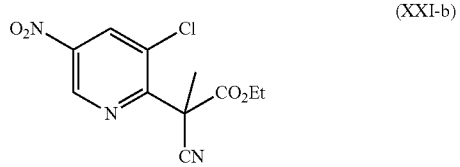 [SMILES: CCOC(=O)C(C)(C#N)c1ncc([N+](=O)[O-])cc1Cl]

(XXI-b)

To a solution of 2,3-dichloro-5-nitropyridine (90 g, 466 mmol) in 500 ml of dimethylformamide, 60 g of ethyl 2-cyanopropanoate (472 mmol) and 150 g of potassium carbonate were added. The resulting reaction mixture was stirred overnight at 60° C. After cooling down, 2.0 L of water were added and the reaction mixture was extracted with ethyl acetate (3×300 ml). The combined organic layers were washed with water (200 ml), brine (200 ml), dried over anhydrous sodium sulphate and concentrated. This afforded 105 g of the title compound (80%), which was used in the next steep without purification.
Step 2:

Synthesis of 2-(3-chloro-5-nitropyridin-2-yl)propanenitrile

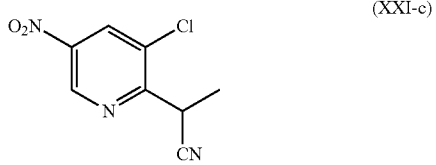

(XXI-c)

A suspension of 105 g of ethyl 2-(3-chloro-5-nitropyridin-2-yl)-2-cyanopropanoate (371 mmol), LiCl (100 g) in dimethylsulfoxide (600 ml) and water (80 ml) were heated at 120° C. overnight. The reaction mixture was then cooled down, diluted with water (3000 ml) and extracted with ethyl acetate (5×300 ml). The combined organic layers were washed with water (2×500 ml), brine (200 ml), dried over anhydrous sodium sulphate and concentrated. The crude product was dissolved in ethanol (500 ml) and charcoal (70 g) was added. The resulting mixture was refluxed overnight under stirring. Then reaction mixture was filtered and concentrated. This afforded 55 g of the title compound (70%).
Step 3:

Synthesis 2-(5-amino-3-chloropyridin-2-yl)propanenitrile

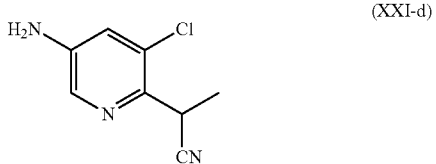

(XXI-d)

To a solution of 55 g of 2-(3-chloro-5-nitropyridin-2-yl)propanenitrile (260 mmol) in mixture of ethanol and water (700 and 5 ml) powdered Fe (146 g, 2.600 mol), NH$_4$Cl (4.5 g) and HCl (10 N, 5 ml) were added. The reaction mixture was stirred for one hour and then refluxed overnight under stirring. On the next day suspension was filtered through a silica pad and the filtrate was concentrated. The residue was dissolved in ethyl acetate (800 ml) and the solution was washed with saturated NaHCO$_3$, water, brine and dried over anhydrous sodium sulphate. Concentration afforded 35 g of the title compound as a crude material which was used in the next step without further purification.
Step 4:

Synthesis 2-(5-bromo-3-chloropyridin-2-yl)propanenitrile

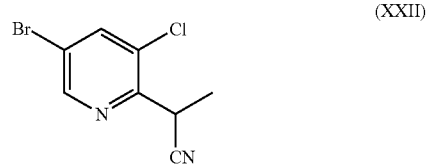

(XXII)

A mixture of CuBr$_2$ (53 g, 237 mmol) and t-BuONO (30 g 291 mmol) in acetonitrile (500 ml) was cooled to −5° C. A solution of 35 g of 2-(5-amino-3-chloropyridin-2-yl)propanenitrile (193 mmol) in acetonitrile was added drop by drop under stirring over 40 min. The reaction mixture was stirred overnight at room temperature and then evaporated. The residue was dissolved in ethyl acetate (800 ml) and 400 ml of saturated aqueous NH$_4$Cl solution were added. The organic layer was separated, washed with water, brine dried over anhydrous sodium sulphate. Evaporation afforded 43 g of the title compound as a crude material which was used in the next step without further purification.
Step 5:

Synthesis 2-(5-bromo-3-chloropyridin-2-yl)-2-fluoropropanenitrile

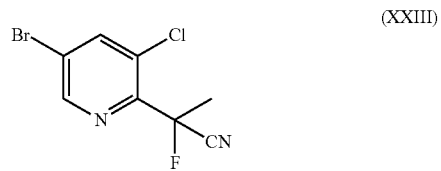

(XXIII)

A solution of 43 g of crude 2-(5-bromo-3-chloropyridin-2-yl)propanenitrile and 61 g of NFSI (N-fluorobenzenesulfonimide) (193 mmol) in tetrahydrofuran (1000 ml) was cooled to −20° C. and 29.4 g of DBU (1,8-diazabicyclo [5.4.0]undec-7-ene) (193 mmol) were added dropwise under stirring. When addition was completed, the reaction mixture was gradually warmed to room temperature during 2 hours. Then the reaction mixture was cooled down to −20° C. again and NFSI (20 g) and DBU (10 g) were added as previously. Then the reaction mixture was stirred for one hour and 1 L of ether was added. The resulting reaction mixture was filtered through a silica pad and the filtrate was concentrated.

The crude material obtained was purified by column on silica to afford 14.5 g of the title compound as a pure material (55 mmol, 31%).

Step 6:

Synthesis 2-(5-bromo-3-chloropyridin-2-yl)-2-fluoropropan-1-amine hydrochloride

(XXIV)

To a solution of 14.5 g of 2-(5-bromo-3-chloropyridin-2-yl)-2-fluoropropanenitrile (55 mmol) in THF (250 ml) at −60° C. a solution of LiAlH$_4$ (2.3 g 60.5 mmol) in THF (300 ml) was added dropwise. The resulting reaction mixture was stirred at the same temperature for one hour. Then a solution of HCl in 1,4-dioxane (10%, 200 ml) was added at −40° C. dropwise under stirring. The resulting solution was evaporated and the residue obtained was purified by chromatography on silica. The material obtained after chromatography column was re-purified by trituration with acetone. This afforded 6.17 g of the title compound (20.3 mmol, 36%).

LC-MS (M+H-HCl)$^+$=267.0

$^1$H-NMR (400 MHz, d6-DMSO); δ 8.69 (s, 1H), 8.44 (s, 1H), 3.72-3.65 (dd, 1H), 3.43-3.36 (t, 1H), 1.81 (d, 3H).

Step 7:

Synthesis of N-[2-(5-bromo-3-chloropyridin-2-yl)-2-fluoropropyl]-2-(trifluoromethyl) benzamide

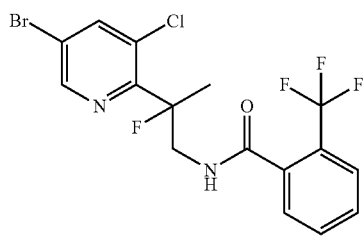 [SMILES: CC(F)(CNC(=O)c1ccccc1C(F)(F)F)c1ncc(Br)cc1Cl]

To a solution of 2-(5-bromo-3-chloropyridin-2-yl)-2-fluoropropan-1-amine hydrochloride (3.0 g, 1.0 eq.) in dichloromethane (50 ml) at room temperature, N—N-diisopropylethylamine (5.2 ml, 3.0 eq.) was added. Then 2-(trifluoromethyl) benzoyl chloride (2.5 g, 1.2 eq.) was added dropwise. After completion of the reaction, the reaction mixture was diluted with water. After dichloromethane extraction, the organic phase was washed with brine and dried over anhydrous sodium sulphate. The solvent was removed under reduced pressure and this afforded 4.6 g of the title compound (97% yield).

LC-MS (M+H)$^+$=439.0; 440.9

$^1$H-NMR (400 MHz, d6-DMSO); δ 8.49 (d, 1H), 7.93 (d, 1H), 7.74-7.48 (m, 4H), 6.42 (s, NH), 4.29-4.14 (m, 2H), 1.90 (d, 3H).

Step 8:

Synthesis of N-{2-[3-chloro-5-(4-fluorophenyl)pyridin-2-yl]-2-fluoropropyl}-2-(trifluoromethyl) benzamide (expl. 21)

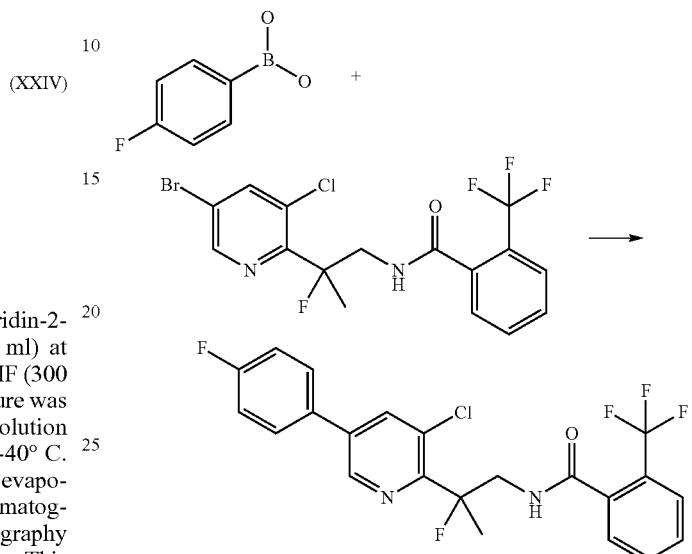

38.5 mg (0.27 mmol) of 4-(fluorophenyl)boronic acid and 120 mg (0.25 mmol) of of N-[2-(5-bromo-3-chloropyridin-2-yl)-2-fluoropropyl]-2-(trifluoromethyl)benzamide from the previous step were dissolved in 3 mL of dioxane followed by addition 0.28 mmol of sodium carbonate (in an aqueous solution), 10.21 mg (0.01 mmol) of 1,1'-bis(diphenylphosphino) ferrocene]dichloropalladium(II) catalyst. The reaction mixture was kept under stirring in a closed vial for 3 h at 80° C. To the reaction mixture was added ethyl acetate. Then the reaction mixture was filtered through a celite layer. The celite was washed with ethyl acetate. The reaction mixture was then dried over anhydrous sodium sulphate. The residue obtained was purified by MPLC on silicagel (solvent gradient cyclohexane/ethylacetate) to afford 53.3 mg the title compound (example 21) (yield: 44%).

For LC-MS (M+H)$^+$ and $^1$H-NMR see example table (example 21).

According to the methods described above, the following compounds of general formula (I) have been prepared.

Compounds of Formula (I-1)

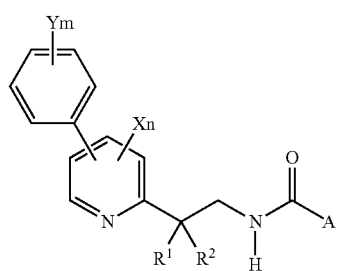

$R^1$, $R^2$, X, Y, n, m and A are as defined by each individual structure.

TABLE 1

| Example no. | Formula | logP [1] (HCOOH) | (M + H)+ (LC/MS) | 1H-NMR |
|---|---|---|---|---|
| 1 | | 3.97[a] | 439.0 | DMSO 8.85 (d, 1H), 8.63 (t, NH), 8.25 (d, 1H), 7.84 (d, 2H), 7.77-7.61 (m, 3H), 7.58 (d, 2H), 7.53 (d, 1H), 3.69-3.64 (qu, 2H), 3.19-3.15 (t, 2H). |
| 2 | | 4.17[a] | 475.0 | NMR peak list |
| 3 | | 4.17[a] | 475.1 | NMR peak list |
| 4 | | 3.78[a] | 507.1 | NMR peak list |
| 5 | | 3.75[a] | 441.0 | NMR peak list |
| 6 | | 3.94[a] | 505.1 | NMR peak list |

TABLE 1-continued

| Example no. | Formula | logP [1]) (HCOOH) | (M + H)+ (LC/MS) | 1H-NMR |
|---|---|---|---|---|
| 7 | | 3.68[a] | 471.1 | NMR peak list |
| 8 | | 3.53[a] | 485.1 | NMR peak list |
| 9 | | 4.00[a] | 455.1 | NMR peak list |
| 10 | | 4.17[a] | 509.1 | NMR peak list |
| 11 | | 4.64[a] | 509.0 511.0 | NMR peak list |
| 12 | | 3.89[a] | 477.1 | NMR peak list |

TABLE 1-continued

| Example no. | Formula | logP [1] (HCOOH) | (M + H)+ (LC/MS) | 1H-NMR |
|---|---|---|---|---|
| 13 | | 3.73[a] | 459.1 | NMR peak list |
| 14 | | 3.84[a] | 477.1 | NMR peak list |
| 15 | | 4.57[a] | 509.0 511.0 | NMR peak list |
| 16 | | 4.00[a] | 475.1 | NMR peak list |
| 17 | | 4.09[a] | 484.1 | NMR peak list |
| 18 | | 3.44[a] | 456.0 | NMR peak list |
| 19 | | 3.51[a] | 460.8 | NMR peak list |

TABLE 1-continued

| Example no. | Formula | logP [1] (HCOOH) | (M + H)+ (LC/MS) | 1H-NMR |
|---|---|---|---|---|
| 20 | | 3.83[a] | 471.9 473.9 | NMR peak list |
| 21 | | 3.96[a] | 455.0 | NMR peak list |
| 22 | | 2.15[a] | 452.0 | NMR peak list |
| 23 | | 3.92[a] | 437.0 | NMR peak list |
| 24 | | 3.74[a] | 459.1 | NMR peak list |
| 25 | | 4.18[a] | 521.1 | NMR peak list |

TABLE 1-continued

| Example no. | Formula | logP [1] (HCOOH) | (M + H)+ (LC/MS) | 1H-NMR |
|---|---|---|---|---|
| 26 | | 3.29[a] | 460.1 | NMR peak list |
| 27 | | 4.38[a] | 470.9 | NMR peak list |
| 28 | | 3.38[a] | 438.0 | NMR peak list |
| 29 | | 4.35[a] | 451.0 | NMR peak list |
| 30 | | 4.83[a] | 510.1 | NMR peak list |
| 31 | | 1.78[a]<br>3.39[b] | 539.0 | NMR peak list |

TABLE 1-continued

| Example no. | Formula | logP [1] (HCOOH) | (M + H)+ (LC/MS) | 1H-NMR |
|---|---|---|---|---|
| 32 | | 3.59[a] | 526.0 | NMR peak list |
| 33 | | 2.65[a] | 519.1 | NMR peak list |
| 34 | | 4.19[a] | 526.9 | NMR peak list |
| 35 | | 4.10[a] | 487.0 | NMR peak list |
| 36 | | 3.39[a] | 470.0 | NMR peak list |
| 37 | | 3.29[a] | 466.0 | NMR peak list |

TABLE 1-continued

| Example no. | Formula | logP [1] (HCOOH) | (M + H)+ (LC/MS) | 1H-NMR |
|---|---|---|---|---|
| 38 | 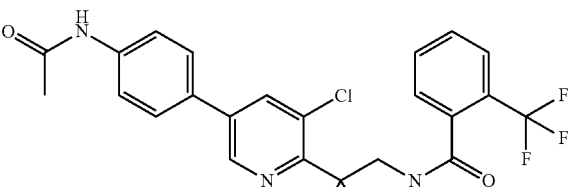 | 2.70[a] | 498.0 | NMR peak list |
| 39 | 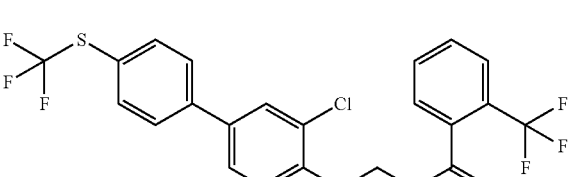 | 4.65[a] | 540.9 | NMR peak list |

Intermediates of Formula (INT-a)

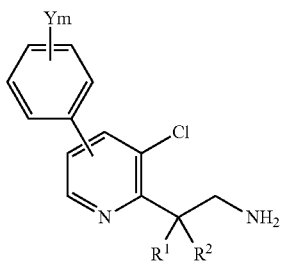

$R^1$, $R^2$, X, Y, n and m are as defined by each individual structure.

In table 1, (M+H)+ or (M−H)− means the molecular ion peak, plus or minus 1 a.m.u. (atomic mass unit) respectively, as observed in mass spectroscopy by electrospray ionization (ESI+ or −).

NMR Peak List of Example Compounds:

1H-NMR-data were determined with a Bruker Avance 400 (Method M1) equipped with a flow cell (60 μl volume) or with a Bruker AVIII 400 equipped with 1.7 mm cryo-CPTCI probe head or with a Bruker AVII 600 (600.13 MHz) equipped with a 5 mm cyroTCI probe head or with a Bruker AVIII 600 (601.6 MHz) equipped with a 5 mm cryo CPMNP probe head with tetramethylsilane as reference (0.0) and the solvents $CD_3CN$, $CDCl_3$ or $D_6$-DMSO.

1H-NMR data of selected examples are written in form of 1H-NMR-peak lists. To each signal peak are listed the

TABLE 2

| Example no. | Formula | logP [1] (HCOOH) | (M + H)+ (LC/MS) | 1H-NMR |
|---|---|---|---|---|
| INT-1 | 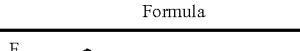 | 1.18[a] 2.61[b] | 287.0 | 1H-NMR (400 MHz, d6-DMSO); δ 8.93 (s, 1H), 8.41 (s, 1H), 7.94-7.90 (dd, 2H), 7.39 (t, 2H), 3.45-3.37 (dd, 2H), 3.33 (m, 2H, $NH_2$). |

[1] Measurement of LogP values was performed according to EEC directive 79/831 Annex V.A8 by HPLC (High Performance Liquid Chromatography) on reversed phase columns with the following methods:
[a] logP value is determined by measurement of LC-UV, in an acidic range, with 0.1% formic acid in water and acetonitrile as eluent (linear gradient from 10% acetonitrile to 95% acetonitrile).
[b] logP value is determined by measurement of LC-UV, in a neutral range, with 0.001 molar ammonium acetate solution in water and acetonitrile as eluent (linear gradient from 10% acetonitrile to 95% acetonitrile).

Calibration was done with straight-chain alkan2-ones (with 3 to 16 carbon atoms) with known Log P values (measurement of Log P values using retention times with linear interpolation between successive alkanones). Lambda-max-values were determined using UV-spectra from 200 nm to 400 nm and the peak values of the chromatographic signals.

δ-value in ppm and the signal intensity in round brackets. Between the δ-value—signal intensity pairs are semicolons as delimiters.

The peak list of an example has therefore the form:

$\delta_1$ (intensity$_1$); $\delta_2$ (intensity$_2$); . . . ; $\delta_i$ (intensity$_i$); . . . ; $\delta_n$ (intensity$_n$)

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily.

The $^1$H-NMR peak lists are similar to classical $^1$H-NMR prints and contains therefore usually all peaks, which are listed at classical NMR-interpretation.

Additionally they can show like classical $^1$H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

Patent Applications" of the Research Disclosure Database Number 564025.

TABLE 3

NMR Peaklist of examples from Table 1

Example 2: $^1$H-NMR (400.0 MHz, d$_6$-DMSO):
δ = 9.012 (2.3); 8.987 (5.1); 8.982 (11.8); 8.476 (9.5); 8.471 (9.7); 8.317 (1.3); 7.927 (1.5); 7.920 (13.4); 7.916 (4.9); 7.904 (4.7); 7.899 (15.7); 7.781 (4.5); 7.762 (6.3); 7.752 (2.2); 7.732 (5.1); 7.714 (3.7); 7.669 (3.7); 7.650 (4.7); 7.631 (3.5); 7.624 (16.0); 7.620 (5.3); 7.608 (4.3); 7.603 (13.7); 7.484 (5.3); 7.465 (4.6); 7.446 (0.3); 4.352 (1.9); 4.336 (2.0); 4.314 (4.6); 4.299 (4.4); 4.277 (2.3); 4.261 (2.2); 3.327 (478.7); 2.676 (1.8); 2.671 (2.6); 2.667 (2.0); 2.542 (0.6); 2.524 (5.2); 2.520 (8.3); 2.511 (138.6); 2.507 (293.7); 2.502 (397.7); 2.498 (296.6); 2.493 (149.3); 2.338 (0.9); 2.333 (1.9); 2.329 (2.6); 2.324 (2.0); 2.075 (0.6); 0.008 (0.5); 0.000 (19.2); −0.008 (0.8)

Example 3: $^1$H-NMR (400.0 MHz, d$_6$-DMSO):
δ = 9.014 (13.8); 9.009 (14.7); 8.988 (3.0); 8.523 (12.4); 8.519 (12.6); 7.989 (11.4); 7.869 (0.6); 7.866 (0.7); 7.859 (3.4); 7.854 (3.6); 7.846 (6.6); 7.841 (4.0); 7.837 (4.4); 7.832 (4.0); 7.826 (1.0); 7.821 (0.7); 7.784 (6.1); 7.765 (8.3); 7.755 (3.0); 7.736 (6.8); 7.717 (4.8); 7.672 (4.8); 7.653 (6.2); 7.634 (2.3); 7.598 (1.1); 7.577 (14.5); 7.573 (9.0); 7.567 (14.8); 7.564 (16.0); 7.553 (1.2); 7.488 (7.2); 7.469 (6.3); 4.356 (2.7); 4.341 (2.8); 4.319 (6.3); 4.303 (6.0); 4.281 (3.1); 4.266 (2.9); 3.328 (168.0); 2.676 (0.9); 2.671 (1.2); 2.667 (0.9); 2.542 (65.1); 2.525 (3.5); 2.511 (72.9); 2.507 (145.5); 2.502 (192.0); 2.498 (143.4); 2.494 (73.0); 2.368 (0.3); 2.334 (0.9); 2.329 (1.3); 2.325 (1.0); 1.259 (0.3); 1.234 (0.7); 0.008 (0.6); 0.000 (16.6); −0.008 (0.7)

Example 4: $^1$H-NMR (400.0 MHz, d$_6$-DMSO):
δ = 9.012 (2.6); 8.997 (5.5); 8.980 (12.6); 8.975 (11.4); 8.457 (10.8); 8.452 (10.7); 7.966 (1.7); 7.958 (14.7); 7.954 (5.2); 7.941 (5.2); 7.936 (16.0); 7.929 (1.8); 7.783 (5.2); 7.764 (7.1); 7.753 (2.5); 7.734 (5.9); 7.715 (4.1); 7.670 (4.1); 7.651 (5.3); 7.632 (1.9); 7.549 (5.4); 7.486 (6.2); 7.468 (5.4); 7.365 (12.4); 7.355 (14.1); 7.333 (13.3); 7.180 (5.6); 4.355 (2.2); 4.340 (2.3); 4.318 (5.2); 4.302 (5.0); 4.280 (2.6); 4.265 (2.4); 3.329 (193.1); 2.676 (0.9); 2.671 (1.2); 2.667 (0.9); 2.541 (71.0); 2.524 (3.5); 2.511 (72.3); 2.507 (143.7); 2.502 (188.2); 2.498 (138.5); 2.494 (68.9); 2.333 (0.9); 2.329 (1.2); 2.324 (0.9); 1.259 (0.4); 1.234 (0.7); 0.008 (0.6); 0.000 (17.9); −0.008 (0.7)

Example 5: $^1$H-NMR (400.0 MHz, d$_6$-DMSO):
δ = 9.012 (3.3); 8.997 (6.9); 8.980 (16.0); 8.975 (14.5); 8.804 (0.6); 8.799 (0.6); 8.566 (0.6); 8.444 (13.5); 8.440 (13.3); 7.872 (13.7); 7.854 (15.5); 7.783 (6.9); 7.763 (9.6); 7.755 (3.9); 7.735 (7.7); 7.716 (5.4); 7.670 (5.6); 7.651 (7.3); 7.631 (2.7); 7.570 (5.4); 7.553 (14.9); 7.534 (12.6); 7.520 (8.3); 7.509 (2.8); 7.503 (7.0); 7.488 (9.4); 7.469 (7.0); 7.448 (0.5); 7.428 (0.4); 6.937 (0.4); 6.916 (0.4); 4.359 (3.1); 4.344 (3.3); 4.322 (7.2); 4.306 (6.9); 4.284 (3.7); 4.269 (3.4); 4.243 (0.5); 4.228 (0.5); 3.968 (0.4); 3.500 (0.4); 3.481 (0.5); 3.470 (0.3); 3.427 (0.6); 3.414 (0.8); 3.396 (0.8); 3.326 (407.9); 3.188 (0.4); 2.711 (0.5); 2.675 (2.9); 2.671 (3.7); 2.541 (93.5); 2.506 (451.1); 2.502 (569.2); 2.497 (433.4); 2.368 (0.5); 2.333 (2.8); 2.328 (3.6); 1.299 (0.4); 1.258 (0.5); 1.235 (1.4); 0.000 (45.4)

Example 5: $^1$H-NMR (400.0 MHz, d$_6$-DMSO):
δ = 9.036 (0.4); 9.016 (3.3); 9.000 (6.9); 8.980 (14.7); 8.975 (14.7); 8.443 (13.7); 8.439 (14.1); 8.318 (0.7); 7.875 (10.6); 7.872 (14.5); 7.854 (16.0); 7.782 (6.7); 7.763 (9.5); 7.755 (3.8); 7.735 (7.7); 7.716 (5.4); 7.670 (5.5); 7.651 (7.2); 7.631 (2.8); 7.574 (3.7); 7.570 (5.7); 7.566 (3.0); 7.553 (15.8); 7.534 (13.2); 7.524 (5.3); 7.520 (8.7); 7.509 (2.8); 7.503 (7.5); 7.489 (9.1); 7.470 (7.9); 4.360 (3.0); 4.345 (3.1); 4.323 (7.0); 4.307 (6.8); 4.286 (3.6); 4.270 (3.5); 3.331 (190.8); 2.676 (0.9); 2.672 (1.3); 2.667 (1.0); 2.525 (3.5); 2.507 (143.9); 2.503 (189.0); 2.498 (143.7); 2.334 (0.9); 2.329 (1.3); 2.325 (1.0); 0.146 (1.1); 0.008 (9.5); 0.000 (222.2); −0.008 (12.3); −0.150 (1.1)

Example 6: $^1$H-NMR (400.0 MHz, d$_6$-DMSO):
δ = 9.004 (0.7); 8.988 (1.6); 8.982 (3.3); 8.977 (3.3); 8.468 (2.9); 8.463 (2.9); 8.028 (3.1); 8.022 (3.3); 7.879 (1.5); 7.874 (1.4); 7.858 (1.6); 7.852 (1.5); 7.784 (1.4); 7.764 (1.9); 7.752 (0.7); 7.734 (1.7); 7.716 (1.1); 7.671 (1.1); 7.652 (1.4); 7.633 (0.5); 7.486 (1.7); 7.468 (1.4); 7.316 (2.7); 7.294 (2.5); 4.345 (0.6); 4.329 (0.6); 4.308 (1.4); 4.292 (1.3); 4.270 (0.7); 4.255 (0.7); 3.932 (16.0); 3.888 (0.7); 3.384 (0.3); 3.335 (333.2); 2.676 (0.6); 2.671 (0.8); 2.667 (0.6); 2.542 (48.9); 2.525 (2.1); 2.511 (47.0); 2.507 (95.3); 2.502 (126.6); 2.498 (93.9); 2.493 (47.0); 2.333 (0.6); 2.329 (0.8); 2.324 (0.6); 1.235 (0.3); 0.000 (2.3)

Example 7: $^1$H-NMR (400.0 MHz, d$_6$-DMSO):
δ = 8.997 (0.5); 8.981 (1.1); 8.966 (0.6); 8.941 (2.3); 8.936 (2.3); 8.383 (2.3); 8.379 (2.3); 7.846 (3.2); 7.841 (1.1); 7.828 (1.1); 7.823 (3.5); 7.816 (0.4); 7.782 (1.1); 7.762 (1.5); 7.752 (0.5); 7.733 (1.3); 7.714 (0.9); 7.669 (0.9); 7.650 (1.2); 7.631 (0.4); 7.485 (1.3); 7.466 (1.1); 7.113 (0.4); 7.106 (3.5); 7.101 (1.1); 7.089 (1.1); 7.084 (3.4); 7.076 (0.3); 4.346 (0.5); 4.330 (0.5); 4.309 (1.1); 4.293 (1.1); 4.271 (0.6); 4.255 (0.5); 3.828 (16.0); 3.334 (278.1); 2.676 (0.6); 2.671 (0.8); 2.667 (0.6); 2.541 (16.1); 2.524 (2.2); 2.511 (47.1); 2.507 (95.8); 2.502 (127.1); 2.498 (93.3); 2.493 (45.7); 2.333 (0.6); 2.329 (0.8); 2.324 (0.6); 0.000 (1.9)

TABLE 3-continued

NMR Peaklist of examples from Table 1

Example 8: $^1$H-NMR (400.0 MHz, d$_6$-DMSO):
δ = 8.998 (1.0); 8.983 (2.1); 8.967 (1.1); 8.925 (4.0); 8.920 (4.2); 8.377 (4.0); 8.372 (4.1); 7.783 (2.1); 7.763 (2.9); 7.752 (1.0); 7.733 (2.4); 7.715 (1.7); 7.670 (1.7); 7.650 (2.2); 7.632 (0.8); 7.513 (4.2); 7.509 (4.6); 7.484 (2.5); 7.465 (2.1); 7.399 (2.2); 7.395 (2.1); 7.379 (2.4); 7.374 (2.4); 7.089 (4.3); 7.069 (3.9); 6.114 (16.0); 4.341 (0.9); 4.325 (1.0); 4.304 (2.1); 4.288 (2.0); 4.266 (1.1); 4.251 (1.0); 3.330 (162.5); 2.675 (0.6); 2.671 (0.8); 2.667 (0.6); 2.541 (25.4); 2.506 (92.9); 2.502 (121.6); 2.498 (92.6); 2.333 (0.6); 2.329 (0.8); 2.325 (0.6); 1.235 (0.4); 0.000 (6.6)

Example 9: $^1$H-NMR (400.0 MHz, d$_6$-DMSO):
δ = 9.023 (0.7); 9.008 (1.5); 8.993 (0.7); 8.643 (3.1); 8.638 (3.3); 8.179 (3.2); 8.175 (3.3); 7.783 (1.6); 7.764 (2.1); 7.750 (0.7); 7.731 (1.8); 7.712 (1.2); 7.671 (1.3); 7.652 (1.6); 7.633 (0.6); 7.485 (1.9); 7.467 (1.6); 7.392 (1.0); 7.386 (1.3); 7.373 (4.7); 7.361 (0.9); 7.357 (0.9); 7.338 (1.6); 7.332 (1.5); 7.324 (3.2); 7.319 (3.0); 7.307 (0.6); 4.375 (0.7); 4.359 (0.7); 4.338 (1.6); 4.322 (1.6); 4.300 (0.8); 4.285 (0.8); 3.392 (0.4); 3.332 (361.5); 2.675 (0.8); 2.671 (1.1); 2.667 (0.8); 2.541 (17.9); 2.524 (3.0); 2.506 (129.9); 2.502 (171.9); 2.497 (129.4); 2.333 (0.8); 2.329 (1.1); 2.324 (0.8); 2.261 (16.0); 1.235 (0.4); 0.000 (2.5)

Example 10: $^1$H-NMR (400.0 MHz, d$_6$-DMSO):
δ = 9.063 (14.6); 9.058 (14.8); 9.025 (3.7); 9.010 (7.6); 8.994 (3.8); 8.605 (15.0); 8.600 (14.8); 8.233 (12.5); 8.194 (6.7); 8.174 (7.3); 7.879 (5.4); 7.859 (8.7); 7.807 (6.4); 7.787 (16.0); 7.767 (13.5); 7.756 (4.2); 7.736 (8.4); 7.718 (6.0); 7.673 (5.9); 7.654 (7.5); 7.635 (2.9); 7.494 (8.7); 7.475 (7.6); 4.366 (3.3); 4.350 (3.5); 4.329 (7.6); 4.313 (7.4); 4.291 (4.0); 4.276 (3.6); 3.413 (0.5); 3.399 (0.5); 3.331 (303.9); 2.676 (1.2); 2.672 (1.5); 2.667 (1.1); 2.542 (44.2); 2.507 (180.9); 2.503 (229.6); 2.498 (173.9); 2.334 (1.2); 2.330 (1.5); 2.325 (1.1); 1.299 (0.3); 1.259 (0.5); 1.234 (1.0); 0.008 (0.8); 0.000 (14.5)

Example 11: $^1$H-NMR (400.0 MHz, d$_6$-DMSO):
δ = 9.053 (6.2); 9.048 (6.4); 9.025 (1.5); 9.010 (3.1); 8.994 (1.5); 8.592 (6.3); 8.587 (6.3); 8.008 (15.3); 8.003 (16.0); 7.787 (3.1); 7.767 (4.3); 7.759 (4.6); 7.755 (8.2); 7.751 (4.1); 7.737 (3.5); 7.718 (2.4); 7.674 (2.4); 7.654 (3.1); 7.636 (1.2); 7.488 (3.6); 7.469 (3.1); 4.352 (1.3); 4.337 (1.4); 4.315 (3.1); 4.300 (2.9); 4.278 (1.5); 4.262 (1.4); 3.331 (112.4); 2.676 (0.4); 2.672 (0.5); 2.667 (0.4); 2.542 (54.2); 2.525 (1.4); 2.512 (29.4); 2.507 (59.2); 2.503 (78.5); 2.498 (58.0); 2.494 (28.6); 2.334 (0.4); 2.329 (0.5); 2.325 (0.4); 1.233 (0.4); 0.000 (5.1)

Example 12: $^1$H-NMR (400.0 MHz, d$_6$-DMSO):
δ = 9.061 (14.8); 9.057 (14.9); 9.025 (3.6); 9.009 (7.4); 8.994 (3.6); 8.569 (14.9); 8.564 (14.6); 7.785 (7.4); 7.765 (10.8); 7.756 (4.9); 7.738 (16.0); 7.723 (12.6); 7.718 (14.5); 7.707 (2.0); 7.673 (6.1); 7.654 (7.7); 7.635 (2.9); 7.484 (8.9); 7.466 (7.8); 7.431 (2.0); 7.426 (3.2); 7.421 (1.9); 7.408 (4.1); 7.403 (6.4); 7.398 (3.7); 7.385 (2.2); 7.380 (3.3); 4.353 (3.3); 4.337 (3.4); 4.316 (7.8); 4.300 (7.4); 4.278 (3.9); 4.262 (3.6); 3.331 (201.9); 2.676 (0.7); 2.672 (1.0); 2.667 (0.7); 2.542 (56.9); 2.525 (2.4); 2.511 (63.7); 2.507 (122.4); 2.503 (158.4); 2.498 (117.2); 2.368 (0.4); 2.334 (0.8); 2.330 (1.1); 2.325 (0.8); 1.258 (0.4); 1.233 (0.8); 0.000 (9.0); −0.008 (0.4)

Example 13: $^1$H-NMR (400.0 MHz, d$_6$-DMSO):
δ = 9.027 (4.1); 9.012 (8.1); 8.996 (3.8); 8.841 (16.0); 8.731 (0.9); 8.726 (0.9); 8.349 (15.0); 8.300 (0.9); 8.295 (0.9); 7.858 (0.9); 7.854 (0.9); 7.783 (8.3); 7.764 (11.5); 7.750 (4.0); 7.743 (4.6); 7.738 (5.5); 7.732 (10.1); 7.723 (8.8); 7.719 (9.7); 7.714 (7.8); 7.704 (4.8); 7.699 (4.7); 7.671 (6.8); 7.652 (8.6); 7.633 (3.3); 7.614 (1.0); 7.609 (1.2); 7.605 (1.6); 7.594 (1.9); 7.590 (2.0); 7.581 (2.3); 7.576 (4.5); 7.572 (4.2); 7.562 (3.4); 7.558 (4.6); 7.555 (5.3); 7.550 (3.2); 7.541 (3.0); 7.537 (2.7); 7.481 (9.8); 7.462 (8.6); 7.445 (6.3); 7.424 (5.2); 7.418 (7.6); 7.413 (8.4); 7.394 (13.1); 7.375 (5.0); 7.373 (4.7); 4.367 (3.8); 4.351 (3.8); 4.330 (8.7); 4.314 (8.3); 4.293 (4.4); 4.277 (4.0); 3.416 (0.4); 3.400 (0.4); 3.331 (276.3); 2.997 (0.4); 2.712 (1.4); 2.676 (1.0); 2.672 (1.4); 2.667 (1.1); 2.542 (314.5); 2.525 (3.9); 2.511 (78.9); 2.507 (156.3); 2.502 (204.1); 2.498 (149.9); 2.494 (74.3); 2.368 (1.4); 2.334 (1.0); 2.329 (1.3); 2.325 (1.0); 1.258 (0.4); 1.234 (0.7); 0.008 (0.5); 0.000 (13.0); −0.009 (0.5)

Example 14: $^1$H-NMR (400.0 MHz, d$_6$-DMSO):
δ = 9.011 (13.8); 9.006 (16.0); 8.987 (3.0); 8.509 (12.3); 8.504 (12.1); 8.101 (2.7); 8.096 (2.8); 8.082 (3.0); 8.076 (3.3); 8.071 (3.1); 8.066 (2.9); 8.052 (2.7); 8.046 (2.7); 7.784 (8.7); 7.776 (3.4); 7.767 (12.0); 7.756 (4.7); 7.735 (7.1); 7.717 (5.0); 7.672 (5.1); 7.663 (3.7); 7.653 (6.7); 7.642 (5.6); 7.637 (5.2); 7.620 (3.0); 7.616 (5.2); 7.594 (2.2); 7.485 (7.4); 7.466 (6.4); 4.351 (2.8); 4.336 (2.8); 4.314 (6.4); 4.298 (6.1); 4.276 (3.2); 4.261 (3.0); 3.331 (234.5); 2.712 (0.4); 2.676 (0.9); 2.672 (1.2); 2.667 (0.9); 2.542 (99.0); 2.525 (3.3); 2.507 (139.2); 2.503 (180.3); 2.498 (132.2); 2.368 (0.4); 2.334 (0.9); 2.329 (1.2); 2.325 (0.9); 1.259 (0.3); 1.234 (0.8); 0.008 (0.4); 0.000 (10.6); −0.008 (0.4)

Example 15: $^1$H-NMR (400.0 MHz, d$_6$-DMSO):
δ = 9.038 (2.3); 9.022 (4.8); 9.007 (2.3); 8.730 (10.3); 8.725 (10.3); 8.317 (0.4); 8.300 (10.6); 8.295 (10.2); 7.860 (9.3); 7.855 (9.7); 7.785 (4.7); 7.765 (6.3); 7.745 (2.0); 7.728 (5.3); 7.709 (3.8); 7.672 (3.9); 7.652 (4.8); 7.635 (3.7); 7.630 (2.6); 7.614 (11.2); 7.609 (12.7); 7.605 (16.0); 7.584 (2.4); 7.475 (5.6); 7.456 (4.8); 6.918 (0.4); 4.374 (2.2); 4.358 (2.2); 4.336 (4.9); 4.321 (4.8); 4.299 (2.6); 4.283 (2.2); 3.966 (0.4); 3.713 (0.4); 3.602 (0.4); 3.581 (0.4); 3.562 (0.4); 3.514 (0.5); 3.501 (0.6); 3.481 (0.6); 3.468 (0.7); 3.450 (0.5); 3.424 (0.9); 3.410 (1.7); 3.395 (1.9); 3.328 (1214.5); 3.189 (0.4); 2.711 (0.9); 2.697 (0.3); 2.675 (4.9); 2.671 (6.6); 2.666 (4.9); 2.646 (0.5); 2.636 (0.4); 2.631 (0.5); 2.625 (0.5); 2.621 (0.5); 2.615 (0.5); 2.604 (0.6); 2.541 (186.3); 2.524 (21.6); 2.510 (396.7); 2.506 (771.2); 2.502 (999.6); 2.497 (728.5); 2.493 (357.4); 2.423 (0.5); 2.408 (0.4); 2.367 (0.8); 2.333 (4.7); 2.328 (6.4); 2.324 (4.7); 2.288 (0.5); 1.299 (0.7); 1.258 (1.0); 1.235 (2.5); 1.056 (0.4); 1.041 (0.4); 0.854 (0.3); 0.008 (2.1); 0.000 (54.0); −0.008 (2.0)

Example 16: $^1$H-NMR (400.0 MHz, d$_6$-DMSO):
δ = 9.040 (3.2); 9.025 (6.9); 9.009 (3.3); 8.732 (13.8); 8.728 (14.6); 8.300 (1.4); 8.295 (1.5); 8.286 (13.3); 8.282 (13.5); 7.859 (1.2); 7.854 (1.2); 7.786 (6.8); 7.767 (9.3); 7.748 (3.0); 7.730 (7.6); 7.711 (5.5); 7.683 (0.8); 7.672 (11.3); 7.667 (6.1); 7.654 (12.5); 7.650 (11.7); 7.635 (3.0); 7.614 (1.4); 7.609 (1.6); 7.605 (2.1); 7.584 (2.4); 7.578 (4.0); 7.572 (3.3); 7.567 (4.0); 7.563 (4.9); 7.555 (10.7); 7.550 (4.2); 7.546 (2.1); 7.538 (10.4); 7.531 (14.1); 7.523 (16.0); 7.513 (8.3); 7.510 (5.9); 7.496 (1.4); 7.491 (1.0); 7.480 (7.9); 7.461 (6.9); 4.382 (2.9); 4.366 (3.0); 4.344 (6.7); 4.329 (6.6); 4.307 (3.5); 4.291 (3.2); 3.413 (0.3); 3.329 (170.9); 2.711 (0.3); 2.676 (0.8); 2.671 (1.1); 2.667 (0.8); 2.542 (80.2); 2.524 (2.8); 2.511 (60.7); 2.507 (122.5); 2.502 (162.2); 2.498 (119.9); 2.493 (59.6); 2.368 (0.4); 2.333 (0.8); 2.329 (1.1); 2.324 (0.8); 1.235 (0.7); 0.008 (0.5); 0.000 (16.0); −0.008 (0.6)

Example 17: $^1$H-NMR (400.0 MHz, d$_6$-DMSO):
δ = 8.980 (0.4); 8.964 (0.7); 8.949 (0.4); 8.901 (1.4); 8.896 (1.4); 8.296 (1.4); 8.291 (1.4); 7.782 (0.7); 7.762 (1.0); 7.750 (0.5); 7.743 (1.9); 7.732 (1.0); 7.726 (0.8); 7.720 (2.1); 7.713 (0.8); 7.668 (0.6); 7.649 (0.7); 7.487 (0.8); 7.468 (0.7); 6.837 (1.8); 6.814 (1.8); 4.298 (0.7); 4.283 (0.7); 4.261 (0.3); 4.246 (0.3); 3.342 (146.2); 2.983 (16.0); 2.526 (0.6); 2.512 (14.0); 2.508 (28.1); 2.503 (37.1); 2.499 (27.5); 2.494 (13.7); 2.075 (0.4); 0.008 (1.5); 0.000 (42.1); −0.009 (1.7)

Example 18: $^1$H-NMR (400.0 MHz, CDCl$_3$):
δ = 8.756 (3.7); 8.745 (3.5); 8.595 (5.9); 8.592 (6.3); 7.915 (9.7); 7.894 (3.9); 7.561 (3.7); 7.554 (5.4); 7.549 (5.7); 7.541 (7.9); 7.532 (7.1); 7.520 (5.4); 7.262 (40.5); 7.222 (0.9); 7.214 (4.9); 7.193 (8.9); 7.171 (4.3); 6.660 (1.3); 6.647 (2.1); 4.383 (0.9); 4.368 (0.9); 4.348 (1.7); 4.332 (2.2); 4.315 (0.9); 4.296 (1.8); 4.280 (1.9); 4.274 (1.9); 4.258 (1.7); 4.239 (2.6); 4.223 (2.6); 4.204 (1.0); 4.189 (0.8); 1.956 (15.9); 1.903 (16.0); 1.843 (0.7); 1.557 (42.0); 1.254 (0.6); 0.000 (38.8)

Example 19: $^1$H-NMR (400.0 MHz, d$_6$-DMSO):
δ = 9.266 (2.5); 9.251 (5.2); 9.235 (2.5); 9.027 (8.2); 9.022 (10.0); 8.973 (10.4); 8.967 (9.5); 8.962 (11.3); 8.958 (10.9); 8.471 (10.9); 8.466 (10.9); 8.317 (2.5); 7.965 (0.8); 7.957 (7.4); 7.952 (3.4); 7.944 (8.3); 7.935 (8.9); 7.927 (3.5); 7.921 (8.1); 7.914 (0.9); 7.426 (0.8); 7.419 (8.4); 7.414 (2.8); 7.396 (16.0); 7.379 (2.6); 7.374 (7.9); 7.366 (0.8); 4.441 (2.4); 4.426 (2.4); 4.404 (5.6); 4.388 (5.4); 4.366 (2.8); 4.350 (2.6); 3.345 (246.7); 2.678 (0.6); 2.673 (0.8); 2.669 (0.6); 2.527 (1.9); 2.513 (46.8); 2.509 (95.8); 2.504 (126.3); 2.500 (92.7); 2.496 (46.2); 2.335 (0.6); 2.331 (0.8); 2.327 (0.6); 2.076 (0.7); 0.146 (0.6); 0.008 (4.6); 0.000 (138.5); −0.009 (5.3); −0.150 (0.6)

TABLE 3-continued

NMR Peaklist of examples from Table 1

Example 20: ¹H-NMR (400.0 MHz, CDCl₃):
δ = 8.608 (0.4); 8.604 (0.5); 7.931 (0.5); 7.926 (0.5); 7.493 (1.3); 7.484 (1.4); 7.265 (17.7); 1.955 (1.2); 1.901 (1.2); 1.638 (6.8); 1.626 (16.0); 0.008 (0.5); 0.000 (15.0)

Example 21: ¹H-NMR (601.6 MHz, CDCl₃):
δ = 8.602 (5.8); 8.599 (5.7); 7.908 (6.2); 7.905 (6.1); 7.771 (1.5); 7.688 (3.3); 7.675 (3.9); 7.588 (1.3); 7.576 (3.5); 7.563 (2.9); 7.554 (0.8); 7.549 (4.9); 7.545 (2.6); 7.540 (7.4); 7.534 (5.9); 7.526 (7.9); 7.516 (5.2); 7.503 (2.8); 7.294 (0.5); 7.289 (0.6); 7.283 (0.6); 7.279 (1.0); 7.274 (0.7); 7.268 (0.9); 7.263 (11.5); 7.208 (0.6); 7.203 (4.9); 7.200 (1.7); 7.189 (8.9); 7.178 (1.7); 7.175 (4.4); 7.170 (0.5); 6.788 (1.0); 6.783 (1.0); 6.774 (1.0); 6.768 (1.0); 6.607 (1.1); 6.597 (1.9); 6.588 (1.1); 4.361 (1.0); 4.351 (1.0); 4.338 (1.6); 4.327 (2.4); 4.317 (1.0); 4.304 (1.6); 4.293 (1.5); 4.259 (1.5); 4.249 (1.6); 4.235 (2.3); 4.224 (2.3); 4.211 (1.1); 4.201 (1.0); 1.946 (16.0); 1.911 (16.0); 1.885 (0.7); 1.849 (0.6); 1.643 (2.5); 1.265 (0.6); 1.254 (1.1); 0.005 (2.4); 0.000 (45.7); −0.005 (2.1)

Example 22: ¹H-NMR (400.0 MHz, CDCl₃):
δ = 8.719 (2.6); 8.714 (2.7); 8.636 (3.0); 8.632 (3.2); 8.219 (0.5); 7.936 (3.3); 7.932 (3.4); 7.785 (1.8); 7.779 (1.8); 7.765 (1.8); 7.759 (1.9); 7.690 (1.7); 7.671 (2.1); 7.596 (0.6); 7.581 (1.7); 7.562 (1.8); 7.542 (1.6); 7.524 (4.5); 7.505 (1.7); 7.307 (2.6); 7.287 (2.6); 7.263 (25.1); 7.162 (0.4); 7.156 (0.4); 7.079 (0.7); 7.058 (0.4); 6.560 (0.6); 6.547 (1.1); 6.532 (0.6); 5.302 (1.7); 4.381 (0.5); 4.365 (0.5); 4.346 (0.9); 4.330 (1.3); 4.315 (0.5); 4.295 (0.9); 4.280 (0.9); 4.271 (0.9); 4.255 (0.9); 4.234 (1.2); 4.219 (1.2); 4.199 (0.5); 4.183 (0.4); 2.654 (0.4); 2.637 (16.0); 2.629 (3.0); 2.497 (3.6); 2.101 (0.4); 2.064 (0.4); 2.057 (0.4); 2.047 (0.5); 2.006 (0.4); 1.959 (8.8); 1.905 (8.7); 0.000 (22.7)

Example 23: ¹H-NMR (400.0 MHz, CDCl₃):
δ = 8.646 (5.4); 8.641 (5.4); 7.951 (6.1); 7.946 (5.9); 7.691 (2.7); 7.672 (3.6); 7.593 (1.0); 7.577 (7.6); 7.572 (3.1); 7.559 (10.8); 7.539 (2.7); 7.521 (9.4); 7.499 (8.7); 7.480 (4.5); 7.468 (2.1); 7.464 (3.4); 7.461 (1.9); 7.453 (1.1); 7.447 (3.2); 7.439 (0.6); 7.428 (0.8); 7.262 (118.1); 6.998 (0.7); 6.585 (1.6); 4.375 (0.8); 4.360 (0.8); 4.340 (1.7); 4.325 (2.3); 4.310 (0.8); 4.290 (1.8); 4.279 (2.0); 4.275 (2.0); 4.264 (1.7); 4.243 (2.2); 4.227 (2.2); 4.207 (0.8); 4.192 (0.7); 1.963 (16.0); 1.910 (16.0); 1.573 (163.5); 1.426 (7.2); 1.413 (1.0); 1.264 (0.5); 1.254 (0.5); 1.248 (0.5); 1.107 (2.9); 0.146 (0.5); 0.000 (114.9); −0.008 (4.1); −0.150 (0.5)

Example 24: ¹H-NMR (400.0 MHz, d₆-DMSO):
δ = 9.014 (2.6); 8.999 (5.4); 8.983 (2.8); 8.970 (11.0); 8.966 (10.9); 8.450 (11.1); 8.445 (10.8); 8.318 (1.1); 7.953 (7.7); 7.948 (3.6); 7.940 (8.7); 7.931 (9.1); 7.923 (3.8); 7.917 (8.1); 7.910 (0.9); 7.783 (5.4); 7.763 (7.4); 7.753 (2.6); 7.734 (6.1); 7.716 (4.3); 7.670 (4.3); 7.651 (5.4); 7.632 (2.0); 7.487 (6.4); 7.468 (5.6); 7.421 (1.0); 7.413 (8.4); 7.408 (2.9); 7.391 (16.0); 7.374 (2.9); 7.369 (7.7); 7.361 (0.8); 4.354 (2.4); 4.338 (2.5); 4.316 (5.4); 4.301 (5.3); 4.279 (2.8); 4.263 (2.6); 3.330 (164.2); 3.307 (0.6); 2.676 (1.1); 2.672 (1.4); 2.667 (1.1); 2.525 (4.4); 2.511 (81.7); 2.507 (159.1); 2.503 (205.4); 2.498 (150.6); 2.334 (1.0); 2.329 (1.3); 2.325 (1.0); 0.008 (2.1); 0.000 (54.6); −0.008 (2.1)

Example 25: ¹H-NMR (400.0 MHz, d₆-DMSO):
δ = 9.022 (3.3); 9.007 (7.0); 8.987 (14.9); 8.982 (14.4); 8.477 (14.1); 8.472 (14.1); 8.316 (3.5); 8.017 (14.8); 8.013 (15.2); 7.784 (6.6); 7.763 (15.0); 7.758 (8.6); 7.742 (9.7); 7.737 (14.8); 7.717 (5.3); 7.672 (5.3); 7.653 (6.7); 7.634 (2.5); 7.607 (16.0); 7.586 (12.5); 7.486 (7.8); 7.467 (6.8); 4.354 (2.9); 4.338 (2.9); 4.316 (6.6); 4.301 (6.4); 4.279 (3.3); 4.263 (3.1); 3.415 (0.4); 3.396 (0.7); 3.344 (778.5); 3.320 (4.2); 2.677 (1.0); 2.673 (1.3); 2.669 (1.0); 2.526 (3.6); 2.513 (74.3); 2.508 (150.5); 2.504 (198.5); 2.499 (145.7); 2.495 (72.1); 2.335 (0.9); 2.331 (1.3); 2.326 (0.9); 0.008 (2.0); 0.000 (61.4); −0.008 (2.3)

Example 26: ¹H-NMR (400.0 MHz, d₆-DMSO):
δ = 9.187 (2.8); 9.172 (5.8); 9.156 (2.8); 8.972 (11.0); 8.967 (11.0); 8.807 (6.0); 8.797 (6.1); 8.460 (11.5); 8.456 (11.2); 8.318 (0.5); 7.955 (11.9); 7.941 (9.9); 7.933 (16.0); 7.925 (5.3); 7.920 (8.6); 7.805 (5.3); 7.793 (5.3); 7.786 (4.5); 7.774 (4.2); 7.417 (8.4); 7.395 (16.0); 7.372 (7.8); 4.386 (2.5); 4.370 (2.6); 4.348 (5.8); 4.333 (5.6); 4.311 (3.0); 4.295 (2.8); 3.330 (144.5); 2.676 (1.1); 2.672 (1.4); 2.667 (1.1); 2.507 (170.5); 2.503 (216.4); 2.498 (161.4); 2.334 (1.1); 2.329 (1.5); 2.325 (1.1); 2.076 (0.4); 0.008 (2.3); 0.000 (51.6); −0.008 (2.8)

Example 27: ¹H-NMR (601.6 MHz, CDCl₃):
δ = 19.953 (0.7); 8.615 (6.1); 8.612 (6.0); 7.916 (6.9); 7.913 (6.7); 7.687 (3.5); 7.675 (3.9); 7.588 (1.3); 7.576 (3.5); 7.563 (2.9); 7.537 (2.6); 7.520 (5.2); 7.509 (7.8); 7.495 (14.7); 7.478 (14.3); 7.464 (5.2); 7.434 (0.7); 7.263 (112.6); 7.087 (0.6); 6.548 (1.7); 5.302 (0.7); 4.351 (1.1); 4.340 (0.9); 4.328 (1.5); 4.318 (2.3); 4.307 (1.1); 4.294 (1.5); 4.284 (1.6); 4.259 (1.6); 4.248 (1.7); 4.234 (2.3); 4.224 (2.2); 4.211 (1.1); 4.201 (0.9); 1.945 (16.0); 1.910 (15.9); 1.597 (17.0); 1.591 (19.7); 1.584 (25.4); 1.578 (30.5); 1.575 (22.7); 1.254 (1.0); 0.000 (86.7); −0.100 (0.5)

Example 28: ¹H-NMR (601.6 MHz, CDCl₃):
δ = 19.949 (0.6); 8.753 (3.0); 8.745 (2.8); 8.634 (4.8); 8.491 (0.5); 7.962 (5.1); 7.959 (5.2); 7.905 (2.7); 7.893 (2.9); 7.572 (4.9); 7.559 (7.0); 7.546 (2.5); 7.541 (2.4); 7.532 (2.0); 7.512 (3.1); 7.501 (6.1); 7.488 (3.7); 7.465 (2.4); 7.453 (2.8); 7.441 (1.0); 7.263 (49.5); 6.688 (1.5); 4.368 (0.7); 4.359 (0.7); 4.345 (1.1); 4.335 (1.5); 4.324 (0.7); 4.311 (1.1); 4.299 (1.1); 4.267 (1.2); 4.256 (1.2); 4.244 (1.9); 4.234 (1.7); 4.222 (0.9); 4.211 (0.8); 1.954 (10.9); 1.919 (10.8); 1.886 (1.1); 1.851 (1.0); 1.604 (16.0); 1.595 (20.2); 1.589 (20.9); 1.587 (21.6); 1.584 (19.8); 1.253 (1.1); 0.069 (2.7); 0.000 (42.7)

Example 29: ¹H-NMR (400.0 MHz, CDCl₃):
δ = 8.626 (3.5); 8.621 (3.6); 7.927 (3.9); 7.922 (3.8); 7.688 (1.8); 7.670 (2.3); 7.590 (0.6); 7.574 (1.9); 7.567 (0.9); 7.555 (2.0); 7.536 (1.7); 7.518 (4.8); 7.500 (1.8); 7.474 (4.7); 7.454 (6.1); 7.309 (4.8); 7.289 (3.8); 7.262 (47.0); 6.605 (0.6); 6.590 (1.1); 6.578 (0.6); 4.365 (0.5); 4.349 (0.5); 4.330 (1.1); 4.315 (1.4); 4.299 (0.5); 4.280 (1.1); 4.271 (1.2); 4.265 (1.2); 4.256 (1.2); 4.235 (1.4); 4.219 (1.4); 4.200 (0.5); 4.184 (0.5); 2.432 (0.4); 2.416 (16.0); 1.956 (10.1); 1.902 (10.1); 1.575 (31.7); 0.008 (1.6); 0.000 (43.9); −0.008 (1.8)

Example 30: ¹H-NMR (400.0 MHz, d₆-DMSO):
δ = 8.974 (1.9); 8.959 (4.1); 8.943 (1.9); 8.892 (7.2); 8.888 (7.5); 8.317 (0.5); 8.278 (7.4); 8.273 (7.4); 7.781 (3.7); 7.761 (5.2); 7.749 (2.0); 7.736 (10.3); 7.732 (7.8); 7.714 (12.6); 7.667 (3.0); 7.648 (3.8); 7.629 (1.0); 7.486 (4.4); 7.468 (4.0); 6.662 (9.2); 6.640 (9.0); 4.331 (1.6); 4.316 (1.6); 4.294 (3.6); 4.279 (3.5); 4.257 (1.8); 4.241 (1.7); 3.327 (205.1); 3.316 (7.1); 3.299 (15.4); 3.283 (5.0); 3.254 (0.4); 3.236 (0.5); 2.983 (0.6); 2.676 (1.1); 2.671 (1.6); 2.667 (1.2); 2.662 (0.6); 2.524 (4.3); 2.511 (84.9); 2.506 (172.8); 2.502 (230.6); 2.497 (172.0); 2.493 (86.4); 2.333 (1.1); 2.329 (1.6); 2.324 (1.2); 2.075 (1.4); 2.010 (0.6); 1.995 (6.0); 1.986 (7.1); 1.979 (16.0); 1.971 (7.1); 1.962 (5.9); 1.948 (1.0); 1.251 (3.7); 1.233 (0.9); 0.146 (1.1); 0.008 (8.6); 0.000 (258.3); −0.009 (10.6); −0.150 (1.2)

Example 31: ¹H-NMR (400.0 MHz, d₆-DMSO):
δ = 8.985 (1.1); 8.970 (2.2); 8.954 (1.1); 8.915 (3.7); 8.911 (3.8); 8.332 (3.8); 8.327 (3.8); 8.317 (0.7); 7.780 (2.2); 7.760 (3.7); 7.754 (5.3); 7.732 (7.2); 7.712 (1.8); 7.667 (1.7); 7.648 (2.2); 7.628 (0.8); 7.484 (2.5); 7.466 (2.2); 7.071 (4.5); 7.049 (4.3); 4.337 (0.9); 4.321 (1.0); 4.300 (2.0); 4.284 (1.9); 4.262 (1.1); 4.247 (1.0); 3.327 (285.7); 3.263 (4.4); 3.251 (6.0); 3.238 (4.7); 2.671 (2.2); 2.506 (242.1); 2.502 (316.4); 2.498 (246.3); 2.465 (5.7); 2.453 (6.8); 2.441 (4.8); 2.329 (2.1); 2.227 (16.0); 2.075 (0.7); 0.146 (1.2); 0.008 (9.8); 0.000 (239.2); −0.150 (1.2)

Example 32: ¹H-NMR (400.0 MHz, d₆-DMSO):
δ = 8.990 (2.4); 8.975 (5.1); 8.959 (2.4); 8.925 (9.4); 8.921 (9.7); 8.344 (9.7); 8.340 (9.7); 8.313 (2.1); 7.779 (14.8); 7.761 (10.5); 7.757 (14.0); 7.732 (5.2); 7.714 (3.6); 7.669 (3.9); 7.650 (4.7); 7.631 (1.6); 7.485 (5.4); 7.467 (4.7); 7.087 (11.5); 7.064 (10.9); 6.543 (0.4); 4.340 (2.1); 4.324 (2.2); 4.303 (4.6); 4.287 (4.4); 4.265 (2.4); 4.250 (2.2); 3.947 (2.2); 3.768 (12.4); 3.756 (16.0); 3.743 (13.7); 3.560 (1.3); 3.361 (5408.7); 3.278 (2.0); 3.231 (12.7); 3.218 (15.6); 3.206 (11.7); 3.168 (0.4); 3.149 (0.4); 2.678 (3.7); 2.673 (5.2); 2.669 (3.9); 2.527 (12.9); 2.522 (20.2); 2.513 (283.3); 2.509 (586.5); 2.504 (782.5); 2.500 (579.1); 2.495 (287.2); 2.335 (3.7); 2.331 (5.2); 2.326 (3.8); 1.262 (0.7); 1.069 (11.0); 0.146 (2.3); 0.008 (17.5); 0.000 (568.5); −0.009 (22.4); −0.150 (2.5)

TABLE 3-continued

NMR Peaklist of examples from Table 1

Example 33: 1H-NMR (400.0 MHz, d6-DMSO):
=9.056 (10.9); 9.034 (2.9); 9.018 (5.7); 9.003 (2.8); 8.572 (10.9); 8.318 (0.5); 8.160 (9.1); 8.139 (15.9); 8.087 (16.0); 8.067 (9.7); 8.056 (4.4); 8.045 (3.7); 8.024 (0.8); 7.784 (5.4); 7.765 (7.5); 7.736 (6.1); 7.717 (4.3); 7.672 (4.4); 7.653 (5.6); 7.634 (2.1); 7.489 (6.4); 7.471 (5.6); 4.367 (2.4); 4.352 (2.6); 4.330 (5.3); 4.315 (5.1); 4.293 (2.8); 4.278 (2.6); 4.038 (0.5); 4.020 (0.5); 3.332 (218.9); 3.299 (45.9); 3.289 (10.5); 2.671 (1.9); 2.503 (284.3); 2.330 (1.9); 1.990 (1.9); 1.193 (0.6); 1.175 (1.0); 1.158 (0.5); 0.000 (34.2)

Example 34: 1H-NMR (400.0 MHz, d6-DMSO):
=9.046 (15.5); 9.041 (16.0); 9.028 (3.8); 9.013 (7.5); 8.997 (3.6); 8.600 (15.9); 8.596 (15.5); 8.318 (0.8); 8.273 (10.8); 8.256 (10.3); 8.251 (8.5); 8.245 (5.3); 7.785 (7.4); 7.766 (10.1); 7.754 (3.5); 7.743 (5.1); 7.736 (9.6); 7.717 (12.8); 7.705 (1.7); 7.693 (4.3); 7.673 (5.9); 7.654 (7.5); 7.635 (2.8); 7.492 (8.8); 7.474 (7.6); 4.361 (3.2); 4.345 (3.3); 4.323 (7.5); 4.307 (7.2); 4.285 (3.8); 4.270 (3.5); 3.331 (126.5); 2.677 (0.9); 2.672 (1.3); 2.668 (0.9); 2.664 (0.5); 2.526 (3.1); 2.512 (71.9); 2.508 (146.0); 2.503 (191.4); 2.499 (139.5); 2.495 (68.0); 2.335 (0.9); 2.330 (1.3); 2.326 (0.9); 1.990 (1.1); 1.398 (3.1); 1.234 (2.5); 1.194 (0.3); 1.176 (0.6); 0.146 (0.7); 0.008 (5.2); 0.000 (152.8); −0.009 (5.7); −0.150 (0.7)

Example 35: 1H-NMR (400.0 MHz, d6-DMSO):
=9.006 (2.6); 8.990 (5.5); 8.971 (11.9); 8.967 (11.3); 8.430 (10.8); 8.425 (10.9); 8.318 (0.7); 7.837 (14.2); 7.816 (16.0); 7.782 (5.1); 7.762 (7.0); 7.752 (2.5); 7.733 (5.8); 7.714 (4.2); 7.669 (4.2); 7.650 (5.3); 7.631 (2.0); 7.486 (6.2); 7.467 (5.4); 7.416 (15.8); 7.394 (14.6); 4.349 (2.3); 4.334 (2.3); 4.312 (5.1); 4.297 (5.0); 4.275 (2.6); 4.259 (2.4); 4.038 (0.4); 4.020 (0.4); 3.332 (182.1); 2.712 (0.4); 2.676 (1.4); 2.672 (1.9); 2.667 (1.4); 2.566 (0.6); 2.538 (71.1); 2.525 (5.4); 2.507 (214.8); 2.503 (279.3); 2.498 (207.1); 2.361 (0.4); 2.334 (1.3); 2.329 (1.8); 2.325 (1.4); 1.989 (1.7); 1.398 (2.4); 1.193 (0.5); 1.175 (0.9); 1.157 (0.5); 0.146 (0.8); 0.008 (6.2); 0.000 (171.7); −0.008 (7.4); −0.150 (0.8)

Example 36: 1H-NMR (400.0 MHz, d6-DMSO):
=8.976 (0.6); 8.961 (1.2); 8.945 (0.6); 8.865 (2.3); 8.860 (2.4); 8.249 (2.4); 8.245 (2.4); 7.781 (1.2); 7.762 (1.6); 7.749 (0.5); 7.731 (1.3); 7.713 (0.9); 7.667 (1.3); 7.660 (3.3); 7.644 (1.6); 7.639 (3.4); 7.631 (0.8); 7.485 (1.4); 7.466 (1.2); 6.662 (3.3); 6.640 (3.3); 6.182 (0.3); 6.169 (1.1); 6.157 (1.0); 6.144 (0.3); 4.330 (0.5); 4.315 (0.5); 4.293 (1.2); 4.277 (1.1); 4.255 (0.6); 4.240 (0.6); 3.937 (2.3); 3.334 (52.0); 2.738 (6.2); 2.726 (6.2); 2.525 (0.7); 2.512 (14.5); 2.507 (29.9); 2.503 (39.5); 2.498 (28.9); 2.494 (14.2); 1.069 (16.0); 0.008 (0.8); 0.000 (25.4); −0.009 (1.0)

Example 37: 1H-NMR (400.0 MHz, d6-DMSO):
=9.056 (8.3); 9.052 (8.6); 9.028 (2.1); 9.013 (4.3); 8.997 (2.0); 8.568 (8.6); 8.564 (8.5); 8.317 (0.4); 8.103 (7.9); 8.082 (16.0); 8.039 (16.0); 8.018 (8.1); 7.781 (4.2); 7.762 (5.8); 7.753 (2.1); 7.733 (4.7); 7.715 (3.3); 7.670 (3.3); 7.651 (4.2); 7.632 (1.6); 7.485 (5.0); 7.466 (4.3); 4.359 (1.8); 4.343 (1.9); 4.322 (4.2); 4.306 (4.0); 4.284 (2.1); 4.269 (2.0); 4.038 (0.4); 4.020 (0.4); 3.332 (190.7); 2.676 (0.8); 2.672 (1.1); 2.668 (0.8); 2.525 (2.7); 2.507 (120.4); 2.503 (157.4); 2.498 (117.3); 2.334 (0.8); 2.330 (1.0); 2.325 (0.8); 1.989 (1.6); 1.193 (0.4); 1.175 (0.9); 1.157 (0.4); 0.008 (1.9); 0.000 (55.8); −0.008 (2.4)

Example 38: 1H-NMR (400.0 MHz, d6-DMSO):
=10.158 (3.6); 9.003 (1.0); 8.987 (2.1); 8.972 (1.1); 8.952 (3.8); 8.949 (3.9); 8.393 (3.8); 8.389 (3.8); 7.840 (3.6); 7.818 (5.9); 7.782 (2.0); 7.761 (3.3); 7.751 (6.3); 7.730 (5.0); 7.715 (1.8); 7.669 (1.6); 7.650 (2.2); 7.631 (1.0); 7.484 (2.4); 7.466 (2.1); 4.346 (0.9); 4.331 (1.0); 4.309 (2.0); 4.294 (1.9); 4.272 (1.1); 4.256 (1.0); 4.038 (0.4); 4.020 (0.4); 3.334 (72.1); 2.672 (0.5); 2.503 (70.3); 2.329 (0.5); 2.082 (16.0); 2.056 (0.7); 1.989 (1.6); 1.193 (0.4); 1.175 (0.8); 1.157 (0.4); 0.000 (19.7)

Example 39: 1H-NMR (400.0 MHz, d6-DMSO):
=9.057 (0.3); 9.036 (10.4); 9.031 (11.4); 9.013 (5.1); 8.998 (2.4); 8.540 (10.2); 8.535 (9.9); 8.318 (0.4); 8.040 (12.0); 8.019 (16.0); 7.936 (0.5); 7.931 (0.4); 7.915 (0.4); 7.894 (13.5); 7.874 (10.4); 7.851 (0.4); 7.783 (4.8); 7.763 (6.6); 7.754 (2.4); 7.734 (5.4); 7.716 (3.8); 7.671 (3.9); 7.652 (5.0); 7.633 (1.9); 7.487 (5.6); 7.468 (4.9); 4.363 (2.1); 4.347 (2.2); 4.326 (4.8); 4.310 (4.6); 4.288 (2.5); 4.273 (2.3); 3.385 (0.4); 3.335 (340.1); 2.677 (0.9); 2.672 (1.2); 2.668 (0.9); 2.525 (3.6); 2.512 (72.9); 2.508 (140.6); 2.503 (180.0); 2.499 (131.9); 2.334 (0.9); 2.330 (1.2); 2.325 (0.9); 1.398 (0.6); 1.311 (3.1); 0.008 (2.8); 0.000 (66.7); −0.008 (2.7)

Biological Examples

In Vitro Assay with *Nippostrongylus brasiliensis* (NIPOBR)

Adult *Nippostrongylus brasiliensis* were washed with saline buffer containing 100 U/ml penicillin, 0.1 mg/ml streptomycin and 2.5 µg/ml amphotericin B. Test compounds were dissolved in DMSO and worms were incubated in medium in a final concentration of 10 µg/ml (10 ppm) respectively 1 µg/ml (1 ppm). An aliquot of the medium was used to determine the acetylcholine esterase activity in comparison to a negative control. The principle of measuring acetylcholine esterase as readout for anthelmintic activity was described in Rapson et al (1986) and Rapson et al (1987).

For the following examples, activity (reduction of AChE compared to negative control) was 60% or higher at 10 ppm: 1, 3, 4, 5, 7, 8, 11, 12, 14, 15, 16, 18, 24

For the following examples, activity (reduction of AChE compared to negative control) was 60% or higher at 1 ppm: 1, 2, 3, 4, 5, 7, 8, 10, 11, 12, 13, 14, 15, 16, 24

In Vitro Assay with *Cooperia curticei* (COOPCU)
Solvent: Dimethyl Sulfoxide

To produce a suitable preparation of active compound, 10 mg of active compound are dissolved in 0.5 ml solvent, and the concentrate is diluted with "Ringer's solution" to the desired concentration.

Approximately 40 nematode larvae (*Cooperia curticei*) are transferred into a test tube containing the compound solution.

After 5 days percentage of larval mortality is recorded. 100% efficacy means all larvae are killed; 0% efficacy means no larvae are killed.

In this test for example, the following compounds from the preparation examples showed good activity of 100% at an application rate of 20 ppm: 1, 2, 3, 4, 5, 6, 7, 8, 9, 10, 11, 12, 13, 14, 15, 16, 17, 18, 19, 24, 30, 31, 32

In Vitro Assay with *Haemonchus contortus* (HAEMCO)
Solvent: Dimethyl Sulfoxide

To produce a suitable preparation of active compound, 10 mg of active compound are dissolved in 0.5 ml solvent, and the concentrate is diluted with "Ringer's solution" to the desired concentration.

Approximately 40 larvae of the red stomach worm (*Haemonchus contortus*) are transferred into a test tube containing compound solution.

After 5 days percentage of larval mortality are recorded. 100% efficacy means all larvae are killed, 0% efficacy means no larvae are killed.

In this test for example, the following compounds from the preparation examples showed good activity of 100% at an application rate of 20 ppm: 1, 2, 3, 4, 5, 6, 7, 8, 9, 10, 11, 12, 13, 14, 15, 16, 17, 18, 19, 24, 31

In this test for example, the following compounds from the preparation examples showed good activity of 90% at an application rate of 20 ppm: 30

*Meloidogyne incognita* (MELGIN) Assay

Solvent: 125.0 parts by weight of acetone

To produce a suitable preparation of active compound, 1 part by weight of active compound is mixed with the stated amount of solvent, and the concentrate is diluted with water to the desired concentration.

Vessels are filled with sand, a solution of the active ingredient, a suspension containing eggs and larvae of the southern root-knot nematode (*Meloidogyne incognita*) and salad seeds. The salad seeds germinate and the seedlings grow. Galls develop in the roots.

After 14 days the nematicidal activity is determined on the basis of the percentage of gall formation. 100% means no galls were found and 0% means the number of galls found on the roots of the treated plants was equal to that in untreated control plants.

In this test, for example, the following compounds from the preparation examples showed good activity of 100% at an application rate of 20 ppm: 1, 4, 7, 8, 9, 14, 18, 21, 24, 26

In this test, for example, the following compounds from the preparation examples showed good activity of 90% at an application rate of 20 ppm: 5, 6, 11, 15, 19

In Vivo Efficacy Test

*Haemonchus contortus/Trichostrongylus Colubriformis/Gerbil*

Gerbils, experimentally infected with *Haemonchus* and/or *Trichostrongylus*, were treated once during late prepatency. Test compounds were formulated as solutions or suspensions and applied parenterally or orally.

Efficacy was determined per group as reduction of worm count in stomach and small intestine, respectively, after necropsy compared to worm count in an infected and placebo-treated control group.

The following examples were tested and had an activity of 75% or higher at the given treatment (see table 4):

TABLE 4

| Treatment | Haemonchus | Trichostrongylus |
| --- | --- | --- |
| 20 mg/kg intraperitoneally | 12, 14 | 14 |
| 10 mg/kg intraperitoneally | 24 | 24 |
| 20 mg/kg subcutaneous | 24 | 24 |
| 50 mg/kg orally | 1 | |

Formulation Examples

An example for a formulation according to the present invention is the following:

| | |
| --- | --- |
| 8 mg | compound of Example 14 |
| 0.2 mL | diethylene glycol monoethyl ether |
| 0.2 mL | Polyoxyl 35 Castor Oil |
| 1.6 mL | physiological sodium chloride solution |

An example for a preparation of such a formulation is as follows. The compound of the present invention was dissolved in 1 part diethylene glycol monoethyl ether and mixed with 1 part Polyoxyl 35 Castor Oil and 8 parts physiological sodium chloride solution.

Such a formulation is suitable for oral or parenteral application.

Formulations of other compounds of the present invention can be prepared in an analogue way and show analogue or identical compositions.

Comparative Example

In Vitro Assay with *Haemonchus contortus* (HAEMCO)

Solvent: Dimethyl Sulfoxide

To produce a suitable preparation of active compound, 10 mg of active compound are dissolved in 0.5 ml solvent, and the concentrate is diluted with "Ringer's solution" to the desired concentration.

Approximately 40 larvae of the red stomach worm (*Haemonchus contortus*) are transferred into a test tube containing compound solution.

After 5 days percentage of larval mortality are recorded. 100% efficacy means all larvae are killed, 0% efficacy means no larvae are killed.

In this test, for example, the following compound from the preparation example show a superior level of activity compared to the prior state of the art: see table 5

TABLE 5

| Substance | Structure | Object | Concentration | % Efficacy | dat |
| --- | --- | --- | --- | --- | --- |
| Ex.-No. 1-49 | | HAEMCO | 20 ppm | 80 | 5dat |
| Known from WO2012/118139 | | | 4 ppm | 60 | 5dat |
| | | | 0.8 ppm | 60 | 5dat |

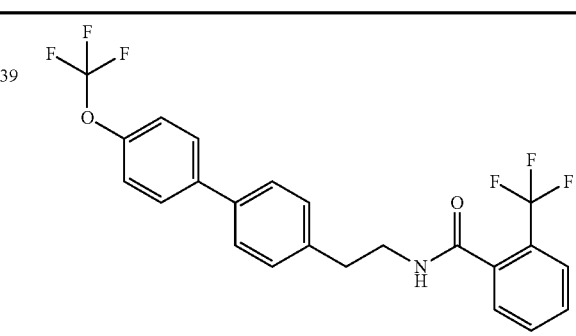

TABLE 5-continued

| Substance | Structure | Object | Concentration | % Efficacy | dat |
|---|---|---|---|---|---|
| Ex.-No. 1 From table 1 | | HAEMCO | 20 ppm<br>4 ppm<br>0.8 ppm | 100<br>100<br>100 | 5dat<br>5dat<br>5dat |
| Ex.-No. 24 From table 1 | | HAEMCO | 20 ppm<br>4 ppm<br>0.8 ppm | 100<br>100<br>100 | 5dat<br>5dat<br>5dat |

The invention claimed is:

1. A compound of formula (I)

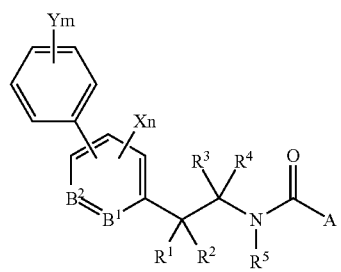

or a salt, N-oxide, metal complex or metalloid complex thereof,
wherein
$B^1$ and $B^2$ are C—X or N, wherein at least one of $B^1$ or $B^2$ is N,
n is 0, 1, 2, 3 or 4, limited by the number of available positions in the ring to which a substituent X can be connected,
each X is independently selected from the group consisting of hydrogen, halogen, nitro, cyano, hydroxy, amino, —SH, —SF$_5$, —CHO, —OCHO, —NHCHO, —COOH, —CONH$_2$, —CONH(OH), —OCONH$_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_8$-halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON($C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(O$C_1$-$C_8$-alkyl), —OCO(O$C_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, ($C_1$-$C_6$-alkoxyimino)-$C_1$-$C_6$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)-$C_1$-$C_6$-alkyl, benzyloxy, —S-benzyl, benzylamino, phenoxy, —S-phenyl and phenylamino,
m is 0, 1, 2, 3, 4 or 5, and
each Y is independently selected from the group consisting of hydrogen, halogen, nitro, cyano, hydroxy, amino, —SH, —SF$_5$, —CHO, —OCHO, —NHCHO, —COOH, —CONH$_2$, —CONH(OH), —OCONH$_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, wherein both alkyl residues may form a 4- to 7-membered heterocycle incorporating the nitrogen bonded to the phenyl system of the compound, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_8$-halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON($C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(O$C_1$-$C_8$-alkyl), —OCO(O$C_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, —CH$_2$—S—$C_1$-$C_8$-alkyl, —CH$_2$—S(O)—$C_1$-$C_8$-alkyl, —CH$_2$—S(O)$_2$—$C_1$-$C_8$-alkyl, ($C_1$-$C_6$-alkoxyimino)-$C_1$-$C_6$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)-$C_1$-$C_6$-alkyl, benzyloxy, —S-benzyl, benzylamino, phenoxy, —S-phenyl and phenylamino, or m is 2, 3, 4 or 5, and at least two substituents Y are vicinal and, together with the carbon atoms to which they are bonded, form an annellated 5- or 6-membered carbocycle or a 5- or 6-membered heterocycle with one or two heteroatoms selected from the group consisting of oxygen and nitrogen, whereat two oxygen atoms are not directly connected, the carbocycle or heterocycle being independently substituted by 0 to 4 halogen atoms, 0 to 2 oxo-groups, 0 to 8 $C_1$-$C_8$-alkyl, 0 to 8 $C_1$-$C_8$-alkoxy or 0 to 4 $C_1$-$C_8$-halogenoalkyl having 1 to 5 halogen atoms, and the remaining substituents Y are independently selected from the group consisting of hydrogen, halogen, nitro, cyano, hydroxy, amino, —SH, —SF$_5$, —CHO, —OCHO, —NHCHO, —COOH, —CONH$_2$, —CONH(OH), —OCONH$_2$, (hydroxyimino)-$C_1$-$C_6$-alkyl, $C_1$-$C_8$-alkyl, $C_1$-$C_8$-halogenoalkyl having 1 to 5 halogen atoms, $C_2$-$C_8$-alkenyl, $C_2$-$C_8$-alkynyl, $C_1$-$C_8$-alkylamino, di-($C_1$-$C_8$-alkyl)amino, $C_1$-$C_8$-alkoxy, $C_1$-$C_8$-halogenoalkoxy having 1 to 5 halogen atoms, $C_2$-$C_8$-alkenyloxy, $C_2$-$C_8$-halogenoalkenyloxy having 1 to 5 halogen atoms, $C_3$-$C_8$-alkynyloxy, $C_3$-$C_8$-halogenoalkynyloxy having 1 to 5 halogen atoms, $C_3$-$C_8$-cycloalkyl, $C_3$-$C_8$-halogenocycloalkyl having 1 to 5 halogen atoms, $C_1$-$C_8$-alkylcarbonyl, $C_1$-$C_8$-halogenoalkylcarbonyl having 1 to 5 halogen atoms, —CONH($C_1$-$C_8$-alkyl), —CON($C_1$-$C_8$-alkyl)$_2$, —CONH(O$C_1$-$C_8$-alkyl), —CON(O$C_1$-$C_8$-alkyl)($C_1$-$C_8$-alkyl), $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, $C_1$-$C_8$-alkylcarbonylamino, $C_1$-$C_8$-halogenoalkylcarbonylamino having 1 to 5 halogen atoms, —OCONH($C_1$-$C_8$-alkyl), —OCON($C_1$-$C_8$-alkyl)$_2$, —OCONH(O$C_1$-$C_8$-alkyl), —OCO(O$C_1$-$C_8$-alkyl), —S—$C_1$-$C_8$-alkyl, —S—$C_1$-$C_8$-halogenoalkyl having 1 to 5 halogen atoms, —S(O)—$C_1$-$C_8$-alkyl, —S(O)—$C_1$-$C_8$-halogenoalkyl having 1 to 5 halogen atoms, —S(O)$_2$—$C_1$-$C_8$-alkyl, —S(O)$_2$—$C_1$-$C_8$-halogenoalkyl having 1 to 5 halogen atoms, —CH$_2$—S—$C_1$-$C_8$-alkyl, —CH$_2$—S(O)—$C_1$-$C_8$-alkyl, —CH$_2$—S(O)$_2$—$C_1$-$C_8$-alkyl, ($C_1$-$C_6$-alkoxyimino)-$C_1$-$C_6$-alkyl, ($C_2$-$C_6$-alkenyloxyimino)-$C_1$-$C_6$-alkyl, ($C_3$-$C_6$-alkynyloxyimino)-$C_1$-$C_6$-alkyl, (benzyloxyimino)-$C_1$-$C_6$-alkyl, benzyloxy, —S-benzyl, benzylamino, phenoxy, —S-phenyl and phenylamino, $R^1$, $R^2$, $R^3$ and $R^4$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-$C_1$-$C_6$-alkyl group, $C_1$-$C_6$-alkyl, $C_2$-$C_6$-alkenyl, $C_2$-$C_6$-alkynyl, $C_1$-$C_6$-alkylamino, di-($C_1$-$C_6$-alkyl)amino, $C_1$-$C_6$-alkoxy, hydroxy-$C_1$-$C_4$-alkyl, $C_1$-$C_4$-alkoxy-$C_1$-$C_3$-alkyl, $C_1$-$C_6$-halogenoalkyl having 1 to 5 halogen atoms, $C_1$-$C_6$-halogenoalkoxy having 1 to 5 halogen atoms, $C_2$-$C_6$-alkenyloxy, $C_2$-$C_6$-halogenoalkenyloxy having 1 to 5 halogen atoms, $C_3$-$C_6$-alkynyloxy, $C_3$-$C_6$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_6$-alkyl, $C_3$-$C_6$-halogenocycloalkyl-$C_1$-$C_6$-alkyl having 1 to 5 halogen atoms, $C_1$-$C_6$-alkylcarbonyl, $C_1$-$C_6$-halogenoalkylcarbonyl having 1 to 5 halogen atoms, —CONH($C_1$-$C_6$-alkyl), —CON($C_1$-$C_6$-alkyl)$_2$, —CONH(O$C_1$-$C_6$-alkyl), —CON(O$C_1$-$C_6$-alkyl)($C_1$-$C_6$-alkyl), $C_1$-$C_6$-alkoxycarbonyl, a $C_1$-$C_6$-halogenoalkoxycarbonyl having 1 to 5 halogen atoms, —OC(O)—$C_1$-$C_6$-alkyl, —OC(O)—$C_1$-$C_6$-halogenoalkyl having 1 to 5 halogen atoms, —NHC(O)—$C_1$-$C_6$-alkyl, —NHC(O)—$C_1$-$C_6$-halogenoalkyl having 1 to 5 halogen atoms, —OCONH($C_1$-$C_6$-alkyl), —OCON($C_1$-$C_6$-alkyl)$_2$, —OCONH(O$C_1$-$C_6$-alkyl), OCO(O$C_1$-$C_6$-alkyl), —S—$C_1$-$C_6$-alkyl, —S—$C_1$-$C_6$-halogenoalkyl having 1 to 5 halogen atoms, —S(O)—$C_1$-$C_6$-alkyl, —S(O)—$C_1$-$C_6$-halogenoalkyl having 1 to 5 halogen atoms, —S(O)$_2$—$C_1$-$C_6$-alkyl, —S(O)$_2$—$C_1$-$C_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino and phenyl, with the proviso that $R^1$ is fluorine and/or $R^2$ is fluorine, $R^5$ is selected from the group consisting of hydrogen, cyano, —CHO, —OH, $C_1$-$C_6$-alkyl, $C_1$-$C_6$-halogenoalkyl having 1 to 5 halogen atoms, $C_1$-$C_6$-alkoxy, $C_1$-$C_6$-halogenoalkoxy having 1 to 5 halogen atoms, $C_3$-$C_7$-cycloalkyl, $C_3$-$C_7$-halogenocycloalkyl having 1 to 5 halogen atoms, $C_3$-$C_7$-cycloalkyl-$C_1$-$C_6$-alkyl, —CONH($C_1$-$C_6$-alkyl), $C_2$-$C_6$-alkenyl, $C_2$-$C_6$-alkynyl, $C_1$-$C_6$-alkoxy-$C_1$-$C_6$-alkyl, $C_3$-$C_7$-cycloalkyl-$C_1$-$C_6$-alkyl, cyano-$C_1$-$C_6$-alkyl, amino-$C_1$-$C_6$-alkyl, $C_1$-$C_6$-alkylamino-$C_1$-$C_6$-alkyl, di-($C_1$-$C_6$-alkyl)amino-$C_1$-$C_6$-alkyl, $C_1$-$C_6$-alkylcarbonyl, $C_1$-$C_6$-halogenoalkylcarbonyl having 1 to 5 halogen atoms, $C_1$-$C_6$-alkoxycarbonyl, $C_1$-$C_6$-benzyloxycarbonyl, $C_1$-$C_6$-alkoxy-$C_1$-$C_6$-alkylcarbonyl, —S—$C_1$-$C_6$-alkyl, S—$C_1$-$C_6$-halogenoalkyl having 1 to 5 halogen atoms, —S(O)$_2$—$C_1$-$C_6$-alkyl, and S(O)$_2$—$C_1$-$C_6$-halogenoalkyl having 1 to 5 halogen atoms, A is a phenyl group of the formula (A1)

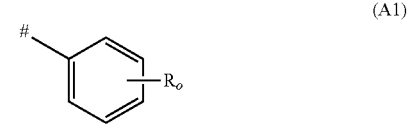

(A1)

wherein o is 0, 1, 2, 3, 4 or 5, and each R is independently selected from the group consisting of halogen, nitro, —OH, NH$_2$, SH, SF$_5$, CHO, OCHO, NHCHO, COOH, cyano, $C_1$-$C_8$-alkyl, $C_1$-$C_8$-halogenoalkyl having 1 to 9 halogen atoms, $C_2$-$C_8$-alkenyl, $C_2$-$C_8$-alkynyl, $C_3$-$C_6$-cycloalkyl, —S—$C_1$-$C_8$-alkyl, —S—$C_1$-$C_8$-halogenoalkyl having 1 to 5 halogen atoms, $C_1$-$C_8$-alkoxy, $C_1$-$C_8$-halogenoalkoxy having 1 to 5 halogen atoms, $C_1$-$C_8$-alkoxy-$C_2$-$C_8$-alkenyl, $C_1$-$C_8$-alkoxycarbonyl, $C_1$-$C_8$-halogenoalkoxycarbonyl having 1 to 5 halogen atoms, $C_1$-$C_8$-alkylcarbonyloxy, $C_1$-$C_8$-halogenoalkylcarbonyloxy having 1 to 5 halogen atoms, —S(O)—C$_1$-C$_8$-alkyl, —S(O)—C$_1$-C$_8$-halogenoalkyl having 1 to 5 halogen atoms, —S(O)$_2$—C$_1$-C$_8$-alkyl, —S(O)$_2$—C$_1$-C$_8$-halogenoalkyl having 1 to 5 halogen atoms, C$_1$-C$_8$-alkylsulfonamide, —NH(C$_1$-C$_8$-alkyl), N(C$_1$-C$_8$-alkyl)$_2$, phenyl (optionally substituted by C$_1$-C$_6$-alkoxy) and phenoxy, or two R bonded to adjacent carbon atoms are taken together to form —O(CH$_2$)$_p$O—, wherein p is 1 or 2, or A is a heterocycle of the formula (Het-1)

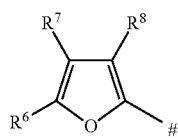
(Het-1)

wherein

R$^6$ and R$^7$ may be the same or different and are selected from the group consisting of hydrogen, halogen, amino, nitro, C$_1$-C$_4$-alkyl and C$_1$-C$_4$-halogenoalkyl having 1 to 5 halogen atoms, and R$^8$ is selected from the group consisting of hydrogen, halogen, nitro, C$_1$-C$_4$-alkyl and C$_1$-C$_4$-halogenoalkyl having 1 to 5 halogen atoms, or A is a heterocycle of the formula (Het-2)

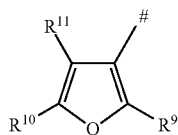
(Het-2)

wherein

R$^9$ is selected from the group consisting of hydrogen, halogen, C$_1$-C$_4$-alkyl and C$_1$-C$_4$-halogenoalkyl having 1 to 5 halogen atoms, and R$^{10}$ and R$^{11}$ may be the same or different and are selected from the group consisting of hydrogen, halogen, amino, C$_1$-C$_4$-alkyl, C$_1$-C$_4$-halogenoalkyl having 1 to 5 halogen atoms and phenyl (optionally substituted by halogen or C$_1$-C$_4$-alkyl), or A is a heterocycle of the formula (Het-3)

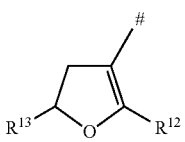
(Het-3)

wherein

R$^{12}$ is selected from the group consisting of halogen, C$_1$-C$_4$-alkyl and C$_1$-C$_4$-halogenoalkyl having 1 to 5 halogen atoms, and R$^{13}$ is selected from the group consisting of hydrogen, C$_1$-C$_4$-alkyl and C$_1$-C$_4$-halogenoalkyl having 1 to 5 halogen atoms, or A is a heterocycle of the formula (Het-4)

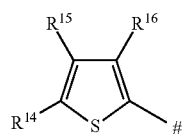
(Het-4)

wherein

R$^{14}$ and R$^{15}$ may be the same or different and are selected from the group consisting of hydrogen, halogen, C$_1$-C$_4$-alkyl, C$_1$-C$_4$-halogenoalkyl having 1 to 5 halogen atoms, —S—C$_1$-C$_4$-alkyl, —S(O)$_2$—C$_1$-C$_4$-alkyl, phenyl optionally substituted by halogen or C$_1$-C$_4$-alkyl and pyridyl (optionally substituted by halogen or C$_1$-C$_4$-alkyl), and R$^{16}$ is selected from the group consisting of hydrogen, halogen, cyano, C$_1$-C$_4$-alkyl, C$_1$-C$_4$-halogenoalkyl having 1 to 5 halogen atoms and C$_1$-C$_4$-halogenoalkoxy having 1 to 5 halogen atoms, or A is a heterocycle of the formula (Het-5)

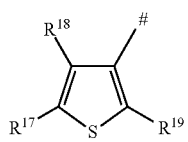
(Het-5)

wherein

R$^{17}$ and R$^{18}$ may be the same or different and are selected from the group consisting of hydrogen, halogen, C$_1$-C$_4$-alkyl, C$_1$-C$_4$-alkyloxy and C$_1$-C$_4$-halogenoalkyl having 1 to 5 halogen atoms, and R$^{19}$ is selected from the group consisting of hydrogen, halogen, C$_1$-C$_4$-alkyl and C$_1$-C$_4$-halogenoalkyl having 1 to 5 atoms, or A is a heterocycle of the formula (Het-6)

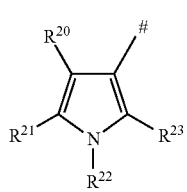
(Het-6)

wherein

R$^{20}$ is selected from the group consisting of hydrogen, halogen, cyano, C$_1$-C$_4$-alkyl and C$_1$-C$_4$-halogenoalkyl having 1 to 5 halogen atoms, and R$^{21}$ and R$^{23}$ may be the same or different and are selected from the group consisting of hydrogen, halogen, C$_1$-C$_4$-alkyl and C$_1$-C$_4$-halogenoalky having 1 to 5 halogen atoms, and R$^{22}$ is selected from the group consisting of hydrogen, cyano, C$_1$-C$_4$-alkyl, C$_1$-C$_4$-halogenoalkyl having 1 to 5 halogen atoms, C$_1$-C$_4$-alkoxy-C$_1$-C$_4$-alkyl, hydroxyl-C$_1$-C$_4$-alkyl, —S(O)$_2$—C$_1$-C$_4$-alkyl, —S(O)$_2$—N(C$_1$-C$_4$-alkyl)$_2$, C$_1$-C$_6$-alkylcarbonyl, —S(O)$_2$-phenyl (optionally substituted by halogen or $C_1$-$C_4$-alkyl) and benzoyl (optionally substituted by halogen or $C_1$-$C_4$-alkyl), or A is a heterocycle of the formula (Het-7)

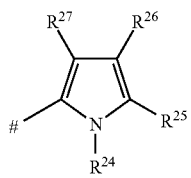
(Het-7)

wherein
$R^{24}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, hydroxy-$C_1$-$C_4$-alkyl, —S(O)$_2$—$C_1$-$C_4$-alkyl, —S(O)$_2$—N($C_1$-$C_4$-alkyl)$_2$, $C_1$-$C_6$-alkylcarbonyl, —S(O)$_2$-phenyl (optionally substituted by halogen or $C_1$-$C_4$-alkyl) and benzoyl (optionally substituted by halogen or a $C_1$-$C_4$-alkyl), and
$R^{25}$, $R^{26}$ and $R^{27}$ may be the same or different and are selected from the group consisting of hydrogen, halogen, cyano, $C_1$-$C_4$-alkyl, $C_1$-$C_4$-halogenalkyl having 1 to 5 halogen atoms and $C_1$-$C_4$-alkylcarbonyl, or A is a heterocycle of the formula (Het-8)

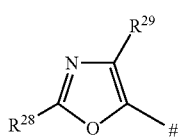
(Het-8)

wherein
$R^{28}$ is selected from the group consisting of hydrogen and $C_1$-$C_4$-alkyl, and
$R^{29}$ is selected from the group consisting of halogen, $C_1$-$C_4$-alkyl and $C_1$-$C_4$-halogenoalkyl having 1 to 5 halogen atoms, or A is a heterocycle of the formula (Het-9)

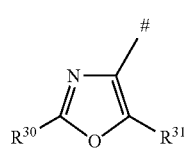
(Het-9)

wherein
$R^{30}$ is selected from the group consisting of hydrogen and $C_1$-$C_4$-alkyl, and
$R^{31}$ is selected from the group consisting of halogen, $C_1$-$C_4$-alkyl, $C_1$-$C_4$-halogenoalkyl having 1 to 5 halogen atoms and phenyl (optionally substituted by halogen or $C_1$-$C_4$-alkyl), or A is a heterocycle of the formula (Het-10)

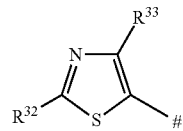
(Het-10)

wherein
$R^{32}$ is selected from the group consisting of hydrogen, halogen, amino, cyano, $C_1$-$C_4$-alkylamino, di-($C_1$-$C_4$-alkyl)amino, $C_1$-$C_4$-alkyl, $C_1$-$C_4$-halogenoalkyl having 1 to 5 halogen atoms and phenyl (optionally substituted by halogen or $C_1$-$C_4$-alkyl), and
$R^{33}$ is selected from the group consisting of halogen, $C_1$-$C_4$-alkyl and $C_1$-$C_4$-halogenoalkyl having 1 to 5 halogen atoms, $C_1$-$C_5$-halogenoalkoxy having 1 to 9 halogen atoms, amino, substituted or unsubstituted $C_1$-$C_5$-alkylamino and substituted or unsubstituted di-($C_1$-$C_5$-alkyl)-amino, or A is a heterocycle of the formula (Het-11)

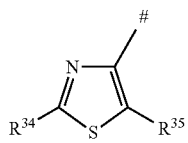
(Het-11)

wherein
$R^{34}$ is selected from the group consisting of hydrogen, halogen, amino, cyano, $C_1$-$C_4$-alkylamino, di-($C_1$-$C_4$-alkyl)amino, $C_1$-$C_4$-alkyl and $C_1$-$C_4$-halogenoalkyl having 1 to 5 halogen atoms, and
$R^{35}$ is selected from the group consisting of halogen, $C_1$-$C_4$-alkyl and $C_1$-$C_4$-halogenoalkyl having 1 to 5 halogen atoms, or A is a heterocycle of the formula (Het-12)

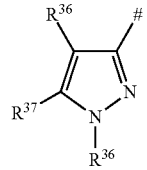
(Het-12)

wherein
$R^{36}$ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 halogen atoms, aminocarbonyl and aminocarbonyl-$C_1$-$C_4$-alkyl, and
$R^{37}$ is selected from the group consisting of hydrogen, halogen, cyano, nitro, $C_1$-$C_4$-alkyl, $C_1$-$C_4$-alkoxy, —S—$C_1$-$C_4$-alkyl, —S(O)—$C_1$-$C_4$-alkyl, and —S(O)$_2$—$C_1$-$C_4$-alkyl, and $R^{38}$ is selected from the group consisting of hydrogen, phenyl, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl and $C_1$-$C_4$-halogenoalkoxy-$C_1$-$C_4$-alkyl having 1 to 5 halogen atoms, or A is a heterocycle of the formula (Het-13)

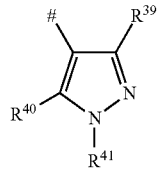

(Het-13)

wherein $R^{39}$ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, S(O)—$C_1$-$C_4$-alkyl, —S(O)$_2$—$C_1$-$C_4$-alkyl, —S—$C_1$-$C_4$-halogenoalkyl having 1 to 5 atoms, aminocarbonyl and aminocarbonyl-$C_1$-$C_4$-alkyl, and $R^{40}$ is selected from the group consisting of hydrogen, halogen, cyano, $C_1$-$C_4$-alkyl, $C_1$-$C_4$-alkoxy, $C_1$-$C_4$-halogenoalkoxy having 1 to 5 halogen atoms, —S—$C_1$-$C_4$-alkylS(O)—$C_1$-$C_4$-alkyl, and —S(O)$_2$—$C_1$-$C_4$-alkyl, and $R^{41}$ is selected from the group consisting of hydrogen, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl, $C_1$-$C_4$-halogenoalkoxy-$C_1$-$C_4$-alkyl having 1 to 5 halogen atoms and phenyl (optionally substituted by halogen, $C_1$-$C_4$-alkyl, $C_1$-$C_4$-alkoxy-$C_1$-$C_4$-alkyl or nitro), or A is a heterocycle of the formula (Het-14)

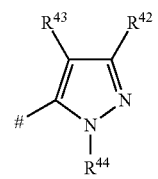

(Het-14)

wherein $R^{42}$ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, S(O)—$C_1$-$C_4$-alkyl, —S(O)$_2$—$C_1$-$C_4$-alkyl, —S—$C_1$-$C_4$-halogenoalkyl having 1 to 5 halogen atoms, aminocarbonyl and aminocarbonyl-$C_1$-$C_4$-alkyl, and $R^{43}$ is selected from the group consisting of hydrogen, halogen, cyano, $C_1$-$C_4$-alkyl, $C_1$-$C_4$-alkoxy, —S—$C_1$-$C_4$-alkyl, S(O)—$C_1$-$C_4$-alkyl, —S(O)$_2$—$C_1$-$C_4$-alkyl, and $C_1$-$C_4$-halogenoalkyl having 1 to 5 halogen atoms, and $R^{44}$ is selected from the group consisting of hydrogen, phenyl, benzyl, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl and $C_1$-$C_4$-halogeno alkoxy-$C_1$-$C_4$-alkyl having 1 to 5 halogen atoms, or A is a heterocycle of the formula (Het-15)

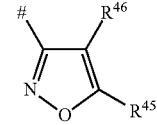

(Het-15)

wherein $R^{45}$ and $R^{46}$ may be the same or different and are selected from the group consisting of hydrogen, halogen, $C_1$-$C_4$-alkyl and $C_1$-$C_4$-halogenoalkyl having 1 to 5 halogen atoms, or A is a heterocycle of the formula (Het-16)

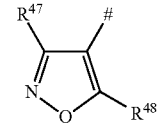

(Het-16)

wherein $R^{47}$ and $R^{48}$ may be the same or different and are selected from the group consisting of hydrogen, halogen, $C_1$-$C_4$-alkyl, $C_1$-$C_4$-halogenoalkyl having 1 to 5 halogen atoms, phenyl (optionally substituted by halogen or a $C_1$-$C_4$-alkyl), and heterocyclyl like pyridyl, pyrimidinyl and thiadiazolyl (each optionally substituted by halogen or $C_1$-$C_4$-alkyl), or A is a heterocycle of the formula (Het-17)

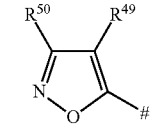

(Het-17)

wherein $R^{49}$ and $R^{50}$ may be the same or different and are selected from the group consisting of hydrogen, halogen, $C_1$-$C_4$-alkyl and $C_1$-$C_4$-halogenoalkyl having 1 to 5 halogen atoms, or A is a heterocycle of the formula (Het-18)

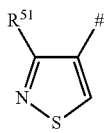
(Het-18)

wherein
R$^{51}$ is selected from the group consisting of halogen, C$_1$-C$_4$-alkyl and C$_1$-C$_4$-halogenoalkyl having 1 to 5 halogen atoms, or
A is a heterocycle of the formula (Het-19)

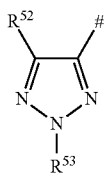
(Het-19)

wherein
R$^{52}$ is selected from the group consisting of halogen, C$_1$-C$_4$-alkyl and C$_1$-C$_4$-halogenoalkyl having 1 to 5 halogen atoms, and
R$^{53}$ is selected from the group consisting of hydrogen, C$_1$-C$_4$-alkyl, C$_1$-C$_4$-halogenoalkyl having 1 to 5 halogen atoms and phenyl (optionally substituted by halogen or C$_1$-C$_4$-alkyl), or
A is a heterocycle of the formula (Het-20)

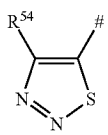
(Het-20)

wherein
R$^{54}$ is selected from the group consisting of halogen, C$_1$-C$_4$-alkyl and C$_1$-C$_4$-halogenoalkyl having 1 to 5 halogen atoms, or
A is a heterocycle of the formula (Het-21)

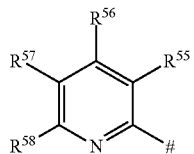
(Het-21)

wherein
R$^{55}$ is selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, S(O)—C$_1$-C$_4$-alkyl, —S(O)$_2$—C$_1$-C$_4$-alkyl, —S—C$_1$-C$_4$-halogenoalkyl having 1 to 5 halogen atoms and C$_1$-C$_4$-halogenoalkoxy having 1 to 5 halogen atoms, and R$^{56}$, R$^{57}$ and R$^{58}$, which may be the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, C$_1$-C$_4$-halogenoalkoxy having 1 to 5 halogen atoms, —S(O)—C$_1$-C$_4$-alkyl and —S(O)$_2$—C$_1$-C$_4$-alkyl, or
A is a heterocycle of the formula (Het-22)

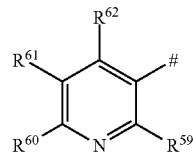
(Het-22)

wherein
R$^{59}$ is selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$ alkoxy, —S—C$_1$-C$_5$-alkyl, S(O)—C$_1$-C$_4$-alkyl, —S(O)$_2$—C$_1$-C$_4$-alkyl, —S—C$_2$-C$_5$-alkenyl, —S—C$_1$-C$_4$-halogenoalkyl having 1 to 5 halogen atoms, C$_1$-C$_4$-halogenoalkoxy having 1 to 5 halogen atoms, phenyloxy (optionally substituted by halogen or C$_1$-C$_4$-alkyl) and —S-phenyl (optionally substituted by halogen or C$_1$-C$_4$-alkyl), and
R$^{60}$, R$^{61}$ and R$^{62}$, which may the same or different, are selected from the group consisting of hydrogen, halogen, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, C$_1$-C$_4$-halogenoalkoxy having 1 to 5 halogen atoms, —S(O)—C$_1$-C$_4$-alkyl, —S(O)$_2$—C$_1$-C$_4$-alkyl, N-morpholine optionally substituted by halogen or C$_1$-C$_4$-alkyl, and thienyl (optionally substituted by halogen or a C$_1$-C$_4$-alkyl), or
A is a heterocycle of the formula (Het-23)

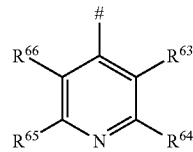
(Het-23)

wherein
R$^{63}$, R$^{64}$, R$^{65}$ and R$^{66}$, which may be the same or different, are selected from the group consisting of hydrogen, halogen, hydroxy, cyano, C$_1$-C$_4$-alkyl, C$_1$-C$_4$-halogenoalkyl having 1 to 5 halogen atoms, C$_1$-C$_4$-alkoxy, —S—C$_1$-C$_4$-alkyl, —S—C$_1$-C$_4$-halogenoalkyl having 1 to 5 halogen atoms, C$_1$-C$_4$-halogenoalkoxy having 1 to 5 halogen atoms, —S(O)—C$_1$-C$_4$-alkyl and —S(O)$_2$—C$_1$-C$_4$-alkyl, or
A is a heterocycle of the formula (Het-24)

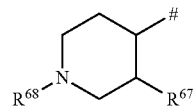
(Het-24)

wherein
R$^{67}$ is selected from the group consisting of hydrogen, halogen, C$_1$-C$_4$-alkyl and C$_1$-C$_4$-halogenoalkyl having 1 to 5 halogen atoms, and $R^{68}$ is selected from the group consisting of hydrogen, $C_1$-$C_4$-alkyl, $C_1$-$C_4$-halogenoalkyl having 1 to 5 halogen atoms, $C_1$-$C_6$-alkoxycarbonyl, benzyl (optionally substituted by 1 to 3 halogen atoms), benzyloxycarbonyl (optionally substituted by 1 to 3 halogen atoms), and heterocyclyl like pyridyl and pyrimidinyl (each optionally substituted by halogen, $C_1$-$C_4$-alkyl, $C_1$-$C_4$-halogenoalkyl having 1 to 5 halogen atoms), or A is a heterocycle of the formula (Het-25)

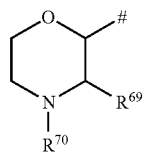

(Het-25)

wherein $R^{69}$ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S—$C_1$-$C_4$-halogenoalkyl having 1 to 5 halogen atoms and $C_1$-$C_4$-halogenoalkoxy having 1 to 5 halogen atoms, and $R^{70}$ is selected from the group consisting of hydrogen, $C_1$-$C_4$-alkyl, $C_1$-$C_4$-halogenoalkyl having 1 to 5 halogen atoms, and benzyl, or A is a heterocycle of the formula (Het-26)

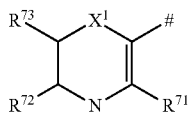

(Het-26)

wherein $X^1$ is selected from the group consisting of sulphur, —SO—, —SO$_2$— and —CH$_2$—, and $R^{71}$ is selected from the group consisting of $C_1$-$C_4$-alkyl and $C_1$-$C_4$-halogenoalkyl having 1 to 5 halogen atoms, and $R^{72}$ and $R^{73}$ may be the same or different and are selected from the group consisting of hydrogen and $C_1$-$C_4$-alkyl, or A is a heterocycle of the formula (Het-27)

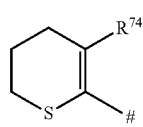

(Het-27)

wherein $R^{74}$ is selected from the group consisting of $C_1$-$C_4$-alkyl and $C_1$-$C_4$-halogenoalkyl having 1 to 5 halogen atoms, or A is a heterocycle of the formula (Het-28)

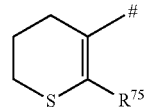

(Het-28)

wherein $R^{75}$ is selected from the group consisting of $C_1$-$C_4$-alkyl and $C_1$-$C_4$-halogenoalkyl having 1 to 5 halogen atoms, or A is a heterocycle of the formula (Het-29)

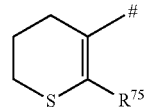

(Het-29)

wherein $R^{76}$ is selected from the group consisting of hydrogen, halogen, $C_1$-$C_4$-alkyl and $C_1$-$C_4$-halogenoalkyl having 1 to 5 halogen atoms.

2. The compound or a salt, N-oxide, metal complex or metalloid complex thereof according to claim 1, wherein $B^1$, $B^2$ are C—X or N, wherein at least one of $B^1$ or $B^2$ is N, n is 1 or 2, limited by the number of available positions in the ring to which a substituent X can be connected, each X is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino, m is 0, 1, 2, 3 or 4 and each Y is independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di- ($C_1$-$C_4$-alkyl)amino, wherein both alkyl residues may form a 4- to 7-membered heterocycle incorporating the nitrogen bonded to the phenyl system of the compound, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, —CH$_2$—S—$C_1$-$C_4$-alkyl, —CH$_2$—S(O)—$C_1$-$C_4$-alkyl, —CH$_2$—S(O)$_2$—$C_1$-$C_4$-alkyl, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino, or m is 2, 3 or 4 and at least two substituents Y are vicinal and, together with the carbon atoms to which they are bonded, form an annellated 5- or 6-membered carbocycle or a 5- or 6-membered heterocycle with one or two heteroatoms selected from the group consisting of oxygen and nitrogen, whereat two oxygen atoms are not directly connected, the carbocycle or heterocycle being independently substituted by 0 to 2 halogen atoms, 0 to 2 oxo-groups, 0 to 4 $C_1$-$C_4$-alkyl, 0 to 4 $C_1$-$C_4$-alkoxy or 0 to 2 $C_1$-$C_4$-halogenoalkyl having 1 to 5 halogen atoms, and the remaining substituents Y are independently selected from the group consisting of hydrogen, halogen, nitro, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, $C_1$-$C_4$-alkylcarbonylamino, $C_1$-$C_4$-halogenoalkylcarbonylamino having 1 to 5 halogen atoms, —OCONH($C_1$-$C_4$-alkyl), —OCON($C_1$-$C_4$-alkyl)$_2$, —OCONH(O$C_1$-$C_4$-alkyl), —OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, —CH$_2$—S—$C_1$-$C_4$-alkyl, —CH$_2$—S(O)—$C_1$-$C_4$-alkyl, —CH$_2$—S(O)$_2$—$C_1$-$C_4$-alkyl, ($C_1$-$C_4$-alkoxyimino)-$C_1$-$C_4$-alkyl, ($C_2$-$C_6$-alkenyloxyimino)-$C_1$-$C_4$-alkyl, ($C_3$-$C_6$-alkynyloxyimino)-$C_1$-$C_4$-alkyl, (benzyloxyimino)-$C_1$-$C_6$-alkyl, benzyloxy, —S-benzyl, benzylamino, phenoxy, —S-phenyl and phenylamino, $R^1$, $R^2$, $R^3$ and $R^4$ are the same or different and are selected from the group consisting of hydrogen, halogen, cyano, hydroxy, amino, —CHO, —COOH, —CONH$_2$, $C_1$-$C_4$-alkyl, $C_2$-$C_4$-alkenyl, $C_2$-$C_4$-alkynyl, $C_1$-$C_4$-alkylamino, di-($C_1$-$C_4$-alkyl)amino, $C_1$-$C_4$-alkoxy, $C_1$-$C_4$-halogenoalkyl having 1 to 5 halogen atoms, $C_1$-$C_4$-halogenoalkoxy having 1 to 5 halogen atoms, $C_2$-$C_4$-alkenyloxy, $C_2$-$C_4$-halogenoalkenyloxy having 1 to 5 halogen atoms, $C_3$-$C_4$-alkynyloxy, $C_3$-$C_4$-halogenoalkynyloxy having 1 to 5 halogen atoms, $C_3$-$C_6$-cycloalkyl, $C_3$-$C_6$-halogenocycloalkyl having 1 to 5 halogen atoms, $C_3$-$C_6$-cycloalkyl-$C_1$-$C_3$-alkyl, $C_3$-$C_6$-halogenocycloalkyl-$C_1$-$C_3$-alkyl having 1 to 5 halogen atoms, $C_1$-$C_4$-alkylcarbonyl, $C_1$-$C_4$-halogenoalkylcarbonyl having 1 to 5 halogen atoms, —CONH($C_1$-$C_4$-alkyl), —CON($C_1$-$C_4$-alkyl)$_2$, —CONH(O$C_1$-$C_4$-alkyl), —CON(O$C_1$-$C_4$-alkyl)($C_1$-$C_4$-alkyl), $C_1$-$C_4$-alkoxycarbonyl, $C_1$-$C_4$-halogenoalkoxycarbonyl having 1 to 5 halogen atoms, —OC(O)—$C_1$-$C_4$-alkyl, —OC(O)—$C_1$-$C_4$-halogenoalkyl having 1 to 5 halogen atoms, —NHC(O)—$C_1$-$C_4$-alkyl, —NHC(O)—$C_1$-$C_4$-halogenoalkyl having 1 to 5 halogen atoms, —OCONH($C_1$-$C_4$-alkyl), —OCON($C_1$-$C_4$-alkyl)$_2$, —OCONH(O$C_1$-$C_4$-alkyl), OCO(O$C_1$-$C_4$-alkyl), —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino and phenyl, with the proviso that $R^1$ is fluorine and/or $R^2$ is fluorine, $R^5$ is selected from the group consisting of hydrogen, —CHO, —OH, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_3$-$C_6$-cycloalkyl, $C_3$-$C_6$-halogenocycloalkyl having 1 to 5 halogen atoms, $C_2$-$C_4$-alkenyl, $C_2$-$C_4$-alkynyl, $C_1$-$C_4$-alkoxy-$C_1$-$C_4$-alkyl, $C_3$-$C_6$-cycloalkyl-$C_1$-$C_3$-alkyl, cyano-$C_1$-$C_4$-alkyl, amino-$C_1$-$C_4$-alkyl, $C_1$-$C_4$-alkylamino-$C_1$-$C_4$-alkyl, di-($C_1$-$C_4$-alkyl)amino-$C_1$-$C_4$-alkyl, $C_1$-$C_4$-alkylcarbonyl, $C_1$-$C_4$-halogenoalkylcarbonyl having 1 to 5 halogen atoms, $C_1$-$C_4$-alkoxycarbonyl, benzyloxycarbonyl, $C_1$-$C_4$-alkoxy-$C_1$-$C_4$-alkylcarbonyl, —S(O)$_2$—$C_1$-$C_4$-alkyl, and —S(O)$_2$—$C_1$-$C_4$-halogenoalkyl having 1 to 5 halogen atoms, A is a phenyl group of formula (A1)

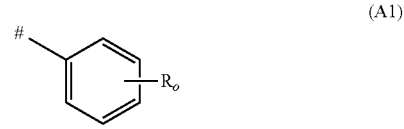

(A1)

wherein o is 0, 1 or 2, and each R is independently selected from the group consisting of halogen, nitro, —OH, CHO, OCHO, NHCHO, cyano, $C_1$-$C_4$-alkyl, $C_1$-$C_4$-halogenoalkyl having 1 to 5 halogen atoms, $C_2$-$C_4$-alkenyl, $C_2$-$C_4$-alkynyl, $C_3$-$C_6$- cycloalkyl, —S—$C_1$-$C_4$-alkyl, —S—$C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-alkoxy-$C_2$-$C_4$-alkenyl, $C_1$-$C_4$-alkoxycarbonyl, $C_1$-$C_4$-halogenoalkoxycarbonyl having 1 to 5 halogen atoms, $C_1$-$C_4$-alkylcarbonyloxy, $C_1$-$C_4$-halogenoalkylcarbonyloxy having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, $C_1$-$C_4$-alkylsulfonamide, —NH($C_1$-$C_4$-alkyl), N($C_1$-$C_4$-alkyl)$_2$, phenyl (optionally substituted by $C_1$-$C_4$-alkoxy) and phenoxy, or two R bonded to adjacent carbon atoms are taken together to form O(CH$_2$)$_p$O—, wherein p is 1 or 2, or A is a heterocycle of the formula (Het-1)

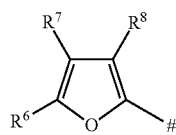

(Het-1)

wherein
$R^6$ and $R^7$ may be the same or different and are selected from the group consisting of hydrogen, halogen, nitro, $C_1$-$C_4$-alkyl and $C_1$-$C_4$-halogenoalkyl having 1 to 5 halogen atoms, and
$R^8$ is selected from the group consisting of hydrogen, halogen, $C_1$-$C_4$-alkyl and $C_1$-$C_4$-halogenoalkyl having 1 to 5 halogen atoms, or
A is a heterocycle of the formula (Het-2)

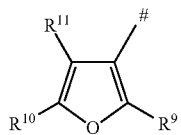

(Het-2)

wherein
$R^9$ is selected from the group consisting of hydrogen, halogen, $C_1$-$C_4$-alkyl and $C_1$-$C_4$-halogenoalkyl having 1 to 5 halogen atoms, and
$R^{10}$ and $R^{11}$ may be the same or different and are selected from the group consisting of hydrogen, halogen, $C_1$-$C_4$-alkyl and $C_1$-$C_4$-halogenoalkyl having 1 to 5 halogen atoms, phenyl optionally substituted by halogen or $C_1$-$C_4$-alkyl), or
A is a heterocycle of the formula (Het-4)

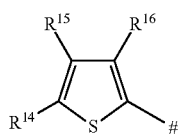

(Het-4)

wherein
$R^{14}$ and $R^{15}$ may be the same or different and are selected from the group consisting of hydrogen, halogen, $C_1$-$C_4$-alkyl, $C_1$-$C_4$-halogenoalkyl having 1 to 5 halogen atoms, —S—$C_1$-$C_4$-alkyl, —S(O)$_2$—$C_1$-$C_4$-alkyl, phenyl (optionally substituted by halogen or $C_1$-$C_4$-alkyl) and pyridyl (optionally substituted by halogen or $C_1$-$C_4$-alkyl), and
$R^{16}$ is selected from the group consisting of hydrogen, halogen, cyano, $C_1$-$C_4$-alkyl, $C_1$-$C_4$-halogenoalkyl having 1 to 5 halogen atoms and $C_1$-$C_4$-halogenoalkoxy having 1 to 5 halogen atoms, or
A is a heterocycle of the formula (Het-5)

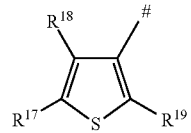

(Het-5)

wherein
$R^{17}$ and $R^{18}$ may be the same or different and are selected from the group consisting of hydrogen, halogen, $C_1$-$C_4$-alkyl, $C_1$-$C_4$-alkyloxy and $C_1$-$C_4$-halogenoalkyl having 1 to 5 halogen atoms, and
$R^{19}$ is selected from the group consisting of hydrogen, halogen, $C_1$-$C_4$-alkyl and $C_1$-$C_4$-halogenoalkyl having 1 to 5 atoms, or
A is a heterocycle of the formula (Het-6)

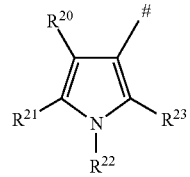

(Het-6)

wherein
$R^{20}$ is selected from the group consisting of hydrogen, halogen, cyano, $C_1$-$C_4$-alkyl and $C_1$-$C_4$-halogenoalkyl having 1 to 5 halogen atoms, and
$R^{21}$ and $R^{23}$ may be the same or different and are selected from the group consisting of hydrogen, halogen, $C_1$-$C_4$-alkyl and $C_1$-$C_4$-halogenoalky having 1 to 5 halogen atoms, and
$R^{22}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, or
A is a heterocycle of the formula (Het-7)

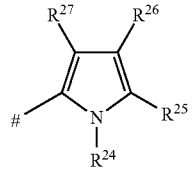

(Het-7)

wherein
$R^{24}$ is selected from the group consisting of hydrogen, cyano, $C_1$-$C_4$-alkyl, $C_1$-$C_4$-halogenoalkyl having 1 to 5 halogen atoms, $C_1$-$C_4$-alkoxy-$C_1$-$C_4$-alkyl, $C_1$-$C_6$-alkylcarbonyl, and benzoyl (optionally substituted by halogen or a $C_1$-$C_4$-alkyl), and $R^{25}$, $R^{26}$ and $R^{27}$ may be the same or different and are selected from the group consisting of hydrogen, halogen, cyano, $C_1$-$C_4$-alkyl, $C_1$-$C_4$-halogenalkyl having 1 to 5 halogen atoms and $C_1$-$C_4$-alkylcarbonyl, or A is a heterocycle of the formula (Het-9)

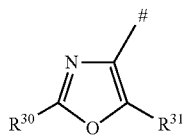

(Het-9)

wherein $R^{30}$ is selected from the group consisting of hydrogen and $C_1$-$C_4$-alkyl, and $R^{31}$ is selected from the group consisting of halogen, $C_1$-$C_4$-alkyl, $C_1$-$C_4$-halogenoalkyl having 1 to 5 halogen atoms and phenyl (optionally substituted by halogen or $C_1$-$C_4$-alkyl), or A is a heterocycle of the formula (Het-10)

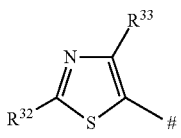

(Het-10)

wherein $R^{32}$ is selected from the group consisting of hydrogen, halogen, amino, cyano, $C_1$-$C_4$-alkylamino, di-($C_1$-$C_4$-alkyl)amino, $C_1$-$C_4$-alkyl, $C_1$-$C_4$-halogenoalkyl having 1 to 5 halogen atoms and phenyl (optionally substituted by halogen or $C_1$-$C_4$-alkyl), and $R^{33}$ is selected from the group consisting of halogen, $C_1$-$C_4$-alkyl and $C_1$-$C_4$-halogenoalkyl having 1 to 5 halogen atoms, $C_1$-$C_5$-halogenoalkoxy comprising 1 to 9 halogen atoms, amino, substituted or unsubstituted $C_1$-$C_5$-alkylamino and substituted or unsubstituted di-($C_1$-$C_5$-alkyl)-amino, or A is a heterocycle of the formula (Het-11)

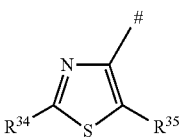

(Het-11)

wherein $R^{34}$ is selected from the group consisting of hydrogen, halogen, $C_1$-$C_4$-alkylamino, di-($C_1$-$C_4$-alkyl)amino, $C_1$-$C_4$-alkyl and $C_1$-$C_4$-halogenoalkyl having 1 to 5 halogen atoms, and $R^{35}$ is selected from the group consisting of halogen, $C_1$-$C_4$-alkyl and $C_1$-$C_4$-halogenoalkyl having 1 to 5 halogen atoms, or A is a heterocycle of the formula (Het-12)

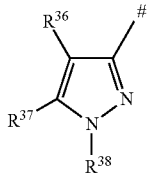

(Het-12)

wherein $R^{36}$ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, —S(O)$_2$—$C_1$-$C_4$-alkyl and —S—$C_1$-$C_4$-halogenoalkyl having 1 to 5 halogen atoms, and $R^{37}$ is selected from the group consisting of hydrogen, halogen, cyano, nitro, $C_1$-$C_4$-alkyl, $C_1$-$C_4$-alkoxy and —S—$C_1$-$C_4$-alkyl, —S(O)—$C_1$-$C_4$-alkyl, —S(O)$_2$—$C_1$-$C_4$-alkyl, and $R^{38}$ is selected from the group consisting of phenyl, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl and $C_1$-$C_4$-halogenoalkoxy-$C_1$-$C_4$-alkyl having 1 to 5 halogen atoms, or A is a heterocycle of the formula (Het-13)

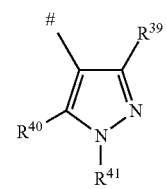

(Het-13)

wherein $R^{39}$ is selected from the group consisting of hydrogen, halogen, cyano, nitro, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 atoms, aminocarbonyl and aminocarbonyl-$C_1$-$C_4$-alkyl, and $R^{40}$ is selected from the group consisting of hydrogen, halogen, cyano, $C_1$-$C_4$-alkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, and —S(O)$_2$—$C_1$-$C_4$-alkyl, and $R^{41}$ is selected from the group consisting of hydrogen, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$- alkyl, $C_1$-$C_4$-halogenoalkoxy-$C_1$-$C_4$-alkyl having 1 to 5 halogen atoms and phenyl optionally substituted by halogen, $C_1$-$C_4$-alkyl, $C_1$-$C_4$-alkoxy-$C_1$-$C_4$-alkyl or nitro, or A is a heterocycle of the formula (Het-14)

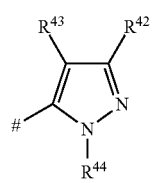

(Het-14)

wherein
$R^{42}$ is selected from the group consisting of hydrogen, halogen, cyano, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1$-$C_4$-halogenoalkoxy having 1 to 5 halogen atoms, —S—$C_1$-$C_4$-alkyl, —S(O)—$C_1$-$C_4$-alkyl, and —S(O)$_2$—$C_1$-$C_4$-alkyl, —S—$C_1$-$C_4$-halogenoalkyl having 1 to 5 halogen atoms, aminocarbonyl and aminocarbonyl-$C_1$-$C_4$-alkyl, and
$R^{43}$ is selected from the group consisting of hydrogen, halogen, cyano, $C_1$-$C_4$-alkyl, $C_1$-$C_4$-alkoxy, —S—$C_1$-$C_4$-alkyl, —S(O)—$C_1$-$C_4$-alkyl, and —S(O)$_2$—$C_1$-$C_4$-alkyl, and $C_1$-$C_4$-halogenoalkyl having 1 to 5 halogen atoms, and
$R^{44}$ is selected from the group consisting of phenyl, benzyl, $C_1$-$C_4$-alkyl, $C_1$-$C_4$-halogenoalkyl having 1 to 5 halogen atoms, hydroxy-$C_1$-$C_4$-alkyl, $C_2$-$C_6$-alkenyl, $C_3$-$C_6$-cycloalkyl, $C_1$-$C_4$-alkylthio-$C_1$-$C_4$-alkyl, $C_1$-$C_4$-alkyl-S(O)—$C_1$-$C_4$-alkyl, $C_1$-$C_4$-alkyl-S(O)$_2$—$C_1$-$C_4$-alkyl, $C_1$-$C_4$-halogenoalkylthio-$C_1$-$C_4$-alkyl having 1 to 5 halogen atoms, $C_1$-$C_4$-alkoxy-$C_1$-$C_4$-alkyl and $C_1$-$C_4$-halogenoalkoxy-$C_1$-$C_4$-alkyl having 1 to 5 halogen atoms, or A is a heterocycle of the formula (Het-15)

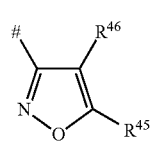

(Het-15)

wherein
$R^{45}$ and $R^{46}$ may be the same or different and are selected from the group consisting of hydrogen, halogen, $C_1$-$C_4$-alkyl and $C_1$-$C_4$-halogenoalkyl having 1 to 5 halogen atoms, or A is a heterocycle of the formula (Het-16)

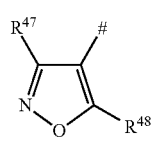

(Het-16)

wherein
$R^{47}$ and $R^{48}$ may be the same or different and are selected from the group consisting of hydrogen, halogen, $C_1$-$C_4$-alkyl, $C_1$-$C_4$-halogenoalkyl having 1 to 5 halogen atoms, phenyl (optionally substituted by halogen or a $C_1$-$C_4$-alkyl), or heterocyclyl like pyridyl, pyrimidinyl and thiadiazolyl (optionally substituted by halogen or $C_1$-$C_4$-alkyl), or A is a heterocycle of the formula (Het-17)

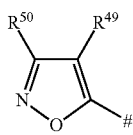

(Het-17)

wherein
$R^{49}$ and $R^{50}$ may be the same or different and are selected from the group consisting of hydrogen, halogen, $C_1$-$C_4$-alkyl and $C_1$-$C_4$-halogenoalkyl having 1 to 5 halogen atoms, or A is a heterocycle of the formula (Het-19)

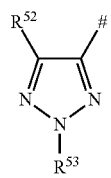

(Het-19)

wherein
$R^{52}$ is selected from the group consisting of halogen, $C_1$-$C_4$-alkyl and $C_1$-$C_4$-halogenoalkyl having 1 to 5 halogen atoms, and
$R^{53}$ is selected from the group consisting of $C_1$-$C_4$-alkyl, $C_1$-$C_4$-halogenoalkyl having 1 to 5 halogen atoms and phenyl (optionally substituted by halogen or $C_1$-$C_4$-alkyl), or A is a heterocycle of the formula (Het-20)

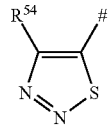

(Het-20)

wherein
$R^{54}$ is selected from the group consisting of halogen, $C_1$-$C_4$-alkyl and $C_1$-$C_4$-halogenoalkyl having 1 to 5 halogen atoms, or A is a heterocycle of the formula (Het-21)

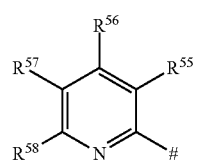

(Het-21)

wherein
$R^{55}$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 halogen atoms and $C_1$-$C_4$-halogenoalkoxy having 1 to 5 halogen atoms, and $R^{56}$, $R^{57}$ and $R^{58}$, which may be the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S(O)—$C_1$-$C_4$-alkyl, —S(O)$_2$—$C_1$-$C_4$-alkyl, $C_1$-$C_4$-halogenoalkoxy having 1 to 5 halogen atoms, —S(O)—$C_1$-$C_4$-alkyl and —S(O)$_2$—$C_1$-$C_4$-alkyl, or A is a heterocycle of the formula (Het-22)

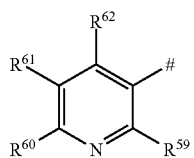

(Het-22)

wherein $R^{59}$ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$ alkoxy, —S—$C_1$-$C_5$-alkyl, —S(O)—$C_1$-$C_4$-alkyl, —S(O)$_2$—$C_1$-$C_4$-alkyl, —S—$C_2$-$C_5$-alkenyl, —S—$C_1$-$C_4$-halogenoalkyl having 1 to 5 halogen atoms, $C_1$-$C_4$-halogenoalkoxy having 1 to 5 halogen atoms, phenyloxy (optionally substituted by halogen or $C_1$-$C_4$-alkyl) and —S-phenyl (optionally substituted by halogen or $C_1$-$C_4$-alkyl), and $R^{60}$, $R^{61}$ and $R^{62}$, which may the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl, —S(O)$_2$—$C_1$-$C_4$-alkyl, N-morpholine (optionally substituted by halogen or $C_1$-$C_4$-alkyl) and thienyl (optionally substituted by halogen or a $C_1$-$C_4$-alkyl), or A is a heterocycle of the formula (Het-23)

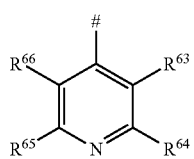

(Het-23)

wherein $R^{63}$, $R^{64}$, $R^{65}$ and $R^{66}$, which may be the same or different, are selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S—$C_1$-$C_4$-halogenoalkyl having 1 to 5 halogen atoms, $C_1$-$C_4$-halogenoalkoxy having 1 to 5 halogen atoms, —S(O)—$C_1$-$C_4$-alkyl and —S(O)$_2$—$C_1$-$C_4$-alkyl, or A is a heterocycle of the formula (Het-24)

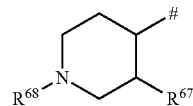

(Het-24)

wherein $R^{67}$ is selected from the group consisting of hydrogen, halogen, $C_1$-$C_4$-alkyl and $C_1$-$C_4$-halogenoalkyl having 1 to 5 halogen atoms, and $R^{68}$ is selected from the group consisting of $C_1$-$C_4$-alkyl, $C_1$-$C_4$-halogenoalkyl having 1 to 5 halogen atoms, $C_1$-$C_6$-alkoxycarbonyl, benzyl (optionally substituted by 1 to 3 halogen atoms), benzyloxycarbonyl (optionally substituted by 1 to 3 halogen atoms) and heterocyclyl like pyrimidinyl, (optionally substituted by halogen, $C_1$-$C_4$-alkyl, $C_1$-$C_4$-halogenoalkyl having 1 to 5 halogen atoms), or A is a heterocycle of the formula (Het-25)

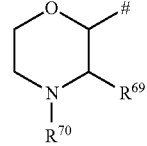

(Het-25)

wherein $R^{69}$ is selected from the group consisting of hydrogen, $C_1$-$C_4$-alkyl and $C_1$-$C_4$-halogenoalkyl having 1 to 5 halogen atoms, and $R^{70}$ is selected from the group consisting of hydrogen, $C_1$-$C_4$-alkyl, $C_1$-$C_4$-halogenoalkyl having 1 to 5 halogen atoms and benzyl, or A is a heterocycle of the formula (Het-26)

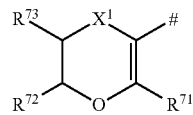

(Het-26)

wherein $X^1$ is selected from the group consisting of sulphur, —SO—, and —SO$_2$—, and $R^{71}$ is selected from the group consisting of $C_1$-$C_4$-alkyl and $C_1$-$C_4$-halogenoalkyl having 1 to 5 halogen atoms, and $R^{72}$ and $R^{73}$ may be the same or different and are selected from the group consisting of hydrogen and $C_1$-$C_4$-alkyl, or A is a heterocycle of the formula (Het-29)

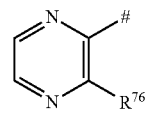

(Het-29)

wherein $R^{76}$ is selected from the group consisting of hydrogen, halogen, $C_1$-$C_4$-alkyl and $C_1$-$C_4$-halogenoalkyl having 1 to 5 halogen atoms.

3. The compound or a salt, N-oxide, metal complex or metalloid complex thereof according to claim 1 or 2, wherein B¹, B² are C—X or N, wherein at least one of B¹ or B² is N, n is 1, X is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, m is 0, 1, 2 or 3, and each Y is independently selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-alkylamino, di-($C_1$-$C_4$-alkyl)amino, wherein both alkyl residues may form a 4- to 7-membered heterocycle incorporating the nitrogen bonded to the phenyl system of the compound, $C_1$-$C_4$-alkylcarbonylamino, —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, —S(O)$_2$—$C_1$-$C_4$-halogenoalkyl having 1 to 5 halogen atoms, or m is 2 or 3, and at least two substituents Y are vicinal and, together with the phenyl ring to which they are bonded, form a structure which is selected from:

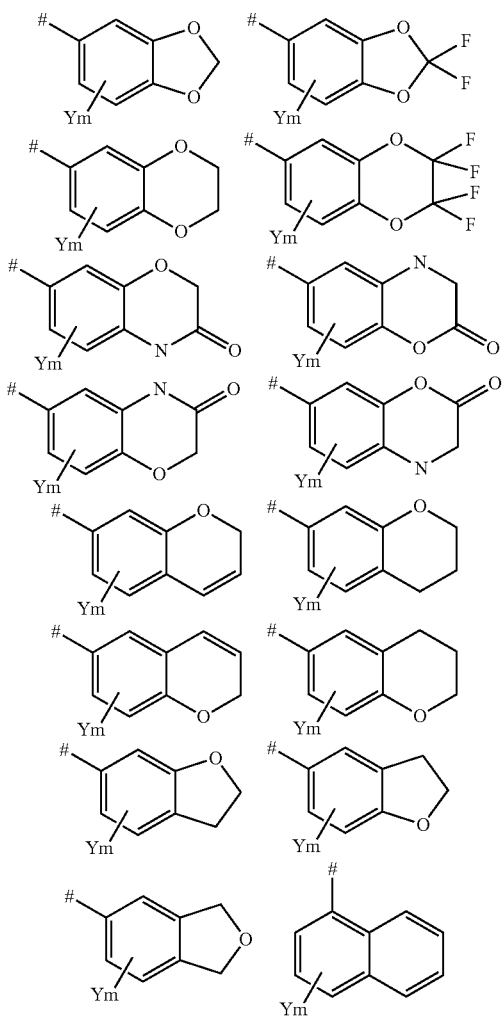

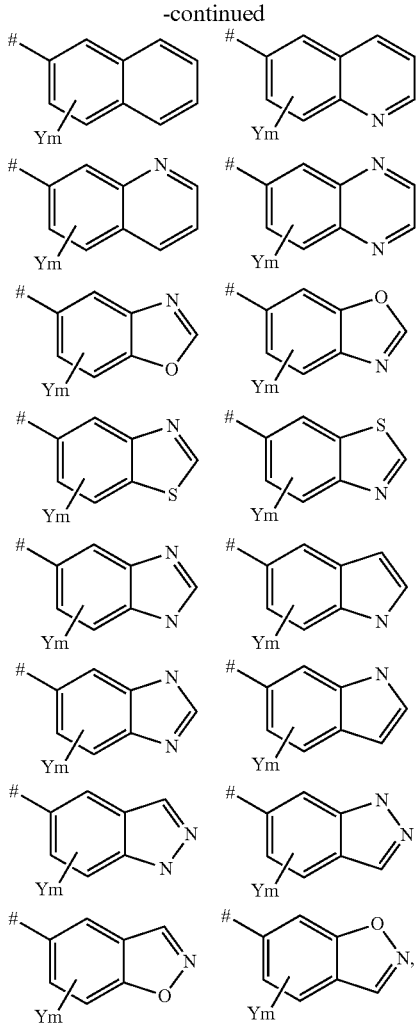

and the remaining substituent Y is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, R¹ and R² are the same or different and are selected from the group consisting of hydrogen, halogen, cyano, 4ydroxyl, $C_1$-$C_4$-alkyl, $C_2$-$C_4$-alkenyl, $C_2$-$C_4$-alkynyl, $C_1$-$C_4$-alkoxy, $C_3$-$C_6$-cycloalkyl-$C_1$-$C_3$-alkyl, $C_1$-$C_4$-alkoxycarbonyl, —OC(O)—$C_1$-$C_4$-alkyl, —NHC(O)—$C_1$-$C_4$-alkyl, and phenyl, with the proviso that R¹ is fluorine and/or R² is fluorine, R³ and R⁴ are the same or different and are selected from the group consisting of hydrogen, —COOH, $C_1$-$C_4$-alkyl, $C_1$-$C_4$-halogeno alkyl $C_1$-$C_4$-alkoxy, 4ydroxyl-$C_1$-$C_4$-alkyl, $C_1$-$C_4$-alkoxy-$C_1$-$C_3$-alkyl, —CONH($C_1$-$C_4$-alkyl), $C_1$-$C_4$-alkoxycarbonyl, —OC(O)—$C_1$-$C_4$-alkyl, and phenyl, R⁵ is selected from the group consisting of hydrogen, $C_3$-$C_6$-cycloalkyl, $C_1$-$C_4$-alkylcarbonyl, and $C_1$-$C_4$-alkoxycarbonyl, A is a phenyl group of formula (A1)

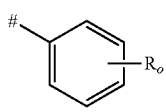

(A1)

wherein
o is 0, 1 or 2, and
each R is independently selected from the group consisting of halogen, nitro, —OH, cyano, $C_1$-$C_4$-alkyl, $C_1$-$C_4$-halogenoalkyl having 1 to 5 halogen atoms, $C_3$-$C_6$-cycloalkyl, $C_1$-$C_4$-alkoxy, $C_1C_1$-$C_4$-alkoxycarbonyl, —NH($C_1$-$C_4$-alkyl), phenyl (optionally substituted by $C_1$-$C_4$-alkoxy) and phenoxy, or A is a heterocycle of the formula (Het-1)

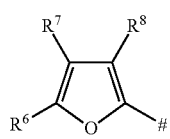

(Het-1)

wherein
$R^6$ and $R^7$ may be the same or different and are selected from the group consisting of hydrogen, halogen, nitro, $C_1$-$C_4$-alkyl and $C_1$-$C_4$-halogenoalkyl having 1 to 5 halogen atoms, and
$R^8$ is selected from the group consisting of hydrogen, halogen, $C_1$-$C_4$-alkyl and $C_1$-$C_4$-halogenoalkyl having 1 to 5 halogen atoms, or A is a heterocycle of the formula (Het-2)

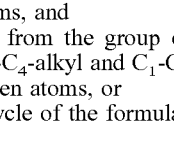

(Het-2)

wherein
$R^9$ is selected from the group consisting of hydrogen, halogen, $C_1$-$C_4$-alkyl and $C_1$-$C_4$-halogenoalkyl having 1 to 5 halogen atoms, and
$R^{10}$ and $R^{11}$ may be the same or different and are selected from the group consisting of hydrogen, halogen, $C_1$-$C_4$-alkyl and $C_1$-$C_4$-halogenoalkyl having 1 to 5 halogen atoms, and
phenyl optionally substituted by halogen or $C_1$-$C_4$-alkyl), or A is a heterocycle of the formula (Het-4)

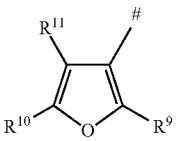

(Het-4)

wherein
$R^{14}$ and $R^{15}$ may be the same or different and are selected from the group consisting of hydrogen, halogen, $C_1$-$C_4$-alkyl, $C_1$-$C_4$-halogenoalkyl having 1 to 5 halogen atoms, —S—$C_1$-$C_4$-alkyl, —S(O)$_2$—$C_1$-$C_4$-alkyl, phenyl (optionally substituted by halogen or $C_1$-$C_4$-alkyl) and pyridyl (optionally substituted by halogen or $C_1$-$C_4$-alkyl), and
$R^{16}$ is selected from the group consisting of hydrogen, halogen, cyano, $C_1$-$C_4$-alkyl, $C_1$-$C_4$-halogenoalkyl having 1 to 5 halogen atoms and $C_1$-$C_4$-halogenoalkoxy having 1 to 5 halogen atoms, or A is a heterocycle of the formula (Het-5)

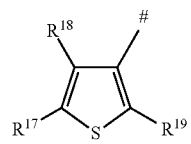

(Het-5)

wherein
$R^{17}$ and $R^{18}$ may be the same or different and are selected from the group consisting of hydrogen, halogen, $C_1$-$C_4$-alkyl, $C_1$-$C_4$-alkyloxy and $C_1$-$C_4$-halogenoalkyl having 1 to 5 halogen atoms, and
$R^{19}$ is selected from the group consisting of hydrogen, halogen, $C_1$-$C_4$-alkyl and $C_1$-$C_4$-halogenoalkyl having 1 to 5 atoms, or A is a heterocycle of the formula (Het-6)

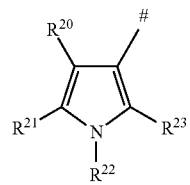

(Het-6)

wherein
$R^{20}$ is selected from the group consisting of hydrogen, halogen, cyano, $C_1$-$C_4$-alkyl and $C_1$-$C_4$-halogenoalkyl having 1 to 5 halogen atoms, and
$R^{21}$ and $R^{23}$ may be the same or different and are selected from the group consisting of hydrogen, halogen, $C_1$-$C_4$-alkyl and $C_1$-$C_4$-halogenoalky having 1 to 5 halogen atoms, and
$R^{22}$ is selected from the group consisting of hydrogen, cyano, $C_1$-$C_4$-alkyl, $C_1$-$C_4$-halogenoalkyl having 1 to 5 halogen atoms, and $C_1$-$C_4$-alkoxy-$C_1$-$C_4$-alkyl, or A represents a heterocycle of the formula (Het-10)

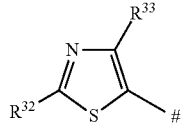

(Het-10)

wherein
$R^{32}$ is selected from the group consisting of hydrogen, halogen, amino, cyano, $C_1$-$C_4$-alkylamino, di-($C_1$-$C_4$-alkyl)amino, $C_1$-$C_4$-alkyl, $C_1$-$C_4$-halogenoalkyl having 1 to 5 halogen atoms and phenyl (optionally substituted by halogen or $C_1$-$C_4$-alkyl), and $R^{33}$ is selected from the group consisting of halogen, $C_1$-$C_4$-alkyl and $C_1$-$C_4$-halogenoalkyl having 1 to 5 halogen atoms, $C_1$-$C_5$-halogenoalkoxy comprising 1 to 9 halogen atoms, amino, substituted or unsubstituted $C_1$-$C_5$-alkylamino and substituted or unsubstituted di-($C_1$-$C_5$-alkyl)-amino, or A represents a heterocycle of the formula (Het-21)

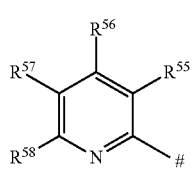

(Het-21)

wherein $R^{55}$ is selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, —S(O)—$C_1$-$C_4$-alkyl, —S(O)$_2$—$C_1$-$C_4$-alkyl, —S—$C_1$-$C_4$-halogenoalkyl having 1 to 5 halogen atoms and $C_1$-$C_4$-halogenoalkoxy having 1 to 5 halogen atoms, and $R^{56}$, $R^{57}$ and $R^{58}$, which may be the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl and —S(O)$_2$—$C_1$-$C_4$-alkyl, or A is a heterocycle of the formula (Het-22)

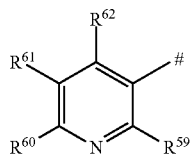

(Het-22)

wherein $R^{59}$ is selected from the group consisting of hydrogen, halogen, hydroxy, cyano, $C_1$-$C_4$-alkyl, $C_1$-$C_4$-halogenoalkyl having 1 to 5 halogen atoms, $C_1$-$C_4$ alkoxy, —S—$C_1$-$C_5$-alkyl, —S(O)—$C_1$-$C_4$-alkyl, —S(O)$_2$—$C_1$-$C_4$-alkyl, —S—$C_2$-$C_5$-alkenyl, —S—$C_1$-$C_4$-halogenoalkyl having 1 to 5 halogen atoms, $C_1$-$C_4$-halogenoalkoxy having 1 to 5 halogen atoms, phenyloxy (optionally substituted by halogen or $C_1$-$C_4$-alkyl) and —S-phenyl (optionally substituted by halogen or $C_1$-$C_4$-alkyl), and $R^{60}$, $R^{61}$ and $R^{62}$, which may the same or different, are selected from the group consisting of hydrogen, halogen, cyano, $C_1$-$C_4$-alkyl, $C_1$-$C_4$-halogenoalkyl having 1 to 5 halogen atoms, $C_1$-$C_4$-alkoxy, —S—$C_1$-$C_4$-alkyl, $C_1$-$C_4$-halogenoalkoxy having 1 to 5 halogen atoms, —S(O)—$C_1$-$C_4$-alkyl, —S(O)$_2$—$C_1$-$C_4$-alkyl, N-morpholine (optionally substituted by halogen or $C_1$-$C_4$-alkyl) and thienyl (optionally substituted by halogen or a $C_1$-$C_4$-alkyl), or A is a heterocycle of the formula (Het-29)

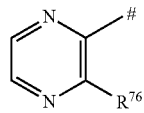

(Het-29)

wherein $R^{76}$ is selected from the group consisting of hydrogen, halogen, $C_1$-$C_4$-alkyl and $C_1$-$C_4$-halogenoalkyl having 1 to 5 halogen atoms.

4. The compound or a salt, N-oxide, metal complex or metalloid complex thereof according to claim 1 or 2, wherein $B^1$ is N, $B^2$ is CH, n is 1, X is selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, and $C_1$-$C_4$-halogenoalkoxy having 1 to 5 halogen atoms, m is 0, 1 or 2, and each Y is independently selected from the group consisting of hydrogen, halogen, nitro, cyano, $C_1$-$C_4$-alkyl, $C_1$-$C_4$-halogenoalkyl having 1 to 5 halogen atoms, $C_1$-$C_4$-alkoxy, $C_1$-$C_4$-halogenoalkoxy having 1 to 5 halogen atoms, $C_1$-$C_4$-alkylamino, di-($C_1$-$C_4$-alkyl)amino, wherein both alkyl residues may form a 4- to 7-membered heterocycle incorporating the nitrogen bonded to the phenyl system of the compound, $C_1$-$C_4$-alkylcarbonylamino, —S—$C_1$-$C_4$-alkyl, —S—$C_1$-$C_4$-halogenoalkyl having 1 to 5 halogen atoms, —S(O)—$C_1$-$C_4$-alkyl, —S(O)—$C_1$-$C_4$-halogenoalkyl having 1 to 5 halogen atoms, —S(O)$_2$—$C_1$-$C_4$-alkyl, and —S(O)$_2$—$C_1$-$C_4$-halogenoalkyl having 1 to 5 halogen atoms, or m is 2 or 3, and at least two substituents Y are vicinal and, together with the phenyl ring to which they are bonded, form a structure which is selected from:

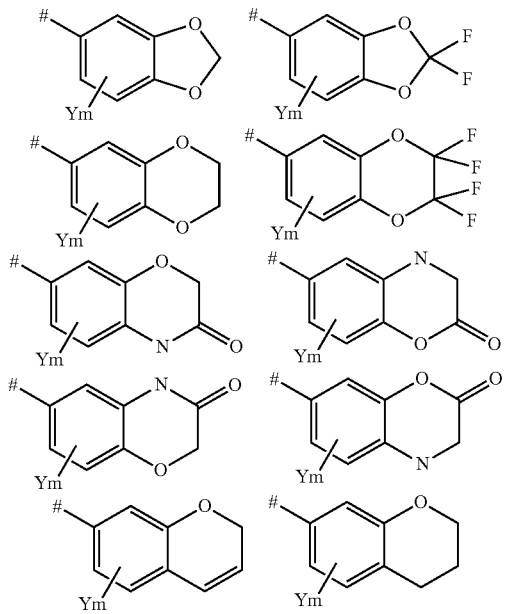

-continued

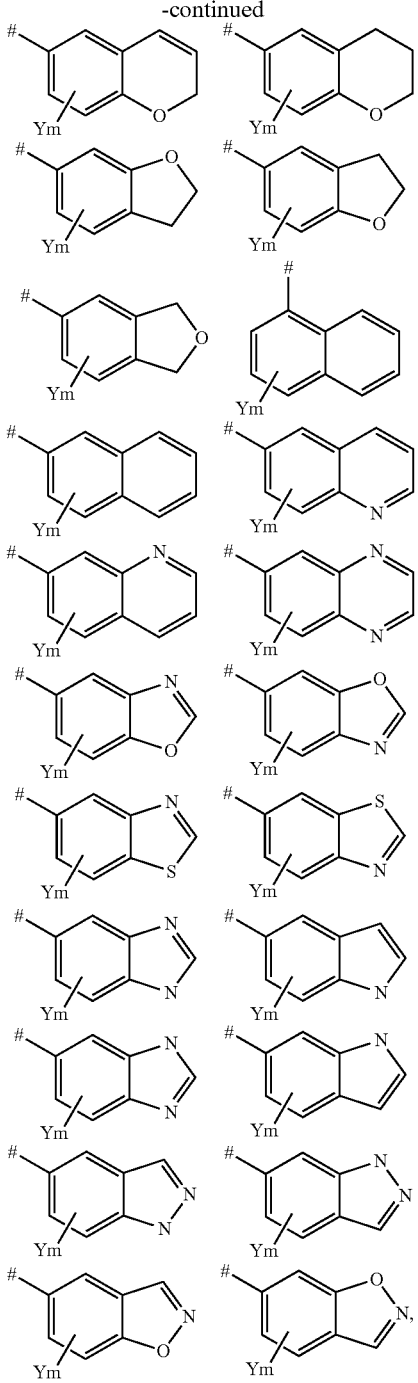

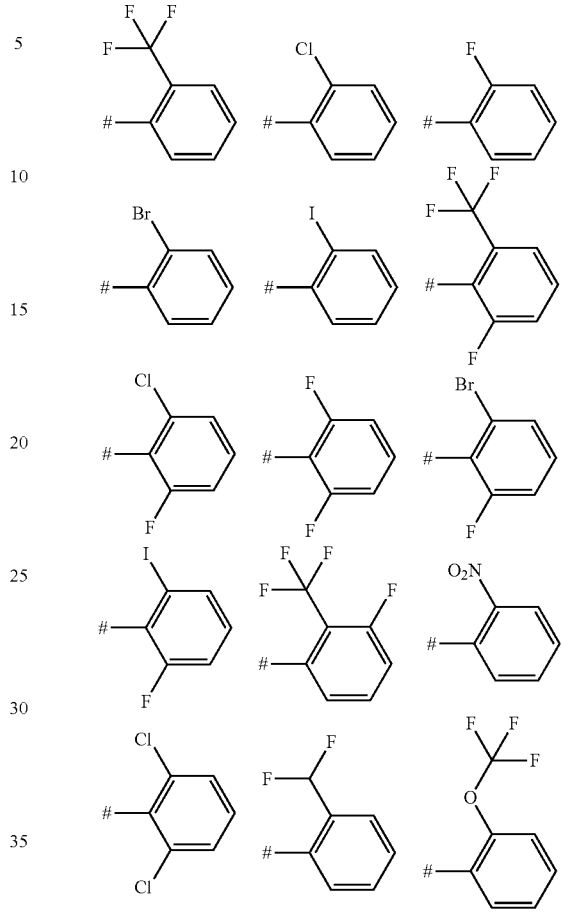

and
  the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl and difluoromethyl,
$R^1$ and $R^2$ are the same or different and are selected from the group consisting of hydrogen, methyl, ethyl, methoxy, ethoxy and fluorine,
  with the proviso that $R^1$ is fluorine and/or $R^2$ is fluorine,
$R^3$ and $R^4$ are the same or different and are selected from the group consisting of hydrogen, methyl and ethyl,
$R^5$ is hydrogen, A is selected from:

or
A is selected from:

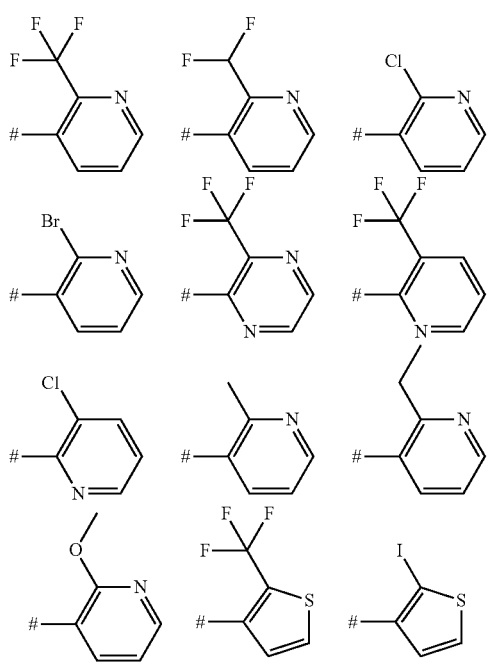

-continued

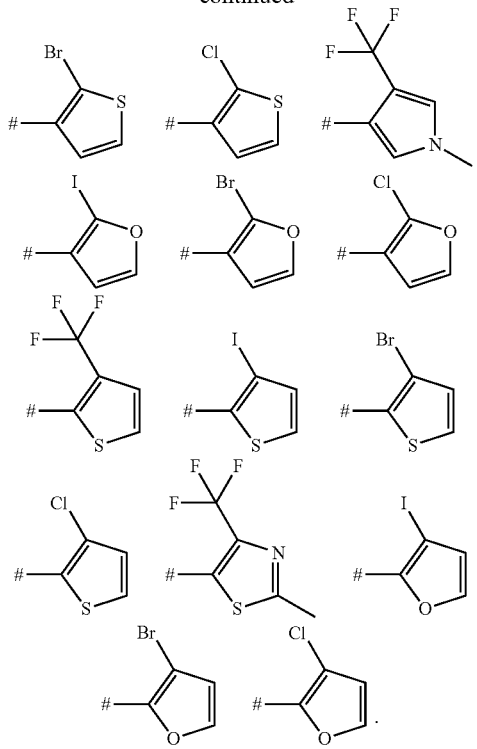

5. The compound or a salt, N-oxide, metal complex or metalloid complex thereof according to claim 1 or 2, wherein
B¹ is N,
B² is CH,
n is 1,
X is selected from the group consisting of hydrogen and chlorine,
m is 0, 1 or 2, and
each Y is independently selected from hydrogen, fluorine, chlorine, bromine, iodine, nitro, cyano, methyl, ethyl, i-propyl, n-propyl, n-butyl, s-butyl, t-butyl, i-butyl, trifluoromethyl, difluoromethyl, methoxy, ethoxy, isopropoxy, n-propoxy, trifluoromethoxy, difluoromethoxy, methylamino, dimethylamino, pyrrolidino, N-methyl-piperazino, morpholino, methylcarbonylamino, methylsulfonyl, methylsulfinyl, methylsulfanyl, trifluoromethylsulfonyl, trifluoromethylsulfinyl or trifluoromethylsulfanyl, or
m is 2 or 3, and
at least two substituents Y are vicinal and, together with the phenyl ring to which they are bonded, form a structure which is selected from:

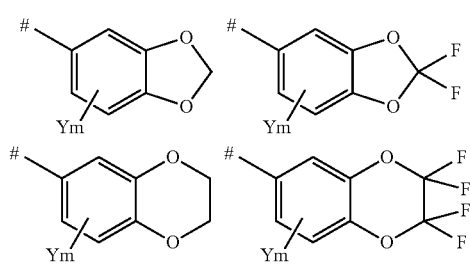

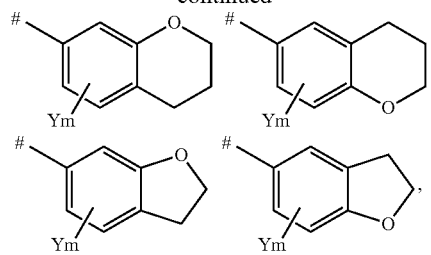

and
the remaining substituent Y is selected from the group consisting of hydrogen, fluorine, chlorine, bromine, iodine, nitro, cyano, methyl, ethyl, i-propyl, n-propyl, n-butyl, s-butyl, t-butyl, i-butyl, methoxy, ethoxy, isopropoxy, n-propoxy, trifluoromethyl and difluoromethyl,
R¹ and R² are independently hydrogen, methyl or fluorine, with the proviso that R¹ is fluorine and/or R² is fluorine,
R³, R⁴ and R⁵ are hydrogen, and
A is

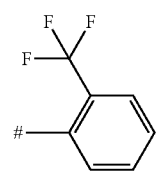

or

or

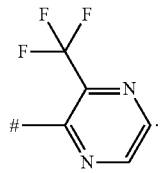

6. The compound or a salt, N-oxide, metal complex or metalloid complex thereof according to claim 1 or 2 which is represented by formula (I-1)

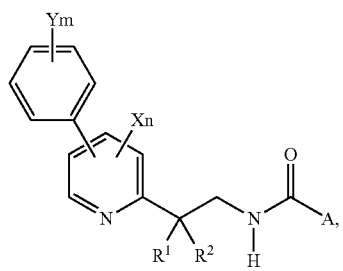

(I-1)

and wherein R¹, R², X, Y, n, m and A are as defined in claim 1 or in claim 2.

7. The compound or a salt, N-oxide, metal complex or metalloid complex thereof according to claim 1 or 2, wherein the phenyl ring bearing the substituent Ym is in para-position.

8. The compound of formula (INT-a)

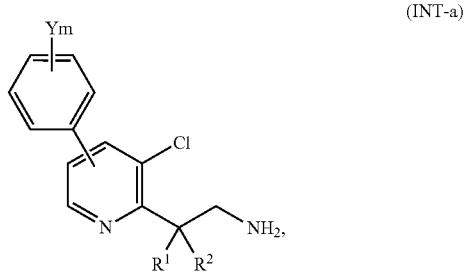

(INT-a)

or a salt, N-oxide, metal complex or metalloid complex thereof,
wherein
R$^1$ and R$^2$ are the same or different and are selected from the group consisting of hydrogen, halogen, cyano, hydroxy, amino, —SH, —CHO, —OCHO, —NHCHO, —COOH, —CONH$_2$, —CONH(OH), —OCONH$_2$, a (hydroxyimino)-C$_1$-C$_6$-alkyl group, C$_1$-C$_6$-alkyl, C$_2$-C$_6$-alkenyl, C$_2$-C$_6$-alkynyl, C$_1$-C$_6$-alkylamino, di-(C$_1$-C$_6$-alkyl)amino, C$_1$-C$_6$-alkoxy, hydroxy-C$_1$-C$_4$-alkyl, C$_1$-C$_4$-alkoxy-C$_1$-C$_3$-alkyl, C$_1$-C$_6$-halogenoalkyl having 1 to 5 halogen atoms, C$_1$-C$_6$-halogenoalkoxy having 1 to 5 halogen atoms, C$_2$-C$_6$-alkenyloxy, C$_2$-C$_6$-halogenoalkenyloxy having 1 to 5 halogen atoms, C$_3$-C$_6$-alkynyloxy, C$_3$-C$_6$-halogenoalkynyloxy having 1 to 5 halogen atoms, C$_3$-C$_6$-cycloalkyl, C$_3$-C$_6$-halogenocycloalkyl having 1 to 5 halogen atoms, C$_3$-C$_6$-cycloalkyl-C$_1$-C$_6$-alkyl, C$_3$-C$_6$-halogenocycloalkyl-C$_1$-C$_6$-alkyl having 1 to 5 halogen atoms, C$_1$-C$_6$-alkylcarbonyl, C$_1$-C$_6$-halogenoalkylcarbonyl having 1 to 5 halogen atoms, —CONH(C$_1$-C$_6$-alkyl), —CON(C$_1$-C$_6$-alkyl)$_2$, —CONH(OC$_1$-C$_6$-alkyl), —CON(OC$_1$-C$_6$-alkyl)(C$_1$-C$_6$-alkyl), C$_1$-C$_6$-alkoxycarbonyl, a C$_1$-C$_6$-halogenoalkoxycarbonyl having 1 to 5 halogen atoms, —OC(O)—C$_1$-C$_6$-alkyl, —OC(O)—C$_1$-C$_6$-halogenoalkyl having 1 to 5 halogen atoms, —NHC(O)—C$_1$-C$_6$-alkyl, —NHC(O)—C$_1$-C$_6$-halogenoalkyl having 1 to 5 halogen atoms, —OCONH(C$_1$-C$_6$-alkyl), —OCON(C$_1$-C$_6$-alkyl)$_2$, —OCONH(OC$_1$-C$_6$-alkyl), OCO(OC$_1$-C$_6$-alkyl), —S—C$_1$-C$_6$-alkyl, —S—C$_1$-C$_6$-halogenoalkyl having 1 to 5 halogen atoms, —S(O)—C$_1$-C$_6$-alkyl, —S(O)—C$_1$-C$_6$-halogenoalkyl having 1 to 5 halogen atoms, —S(O)$_2$—C$_1$-C$_6$-alkyl, —S(O)$_2$—C$_1$-C$_6$-halogenoalkyl having 1 to 5 halogen atoms, benzyl, benzyloxy, —S-benzyl, —S(O)-benzyl, —S(O)$_2$-benzyl, benzylamino, phenoxy, —S-phenyl, —S(O)-phenyl, —S(O)$_2$-phenyl, phenylamino, phenylcarbonylamino and phenyl,
with the proviso that R$^1$ is fluorine and/or R$^2$ is fluorine,
Y is independently selected from the group consisting of hydrogen, halogen, nitro, cyano, hydroxy, amino, —SH, —SF$_5$, —CHO, —OCHO, —NHCHO, —COOH, —CONH$_2$, —CONH(OH), —OCONH$_2$, (hydroxyimino)-C$_1$-C$_6$-alkyl, C$_1$-C$_8$-alkyl, C$_1$-C$_8$-halogenoalkyl having 1 to 5 halogen atoms, C$_2$-C$_8$-alkenyl, C$_2$-C$_8$-alkynyl, C$_1$-C$_8$-alkylamino, di-(C$_1$-C$_8$-alkyl)amino, wherein both alkyl residues may form a 4- to 7-membered heterocycle incorporating the nitrogen bonded to the phenyl system of the compound, C$_1$-C$_8$-alkoxy, C$_1$-C$_8$-halogenoalkoxy having 1 to 5 halogen atoms, C$_2$-C$_8$-alkenyloxy, C$_2$-C$_8$-halogenoalkenyloxy having 1 to 5 halogen atoms, C$_3$-C$_8$-alkynyloxy, C$_3$-C$_8$-halogenoalkynyloxy having 1 to 5 halogen atoms, C$_3$-C$_8$-cycloalkyl, C$_3$-C$_8$-halogenocycloalkyl having 1 to 5 halogen atoms, C$_1$-C$_8$-alkylcarbonyl, C$_1$-C$_8$-halogenoalkylcarbonyl having 1 to 5 halogen atoms, —CONH(C$_1$-C$_8$-alkyl), —CON(C$_1$-C$_8$-alkyl)$_2$, —CONH(OC$_1$-C$_8$-alkyl), —CON(OC$_1$-C$_8$-alkyl)(C$_1$-C$_8$-alkyl), C$_1$-C$_8$-alkoxycarbonyl, C$_1$-C$_8$-halogenoalkoxycarbonyl having 1 to 5 halogen atoms, C$_1$-C$_8$-alkylcarbonyloxy, C$_1$-C$_8$-halogenoalkylcarbonyloxy having 1 to 5 halogen atoms, C$_1$-C$_8$-alkylcarbonylamino, C$_1$-C$_8$-halogenoalkylcarbonylamino having 1 to 5 halogen atoms, —OCONH(C$_1$-C$_8$-alkyl), —OCON(C$_1$-C$_8$-alkyl)$_2$, —OCONH(OC$_1$-C$_8$-alkyl), —OCO(OC$_1$-C$_8$-alkyl), —S—C$_1$-C$_8$-alkyl, —S—C$_1$-C$_8$-halogenoalkyl having 1 to 5 halogen atoms, —S(O)—C$_1$-C$_8$-alkyl, —S(O)—C$_1$-C$_8$-halogenoalkyl having 1 to 5 halogen atoms, —S(O)$_2$—C$_1$-C$_8$-alkyl, —S(O)$_2$—C$_1$-C$_8$-halogenoalkyl having 1 to 5 halogen atoms, —CH$_2$—S—C$_1$-C$_8$-alkyl, —CH$_2$—S(O)—C$_1$-C$_8$-alkyl, —CH$_2$—S(O)$_2$—C$_1$-C$_8$-alkyl, (C$_1$-C$_6$-alkoxyimino)-C$_1$-C$_6$-alkyl, (C$_2$-C$_6$-alkenyloxyimino)-C$_1$-C$_6$-alkyl, (C$_3$-C$_6$-alkynyloxyimino)-C$_1$-C$_6$-alkyl, (benzyloxyimino)-C$_1$-C$_6$-alkyl, benzyloxy, —S-benzyl, benzyl amino, phenoxy, —S-phenyl and phenylamino, and
m is 0, 1, 2, 3, 4 or 5.

9. The compound or a salt, N-oxide, metal complex or metalloid complex thereof according to claim 8, wherein the phenyl ring bearing the substituent Ym is in para-position.

10. The compound or a salt, N-oxide, metal complex or metalloid complex thereof according to claim 8 or 9 which is represented by formula (INT-1)

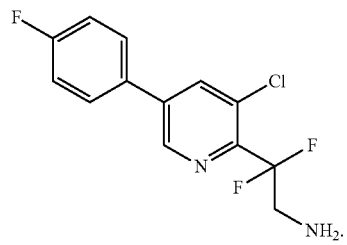

(INT-1)

11. A formulation comprising at least one compound of formula (I) or a salt, N-oxide, metal complex or metalloid complex thereof according to claim 1.

12. The formulation according to claim 11 which further comprises at least one extender and/or at least one surfactant.

13. The formulation according to claim 11 or 12, wherein the compound of the formula (I), or a salt, N-oxide, metal complex or metalloid complex thereof, is present in a mixture with at least one other active compound.

14. A method for controlling an animal pest, wherein a compound of formula (I) or a salt, N-oxide, metal complex or metalloid complex thereof according to claim 1, or a formulation according to claim 11 is allowed to act on the animal pest and/or their habitat.

15. The method according to claim 14, wherein the animal pest comprises a nematode or is a nematode.

16. A method for protecting a seed and/or a germinating plant from attack by a pest, particularly a nematode, comprising the step of contacting the seed with a compound of formula (I) or a salt, N-oxide, metal complex or metalloid complex thereof according to claim 1, or with a formulation according to claim 11.

17. A seed obtained by a method according to claim 16.

* * * * *